(12) United States Patent
Buggy et al.

(10) Patent No.: US 7,838,234 B2
(45) Date of Patent: Nov. 23, 2010

(54) METHODS FOR DETERMINING CANCER RESISTANCE TO HISTONE DEACETYLASE INHIBITORS

(75) Inventors: Joseph J. Buggy, Mountain View, CA (US); Sriram Balasubramanian, San Carlos, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 203 days.

(21) Appl. No.: 12/022,977

(22) Filed: Jan. 30, 2008

(65) Prior Publication Data
US 2009/0123374 A1 May 14, 2009

Related U.S. Application Data

(60) Provisional application No. 60/887,318, filed on Jan. 30, 2007, provisional application No. 60/911,855, filed on Apr. 13, 2007.

(51) Int. Cl.
*C12Q 1/68* (2006.01)
(52) U.S. Cl. ............................................. 435/6; 435/7.1
(58) Field of Classification Search ........................ None
See application file for complete search history.

(56) References Cited

U.S. PATENT DOCUMENTS

2003/0166026 A1   9/2003   Goodman

FOREIGN PATENT DOCUMENTS

| EP | 1400806 A1 | 3/2004 |
|---|---|---|
| EP | 1426054 A1 | 6/2004 |
| EP | 1595952 A1 | 11/2005 |
| WO | WO 2005-059108 A2 | 6/2005 |

OTHER PUBLICATIONS

LePage, C. et al., "From gene profiling to diagnostic markers: IL-18 and FGF-2 complement CA125 as serum-based markers in epithelial ovarian cancer," Int. J. Cancer 118(7):1750-1758 (2006).
Natrajan, R. et al., "Array CGH profiling of favourable histology Wilms tumours reveals novel gains and losses associated with relapse," J. Pathol. 210(1):49-58 (2006).
PCT/US08/52540 Search Report dated Jun. 17, 2008.
Hardiman, "Microarray Platforms-Comparisons and Contrasts," Pharmacogenomics 5(5):487-502 (20040.
Piekarz et al. "T-cell lymphoma as a model for the use of histone deacetylase inhibitors in cancer therapy: impact of depsipeptide on molecular markers, therapeutic targets, and mechanisms of resistance," Blood 103(12):4636-4643 (2004).
Sasakawa et al., "Marker genes to predict sensitivity to FK 228, a histone deacetylase inhibitor," Biochem. Pharmacol. 69(4):603-616 (2005).
EP 08728620 Supplementary Search Report mailed Aug. 24, 2010.

*Primary Examiner*—James Martinell
(74) *Attorney, Agent, or Firm*—Wilson Sonsini Goodrich & Rosati

(57) ABSTRACT

Described herein are methods and compositions for determining whether a particular cancer is resistant to or susceptible to a histone deacetylase inhibitor or to histone deacetylase inhibitors. The methods include analysis of the expression levels of at least four biomarker genes associated with response to a histone deacetylase inhibitor. Also described herein are methods and compositions for increasing the likelihood of a therapeutically effective treatment in a patient, comprising an analysis of the expression levels of at least four biomarker genes associated with response to a histone deacetylase inhibitor. Also described herein are isolated populations of nucleic acids derived from a cancer sensitive to or resistant to a histone deacetylase inhibitor. Further described are kits and indications that are optionally used in conjunction with the aforementioned methods and compositions.

17 Claims, 11 Drawing Sheets

FGF 15

Synaptogyrin 2

METHODS FOR DETERMINING CANCER RESISTANCE TO HISTONE DEACETYLASE INHIBITORS

RELATED APPLICATIONS

This application claims the benefit of U.S. Provisional Patent Application No. 60/887,318, entitled "Methods for determining cancer resistance to histone deacetylase inhibitors," filed Jan. 30, 2007, and U.S. Provisional Patent Application No. 60/911,855 entitled "Methods for determining cancer resistance to histone deacetylase inhibitors," filed Apr. 13, 2007, the contents of both of which are incorporated by reference in their entirety.

BACKGROUND OF THE INVENTION

The highly heterogeneous response of the same type of cancer (e.g., colon cancer) to a given anti-cancer compound in different patients is one of the most vexing and tragic problems of modern medicine. It is widely thought that human genetic and epigenetic diversity underlies much of the variation in response to chemotherapy. Thus, there is an ongoing effort to identify in the human population the molecular genetic correlates (i.e., molecular signatures) of cancer resistance and sensitivity to specific therapeutic agents. It is hoped that such efforts will ultimately enable physicians to predetermine the likelihood that a patient's cancer can be effectively treated with a particular anti-cancer compound.

SUMMARY OF THE INVENTION

Described herein are methods and compositions for classifying a cancer in a patient as resistant or sensitive to a histone deacetylase inhibitor (HDACi) compound by (i) comparing the expression levels of at least four biomarker genes to a first set of biomarker gene expression level values, which was determined in cancer cells known to be resistant to the HDACi compound, or by comparing the expression levels to a second set of biomarker gene expression level values, which was determined in cancer cells known to be sensitive to the HDACi compound, and (ii) indicating that the cancer is sensitive to the HDACi compound if the biomarker gene expression levels are significantly lower than the first set of expression level values, or indicating that the cancer is resistant to the HDACi compound if the biomarker gene expression levels are greater than the second set of expression level values. The referred-to biomarker genes include PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2.

Accordingly, in one aspect provided herein is a method for classifying a cancer in a patient, comprising comparing the expression levels of at least four biomarker genes in the cancer to expression level to a first or second set of expression level threshold values for the biomarker genes, and indicating that the cancer is sensitive to a HDAC inhibitor if the expression levels of the biomarker genes are lower than the first set of expression level threshold values, or indicating that the cancer is resistant to a HDAC inhibitor if the expression levels are greater than the second set of expression level threshold values, wherein the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA 1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2. In some embodiments, the at least four marker genes are selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the at least four biomarker genes include at least one of DEFA6, RAB25, TM4SF4, or IL18. In some embodiments, the at least four biomarker genes include DEFA6, ITGB4, TM4SF3, SYK, PPAP2C, and RAB25. In some embodiments, the at least four biomarker genes include DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, one or more of the above-mentioned expression levels is an mRNA expression level. In some embodiments, one or more of the expression levels is a polypeptide expression level. In some embodiments, the patient's cancer is a colon cancer. In some embodiments, the method for classifying the cancer further comprises determining the level of expression of the at least four biomarker genes in the cancer prior to the step of comparing. In some embodiments, the referred-to HDAC inhibitor is PCI-24781. In some embodiments, the expression levels of the at least four biomarker genes are compared to the first set and the second set of biomarker gene expression level threshold level values.

In another aspect provided herein is a method for classifying a cancer in a patient, comprising determining the expression levels of at least four biomarker genes in the cancer, comparing the expression levels of the at least four biomarker genes in the cancer to expression level to a first or second set of expression level threshold values for the biomarker genes, and indicating that the cancer is sensitive to a HDAC inhibitor if the expression levels of the biomarker genes are lower than the first set of expression level threshold values, or indicating that the cancer is resistant to a HDAC inhibitor if the expression levels are greater than the second set of expression level threshold values, wherein the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2.

In some embodiments, at least one of the at least four marker genes are selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the at least four biomarker genes include at least one of DEFA6, RAB25, TM4SF4, or IL18. In some embodiments, the at least four biomarker genes include DEFA6, ITGB4, TM4SF3, SYK, PPAP2C, and RAB25. In some embodiments, the at least four biomarker genes include DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, wherein one or more of the expression levels of the referred-to biomarker genes is an mRNA expression level. In some embodiments, one or more of the expression levels is a polypeptide expression level. In some embodiments, the patient's cancer is a colon cancer. In some embodiments, the HDAC inhibitor is PCI-24781. In some embodiments, the method further comprises prescribing or administering an HDAC inhibitor to the patient based on the comparison of the biomarker gene expression levels. In some embodiments, the expression levels of the at least four biomarker genes are compared to the first set and the second set of biomarker gene expression level threshold level values.

In a further aspect provided herein is an isolated population of nucleic acids comprising a plurality of nucleic acids derived from a cancer cell, wherein the cancer cell is a type of cancer cell that is sensitive to an HDAC inhibitor compound. In some embodiments, the isolated population contains RNAs. In some embodiments, the isolated population contains cDNAs. In some embodiments, the referred-to HDAC inhibitor is PCI-24781. In some embodiments, the referred-to cancer cell was isolated from a population of cells grown in vitro. In some embodiments, the cancer cell is a colon carcinoma cell. In some embodiments, the colon carcinoma cell is derived from colon carcinoma R1059261097, R4498160614, R5456781761, R7424107588, or R0948311023. In some embodiments, the nucleotide sequences of at least four of DEFA6, ITGB4, TM4SF4, SYK, PPAP2C, RAB25, HEPH, NOXO1, TM4SF4, PTPN3, EPHA2, FGFBP1, ABCC3, TPMT, IL18, or DPEP1 are represented in the isolated population of nucleic acids.

In a related aspect provided herein is an isolated population of nucleic acids comprising a plurality of nucleic acids derived from a cancer cell, wherein the cancer cell is a type of cancer cell that is resistant to an HDAC inhibitor compound. In some embodiments, the isolated population contains RNAs. In some embodiments, the isolated population contains cDNAs. In some embodiments, the referred-to HDAC inhibitor is PCI-24781. In some embodiments, the referred-to cancer cell was isolated from a population of cells grown in vitro. In some embodiments, the cancer cell is a colon carcinoma cell. In some embodiments, the colon carcinoma cell is derived from colon carcinoma R1059261097, R4498160614, R5456781761, R7424107588, or R0948311023. In some embodiments, the nucleotide sequences of at least four of DEFA6, ITGB4, TM4SF4, SYK, PPAP2C, RAB25, HEPH, NOXO1, TM4SF4, PTPN3, EPHA2, FGFBP1, ABCC3, TPMT, IL18, or DPEP1 are represented in the isolated population of nucleic acids.

In some embodiments provided herein is a kit comprising the above referred-to isolated population of nucleic acids and an insert indicating the ratio of a biomarker gene nucleic acid level in the population to an internal expression control gene nucleic acid level in the population.

In some embodiments provided herein is a kit comprising the above referred-to isolated population of nucleic acids and an insert indicating the ratio of a biomarker gene nucleic acid level in the population to a nucleic acid level of the biomarker gene in a population of nucleic acids derived from a cancer cell, wherein the cancer cell is a type of cancer cell that is sensitive to the HDAC inhibitor compound.

In another aspect provided herein is a method for generating an expression level reference population of nucleic acids for expression profiling, comprising deriving an isolated population of nucleic acids from a cancer cell, wherein the cancer cell is a type of cancer cell that is sensitive to an HDAC inhibitor compound. In some embodiments, the isolated population contains RNAs. In some embodiments, the isolated population contains cDNAs. In some embodiments, the just-referred to HDAC inhibitor compound is PCI-24781. In some embodiments, the cancer cell is present in a biopsy sample. In some embodiments, the cancer cell is present in a population of cells grown in vitro. In some embodiments, the cancer cell is a colon carcinoma cell. In some embodiments, the carcinoma cell is derived from colon carcinoma R1059261097, R4498160614, R5456781761, R7424107588, or R0948311023. In some embodiments, the nucleotide sequences of at least four of DEFA6, ITGB4, TM4SF4, SYK, PPAP2C, RAB25, HEPH, NOXO1, TM4SF4, PTPN3, EPHA2, FGFBP1, ABCC3, TPMT, IL18, or DPEP1 are represented in the above referred-to isolated population of nucleic acids. In some embodiments, the method further comprises determining, prior to the isolating step, that the type of cancer cell is sensitive to an HDAC inhibitor compound. In some embodiments, the type of cancer cell determined to be sensitive to an HDAC inhibitor compound HDAC inhibitor compound in vitro. In some embodiments, the HDAC inhibitor compound is PCI-24781.

In a related aspect provided herein is a method for generating an expression level reference sample for expression profiling, comprising deriving an isolated population of nucleic acids from a cancer cell, wherein the cancer cell is a type of cancer cell that is resistant to an HDAC inhibitor compound. In some embodiments, the isolated population contains RNAs. In some embodiments, the isolated population contains cDNAs. In some embodiments, the just-referred to HDAC inhibitor compound is PCI-24781. In some embodiments, the cancer cell is present in a biopsy sample. In some embodiments, the cancer cell is present in a population of cells grown in vitro. In some embodiments, the cancer cell is a colon carcinoma cell. In some embodiments, the carcinoma cell is derived from colon carcinoma R1059261097, R4498160614, R5456781761, R7424107588, or R0948311023. In some embodiments, the nucleotide sequences of at least four of DEFA6, ITGB4, TM4SF4, SYK, PPAP2C, RAB25, HEPH, NOXO1, TM4SF4, PTPN3, EPHA2, FGFBP1, ABCC3, TPMT, IL18, or DPEP1 are represented in the above referred-to isolated population of nucleic acids. In some embodiments, the method further comprises determining, prior to the isolating step, that the type of cancer cell is resistant to an HDAC inhibitor compound. In some embodiments, the type of cancer cell determined to be resistant to an HDAC inhibitor compound HDAC inhibitor compound in vitro. In some embodiments, the HDAC inhibitor compound is PCI-24781.

In another aspect provided herein is a human cancer cell line that is resistant to an HDAC inhibitor compound in vitro. In some embodiments, the human cell line expresses DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the HDAC inhibitor compound to which the referred-to human cancer cell line is resistant is PCI-24781. In some embodiments, the PCI-24781-resistant human cancer cell line is resistant to a PCI-24781 concentration of at least about 1 μM. In some embodiments, the human cancer cell line is a colon carcinoma cell line. In some embodiments, the colon carcinoma cell line is R5247682266, R9866135153, R1078103114, or R4712781606.

In a further aspect provided herein is a method for increasing the likelihood of therapeutically effective treatment of a cancer with an HDAC inhibitor, comprising providing an indication that a cancer in a patient is sensitive to treatment with an HDAC inhibitor if expression levels of at least four biomarker genes in a sample from the patient's cancer are lower than expression level threshold values for the four biomarker genes, or providing an indication that the cancer is resistant to treatment with the HDAC inhibitor if the expression levels of the biomarker genes are higher than the expression level threshold values, wherein the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MSTIR, ITGB4, ANXA3, CCL15, DPEP1, NOXO1, IF127, CYP3A43, and PKP2, whereby the likelihood of therapeutically effective treatment of the cancer with the HDAC inhibitor is increased. In some embodiments, the indication is provided in a digital medium. In some embodiments, the indication is provided in a hardcopy medium. In some embodiments, the indication is a biomedical publication reference. In some embodiments, the indication refers to expression levels of at least two of the biomarker genes. In some embodiments, the at least four biomarker genes include DEFA6, RAB25, TM4SF4, or IL18. In some embodiments, the at least four biomarker genes include DEFA6, ITGB4, TM4SF3, SYK, PPAP2C, and RAB25. In some embodiments, the at least four biomarker genes include DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the cancer is colon cancer. In some embodiments, the HDAC inhibitor is PCI-24781.

In yet another aspect provided herein is a method for optimizing selection of an anti-cancer agent for treating a cancer in combination with an HDAC inhibitor compound, by: (i) comparing a first set of biomarker genes the expression of which is correlated to resistance or sensitivity of the cancer to the anti-cancer agent to a second set of biomarker genes the expression of which is correlated with resistance to the HDAC inhibitor compound; and (ii) selecting the anti-cancer agent for treatment of the cancer in combination with the HDAC inhibitor if the biomarker genes in the first set are different from the biomarker genes in the second set, where the biomarker genes in the second set are DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1. In some embodiments, the method further comprises comparing the expression level of the second set of biomarker genes in a plurality of cancer cells treated with the HDAC inhibitor together with a second anti-cancer agent.

In a further aspect provided herein is an indication of the likelihood of a therapeutically effective treatment of a cancer with an HDAC inhibitor compound, comprising a means of communicating an interpretation of expression levels of at least four biomarker genes selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP. In some embodiments, the indication further comprises the expression levels of the at least four biomarker genes. In some embodiments, the means of communicating is a paper document or an electronic document. In some embodiments, the interpretation includes a biomedical publication reference. In some embodiments, the interpretation includes a graph. In some embodiments, the interpretation includes information that indicates that a cancer in a patient is sensitive to treatment with an HDAC inhibitor if expression levels of the biomarker genes in a sample from the patient's cancer are lower than expression level threshold values for the four biomarker genes, or information that indicates that the cancer is resistant to treatment with the HDAC inhibitor if the expression levels of the biomarker genes are higher than the expression level threshold values.

In another aspect provided herein is a method for determining the likelihood of effectively treating a cancer in a patient with an HDAC inhibitor compound, comprising: (i) determining in the cancer the expression levels of at least four biomarker genes selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP; and (ii) comparing the expression levels of that at least four biomarker genes in the cancer to expression levels of the at least four biomarker genes in an expression level reference sample derived from cancer cells previously determined to be resistant to the HDAC inhibitor compound, wherein the likelihood of effectively treating the cancer is higher if the expression level of the at least four biomarkers in the cancer from the patient is lower than the expression levels of the biomarker genes in the expression level reference sample. In some embodiments, the method further comprises selecting an anti-cancer agent other than an HDAC inhibitor compound for treating the cancer.

In yet another aspect provided herein is a method for classifying a cancer in a patient, comprising comparing the expression levels of at least four biomarker genes in the cancer to a first or second set of expression level values for the biomarker genes, and for each comparison assigning a probability to the biomarker gene expression level that the cancer in the patient is resistant to a histone deacetylase inhibitor compound, where: (i) the first set of expression level values were measured in cancer cells determined to be resistant to the histone deacetylase inhibitor compound; (ii) the second set of expression level values were measured in cancer cells determined to be sensitive to the histone deacetylase inhibitor compound; (iii) the assigned probability is inversely proportional to a negative deviation of the biomarker gene expression level from the first set of expression level values and directly proportional to a positive deviation of the biomarker gene expression level from the second set of expression level values; and (iv) the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA 1, EPHA2, ITGA6, TNFRSF21, TM4SF3, IL18, BMP4, SMPDL3B, TMPRSS2, GDA, MSTIR, ITGB4, ANXA3, CCL15, DPEP1, NOXO1, IF127, CYP3A43, and PKP2.

In another aspect provided herein is a method for classifying a population of cells, comprising comparing the expression levels of at least four biomarker genes in the population of cells to a first or second set of expression level threshold values for the biomarker genes, and indicating that the population of cells is sensitive to a HDAC inhibitor if the expression levels of the biomarker genes are lower than the first set of expression level threshold values, or indicating that the population of cells is resistant to a HDAC inhibitor if the expression levels are greater than the second set of expression level threshold values, wherein the at least four biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA 1, EPHA2, ITGA6, TNFRSF21, TM4SF3, IL18, BMP4, SMPDL3B, TMPRSS2, GDA, MSTIR, ITGB4, ANXA3, CCL15, DPEP1, NOXO1, IF127, CYP3A43, and PKP2.

In another aspect provided herein is a method for determining HDAC inhibition in vivo, comprising determining the expression level of an HDAC inhibitor-responsive biomarker gene in a biological sample obtained from a subject after the subject had been administered an HDAC inhibitor compound, wherein the HDAC inhibitor-responsive biomarker genes are any of the genes listed in Table 5.

In another aspect provided herein is a method for determining the most responsive tissues and the tumors derived therefrom to an HDAC inhibitor, comprising: (i) providing a first tissue of the tissue type (including blood) at a first time point and administration of HDAC inhibitor compound to the first tissue by any applicable route at a first time point, (ii) providing a second tissue of the tissue type (including blood) at a second time point and administration of HDAC inhibitor compound to the second tissue by any applicable route at a second time point, and (iii) determining expression profiles in the first and second tissues for any of the genes listed in Table 5.

In a further aspect provided herein is a method for classifying one or more cells, comprising determining the expression levels of no more than four to fifty biomarker genes in the one or more cells, wherein at least four of the biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA 1, EPHA2, ITGA6, TNFRSF21, TM4SF3, IL18, BMP4, SMPDL3B, TMPRSS2, GDA, MSTIR, ITGB4, ANXA3, CCL15, DPEP1, NOXO1, IF127, CYP3A43, and PKP2. In some embodiments, the method further comprises comparing the expression levels of the four to fifty biomarker genes to a first or second set of expression level threshold values for the biomarker genes, and indicating that the cancer is sensitive to a HDAC inhibitor if the expression levels of the biomarker genes are lower than the first set of expression level threshold values, or indicating that the cancer is resistant to a HDAC inhibitor if the expression levels are greater than the second set of expression level threshold values. In some embodiments, the one or more cells are cancer cells. In some embodiments, the at least four biomarker genes are selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP. In some embodiments, the method further comprises determining the expression levels of no more than four to twenty biomarker genes. In some embodiments, the method comprises determining the expression levels of no more than four biomarker genes. In some embodiments, the four biomarker genes consist of DEFA6, RAB25, TM4SF4, and IL18.

In yet another aspect provided herein is a nucleic acid hybridization array comprising nucleic acid probes that hybridize under high stringency hybridization conditions to nucleic acids of no more than four to fifty biomarker genes, wherein at least four of the biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MSTIR, ITGB4, ANXA3, CCL15, DPEP1, NOXO1, IF127, CYP3A43, and PKP2. In some embodiments, the nucleic acid hybridization array comprises at least four biomarker genes selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP. In some embodiments, the at least four biomarker genes consist of DEFA6, RAB25, TM4SF4, and IL18.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a,", "an," and "the" include plural reference unless the context clearly indicates otherwise.

The term "biomarker gene" refers to a gene whose expression or activity yields at least one expression product the level of which is quantitatively correlated to a phenotypic state of interest (e.g., drug resistance, pathology).

The term "detectable label" refers to a label which is observable using analytical techniques including, but not limited to, fluorescence, chemiluminescence, electron-spin resonance, ultraviolet/visible absorbance spectroscopy, mass spectrometry, nuclear magnetic resonance, magnetic resonance, and electrochemical methods.

The terms "differentially expressed gene," "differential gene expression," and their synonyms, which are used interchangeably, refer to a gene whose expression is upregulated or downregulated in a first cell population relative to the expression of the same gene in a second population of cells. Such differences are evidenced by, e.g., a change in mRNA levels, surface expression, secretion or other partitioning of a polypeptide. Differential gene expression includes, in some embodiments, a comparison of expression between two or more genes or their gene products, or a comparison of the ratios of the expression between two or more genes or their gene products, or even a comparison of two differently processed products of the same gene, which differ between two populations of cells. Differential expression includes both quantitative, as well as qualitative, differences in the temporal or cellular expression pattern in a gene or its expression products among, for example, normal and diseased cells, or among cells which have undergone different disease events or disease stages, or cells that are significantly sensitive or resistant to certain therapeutic drugs.

The term "fluorophore" refers to a molecule which upon excitation emits photons and is thereby fluorescent.

The phrase "gene amplification" refers to a process by which multiple copies of a gene or gene fragment are formed in a particular cell or cell line. The duplicated region (a stretch of amplified DNA) is often referred to as "amplicon." Frequently, the amount of the messenger RNA (mRNA) produced, i.e., the level of gene expression, also increases in proportion to the number of copies made of the particular gene.

The term "gene expression profiling," unless otherwise specified, is used in the broadest sense, and includes methods of quantification of a gene's mRNA or nucleic acids derived therefrom, and/or protein levels or peptides derived therefrom and/or protein functions in a biological sample.

The term "high stringency hybridization" refers to hybridization conditions of incubating at 68° C. for an hour, followed by washing 3 times for 20 minutes each at room temperature in 2×SSC and 0.1% SDS and twice at 50° C. in 0.1×SSC and 0.1% SDS, or any art-recognized equivalent hybridization conditions.

The term "internal expression control gene" refers to a gene the expression level of which is known to or expected to be very similar in cells that differ in one or more phenotypes, or which have been subjected to differing experimental treatments. For example, the expression of the gene HDAC3 is shown to be to very similar in colon cancer cells that are resistant or sensitive to treatment with an HDACi compound.

The term "isolated" refers to separating and removing a component of interest from components not of interest. Isolated substances are optionally in either a dry or semi-dry state, or in solution, including but not limited to an aqueous solution. The isolated component is optionally in a homogeneous state or the isolated component is optionally a part of a pharmaceutical composition that comprises additional pharmaceutically acceptable carriers and/or excipients. Purity and homogeneity are determined, for example, using analytical chemistry techniques including, but not limited to, polyacrylamide gel electrophoresis or high performance liquid chromatography. In addition, when a component of interest is isolated and is the predominant species present in a preparation, the component is described herein as substantially purified. The term "purified," as used herein, refers to a component of interest which is at least 85% pure, at least 90% pure, at least 95% pure, at least 99% or greater pure. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production.

The term "label" refers to a substance which is incorporated into a compound and is readily detected, whereby its physical distribution is detected and/or monitored.

The term "microarray" refers to an ordered arrangement of hybridizable array elements, preferably polynucleotide probes, on a substrate.

The term "nucleic acid" or "nucleic acid probe," when used in singular or plural, generally refers to any polyribonucleotide or polydeoxyribonucleotide, which includes unmodified RNA or DNA or modified RNA or DNA. Thus, for instance, nucleic acids as defined herein include, without limitation, single- and double-stranded DNA, DNA including single- and double-stranded regions, single- and double-stranded RNA, and RNA including single- and double-stranded regions, hybrid molecules comprising DNA and RNA that are optionally single-stranded or, more typically, double-stranded or include single- and double-stranded regions. In addition, the term "nucleic acid" as used herein refers to triple-stranded regions comprising RNA or DNA or both RNA and DNA. The strands in such regions are optionally from the same molecule or from different molecules. The regions optionally include all of one or more of the molecules, but more typically involve only a region of some of the molecules. One of the molecules of a triple-helical region often is an oligonucleotide. The term "nucleic acid" specifically includes cDNAs. The term includes DNAs (including cDNAs) and RNAs that contain one or more modified bases. Thus, DNAs or RNAs with backbones modified for stability or for other reasons are "nucleic acids" as referred to herein. DNAs or RNAs comprising unusual bases, such as inosine, or modified bases, such as tritiated bases, are included within the term "nucleic acid" as defined herein. In general, the term "nucleic acid" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides are optionally made by a variety of other methods, including in vitro recombinant DNA-mediated techniques and by expression of DNAs in cells and organisms.

The terms "prediction," "predicting," "prognostic," or "prognosis" are used herein to refer to the likelihood that a patient will respond either favorably or unfavorably to a drug (e.g., an anti-cancer compound) or set of drugs, and also the extent of those responses. The predictive methods of described herein are valuable tools in predicting if a patient suffering from a cancer is likely to respond favorably to an HDAC inhibitor compound treatment regimen alone or in combination with another therapeutic agent (e.g., a second anti-cancer compound).

The term "subject" or "patient" refers to an animal which is the object of treatment, observation or experiment. By way of example only, a subject includes, but is not limited to, a mammal including, but not limited to, a human.

The term "substantially purified" refers to a component of interest that is substantially or essentially free of other components which normally accompany or interact with the component of interest prior to purification. By way of example only, a component of interest is "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest optionally has a purity level of about 70%, about 75%, about 80%, about 85%, about 90%, about 95%, about 96%, about 97%, about 98%, about 99% or greater.

The term "therapeutically effective amount" refers to the amount of a composition administered to a patient already suffering from a disease, condition or disorder, sufficient to cure or at least partially arrest, or relieve to some extent one or more of the symptoms of the disease, disorder or condition being treated. The effectiveness of such compositions depend conditions including, but not limited to, the severity and course of the disease, disorder or condition, previous therapy, the patient's health status and response to the drugs, and the judgment of the treating physician. By way of example only, therapeutically effective amounts are determined by methods, including but not limited to a dose escalation clinical trial.

The terms "treat," "treating" or "treatment," include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

The term "tumor" or "cancer" refers to all neoplastic cell growth and proliferation, whether malignant or benign, and all pre-cancerous and cancerous cells and tissues.

Unless otherwise indicated, conventional methods of cell culture, protein chemistry, biochemistry, recombinant DNA techniques including gene amplification and hybridization techniques, mass spectroscopy, and pharmacology, are employed.

DETAILED DESCRIPTION OF THE INVENTION

Figure 1:
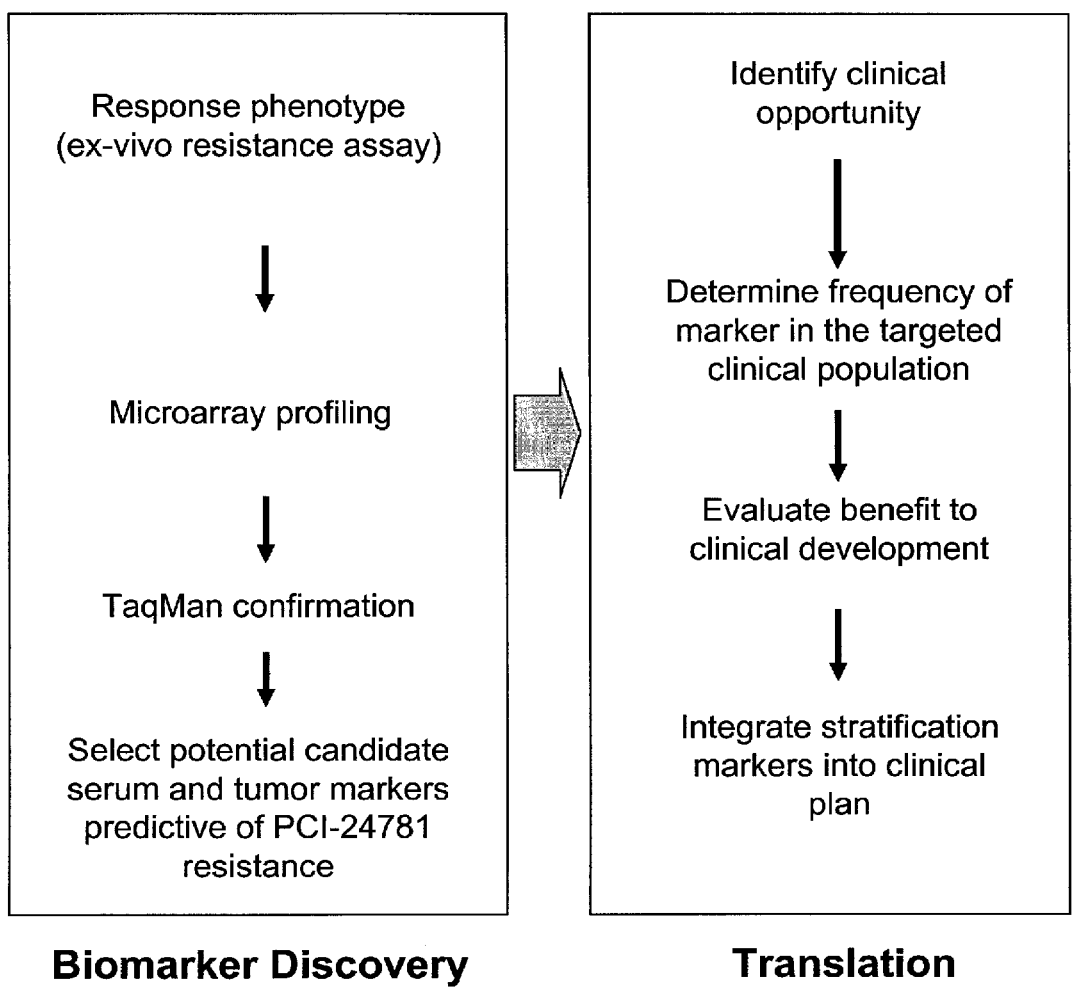
FIG. 1 is an illustrative schematic flow diagram of a method for identifying biomarker genes for HDACi compound resistance in cancer cells based on gene expression profiling, and the clinical application of expression profiling of the identified biomarker genes.

The methods described herein include classifying a cancer in a patient as resistant or sensitive to a histone deacetylase inhibitor (HDACi) compound by comparing the expression levels of at least four biomarker genes expressed in the cancer to biomarker gene expression level threshold values, as described herein. Where the expression levels of at least four biomarker genes are greater than the expression level threshold values, the cancer is indicated as being resistant to the HDACi compound. Conversely, if the expression levels of the at least four biomarker genes are lower than the expression level threshold values, the cancer is indicated to be sensitive to the HDACi compound.

Also described herein is a population of nucleic acids derived from a cancer cell, where the cancer cell is a type of cancer cell that is resistant to an HDACi compound. Further described herein is a population of nucleic acids derived from a cancer cell, where the cancer cell is a type of cancer cell that is sensitive to an HDACi compound. Also described herein are methods for generating these populations of nucleic acids. Such populations of nucleic acids are optionally used as expression level reference standards for setting biomarker gene expression threshold levels as described herein. Further described herein are cell lines determined to be resistant to an HDACi compound. Also described herein are cell lines determined to be sensitive to an HDACi compound.

Also described herein is a method for increasing the likelihood of therapeutically effective treatment of a cancer with an HDACi compound by providing an indication that a cancer is sensitive to treatment with an HDACi compound if the expression levels of at least four of the biomarker genes described herein are lower than the expression level threshold values for those biomarker genes, or providing an indication that a cancer is resistant to treatment with an HDACi compound If the expression levels of at least four of the biomarker genes described herein are higher than the expression level threshold values for those biomarker genes.

Further described herein are methods for optimizing selection of an anti-cancer agent for treating cancer in combination with an HDACi compound by comparing a first set of biomarker genes the expression of which is correlated to resistance or sensitivity of the cancer to the anti-cancer agent to a second set of biomarker genes the expression of which is correlated with resistance to the HDACi compound, and then selecting the anti-cancer agent for treatment of the cancer in combination with the HDAC inhibitor only if all of the biomarker genes in the first set are different from the biomarker genes in the second set.

Identification of HDACi Compound Resistance Biomarker Genes (HDACiR-BGs)

Described herein are methods for identifying genes whose expression levels in cancer cells are significantly and consistently correlated with resistance of the cells to an HDACi compound. Such genes are termed HDACi compound resistance biomarker genes (HDACiR-BGs). In an exemplary embodiment, HDACiR-BGs are identified as follows.

The ex-vivo response of primary tumor cells (e.g., colon cancer cells) from various patients to an HDAC inhibitor is determined by culturing the cells in the presence of varying concentrations of the HDACi compound.

After determining the HDACi compound sensitivity the cancer cells from each patient, mRNA expression profiles are determined for HDACi-resistant and sensitive tumors. Total RNA is isolated and fluorescent probes are prepared and hybridized to a whole genome cDNA microarray (e.g., Codelink Human Whole Genome oligonucleotide microarrays containing ~55,000 unique probes; GE Healthcare Bio-Sciences Corp., Piscataway, N.J.) according to the manufacturer's instructions. Following hybridization, the microarrays are scanned (e.g., in a GenePix 4000B scanner; Molecular Devices Corporation, Sunnyvale Calif.). The images are then processed with Codelink software and the data are normalized to the median.

The median-normalized microarray data are imported into a microarray data analysis program for principal component analysis (PCA) and hierarchical clustering analysis (e.g., Genespring software from Agilent). Multiple analysis methods are employed to provide additional confidence in the mRNA expression analysis. For multiple hypothesis correction, the q-values approach for false discovery rates (FDR) are optionally used as described in Storey et al. (2003), *Proc. Nat. Acad. Sci. USA*, 100:9440-9445. As a second analytical approach the Bayesian ANOVA approach described in Ishwaran et al. (2003), *J. Amer. Stat. Assoc.*, 98:438-455 is optionally used.

In the Bayesian ANOVA method, the contributions of irrelevant genes to the ANOVA model are selectively shrunk to balance total false detections against total false non-detections. The output is a Zcut score which identifies genes whose contribution to the ANOVA model is larger than the standard z-score. See Ishwaran et al., ibid., and the website at bamarray.com.

The just-described method and variants thereof is optionally used to identify biomarker genes for other specific phenotypic states, e.g., resistance to anti-cancer agents other than HDACi compounds.

HDACiR-BGs identified by the just-described methods include those listed in Table 1. The sequence for the mRNA of each of the listed genes is included herein in an appendix.

TABLE 1

HDACi Compound Resistance Biomarker Genes (HDACiR-BGs)

| Gene Name | Gene Symbol | GenBank Accession # | SEQ ID NO |
|---|---|---|---|
| PTPN3 | PTPN3 | AK096975 | 1 |
| ATP-binding cassette, sub-family C (CFTR/MRP), member 3 | ABCC3 | NM_020037 | 2 |
| specifically androgen-regulated protein | SARG | NM_023938 | 3 |
| phosphatidic acid phosphatase type 2C | PPAP2C | NM_177526 | 4 |
| neural proliferation, differentiation and control, 1 | NPDC1 | NM_015392 | 5 |
| C-terminal tensin-like | CTEN | NM_032865 | 6 |
| RAB25, member RAS oncogene family | RAB25 | NM_020387 | 7 |
| Hephaestin | HEPH | NM_138737 | 8 |
| thiopurine S-methyltransferase | TPMT | NM_000367 | 9 |
| plakophilin 3 | PKP3 | NM_007183 | 10 |
| UDP-N-acetyl-alpha-D-galactosamine:polypeptide N-acetylgalactosaminyltransferase 5 (GalNAc-T5) | GALNT5 | NM_014568 | 11 |
| calmodulin-like 4 | CALML4 | NM_033429 | 12 |
| UDP-N-acetyl-alpha-D-galactosamine:polypeptide N-acetylgalactosaminyltransferase 12 (GalNAc-T12) | GALNT12 | AK024865 | 13 |
| thiamin pyrophosphokinase 1 | TPK1 | NM_022445 | 14 |
| defensin, alpha 6, Paneth cell-specific | DEFA6 | NM_001926 | 15 |
| epithelial protein lost in neoplasm beta | EPLIN | NM_016357 | 16 |
| chloride intracellular channel 5 | CLIC5 | NM_016929 | 17 |
| PERP, TP53 apoptosis effector | PERP | NM_022121 | 18 |
| spleen tyrosine kinase | SYK | NM_003177 | 19 |
| solute carrier family 12 (sodium/potassium/chloride transporters), member 2 | SLC12A2 | NM_001046 | 20 |
| guanylate cyclase 2C (heat stable enterotoxin receptor) | GUCY2C | NM_004963 | 21 |
| transmembrane 4 superfamily member 4 | TM4SF4 | NM_004617 | 22 |
| transforming growth factor, alpha | TGFA | NM_003236 | 23 |
| fibroblast growth factor binding protein 1 | FGFBP1 | NM_005130 | 24 |
| PTK6 protein tyrosine kinase 6 | PTK6 | NM_005975 | 25 |
| epithelial V-like antigen 1 | EVA1 | NM_005797 | 26 |
| EPH receptor A2 | EPHA2 | NM_004431 | 27 |
| integrin, alpha 6 | ITGA6 | NM_000210 | 28 |
| tumor necrosis factor receptor superfamily, member 21 | TNFRSF21 | NM_014452 | 29 |
| transmembrane 4 superfamily member 3 | TM4SF3 | NM_004616 | 30 |
| interleukin 18 (interferon-gamma-inducing factor) | IL18 | NM_001562 | 31 |

TABLE 1-continued

HDACi Compound Resistance Biomarker Genes (HDACiR-BGs)

| Gene Name | Gene Symbol | GenBank Accession # | SEQ ID NO |
|---|---|---|---|
| bone morphogenetic protein 4 | BMP4 | NM_130850 | 32 |
| sphingomyelin phosphodiesterase, acid-like 3B | SMPDL3B | NM_014474 | 33 |
| transmembrane protease, serine 2 | TMPRSS2 | NM_005656 | 34 |
| guanine deaminase | GDA | NM_004293 | 35 |
| macrophage stimulating 1 receptor (c-met-related tyrosine kinase) | MST1R | NM_002447 | 36 |
| integrin, beta 4 | ITGB4 | NM_000213 | 37 |
| annexin A3 | ANXA3 | NM_005139 | 38 |
| chemokine (C—C motif) ligand 15 | CCL15 | NM_032965 | 39 |
| dipeptidase 1 (renal) | DPEP1 | NM_004413 | 40 |
| NADPH oxidase organizer 1 | NOXO1 | NM_172167 | 41 |
| interferon, alpha-inducible protein 27 | IFI27 | NM_005532 | 42 |
| cytochrome P450, family 3, subfamily A, polypeptide 43 | CYP3A43 | NM_057095 | 43 |
| plakophilin 2 | PKP2 | NM_004572 | 44 |

Classification of Individual Patient Cancers as Resistant or Sensitive to an HDACi Compound In some embodiments, gene expression profiling is performed on a biological sample obtained from an individual patient suffering from a cancer (e.g., a colon cancer tumor) to classify the cancer in the patient as resistant or sensitive to an HDACi compound. The gene expression profiling includes profiling the expression of at least one of the HDACi compound resistance biomarker genes (HDACiR-BGs) listed in Table 1, which were identified as described herein.

In some embodiments the HDACiR-BG is selected from among DEFA6, TM4SF4, TGFA, FGFBP1, EPHA2, TNFRSF2, TM4SF3, IL18, TMPRSS2, and CCL15.

In some embodiments, at least four of the HDACiR-BGs are expression profiled. In some embodiments, at least one of the four HDACiR-BGs are selected from among DEFA6, ITGB4, TM4SF4, SYK, PPAP2C, RAB25, HEPH, NOXO1, TM4SF3, PTPN3, EPHA2, FGFBP1, ABCC3, TPMT, IL18, or DPEP 1. In some embodiments, all of the at least four HDACiR-BGs are selected from among DEFA6, ITGB4, TM4SF4, SYK, PPAP2C, RAB25, HEPH, NOXO1, TM4SF3, PTPN3, EPHA2, FGFBP1, ABCC3, TPMT, IL18, or DPEP1.

In some embodiments, the expression of at least sixteen of the HDACiR-BGs is profiled. In some embodiments, the at least sixteen HDACiR-BGs include one or more of DEFA6, ITGB4, TM4SF4, SYK, PPAP2C, RAB25, HEPH, NOXO1, TM4SF3, PTPN3, EPHA2, FGFBP1, ABCC3, TPMT, IL18, or DPEP1. In some embodiments, the at least 16 HDACiR-BGs include DEFA6, ITGB4, TM4SF4, SYK, PPAP2C, RAB25, HEPH, NOXO1, TM4SF3, PTPN3, EPHA2, FGFBP1, ABCC3, TPMT, IL18, or DPEP1.

In various embodiments, the types of cancers and tumors that are optionally classified (from individual patients) for resistance or sensitivity to an HDACi compound include, but are not limited to, colorectal cancer, ovarian cancer, pancreatic cancer biliary tract cancer; bladder cancer; bone cancer; brain and CNS cancer; breast cancer; cervical cancer; choriocarcinoma; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Types of cancer cells that are optionally classified in various embodiments include, but are not limited to, squamous cell papilloma, squamous cell carcinoma, basal cell tumor, basal cell carcinoma, transitional cell papilloma, transitional cell carcinoma, glandular epithelium adenoma, melanocytes glomus tumor, melanocytic nevus, malignant melanoma, fibroma, fibrosacroma, an adenocarcinoma, gastrinoma, malignant gastrinoma, an oncocytoma, cholangiocellular adenoma, cholangiocellular carcinoma, hepatocellular adenoma, hepatocellular carcinoma, renal tubular adenoma, renal cell carcinom (Grawitz tumor), myxoma, myxosarcoma, lipoma, liposarcoma, leiomyoma, leiomyosarcoma, rhabdomyoma, rhabdomyosarcoma, benign teratoma, malignant teratoma, hemangioma, hemangiosarcoma, Kaposi sarcoma, lymphangioma, lymphangiosarcoma, an osteoma, an osteosarcoma, an osteogenic sarcoma, cartilage chondroma, chondrosarcoma, meninges meningioma, malignant meningioma, oligoastrocytoma, an ependymoma, an astrocytoma, pilocytic astrocytoma, glioblastommultiforme, an oligodendroglioma, neuroblastoma, schwanoma, retinoblastoma, or neurofibroma. Other types of cancers and tumors include those described in reference sources, e.g., the "International Classification of Diseases for Oncology," 3rd Edition, International Association of Cancer Registries.

A biological sample is any biological sample that includes cellular material from which DNA, RNA or protein are optionally isolated, e.g., solid tissue samples, such as a biopsy specimen or tissue cultures or cells derived therefrom and the progeny thereof, blood and other liquid samples of biological origin, e.g., sputum (including saliva, buccal wash, or bronchial brush), stool, semen, urine, ascitic fluid, cerebral spinal fluid, bladder wash, or pleural fluid. The term "biological sample" also encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples, e.g., freshly collected tissue, frozen tissue, archived tissue, orbiological fluids In some embodiments, the biological sample is a tumor biopsy (e.g., a core biopsy, a needle biopsy, or an excisional biopsy) containing one or more cancer cells. In one embodiment the biological sample is a population of cancer cells obtained by laser capture dissection from a tumor tissue section as described in, e.g., U.S. Pat. No. 6,040,139. Methods for optimizing tissue sample preparation and processing for expression profiling include, e.g., Bova et al. (2005), *Methods Mol. Med.*, 103:15-66.

In some embodiments, one or more cells (e.g., from a cultured cancer cell line), are classified by determining the expression levels of no more than four to fifty biomarker genes described herein., e.g., 5, 6, 7, 8, 9, 10, 12, 16, 18, 20, 24, 30, 32, 35, 40, 44, 45, 47, or any other number of biomarker genes from four to fifty. In some embodiments, four to forty four of the biomarker genes are selected from Table 3, e.g., 5, 6, 7, 8, 9, 10, 12, 16, 18, 20, 24, 30, 32, 35, 40, or any other number of biomarker genes from four to forty four is selected from Table 3. In some embodiments, at least four of the biomarker genes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2. In some embodiments, the four to fifty biomarker comprises one or more genes selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP In some embodiments, classification of the cells comprises comparing the determined expression levels to a first or second set of expression level threshold values for the biomarker genes, and indicating that the one or more cells are sensitive to a HDAC inhibitor if the expression levels of the biomarker genes are lower than the first set of expression level threshold values, or indicating that the one or more cells are resistant to a HDAC inhibitor if the expression levels are greater than the second set of expression level threshold values. In some embodiments, the expression of no more than four to twenty biomarker genes is determined. In some embodiments, the expression levels of no more than four biomarker genes is determined. In some embodiments, the four biomarker genes the expression level of which is determined are: DEFA6, RAB25, TM4SF4, and IL18.

Methods for HDACiR-BG Expression Profiling

HDACiR-BG expression profiles are optionally generated by any convenient means for determining differential gene expression between two samples, e.g. quantitative hybridization of mRNA, labeled mRNA, amplified mRNA, cRNA, etc., quantitative PCR, ELISA for protein quantitation, and the like.

In some embodiments, HDACiR-BG mRNA levels (including cDNA copy or aRNA copies) are quantified. The expression profile is optionally generated from the initial nucleic acid sample using any convenient protocol. While a variety of different manners of generating expression profiles are known, such as those employed in the field of differential gene expression analysis, one representative and convenient type of protocol for generating expression profiles is array based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation optionally includes labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. HDACiR-BG hybridization complexes are then detected and quantified.

Specific hybridization technologies which are optionally practiced to generate the HDACiR-BG expression profiles employed in the methods described herein includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions as those conditions are practiced in the art, and unbound nucleic acid is then removed. The resultant pattern of hybridized nucleic acid provides quantitative information regarding expression for each of the HDACiR-BGs that have been probed.

Evaluation of differences in expression values is optionally performed using any convenient methodology, e.g., by comparing digital images of the expression profiles, by comparing databases of expression data, etc. Patents describing ways of comparing expression profiles include, but are not limited to, U.S. Pat. Nos. 6,308,170 and 6,228,575 and U.S. patent application Ser. No. 10/858,867.

In some embodiments, the methods described herein are performed on nucleic acid hybridization arrays comprising nucleic acid probes that hybridize under high stringency hybridization conditions to nucleic acids of no more than four to fifty biomarker genes, e.g., 5, 6, 7, 8, 9, 10, 12, 16, 18, 20, 24, 30, 32, 35, 40, 44, 45, 47, or any other number of biomarker genes from four to fifty. In some embodiments, four to forty four of the biomarker genes are selected from Table 3, e.g., 5, 6, 7, 8, 9, 10, 12, 16, 18, 20, 24, 30, 32, 35, 40, or any other number of biomarker genes from four to forty four is selected from Table 3. In some embodiments, at least four of the biomarker genes for the array probes are selected from PTPN3, ABCC3, SARG, PPAP2C, NPDC1, CTEN, RAB25, HEPH, TPMT, PKP3, GALNT5, CALML4, GALNT12, TPK1, DEFA6, EPLIN, CLIC5, PERP, SYK, SLC12A2, GUCY2C, TM4SF4, TGFA, FGFBP1, PTK6, EVA1, EPHA2, ITGA6, TNFRSF21, TM4SF3, IL18, BMP4, SMPDL3B, TMPRSS2, GDA, MST1R, ITGB4, ANXA3, CCL15, DPEP1, NOXO1, IF127, CYP3A43, and PKP2. In some embodiments, the at least four biomarker genes are selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP In some embodiments, the at least four biomarker genes are DEFA6, RAB25, TM4SF4, and IL18.

Alternatively, non-array based methods for quantitating the levels of one or more nucleic acids in a sample are employed, including quantitative PCR, and the like.

In some embodiments, expression profiling of HDACiR-BGs expressed in a biological sample (e.g., a tumor biopsy) is done by a quantitative reverse transcription PCR assay (qRT-PCR). In this method, RNA from a biological sample is reverse transcribed to generate segments of cDNA which are then be amplified by gene-specific quantitative PCR. The rate of accumulation of specific PCR products is optionally correlated to the abundance of the corresponding RNA species in the original sample and thereby provide an indication of gene expression levels.

In one embodiment, the qPCR assay is a TaqMan™ assay. In brief, PCR typically utilizes the 5' exonuclease activity of Taq or Tth polymerase to hydrolyze a fluorescently-labelled hybridization probe bound to its target amplicon, but any enzyme with equivalent 5' exonuclease activity is optionally used. Two oligonucleotide primers are used to generate an amplicon typical of a PCR reaction. A third oligonucleotide, or probe, is designed to hybridize to a nucleotide sequence located between the two PCR primers. The probe is non-extendible by Taq DNA polymerase enzyme, and is 5' labeled with a reporter fluorescent dye and a 3' labeled with a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second chromophore. One molecule of reporter dye is liberated for each new molecule synthesized, and detection of the unquenched reporter dye provides the basis for quantitative interpretation of the data.

qRT-PCR is optionally performed using commercially available equipment, such as, for example, the ABI PRISM 7900™ Sequence Detection System™ (Perkin-Elmer-Applied Biosystems, Foster City, Calif.), or LightCycler™. (Roche Molecular Biochemicals, Mannheim, Germany). In one embodiment, the 5' exonuclease procedure is run on a real-time quantitative PCR device such as the ABI PRISM 7900™ Sequence Detection System™ or one of the similar systems in this family of instruments. The system consists of a thermocycler, laser, charge-coupled device (CCD), camera and computer. The system amplifies samples in 96-well or 384 well formats on a thermocycler. During amplification, laser-induced fluorescent signal is collected in real-time through fiber optic cables for all reaction wells, and detected at the CCD. The system includes software for running the instrument and for analyzing the data.

Exonuclease assay data are initially expressed as a $C_T$ value, i.e., the PCR cycle at which the fluorescent signal is first recorded as statistically significant.

In order to minimize errors and the effects of sample-to-sample variation and process variability mRNA level measurements are generally normalized to the expression level of an internal expression control gene. Methods for normalizing qPCR assays include, see, e.g., the website at normalisation-.gene-quantification.info. The ideal internal expression control gene is one that is expressed at a relatively constant level among different patients or subjects, and is unaffected by the experimental treatment.

In some embodiments, the internal expression control gene is RNA polymerase II (GenBank Accession No. X74870).

In other embodiments, the internal expression control gene is HDAC3 (NM_003883).

In further embodiments, the internal expression control gene is ZNF217 (NM_006526).

In some embodiments, HDAiR-BG mRNA expression levels for each sample are normalized by the total amount of RNA in each sample. The amount of RNA in a sample is optionally determined, e.g., by UV-spectrophotometry or by using an RNA detection reagent, e.g., RiboGreen® from Invitrogen (Carlsbad, Calif.).

Where the HDACiR-BG expression profile to be determined is a protein expression profile, any convenient protein quantitation protocol is optionally employed, where the levels of one or more proteins in the assayed sample are determined. Representative methods include, but are not limited to; proteomic arrays, mass spectrometry, or standard immunoassays (e.g., RIA or ELISA). See, e.g., the methods set forth in R. Scopes, *Protein Purification*, Springer-Verlag, N.Y. (1982); Sandana (1997) *Bioseparation of Proteins*, Academic Press, Inc.; Bollag et at (1996) Protein Methods. 2nd Edition Wiley-Liss, NY; Walker (1996) The Protein Protocols Handbook Humana Press, NJ, Harris and Angal (1990) Protein Purification: Principles and Practice 3rd Edition Springer Verlag, NY; Janson and Ryden (1998) Protein Purification: Principles, High Resolution Methods and Applications, Second Edition Wiley-VCH, NY; and Satinder Ahuja ed., *Handbook of Bioseparations*, Academic Press (2000); Harlow et al., *Antibodies: A Laboratory Manual*, Cold Spring Harbor Laboratory, Cold Spring Harbor, N.Y., 353-355 (1988).

Proteomic expression profiling methods detection methods include various multidimensional electrophoresis methods (e.g., 2-D gel electrophoresis), mass spectrometry based methods e.g., SELDI, MALDI, electrospray, etc.), or surface plasmon reasonance methods. For example, in MALDI, a sample is usually mixed with an appropriate matrix, placed on the surface of a probe and examined by laser desorption/ ionization. See, e.g., U.S. Pat. Nos. 5,045,694, 5,202,561, and 6,111,251. Similarly, for SELDI, a first aliquot is contacted with a solid support-bound (e.g., substrate-bound) adsorbent. A substrate is typically a probe (e.g., a biochip) that is optionally positioned in an interrogatable relationship with a gas phase ion spectrometer. SELDI has been applied to diagnostic proteomics. See, e.g. Issaq et al. (2003), *Anal. Chem.* 75: 149A-155A.

In one embodiment, any of the just-described protein detection methods are used to determine the expression level of one or more HDACiR-BG proteins that are known to be secreted proteins, e.g., DEFA6, TM4SF4, TM4SF3, TGFA, FGFBP1, EPHA2, TNFRSF2, IL18, CCL15, or TMPRSS2.

Expression Level Reference Samples

In some embodiments, expression profiles of HDACiR-BGs in a biological sample of interest (e.g., a colon cancer biopsy) are compared to HDACiR-BG expression profiles in an expression level reference sample. The expression level reference sample is a biological sample derived from one or more cancer patients determined to be suffering from a particular cancer or tumor for which sensitivity or resistance to treatment with an HDACi compound (e.g., PCI-24781) has been determined. In other words, the expression level reference sample serves as a standard with which to compare expression level values for each HDACiR-BG in a test sample. The deviation of HDACiR-BG expression levels from the expression level values in a reference sample indicates whether the cancer in the patient from the biological sample was derived is sensitive or resistant to treatment with an HDACi compound. In some embodiments, HDACiR-BG threshold expression level values are optionally set based on one or more statistical criteria for deviation from HDACiR- BG expression level values in an expression level reference sample, e.g., two or more SDs away from the value for a reference sample HDACiR-BG expression level.

In some embodiments, the expression level reference sample is a "negative" reference sample, i.e., a sample derived from a patient having a cancer or tumor determined to be sensitive to an HDACi compound. Thus, where expression levels of multiple HDACiR-BGs (e.g. at least 4, 5, 6, 8, 10, 12, or 16) are significantly greater than the threshold expression level values based on the negative reference sample, the patient's cancer is indicated as resistant to the HDACi compound.

In some embodiments, the expression level reference sample is a "positive" reference sample, i.e., a sample derived from a patient having a cancer or tumor determined to be resistant to an HDACi compound. Thus, where expression levels of multiple HDACiR-BGs (e.g. at least 4, 5, 6, 8, 10, 12, or 16) are significantly lower than the threshold expression level values based on the negative reference sample, the patient's cancer is indicated as sensitive to the HDACi compound.

In some embodiments, HDACiR-BG expression profiles are compared to those in both positive and negative reference samples.

In some embodiments, HDACiR-BGs expression level measurements are performed in parallel for the biological sample of interest and the (positive or negative) expression level reference. For example, where an array hybridization method is used, HDACiR-BG mRNA levels in the biological sample of interest and in an expression level reference sample are optionally measured simultaneously by separately labeling nucleic acid populations (e.g., mRNA, cDNA, aRNA populations) from each with a detectably distinct fluorophore, and then hybridizing the fluorescently labeled nucleic acids to the same array.

In some embodiments an expression level reference sample is a population of nucleic acids (e.g., mRNAs, aRNAs, cDNAs, or aRNAs) derived from a cancer biopsy sample within which the sequences of at least four HDACiR-BGs are represented, and for which sensitivity to an HDACi compound has been determined. In some embodiments, the population of nucleic acids is derived from patient tumor cells cultivated in culture. In other embodiments, the population is derived directly from a biopsy without a cell culture step.

In some embodiments, the population of nucleic acids serving as an expression level reference sample is generated as follows. A cancer biopsy is obtained from a patient as described above, and afterwards viable tumors cells are then isolated and grown in culture as described in, e.g., Kern et al. (1990), *J. Natl. Cancer Inst.*, 82:582-588. In order to determine if cancer cells are sensitive to an HDACi compound, they are then grown in the presence of the HDACi compound at a range of concentrations, e.g., (0-10 μM), and cell proliferation is measured by any number of methods, e.g., tritiated thymidine incorporation. Inhibition of tumor cell proliferation by the HDACi compound is measured relative to tumor cell proliferation in the absence of the compound (i.e., no inhibition). Assignment of the cancer as sensitive or resistant is optionally determined based on a number of cell proliferation criteria. For example, if the $IC_{50}$ of the HDACi compound in the tested cancer cells is significantly lower (e.g., by 2 SDs) than that observed for cells known to be sensitive to the compound, the cancer is characterized as resistant. Thus, cells derived from the resistant cancer (e.g., directly or after passage in culture) are optionally used to generate a population of nucleic acids serving as an expression level (positive) reference sample used for setting HDACiR-BG expression level threshold values as described above. Conversely, tumor cells found to be sensitive to an HDACi compound are used generate a population of nucleic acids serving as an expression level (negative) reference sample.

Methods for obtaining RNA from biological samples (e.g., tissues or cells) including linear aRNA amplification from single cells include, e.g., Luzzi et al. (2005), *Methods Mol. Biol.*, 293:187-207. Further, diverse kits for high quality RNA purification are available commercially, e.g., from Qiagen (Valencia, Calif.), Invitrogen (Carlsbad, Calif.), Clontech (Palo Alto, Calif.), and Stratagene (La Jolla, Calif.).

In some embodiments, the expression level reference sample is an RNA sample isolated from one or more HDACi compound-resistant colon cancer cells. In one embodiment, the cells were derived from colon carcinoma biopsy R5247682266, R9866135153, R1078103114, or R4712781606 described herein.

HDACi Inhibitor Compounds

In another embodiment, HDACi inhibitor tumor compounds for which cancer resistance or sensitivity include, but are not limited to carboxylates, short-chain fatty acids, hydroxamic acids, electrophilic ketones, epoxides, cyclic peptides, and benzamides. In a further embodiment, HDACi inhibitor tumor compounds for which cancer resistance or sensitivity include, but are not limited to hydroxamic acids having the structure of Formula (A):

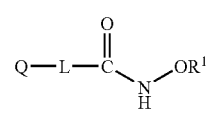

Formula (A)

wherein
Q is an optionally substituted $C_{5-12}$ aryl or an optionally substituted $C_{5-12}$ heteroaryl;
L is a linker having at least 4 atoms;
$R^1$ is H or alkyl;

and a pharmaceutically acceptable salt, pharmaceutically acceptable N-oxide, pharmaceutically active metabolite, pharmaceutically acceptable prodrug, pharmaceutically acceptable solvate thereof.

HDACi inhibitor tumor compounds for which cancer resistance or sensitivity include, but are not limited to compounds having the structure of Formula (I):

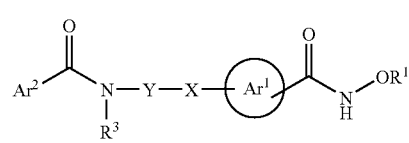

Formula (I)

wherein:
$R^1$ is hydrogen or alkyl;
X is —O—, —$NR^2$—, or —$S(O)_n$— where n is 0-2 and $R^2$ is hydrogen or alkyl;
Y is alkylene optionally substituted with cycloalkyl, optionally substituted phenyl, alkylthio, alkylsulfinyl, alkysulfonyl, optionally substituted phenylalkylthio, optionally substituted phenylalkylsulfonyl, hydroxy, or optionally substituted phenoxy;

Ar¹ is phenylene or heteroarylene wherein said Ar¹ is optionally substituted with one or two groups independently selected from alkyl, halo, hydroxy, alkoxy, haloalkoxy, or haloalkyl;

R³ is hydrogen, alkyl, hydroxyalkyl, or optionally substituted phenyl; and

Ar² is aryl, aralkyl, aralkenyl, heteroaryl, heteroaralkyl, heteroaralkenyl, cycloalkyl, cycloalkylalkyl, heterocycloalkyl, or heterocycloalkylalkyl;

and individual stereoisomers, individual geometric isomers, or mixtures thereof; or a pharmaceutically acceptable salt thereof.

In another embodiment, HDACi inhibitor tumor compounds for which cancer resistance or sensitivity include, but are not limited to, PCI-24781.

In some embodiments, a patient is prescribed or administered an HDAC inhibitor to the patient based on a classification of the patient's cancer as being sensitive or resistant to an HDAC inhibitor according to the methods described herein.

In some embodiments, the methods described herein are used to optimize the selection of an anti-cancer agent for use in combination with an HDACI compound. In some embodiments, optimized selection of the second anti-cancer agent is performed by first comparing the set of known biomarker genes for resistance to the HDACi compound to sets of biomarker genes identified for other anti-cancer agents. The second anti-cancer agent is then selected for use in combination with the HDACi compound based on minimal overlap of the respective sets of resistance biomarker genes.

Examples of anti-cancer agents that are optionally used in combination with an HDACi compound include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", is an anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and are optionally useful for treating cancer in combination with the compounds described herein.

Further examples of anti-cancer agents for use in combination with an HDACi compound include inhibitors of mitogen-activated protein kinase signaling, e.g., U0126, PD98059, PD184352, PD0325901, ARRY-142886, SB239063, SP600125, BAY 43-9006, wortmannin, or LY294002.

Other anti-cancer agents that are optionally employed in combination with an HDACi compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that are optionally employed in combination with an HDACi compound include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that are optionally employed in combination with an HDACi compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with an HDACi compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that are optionally employed in combination an HDACi compound include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with an HDACi compound include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which are optionally used in combination with an HDACi compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-10, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Applications of HDACiR-BGs

The methods and compositions described herein are optionally used to increase the likelihood of a therapeutically effective treatment of a patient's cancer with an HDACi compound by providing an indication (e.g. by oral or written communication in any analog or digital medium) of which genes are HDACiR-BGs, as well as HDACiR-BG expression level reference values (e.g., expression level threshold values) above which HDACi compound resistance is likely (i.e., greater than the probability by chance) or below which HDACi compound sensitivity is likely.

In some embodiments, the indication includes a document with an interpretation of expression levels of at least four biomarker genes selected from Table 1 as to the likelihood that a patient's cancer is resistant or sensitive to treatment with an HDACi compound.

In some embodiments, the document includes an interpretation of the expression levels of at least one HDACiR-BG selected from DEFA6, ITGB4, TM4SF4, SYK, PPAP2C, RAB25, HEPH, NOXO1, TM4SF4, PTPN3, EPHA2, FGFBP1, ABCC3, TPMT, IL18, and DPEP1.

In some embodiments an indication is provided in one or more databases containing information concerning one or more HDACiR-BGs, including one or more expression level threshold values that permit the interpretation of the effect of HDACiR-BG expression levels on the resistance or sensitivity of a cancer to an HDACi compound according to any of the methods described herein. Such expression level threshold values include those set based on, e.g., deviation of HDACiR-BG expression levels in a test sample from the corresponding HDACiR-BG expression levels in an expression level (positive or negative) reference sample as described herein. Alternatively, or in addition, expression level threshold values are optionally set based on deviation of the expression ratios of HDACiR-BGs to one or more internal expression control genes (e.g., RNA polymerase II, HDAC3, or ZNF217). For example, as described herein, the mean expression ratio (based on TaqMan fluorescence intensity) of the HDACiR-BG DEFA6 to the internal expression control gene ZNF217 is 5.83 in HDACi-resistant colon cancer cells and 0.24 in HDACi-sensitive colon cancer cells.

In some embodiments, the databases include HDACiR-BG expression level profiles or thresholds associated with resistance to one or more HDACi compounds for one or more types of cancer.

Other information that is optionally included in the databases or in other types of indication include, but are not limited to, HDACiR-BG sequence information, frequency distributions of HDACiR-BG expression levels in a particular cancer population, descriptive information concerning the clinical status of a biological sample analyzed for HDACiR-BG expression profiles, or the clinical status of the patient from which the sample was derived. The database is optionally be designed to include different parts, for instance an HDACiR-BG list database, and an informative HDACiR-BG expression profile database, e.g., a database associating with each HDACiR-BG expression profile record the probability that the expressin profile is associated with resistance to an HDACi compound. Methods for the configuration and construction of databases are widely available, for instance, see U.S. Pat. No. 5,953,727.

The databases described herein are optionally linked to an outside or external database. In some embodiments, the database optionally communicates with outside data sources, such as database of the developmental therapeutics program of the national cancer institute or the National Center for Biotechnology Information through the internet.

Any appropriate computer platform is used to perform the methods for interpreting one or more HDACiR-BG expression profiles by the methods described herein. In some embodiments, the computer platform receive direct input from a database, e.g., one of the databases described herein. For example, a large number of computer workstations are available from a variety of manufacturers, such has those available from Silicon Graphics. Client-server environments, database servers and networks are also widely available and are appropriate platforms for the databases described herein.

The databases described herein are optionally used to present information identifying a set of HDACiR-BG expression profiles in an individual and such a presentation is optionally used to predict or diagnose the likelihood of a effective therapeutic treatment of the individual's cancer with a particular HDACi compound based on a statistical comparison of the individual's expression profile to HDACiR-BG expression level thresholds as described herein. Accordingly, one chooses to partition cancer patients into subgroups at any threshold value of the measured HDACiR-BG expression, where all patients with expression values above the threshold have higher risk, and all patients with expression values below the threshold have lower risk, of and HDACi compound-resistant cancer resistanceor vice versa, depending on whether the expression level threshold is based on an expression level in a cancer determined to be resistant to an HDACi compound treatment (i.e., a positive reference sample) or sensitive to the HDACi compound treatment (i.e., a negative reference sample). Alternatively, HDACiR-BG expression profiles ranked on a probability continuum, where the more an HDACiR-BG expression level deviates negatively from (i.e., is less than) an expression level positive reference value, the higher the probability that the cancer is sensitive to treatment with an HDACi compound. Conversely, the more an HDACiR-BG expression level deviates positively from (i.e., is greater than) an expression level negative reference value, the higher the probability that the cancer is resistant to treatment with an HDACi compound.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Example 1 mRNA Expression Profiling of HDACi Sensitive Versus Resistant Colorectal Tumor Cells Ex Vivo We and others previously developed several pharmacodynamic markers for HDACi compounds (such as tubulin or histone acetylation, p21 expression etc). However, there is currently no clinically predictive biomarker for response to these agents available. In this work, we developed a strategy to identify such biomarkers for the HDACi compound PCI-24781 in primary human colorectal tumors.

The method used soft agar chemosensitivity assays in which primary human tumors were exposed in culture to PCI-24781. Either a trititated thymidine or alamar blue assay was then used to estimate the percentage of resistance to PCI-24781. For example in the trititated thymidine assay, sensitive tumor cells affected by the drug divided less and therefore incorporated less thymidine, whereas resistant tumor cells continued to grow and divide and therefore incorporated more thymidine into their DNA. It has been shown historically that under the optimized conditions of this assay, a patient whose tumor is classified as resistant to a given drug has <1% probability of response to that drug in the clinic (in published correlations to clinical outcome, these assays predicted resistance with an accuracy of 99% in solid cancers and 92% in blood cancers). For example, a recent paper correlated in vitro sensitivity or resistance to fludarabine in the DiSC assay in B-cell CLL patients with clinical outcome (median survival 7.9 months in resistant vs 41.7 months in sensitive patients). Similar data has also been published for solid tumors: e.g., for sensitivity or resistance to Pt in ovarian tumors, and to CPX and DOX in breast tumors.

After determining ex vivo sensitivity or resistance to PCI-24781 for each tumor, RNA isolated from tumor cells was then profiled on microarrays and a marker set was identified by statistical analysis of the data. This marker set was validated by RT-PCR (TaqMan™) analysis. Such pharmacogenomic biomarkers that are used for patient stratification in the clinic provide a competitive advantage in the development of PCI-24781. A graphic summary of the method and its clinical applications is illustrated in FIG. 1.

We examined the ex-vivo response of primary colorectal tumors from various patients to an HDAC inhibitor, PCI-24781, and subsequently determined whether there were robust differences in the mRNA expression profiles of sensitive versus resistant tumor cells prior to HDACi treatment.

Figure 2:
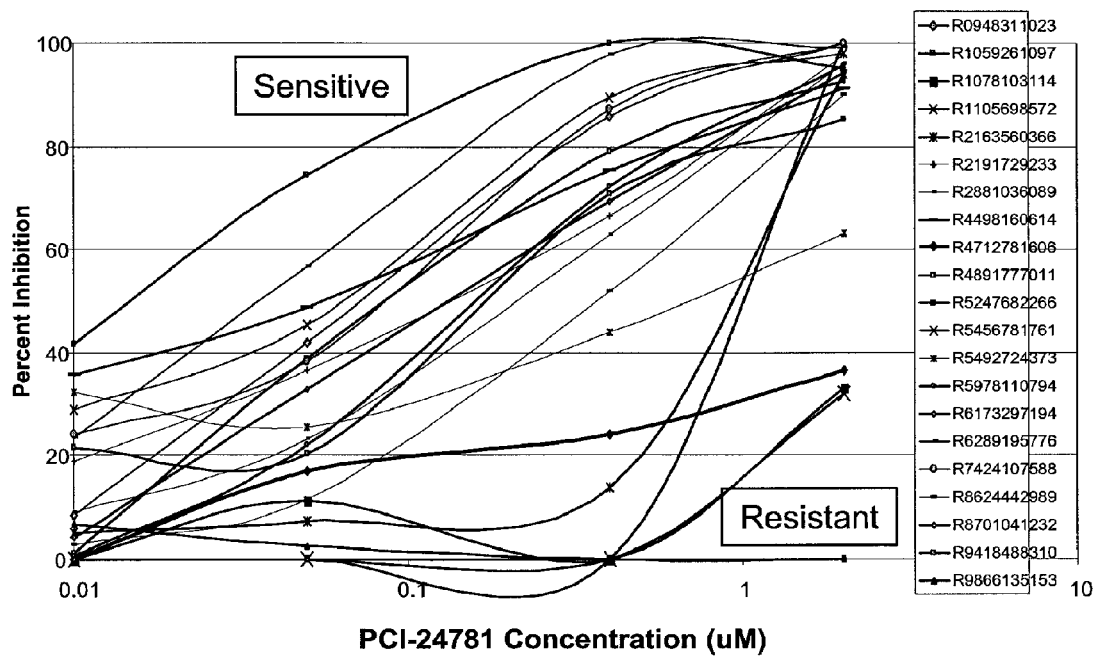
FIG. 2 is an illustrative graph showing in vitro inhibition of cell proliferation versus concentration of the HDACi compound PCI-24781 for a series of colon carcinoma cell lines.

Primary colorectal cancer (CRC) samples were obtained from patient biopsies (Table 2). Viable tumor cells were plated and cultured in soft agar as described in Kern et al. (1990), *J. Natl. Cancer Inst.*, 82:582-588, and were treated with a range of PCI-24781 concentrations (0.01-2 µM). Trititated thymidine was added to the culture after 3 days of exposure to the drug, and the amount of radioactivity incorporated into the cells after a further 2 days was quantified. The percentage of cell growth inhibition (% GI) was calculated by comparing the treated cells to the control cells, and from these growth profiles the tumors were classified as either sensitive or resistant based on deviation from the median profile. As shown in FIG. 2, primary tumors displayed a spectrum of growth inhibition phenotypes from 100% to 0% relative to control at the PCI-24781 concentrations tested (up to 2 µM).

TABLE 2

Clinical data for colorectal cancer biopsies

| Research ID | Cancer Name | Age | Sex | Site | Clinical Diagnosis | Histology | Specimen Type |
|---|---|---|---|---|---|---|---|
| R1078103114 | Colon Carcinoma | 54 | F | R Ovary | Colon Carcinoma | ADENOCARCINOMA | Solid Tumor Biopsy |
| R1105698572 | Colon Carcinoma | 72 | F | Portion of Terminal Ileum | Colon Carcinoma | NA | Solid Tumor Biopsy |
| R2163560366 | Colon Carcinoma | 58 | F | Uterus | Rectal Cancer | NA | Solid Tumor Biopsy |
| R4712781606 | Colon Carcinoma | 59 | M | Colon Resection | Colon Carcinoma | NA | Solid Tumor Biopsy |
| R5247682266 | Colon Carcinoma | 51 | F | Upper Lobe Lung | Colon Carcinoma | ADENOCARCINOMA | Solid Tumor Biopsy |
| R5891015174 | Colon Carcinoma | 43 | F | Colon | Cecal Carcinoma | NA | Solid Tumor Biopsy |
| R6173297194 | Colon Carcinoma | 65 | M | Omentum | Colon Carcinoma | ADENOCARCINOMA | Solid Tumor Biopsy |
| R7103644976 | Colon Carcinoma | 52 | F | R Tube & Ovary | Colon Cancer | NA | Solid Tumor Biopsy |
| R9886135153 | Colon Carcinoma | 55 | F | R Hepatic Lobe | Colon Carcinoma | ADENOCARCINOMA | Solid Tumor Biopsy |
| R2881036089 | Colon Carcinoma | 79 | F | Colon | Colon Carcinoma | CARCINOMA, PD | Solid Tumor Biopsy |
| R5492724373 | Colon Carcinoma | 55 | F | Cecum | Colon Carcinoma | COLON CARCINOMA | Solid Tumor Biopsy |
| R8624442989 | Colon Carcinoma | 47 | F | Brain | Colon Carcinoma | NA | Solid Tumor Biopsy |
| R0948311023 | Colon Carcinoma | 33 | F | L Lower Lung Lobe Nodule | Colon Carcinoma | ADENOCARCINOMA | Solid Tumor Biopsy |
| R1059261097 | Colon Carcinoma | 50 | M | Liver | Colon Cancer | ADENOCARCINOMA | Solid Tumor Biopsy |
| R2191729233 | Colon Carcinoma | 62 | F | Ovary | Colon Cancer | ADENOCARCINOMA | Solid Tumor Biopsy |
| R4498160614 | Colon Carcinoma | 40 | F | L Ovary | Colon Carcinoma | ADENOCARCINOMA | Solid Tumor Biopsy |
| R4891777011 | Colon Carcinoma | 53 | F | R Abdominal Sidewall | Colon Carcinoma | ADENOCARCINOMA | Solid Tumor Biopsy |
| R5456781761 | Colon Carcinoma | 65 | F | Liver Lobes 5&6 | Met. Colon CA to L | NA | Solid Tumor Biopsy |
| R5978110794 | Colon Carcinoma | 63 | F | Sigmoid Rectum | Colon Carcinoma | NA | Solid Tumor Biopsy |
| R6289195776 | Colon Carcinoma | 56 | M | Liver | Colon Carcinoma | ADENOCARCINOMA | Solid Tumor Biopsy |
| R6324805249 | Colon Carcinoma | 55 | F | Ovary | Colon Carcinoma | ADENOCARCINOMA | Solid Tumor Biopsy |
| R7424107588 | Colon Carcinoma | 48 | M | Lumbar/Spine Biopsy | Colon Carcinoma | NA | Solid Tumor Biopsy |
| R8701041232 | Colon Carcinoma | 65 | M | Sigmoid Colon | Colon Carcinoma | ADENOCARCINOMA | Solid Tumor Biopsy |
| R9418488310 | Colon Carcinoma | 55 | F | Cecum | Colon Carcinoma | ADENOCARCINOMA | Solid Tumor Biopsy |

After determining tumor sensitivity to PCI-24781, gene expression profiles were determined for resistant and sensitive tumors that were treated with PCI-24781 (2 µM) or untreated. Total RNA was isolated using Qiagen procedures (Qiagen, Inc., Valencia, Calif.) and fluorescent probes were prepared and hybridized to Codelink Human Whole Genome oligonucleotide microarrays containing ~55,000 unique probes (GE Healthcare Bio-Sciences Corp., Piscataway, N.J.) according to the manufacturer's instructions. The microarrays were scanned in a GenePix 4000B scanner (Molecular Devices Corporation, Sunnyvale Calif.). The images were processed with Codelink software and the exported data was analyzed as follows.

The median-normalized microarray data were imported into Genespring software (Agilent), and principal component analysis (PCA) and hierarchical clustering analysis were performed. We looked for consistent results from multiple analysis methods to provide additional confidence in our results. For multiple hypothesis correction, we used the q-values approach for false discovery rates (FDR) as described in Storey et al. (2003), *Proc. Nat. Acad. Sci. USA*, 100:9440-9445. As a second analytical approach we adopted the Bayesian ANOVA approach described in Ishwaran et al. (2003), *J. Amer. Stat. Assoc.*, 98:438-455.

Figure 3:
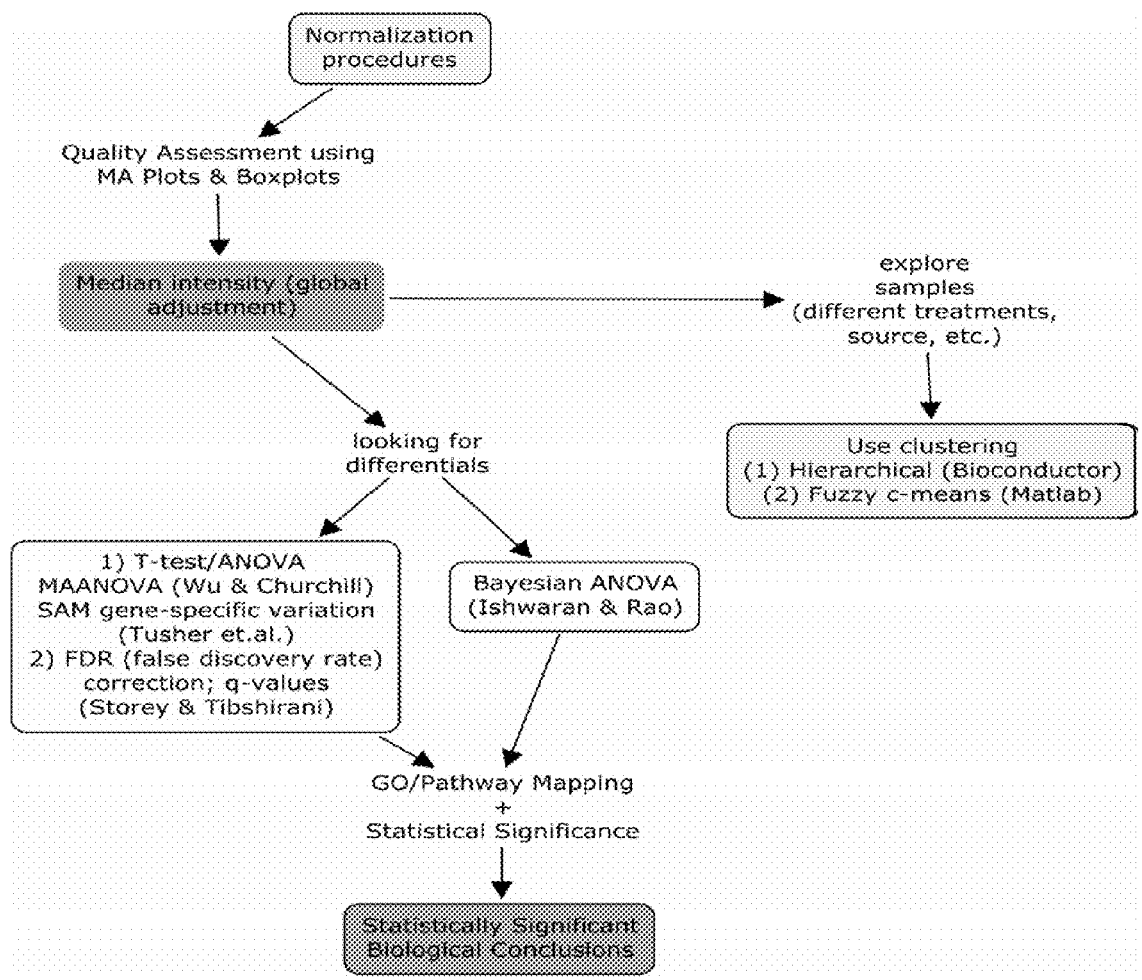
FIG. 3 is an illustrative flow diagram illustrating the statistical approach used to analyze microarray data to identify differentially expressed genes in populations of cancer cells resistant to a HDACi compound versus cancer cells that are sensitive to the compound.

In the Bayesian ANOVA method, the contribution of irrelevant genes to the ANOVA model are selectively shrunk to balance total false detections against total false non-detections. The output is a Zcut score which identifies genes whose contribution to the ANOVA model is larger than the standard z-score. See Ishwaran et al., ibid., and the website at bamarray.com. For the identification of biomarkers predictive of PCI-24781 resistance, we used only the untreated control samples divided into pools based on the sensitivity or resistance classification in the assay described above. This analytical approach is summarized in FIG. 3.

Figure 4:
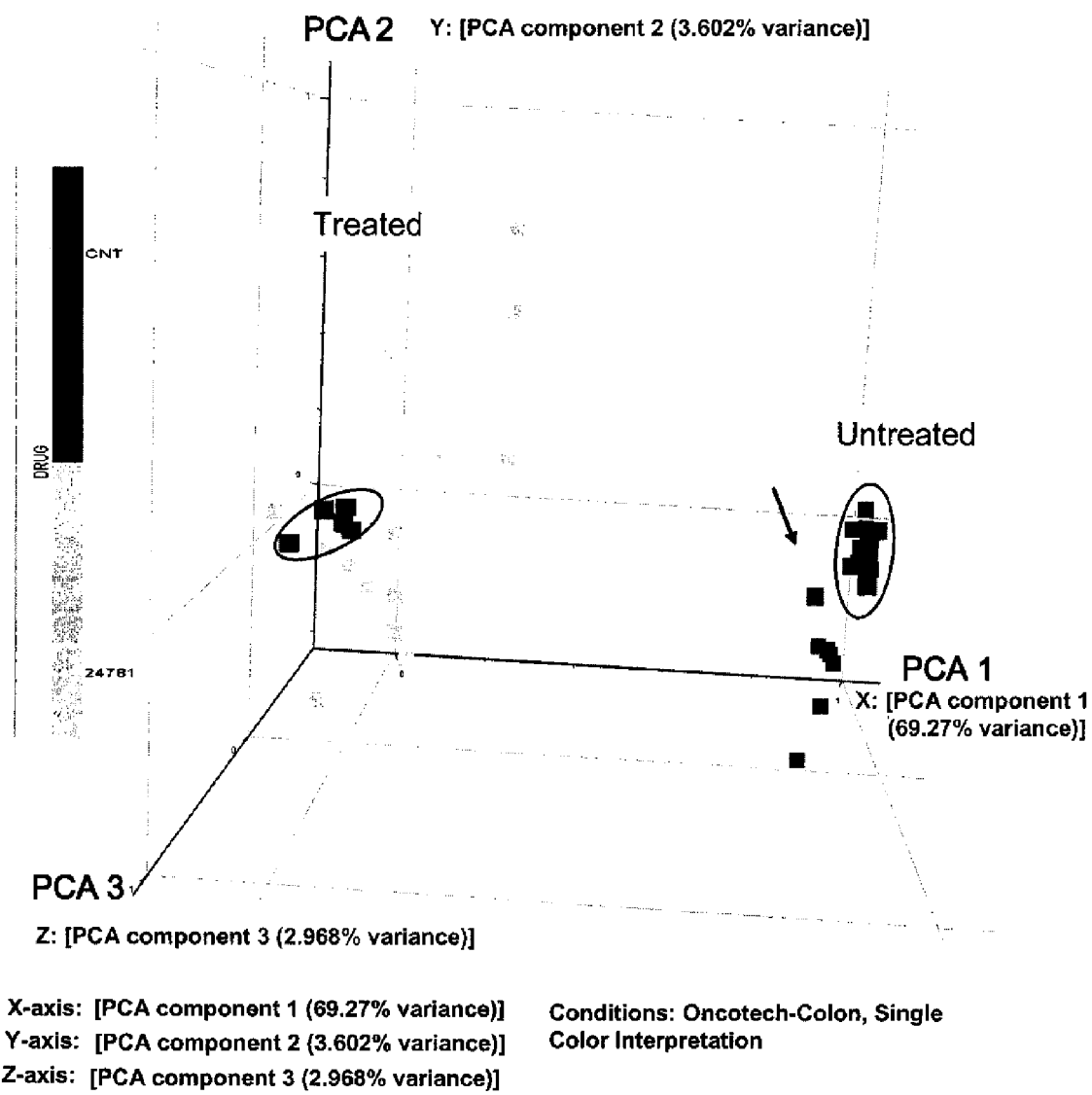
FIG. 4 is an illustrative scatter plot illustrating principal component analysis of gene expression microarray data in HDACi compound-treated and untreated cancer cells, and sensitive and resistant cancer cells.
Figure 5:
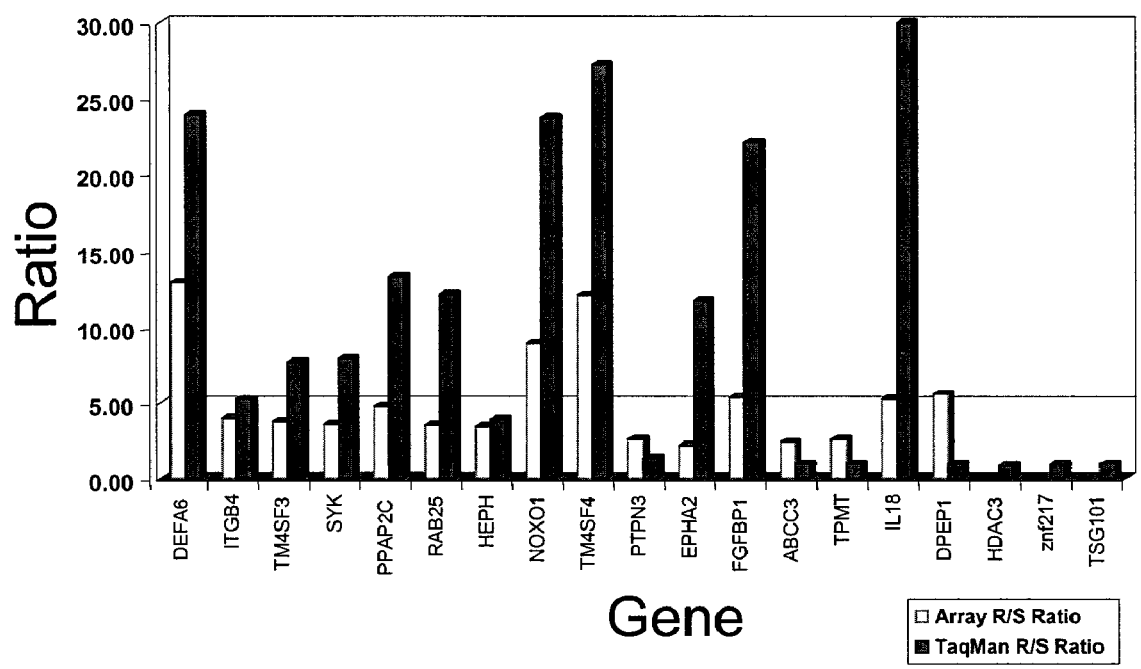
FIG. 5 is an illustrative bar graph comparing the results of a microarray method versus TaqMan® quantitative RT-PCR method for determining the ratio of mRNA expression levels for a series of identified HDACi compound resistance biomarker genes in PCI-24781-resistant versus PCI-24781 colon carcinoma cells.
Figure 6:
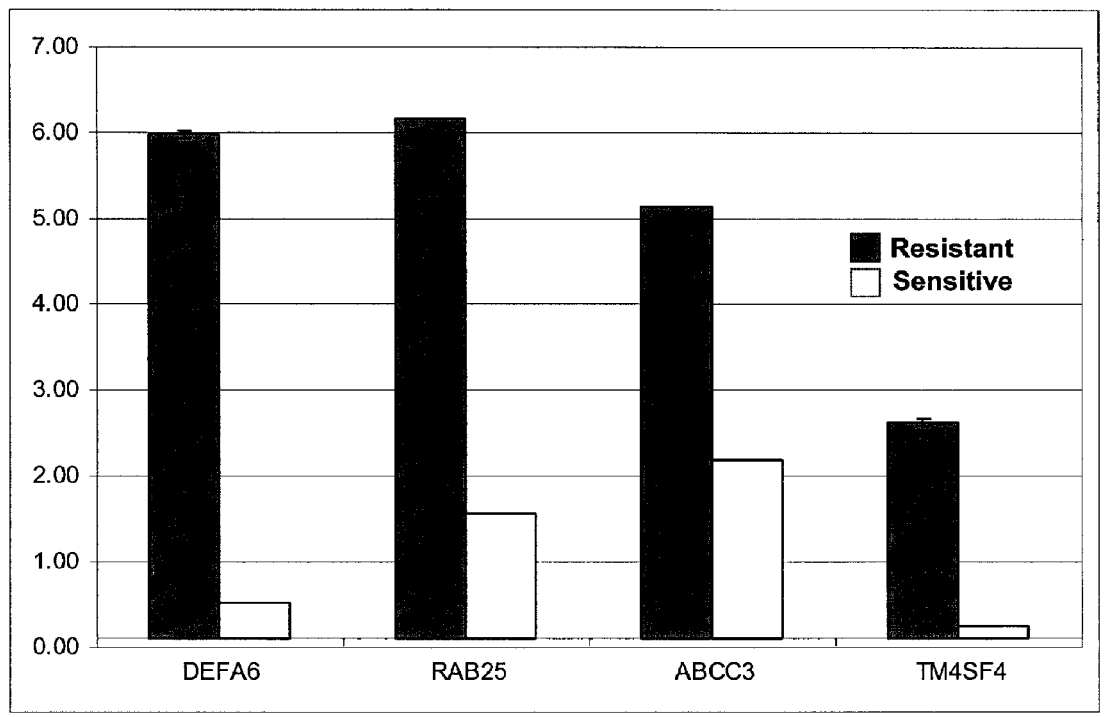
FIG. 6 is an illustrative bar graph comparing relative expression levels of four HDACi compound resistance biomarker genes in cancer cells that are resistant to the HDAC inhibitor compound (PCI-24781) versus expression of the biomarker genes in cancer cells that are sensitive to the compound.

As shown in FIG. 4, principal components analysis clearly distinguished untreated cell expression profiles from treated cell expression profiles. Controls (arrowhead) are more similar to each other and well separated from the treated samples. The major component PCA 1 clearly resolves treated from control samples. Interestingly, the resistant cell expression profiles (circled in both the treated and untreated samples) clustered together before and after treatment, whereas the sensitive samples varied widely in their profiles after treatment with PCI-24781. This suggested that it is easier to identify patients with the most resistant tumors and exclude them from a clinical trial rather than to identifying patients with sensitive tumors.

Based on the microarray analysis, we identified a total of 44 genes (see table 3) whose level of expression was significantly higher (z-score greater than 3.5) in PCI-24781 resistant cells than in PCI-24781 sensitive cells (data not shown). Of note, the expression of the identified biomarker genes was not altered by treatment with PCI-24781.

TABLE 3

Microarray Analysis: Upregulated Genes in PCI-24781-resistant Colorectal Tumor Cells

| Gene Name | Gene Symbol | GenBank Accession # | z-score | Res./Sens. Fold Expression Difference |
|---|---|---|---|---|
| PTPN3 | PTPN3 | AK096975 | 14.19 | 2.58 |
| ATP-binding cassette, sub- | ABCC3 | NM_020037 | 13.24 | 2.37 |

TABLE 3-continued

Microarray Analysis: Upregulated Genes in
PCI-24781-resistant Colorectal Tumor Cells

| Gene Name | Gene Symbol | GenBank Accession # | z-score | Res./Sens. Fold Expression Difference |
|---|---|---|---|---|
| family C (CFTR/MRP), member 3 | | | | |
| specifically androgen-regulated protein | SARG | NM_023938 | 13.04 | 4.00 |
| phosphatidic acid phosphatase type 2C | PPAP2C | NM_177526 | 12.95 | 4.75 |
| neural proliferation, differentiation and control, 1 | NPDC1 | NM_015392 | 11.88 | 2.45 |
| C-terminal tensin-like | CTEN | NM_032865 | 11.32 | 3.83 |
| RAB25, member RAS oncogene family | RAB25 | NM_020387 | 10.96 | 3.51 |
| hephaestin | HEPH | NM_138737 | 10.49 | 3.38 |
| Thiopurine S-methyltransferase | TPMT | NM_000367 | 9.97 | 2.56 |
| plakophilin 3 | PKP3 | NM_007183 | 9.31 | 3.13 |
| UDP-N-acetyl-alpha-D-galactosamine:polypeptide N-acetylgalactosaminyltransferase 5 (GalNAc-T5) | GALNT5 | NM_014568 | 9.31 | 2.54 |
| calmodulin-like 4 | CALML4 | NM_033429 | 9.14 | 3.51 |
| UDP-N-acetyl-alpha-D-galactosamine:polypeptide N-acetylgalactosaminyltransferase 12 (GalNAc-T12) | GALNT12 | AK024865 | 8.86 | 2.51 |
| thiamin pyrophosphokinase 1 | TPK1 | NM_022445 | 8.81 | 3.55 |
| defensin, alpha 6, Paneth cell-specific | DEFA6 | NM_001926 | 8.58 | 12.92 |
| epithelial protein lost in neoplasm beta | EPLIN | NM_016357 | 8.49 | 2.33 |
| chloride intracellular channel 5 | CLIC5 | NM_016929 | 7.20 | 3.60 |
| PERP, TP53 apoptosis effector | PERP | NM_022121 | 6.94 | 2.60 |
| spleen tyrosine kinase | SYK | NM_003177 | 6.90 | 3.59 |
| solute carrier family 12 (sodium/potassium/chloride transporters), member 2 | SLC12A2 | NM_001046 | 6.75 | 4.85 |
| guanylate cyclase 2C (heat stable enterotoxin receptor) | GUCY2C | NM_004963 | 6.72 | 3.53 |
| transmembrane 4 superfamily member 4 | TM4SF4 | NM_004617 | 6.54 | 12.09 |
| transforming growth factor, alpha | TGFA | NM_003236 | 6.44 | 3.11 |
| fibroblast growth factor binding protein 1 | FGFBP1 | NM_005130 | 6.27 | 5.35 |
| PTK6 protein tyrosine kinase 6 | PTK6 | NM_005975 | 6.24 | 3.10 |
| epithelial V-like antigen 1 | EVA1 | NM_005797 | 5.96 | 4.55 |
| EPH receptor A2 | EPHA2 | NM_004431 | 5.90 | 2.18 |
| integrin, alpha 6 | ITGA6 | NM_000210 | 5.53 | 4.09 |
| tumor necrosis factor receptor superfamily, member 21 | TNFRSF21 | NM_014452 | 5.47 | 2.16 |
| transmembrane 4 superfamily member 3 | TM4SF3 | NM_004616 | 5.32 | 3.75 |
| interleukin 18 (interferon-gamma-inducing factor) | IL18 | NM_001562 | 5.24 | 5.22 |
| bone morphogenetic protein 4 | BMP4 | NM_130850 | 4.82 | 3.91 |
| sphingomyelin phosphodiesterase, acid-like 3B | SMPDL3B | NM_014474 | 4.62 | 5.49 |
| transmembrane protease, serine 2 | TMPRSS2 | NM_005656 | 4.62 | 3.51 |
| guanine deaminase | GDA | NM_004293 | 4.56 | 6.52 |
| macrophage stimulating 1 receptor (c-met-related tyrosine kinase) | MST1R | NM_002447 | 4.49 | 4.52 |
| integrin, beta 4 | ITGB4 | NM_000213 | 4.41 | 3.98 |
| annexin A3 | ANXA3 | NM_005139 | 4.11 | 3.34 |
| chemokine (C—C motif) ligand 15 | CCL15 | NM_032965 | 3.87 | 3.74 |
| dipeptidase 1 (renal) | DPEP1 | NM_004413 | 3.72 | 5.53 |
| NADPH oxidase organizer 1 | NOXO1 | NM_172167 | 3.71 | 8.92 |
| interferon, alpha-inducible protein 27 | IFI27 | NM_005532 | 3.69 | 3.65 |

TABLE 3-continued

Microarray Analysis: Upregulated Genes in
PCI-24781-resistant Colorectal Tumor Cells

| Gene Name | Gene Symbol | GenBank Accession # | z-score | Res./Sens. Fold Expression Difference |
|---|---|---|---|---|
| cytochrome P450, family 3, subfamily A, polypeptide 43 | CYP3A43 | NM_057095 | 3.65 | 3.40 |
| plakophilin 2 | PKP2 | NM_004572 | 3.54 | 3.45 |

Analysis of the biological pathways associated with these genes showed that homologous recombination, nucleotide excision repair, cell cycle, and apoptosis were among those that affect sensitivity to PCI-24781.

a further validation of our microarray analysis, we performed TaqMan assays for three genes whose expression, as measured by microarray hybridization, was not found to correlate with PCI-24781 resistance (see last three genes in Table 3).

TABLE 4

Microarray vs TaqMan Analysis of Genes Upregulated in PCI-24781-Resistant vs Sensitive Colorectal Tumor Cells

| | | Microarrays | | | | Taqman | | | | |
|---|---|---|---|---|---|---|---|---|---|---|
| GeneName | GeneCards | Zcut | Resist mean | Sens mean | Ratio ArR/S | Sens Ct | ResistAvg | SensAvg | Ratio TaqR/S | Taq/Arr |
| defensin, alpha 6, Paneth cell-specific | DEFA6 | 8.58 | 8.57 | 0.65 | 12.92 | 37.20 | 1.34 | 0.06 | 23.94 | 1.85 |
| Integrin, beta 4 | ITGB4 | 4.41 | 0.67 | 0.17 | 3.98 | 28.99 | 86.18 | 16.59 | 5.20 | 1.31 |
| transmembrane 4 superfamily member 3 | TM4SF3 | 5.32 | 239.99 | 65.01 | 3.75 | 29.21 | 108.96 | 14.30 | 7.62 | 2.03 |
| spleen tyrosine kinase | SYK | 6.90 | 5.16 | 1.48 | 3.59 | 35.45 | 1.50 | 0.19 | 7.90 | 2.20 |
| phosphatidic acid phosphatase type 2C | PPAP2C | 12.95 | 5.35 | 1.14 | 4.75 | 36.45 | 1.26 | 0.09 | 13.31 | 2.80 |
| RAB25, member RAS oncogene family | RAB25 | 10.96 | 55.31 | 15.92 | 3.51 | 32.56 | 16.97 | 1.40 | 12.10 | 3.45 |
| hephaestin | HEPH | 10.49 | 8.11 | 2.46 | 3.38 | 32.90 | 4.34 | 1.11 | 3.93 | 1.16 |
| NADPH oxidase organizer 1 | NOXO1 | 3.71 | 0.98 | 0.11 | 8.92 | 35.41 | 4.60 | 0.19 | 23.76 | 2.66 |
| transmembrane 4 superfamily member 4 | TM4SF4 | 6.54 | 2.06 | 0.18 | 12.09 | 40.00 | 0.22 | 0.01 | 27.22 | 2.25 |
| PTPN3 | PTPN3 | 14.19 | 5.45 | 2.16 | 2.58 | 30.71 | 6.60 | 5.04 | 1.31 | 0.51 |
| EPH receptor A2 | EPHA2 | 5.90 | 29.27 | 13.49 | 2.18 | 31.91 | 25.80 | 2.20 | 11.73 | 5.37 |
| fibroblast growth factor binding protein 1 | FGFBP1 | 6.27 | 27.93 | 5.30 | 5.35 | 37.76 | 0.84 | 0.04 | 22.08 | 4.13 |
| ATP-binding cassette, sub-family C, member 3 | ABCC3 | 13.24 | 4.14 | 1.82 | 2.37 | 40.00 | 0.01 | 0.01 | 0.96 | 0.41 |
| thiopurine S-methyltransferase | TPMT | 9.97 | 26.21 | 10.11 | 2.56 | 40.00 | 0.01 | 0.01 | 0.96 | 0.38 |
| interleukin 18 (interferon-gamma-inducing factor) | IL18 | 5.24 | 26.57 | 5.04 | 5.22 | 40.00 | 0.62 | 0.01 | 77.06 | 14.77 |
| dipeptidase 1 (renal) | DPEP1 | 3.72 | 2.93 | 0.54 | 5.53 | 40.00 | 0.01 | 0.01 | 0.98 | 0.17 |
| HDAC3 | HDAC3 | | Not significant | | | 25.66 | 141.70 | 167.11 | 0.85 | |
| Zinc Finger Protein znt217 | ZNF217 | | Not significant | | | 35.07 | 0.23 | 0.25 | 0.93 | |
| TSG101 | TSG101 | | Not significant | | | 40.00 | 0.01 | 0.01 | 0.98 | |

In order to validate the higher expression of each resistance biomarker gene identified by microarray analysis, we analyzed the expression of each biomarker gene by the TaqMan® quantitave RT-PCR method as described below.

TaqMan® Gene Expression Assays for selected genes were obtained from Applied Biosystems (Foster City, Calif.). One-step RT-PCR was carried out in triplicate on 25 ng of total RNA from each sample on an ABI PRISM® 7900HT sequence detection system. The mRNA levels for each gene were normalized to the amount of RNA in the well as measured in parallel using Ribogreen (Invitrogen, Inc., Carlsbad, Calif.). We then calculated the ratios of expression levels of the biomarker genes in the resistant & sensitive samples (R/S) and compared them to the corresponding ratios obtained from the microarray analysis. The comparative analysis for 16 of the biomarker genes listed in Table 3 is shown in Table 4. As The comparison of microarray versus results is graphically summarized in FIG. 2. As shown in Table 4 and FIG. 2, genes found to be significantly upregulated by the microarray method were also found to be upregulated by the TaqMan method, though the latter generally yielded higher R/S ratios. Likewise, three genes whose expression did not differ significantly in the microarray analysis also showed no significant difference in the TaqMan assay.

Interestingly, several of the identified biomarker genes have previously been studied in relation to cancer, e.g., DEFA6, RAB25 small GTPase, MRP3 (ABCC3), and TM4SF4. Further, a number of the identified genes encode secreted proteins or transmembrane proteins that shed their extracellular domains. Genes encoding secretable proteins include, e.g., DEFA6 (NM_001926), TM4SF4 (NM 004617), TGFA (NM_003236), FGFBP1 (NM_005130), EPHA2 (NM_004431), TNFRSF21 (NM_014452), TMF4SF3 (NM_004616), IL18 (NM_001562), TMPRSS2 (NM_005656), and CCL15 (NM_032965).

Based on these data, we concluded that the expression pattern of subsets (e.g., four or more) of the identified biomarker genes provide "resistance signatures" that are optionally used to reliably identify colorectal tumors that are resistant or susceptible to the HDAC inhibitor PCI-24781.

Figure 11:
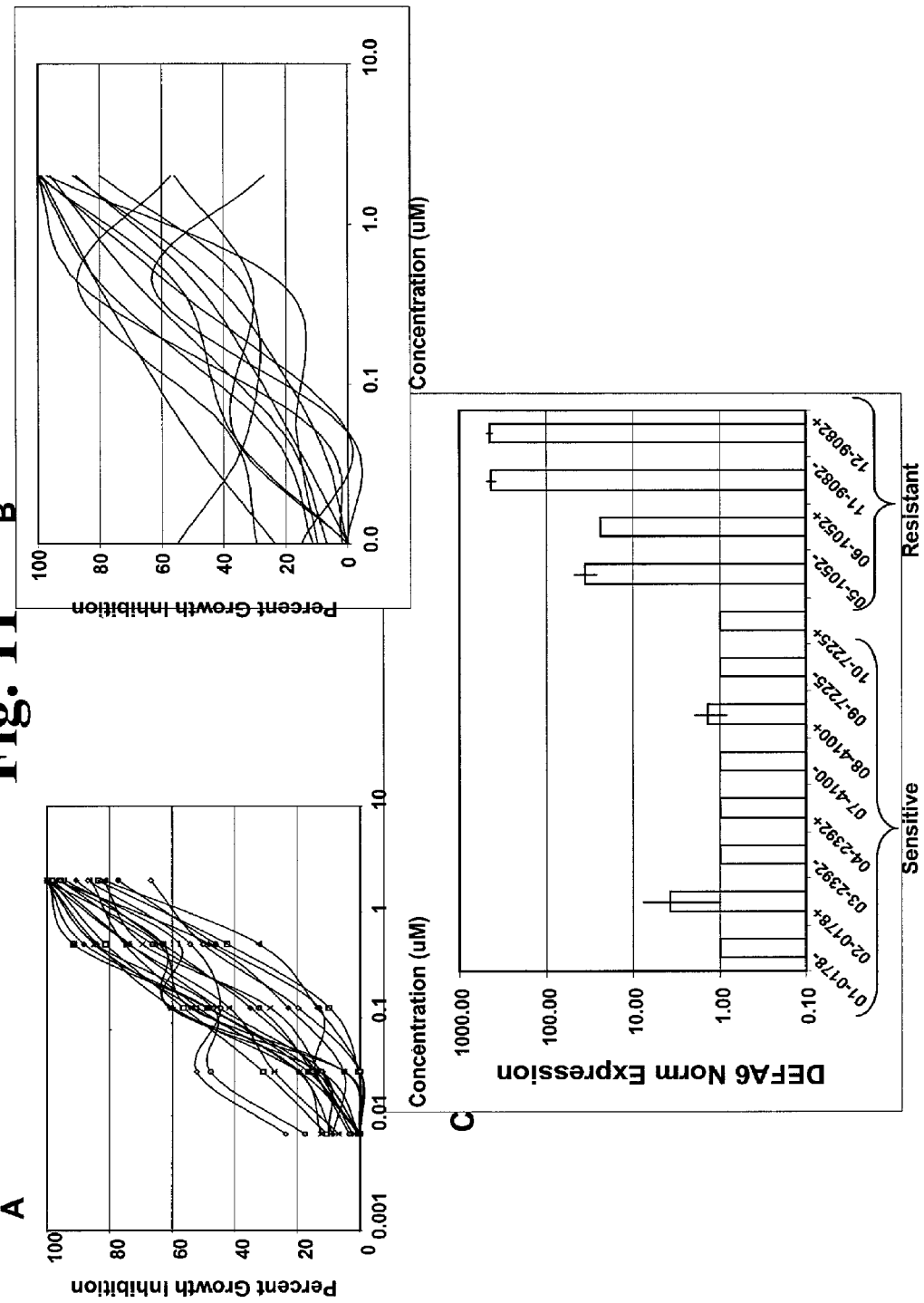

In a validation experiment, we found that ex vivo cultured primary colon tumor cells from twelve newly diagnosed, naive patients were all sensitive to growth inhibition by the HDAC inhibitor PCI-24781 (FIG. 11A). In contrast, we found that in a number of cases, advanced metastatic colon tumor cells were resistant to growth inhibition by the HDAC inhibitor PCI-24781 (FIG. 11B), and the DEFA6 mRNA expression levels were higher in HDAC-resistant cells than in HDAC-sensitive cells (FIG. 11C).

Example 2

Identification and Cross-Validation of Functional Biomarkers for HDAC Inhibitor Compounds and Selection Of Clinical Indications In order to determine relevant tumor types and to identify pharmacodynamic (PD) markers that are useful in the clinic, we first identified biomarkers of HDAC inhibition in mice and used these to identify HDACi-"sensitive" tissues. This was done by identifying, in HDACi-treated mice, genes in peripheral blood mononuclear cells (PBMC) whose mRNA levels showed the same timecourse as acetylated tubulin levels, an index of HDAC inhibition. These biomarker genes were then used to identify HDACi responsive mouse tissues. Primary human tumors corresponding to sensitive tissues were then tested ex-vivo with PCI-24781, and it was found that tumors from tissues that showed higher levels of activity were sensitive to inhibition by PCI-24781, thus validating that this technique does indeed predict sensitive tumor types.

In brief, female BALB/c mice were injected IV with 50 mg/kg PCI-24781 or vehicle. Blood and various tissues were collected at 0.25, 0.5, 1, 2, 3 & 8 hours after dosing. For acetylated histone and tubulin detection, organs/tissues were pooled for each vehicle and drug-treated organ group. RNA and protein were extracted from the samples with the PARIS Protein and RNA Isolation System (Ambion). Levels of acetylated and total α-tubulin & histones were evaluated by immunoblotting.

RNA expression profiles were determined using on a GE-Codelink Mouse Unisetl 10K oligonucleotide arrays in duplicate. Each treated sample was normalized to the corresponding vehicle control. In order to validate the expression profile of HDADi-responsive genes identified by the gene expression array assays, Taqman gene expression assays were performed using Applied Biosystems Inc. assays. One-step RT-PCR was carried out in triplicate on 25 ng of total RNA from each sample on a ABI PRISM 7700 instrument. The mRNA levels for each gene were normalized to the amount of RNA in the well as measured in parallel using Ribogreen (Molecular Probes). The treated samples were then normalized to the vehicle control at that time point.

Figure 7:
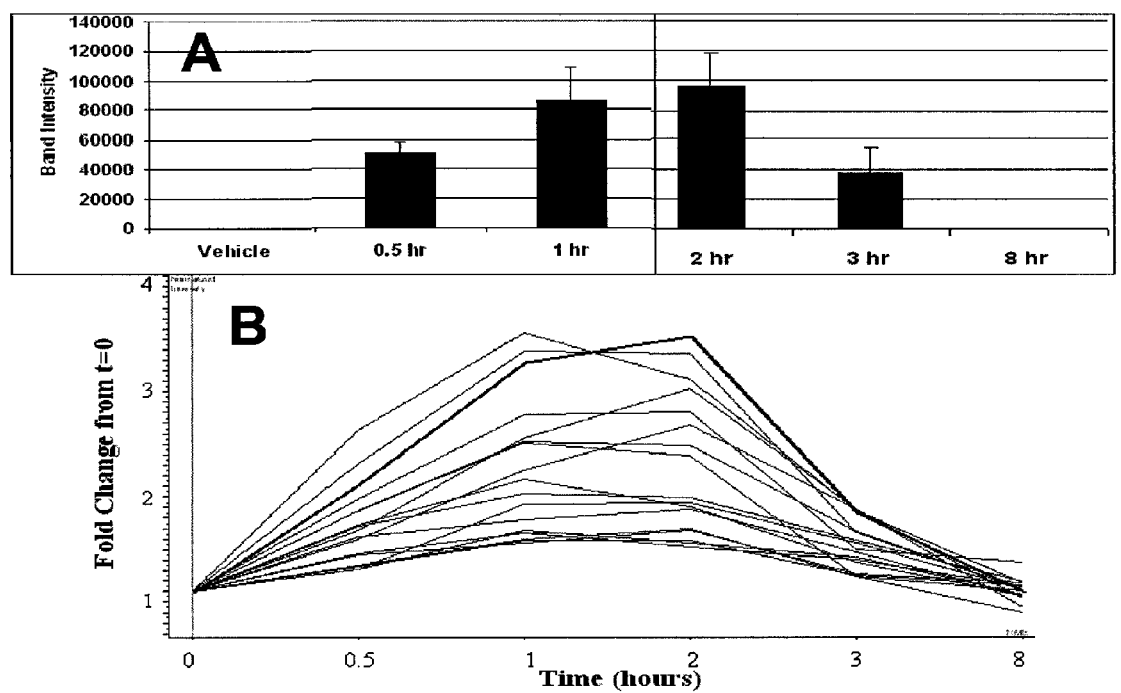
FIG. 7 (A) is an illustrative bar graph showing the time course of tubulin acetylation in peripheral blood mononuclear cells from mice treated with the HDAC inhibitor compound PCI-24781; (B) is a time course of the expression profile of genes whose mRNA levels are correlated with changes in tubulin acetylation.

A set of 16 genes (Table 5) whose expression profile in PBMC (FIG. 7A) closely tracked increases in tubulin acetylation levels (FIG. 7B) following treatment with the HDAC inhibitor PCI-24781.

TABLE 5

HDAC Inhibitor (HDACi)-Responsive Biomarker Genes

| Common | Description | Function |
|---|---|---|
| Slc9a3r1 | solute carrier family 9 isoform 3 regulator 1 | ION TRANSPORT |
| Ing11 | inhibitor of growth family, member 1-like | CELL PROLIFERATION AND DIFFERENTIATION |
| Gadd45g | growth arrest and DNA-damage-inducible 45 gamma | CELL PROLIFERATION AND DIFFERENTIATION; APOPTOSIS |
| Plaur | urokinase plasminogen activator receptor | MULTIPLE |
| EST | RIKEN cDNA 2810405O22 gene | UNKNOWN |
| Insl6 | insulin-like 6 | BIOLOGICAL PROCESS UNKNOWN |
| Luc7l | Luc7 homolog (S. cerevisiae)-like | RNA PROCESSING |
| Taf9 | TAF9 RNA polymerase II | MRNA TRANSCRIPTION |
| Gadd45b | growth arrest and DNA-damage-inducible 45 beta | CELL PROLIFERATION AND DIFFERENTIATION |
| Syngr2 | synaptogyrin 2 | UNKNOWN |
| Polr2e | polymerase (RNA) II (DNA directed) polypeptide E | MRNA TRANSCRIPTION |
| Kras2 | Mouse c-Ki-ras oncogene | ONCOGENE |
| Hspa5 | heat shock 70 kD protein 5 | STRESS RESPONSE |
| Fgf15 | fibroblast growth factor 15 | CELL PROLIFERATION AND DIFFERENTIATION |
| Tuba4 | tubulin, alpha 4 | CELL STRUCTURE |
| H2afz | H2A histone family, member Z | CHROMATIN PACKAGING |

Figure 8:
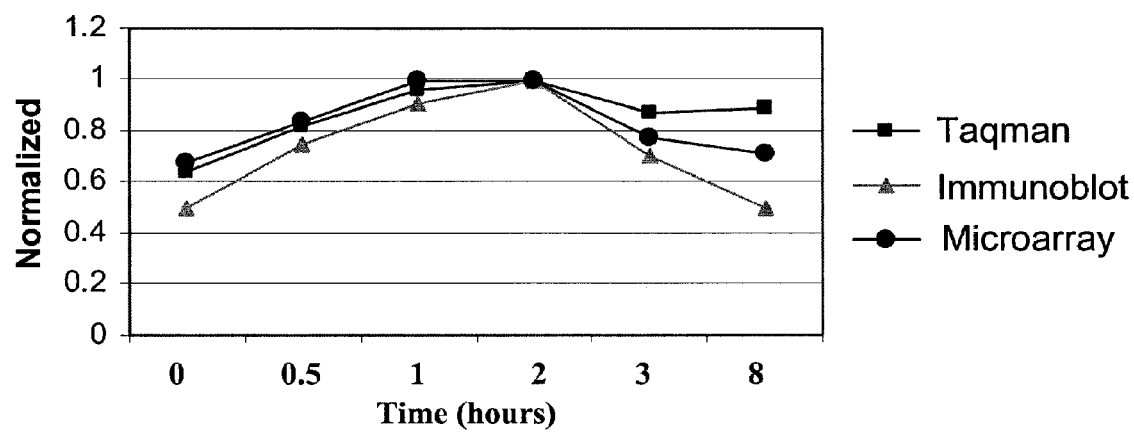
FIG. 8 is an illustrative set of two line graphs illustrating the expression profiles of two HDAC inhibitor-responsive biomarker genes as determined by microarray analysis, quantitative RT-PCR, and immunoblotting.
Figure 8:
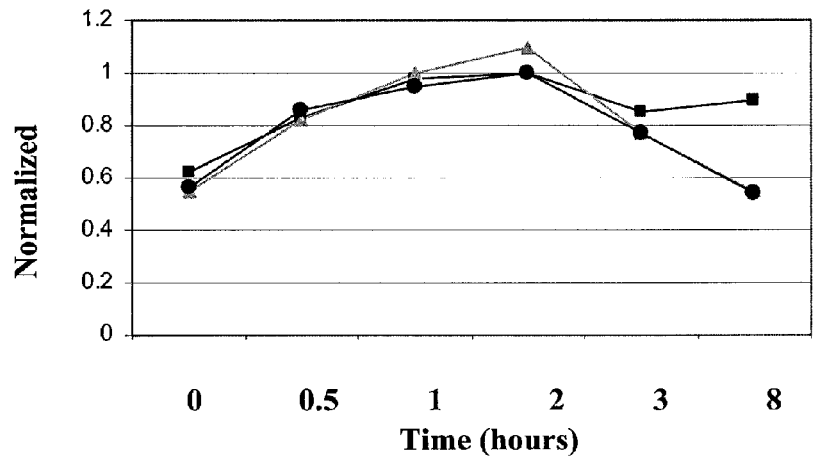

Subsequently, we validated the expression profile of two of HDACi-responsive genes, Fgf15 and Syngr2, by quantitative RT-PCR and immunoblotting. As shown in FIG. 8, the expression profiles obtained the three different methods closely matched one another, suggesting that the microarray analysis identified HDACi-responsive genes reliably.

Figure 9:
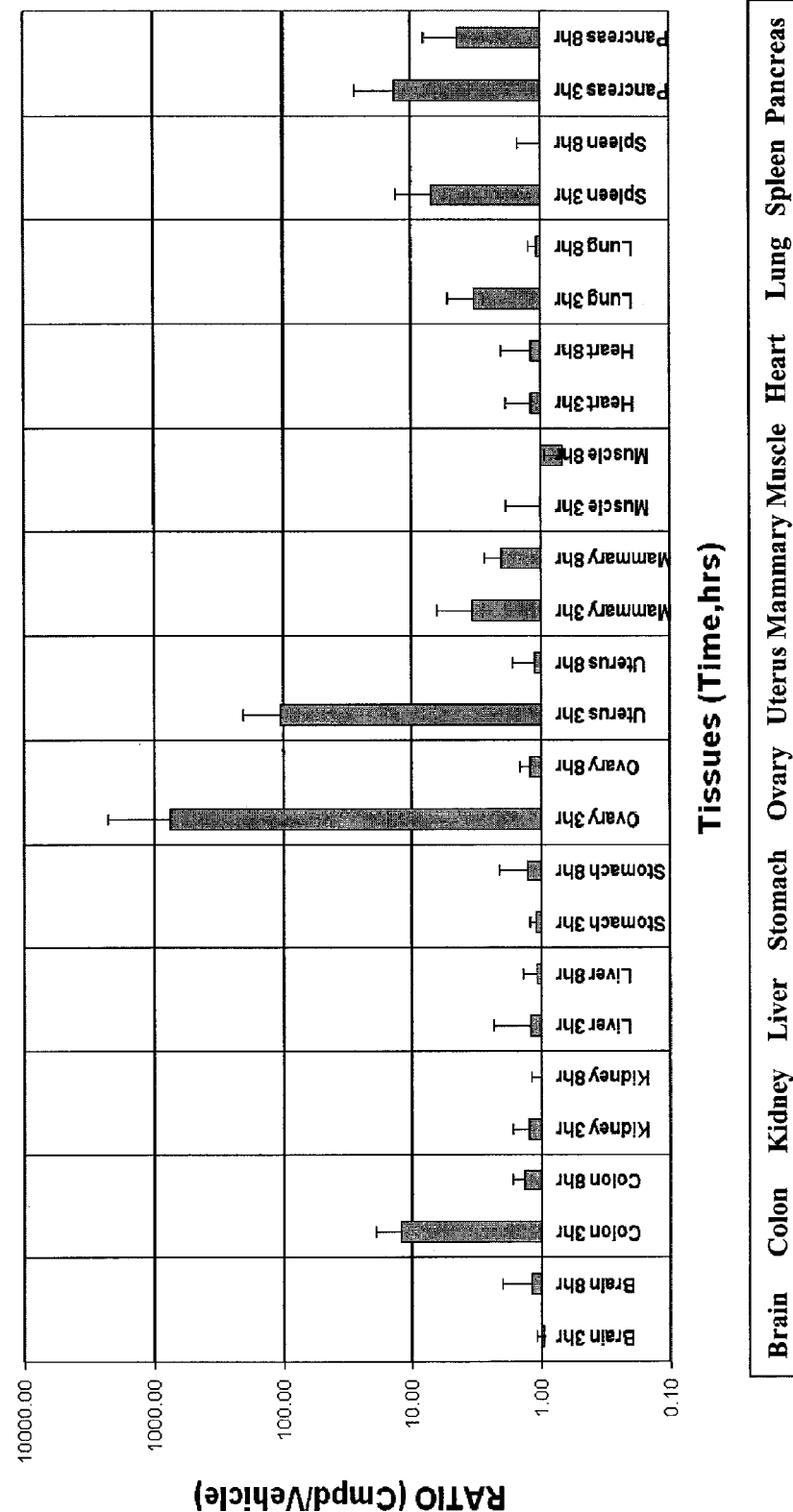
FIG. 9 is an illustrative bar graph showing average in vivo mRNA levels in various tissues of five of the HDAC inhibitor-responsive biomarker genes at 3 and 8 hours post-HDAC inhibitor treatment.

We then determined the in vivo expression levels for five of the RDACi-responsive biomarker genes in various tissues following 3 hours or 8 hours following administration of PCI-24781 (50 mg/kg). A Taqman assay was performed to determine mRNA expression levels in brain, colon, kidney, liver, stomach, ovary, uterus, mammary, muscle, heart, lung, spleen, and pancreas. The mean and SD for mRNA expression levels of all 5 genes in each tissue at each time point are shown in FIG. 9. The issue distribution pattern was very reproducible across the biomarker set. Ovary showed the highest level of induction, followed by uterus.

Subsequently, primary human tumor samples were obtained and viable tumor cells were plated in soft agar and treated with the HDAC inhibitor PCI-24781. Tritiated thymidine was added after 3 days, and 2 days later the radioactivity incorporated into the DNA was quantified. The tumors were then classified as either resistant (EDR: Extreme Drug Resistance), sensitive (LDR) or intermediate (IDR) based on deviation from the median profile (Oncotech, Inc. Tustin, Calif.).

Figure 10:
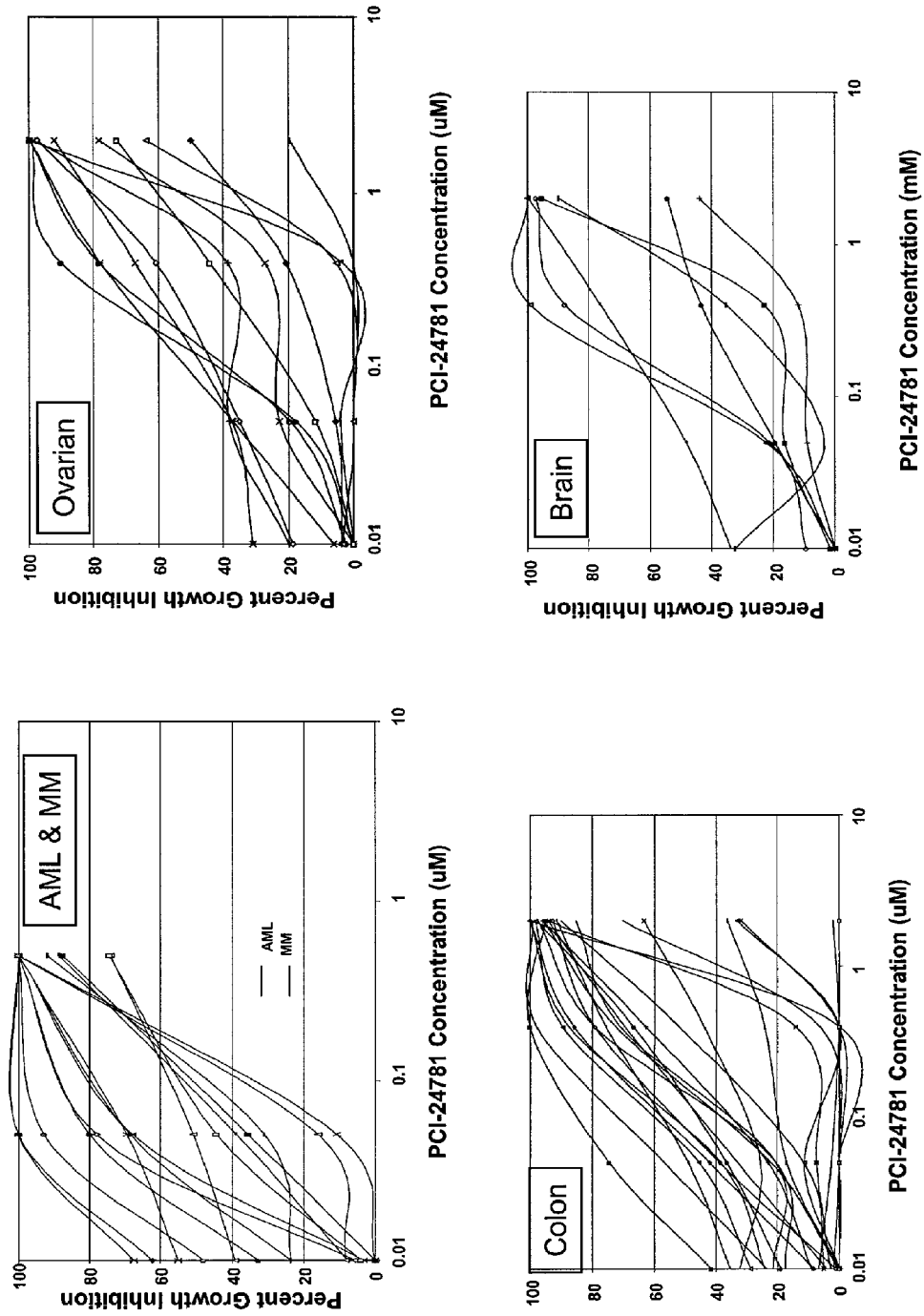
FIG. 10 is an illustrative series of dose response curves for the effect of the HDAC inhibitor PCI-24781 on tumors derived from the indicated tumors FIG. 11 (A) is a series of line graphs illustrating the amount of in vitro growth inhibition by the HDAC inhibitor PCI-24781 of primary colon tumor cells derived from newly diagnosed, naive colon cancer patients; (B) is a series of line graphs illustrating the amount of in vitro growth inhibition by the HDAC inhibitor PCI-24781 of colon cancer cells derived from patients having advanced, metastatic colon tumors; (C) is a bar graph illustrating the correlation between metastatic tumor cell resistance to an HDAC inhibitor in vitro and the mRNA expression level of the HDAC resistance biomarker gene DEFA6.

As predicted based on the HDACi responsive biomarker gene profiles hematopoietic tumors had the lowest proportion of resistant (EDR) tumors, and colon the most (38%). See FIG. 10 and Table 6. Among the solid tumors, ovarian had the lowest proportion of resistant tumors, consistent with the high HDACi-biomarker responsiveness of this tissue.

TABLE 6

Tumor Resistance to HDAC Inhibitor PCI-24781

| Tumor Type | Resistant EDR | Interme-diate IDR | Sensitive LDR | Total | % Resis-tance |
|---|---|---|---|---|---|
| AML | 1 | 4 | 5 | 10 | 10 |
| Multiple Myeloma | 2 | 0 | 4 | 6 | 33 |
| Ovarian | 3 | 4 | 5 | 12 | 25 |
| Glioblastoma | 2 | 1 | 4 | 7 | 29 |
| Colon | 9 | 3 | 12 | 24 | 38 |

Note:
EDR/LDR status as determined by Oncotech's algorithm from their assay data Based on the above results, we concluded that expression profiles of the orthologous human biomarkers will reflect PCI-24781 activity in human blood, and serve as PD markers in the clinic. Further, the identified set of HDACi-responsiveness biomarker genes accurately predicts tumor sensitivity to treatment with HDAC inhibitors.

APPENDIX

Nucleotide Sequences for HDACi Compound Resistance Biomarker Genes

| Gene Name | Gene Symbol | GenBank Accession # | SEQ ID NO |
|---|---|---|---|
| PTPN3 | PTPN3 | AK096975 | 1 |

```
   1 tgaatagttt gctggtagca agacggatga agacctatat gggagattct ttatctctag
  61 agctagcata tttacttgca tactttgttt cttttccaca tggatatttt actgctaaat
 121 ggcagaggtg ggagggagat gtcacacagt accataaccc catattgaaa acaagaaacc
 181 accagaaagt ttgcagctaa ggggcagggg attcagttcc tacgcccact cagcactaac
 241 tacttgcggg cctggttgct tagaagctct acctctcttt cattatctgt aaaatagaaa
 301 caatacttag gactttagtt ggaacatgag gattgaataa gatcacgcta ttcatgtgac
 361 ttttttatcgg ctagaacagc aacagacact gctgtgggtg agttacttag aaaagtttag
 421 ttatcagtga ttagcccaaa aacacatcag tcaaaaatag aatccactgg atttttgtct
 481 ctcttttag agacagggtc tcactgtcgc ccaggctgga gtacagtggc atgatcattg
 541 ttcactgcag cctcaaattc ctgggctcaa gcaatcctcg cacctcagcc tcctgagtag
 601 ccgggactat aggcacatgc cacctcacct ggcttgtgtg tgtgtgtgtg tgtgtgtgtg
 661 tgtgtgtgtg tgtgtgtgta gagacaggat cttgatgtgt cgcctaggct ggtctcaaac
 721 tcctggcctc aagtgatctt cccacctcag cctccaaaac tgtgggatt ataggcgtga
 781 gccactgtgc ccagcctaac tgggttttta tgagaggaaa atagaaaatg ctcttctaga
 841 agagagagaa caagagcaca aaataatctg gactcacaaa aattcagcaa gctccaagaa
 901 aggggatgg agggaacgct ggcaaaaatt taaatgccat taggatattt agcaagttat
 961 tactgtttgg taaaaatgca tcatcaccct gtgtgcaaaa tgcttgcaaa gtagtctaaa
1021 tgtctttgga gatgggtgtt ttactgcttt tttccaaaaa caaattgttt attatggttg
1081 cagaaatgca gccattacgg tcacataaat ttctaaaaag cctaccaaag gttgcaagca
1141 gtcttctgcc actgggcagg ccagcagttc agacccagcg aggttgccag gaacaaatcc
1201 aggaaatact gggaagaaca agacaagaga attacctaaa agagcaaaca attcaagtaa
1261 atcctgtagc tattaccact taaaatccgt agctcaagat tcctgtttca ccaccttata
1321 cacttaagca attatactta agccttttt tagtcctaag tgaagaacta catcagaatc
1381 aggataagta ttttgcctgg gaaatttggc tgcatatgaa tggagaagac atttacatcc
1441 tatgttctgg cactttctga aagatctaat taaacatgtt gatgtgccaa tttaatcaag
```

APPENDIX-continued

Nucleotide Sequences for HDACi Compound Resistance Biomarker Genes

```
1501 atgagagatc cctgctggtg tcaccctcta gaacctgcac ttggtgtttt gactttccag 1561 aagaaaaaaa tgcaactttg gttagggggc agtggttgga tcacacagtt gtctttcgtt 1621 tcctaccaca gtaattcata tttaaatatg cttttagatt agtgtggata ctattgctgc 1681 tgtgttgcta cctgaccttt ttctgggggg ggtacctcag aaatgagcat ttgagggcaa 1741 gcgaaaaagc cctcttcatc ctccagaggc aacaaagagg cagcagaaat ggggaaagat 1801 tgtgagaggc agggcttggg tctagacctg gacttaggca agatatgttg ccctcaaccc 1861 tgagttttct tatatgtaaa aagggaaggt tgggctggac tagatgaggt caagatttgc 1921 cattctggga ggctgatatt ccagagaatc aaaattaatc ctaaaccaaa gctttatggc 1981 tgctacagag acatgtcaca tttctgagac ttgtcaccaa gagtttgtcc ctcagacttt 2041 ggcgctgttg aatgcaaaga caaggatggc caccttctgg ttcttgcctg ttgtcctcag 2101 ctgagagcag tctcggtaaa ggtggcaaag attctgtgac ctcagaccgg ggaccaaatg 2161 cttgggagtc tgatggccgg gctgggccac cattctcata gctctcattc tgtttggagc 2221 aaccaaagga tttgtgtgaa gttatttgga aaaggacctt aactgagcag taatcttttt 2281 tctgtatatt tggaatgttt ttcattctga cctgttctgt cagtgattct actgaaaaac 2341 aatttaatca atataaaaat gttcaagcta tgcaac
```

| Gene Name | Gene Symbol | GenBank Accession # | SEQ ID NO |
|---|---|---|---|
| ATP-binding cassette, sub-family C (CFTR/MRP), member 3 | ABCC3 | NM_020037 | 2 |

```
   1 ctccggcgcc cgctctgccc gccgctgggt ccgaccgcgc tcgccttcct tgcagccgcg 61 cctcggcccc atgacgcccc tgtgcggttc cggggagctc ggctccaagt tctgggactc 121 caacctgtct gtgcacacag aaaacccgga cctcactccc tgcttccaga actccctgct 181 ggcctgggtg ccctgcatct acctgtgggt cgccctgccc tgctacttgc tctacctgcg 241 gcaccattgt cgtggctaca tcatcctctc ccacctgtcc aagctcaaga tggtcctggg 301 tgtcctgctg tggtgcgtct cctgggcgga cctttttttac tccttccatg gcctggtcca 361 tggccgggcc cctgccccctg ttttctttgt caccccccttg gtggtggggg tcaccatgct 421 gctggccacc ctgctgatac agtatgagcg gctgcagggc gtacagtctt cggggggtcct 481 cattatcttc tggttcctgt gtgtggtctg cgccatcgtc ccattccgct ccaagatcct 541 tttagccaag gcagagggtg agatctcaga ccccttccgc ttcaccacct tctacatcca 601 ctttgccctg gtactctcta ccctcatctt ggcctgcttc agggagaaac ctccattttt 661 ctccgcaaag aatgtcgacc ctaaccccta ccctgagacc agcgctggct ttctctcccg 721 cctgttttc tggtggttca caaagatggc catctatggc taccggcatc ccctggagga 781 gaaggacctc tggtccctaa aggaagagga cagatcccag atggtggtgc agcagctgct 841 ggaggcatgg aggaagcagg aaaagcagac ggcacgacac aaggcttcag cagcacctgg 901 gaaaaatgcc tccggcgagg acgaggtgct gctgggtgcc cggccaggc cccggaagcc 961 ctccttcctg aaggccctgc tggccacctt cggctccagc ttcctcatca gtgcctgctt 1021 caagcttatc caggacctgc tctccttcat caatccacag ctgctcagca tcctgatcag 1081 gtttatctcc aaccccatgg ccccctcctg gtggggcttc ctggtggctg ggctgatgtt
```

APPENDIX-continued

Nucleotide Sequences for HDACi Compound Resistance Biomarker Genes

```
1141 cctgtgctcc atgatgcagt cgctgatctt acaacactat taccactaca tctttgtgac
1201 tggggtgaag tttcgtactg ggatcatggg tgtcatctac aggaaggctc tggttatcac
1261 caactcagtc aaacgtgcgt ccactgtggg ggaaattgtc aacctcatgt cagtggatgc
1321 ccagcgcttc atggaccttg ccccttcct caatctgctg tggtcagcac ccctgcagat
1381 catcctggcg atctacttcc tctggcagaa cctaggtccc tctgtcctgg ctggagtcgc
1441 tttcatggtc ttgctgattc cactcaacgg agctgtggcc gtgaagatgc gcgccttcca
1501 ggtaaagcaa atgaaattga aggactcgcg catcaagctg atgagtgaga tcctgaacgg
1561 catcaaggtg ctgaagctgt acgcctggga gcccagcttc ctgaagcagg tggagggcat
1621 caggcagggt gagctccagc tgctgcgcac ggcggcctac ctccacacca caaccaccct
1681 cacctggatg tgcagcccct tcctggtgac cctgatcacc ctctgggtgt acgtgtacgt
1741 ggacccaaac aatgtgctgg acgccgagaa ggcctttgtg tctgtgtcct tgtttaatat
1801 cttaagactt cccctcaaca tgctgcccca gttaatcagc aacctgactc aggccagtgt
1861 gtctctgaaa cggatccagc aattcctgag ccaagaggaa cttgaccccc agagtgtgga
1921 aagaaagacc atctccccag gctatgccat caccatacac agtggcacct tcacctgggc
1981 ccaggacctg ccccccactc tgcacagcct agacatccag gtcccgaaag gggcactggt
2041 ggccgtggtg gggcctgtgg gctgtgggaa gtcctccctg gtgtctgccc tgctgggaga
2101 gatggagaag ctagaaggca aagtgcacat gaagggctcc gtggcctatg tgccccagca
2161 ggcatggatc cagaactgca ctcttcagga aaacgtgctt ttcggcaaag ccctgaaccc
2221 caagcgctac cagcagactc tggaggcctg tgccttgcta gctgacctgg agatgctgcc
2281 tggtggggat cagacagaga ttggagagaa gggcattaac ctgtctgggg ccagcggca
2341 gcgggtcagt ctggctcgag ctgtttacag tgatgccgat attttcttgc tggatgaccc
2401 actgtccgcg gtggactctc atgtggccaa gcacatcttt gaccacgtca tcgggccaga
2461 aggcgtgctg gcaggcaaga cgcgagtgct ggtgacgcac ggcattagct tcctgcccca
2521 gacagacttc atcattgtgc tagctgatgg acaggtgtct gagatgggcc cgtacccagc
2581 cctgctgcag cgcaacggct cctttgccaa ctttctctgc aactatgccc ccgatgagga
2641 ccaagggcac ctgaggaca gctggaccgc gttggaaggt gcagaggata aggaggcact
2701 gctgattgaa gacacactca gcaaccacac ggatctgaca gacaatgatc cagtcaccta
2761 tgtggtccag aagcagtta tgagacagct gagtgccctg tcctcagatg ggagggaca
2821 gggtcggcct gtaccccga ggcacctggg tccatcagag aaggtgcagg tgacagaggc
2881 gaaggcagat ggggcactga cccaggagga gaaagcagcc attggcactg tggagctcag
2941 tgtgttctgg gattatgcca aggccgtggg gctctgtacc acgctggcca tctgtctcct
3001 gtatgtgggt caaagtgcgg ctgccattgg agccaatgtg tggctcagtg cctggacaaa
3061 tgatgccatg gcagacagta gacagaacaa cacttccctg aggctgggcg tctatgctgc
3121 tttaggaatt ctgcaagggt tcttggtgat gctggcagcc atggccatgg cagcgggtgg
3181 catccaggct gcccgtgtgt tgcaccaggc actgctgcac aacaagatac gctcgccaca
3241 gtccttcttt gacaccacac catcaggccg catcctgaac tgcttctcca aggacatcta
3301 tgtcgttgat gaggttctgg ccctgtcat cctcatgctg ctcaattcct tcttcaacgc
3361 catctccact cttgtggtca tcatggccag cacgccgctc ttcactgtgg tcatcctgcc
```

APPENDIX-continued

Nucleotide Sequences for HDACi Compound Resistance Biomarker Genes

```
3421 cctggctgtg ctctacacct tagtgcagcg cttctatgca gccacatcac ggcaactgaa
3481 gcggctggaa tcagtcagcc gctcacctat ctactcccac ttttcggaga cagtgactgg
3541 tgccagtgtc atccgggcct acaaccgcag ccgggatttt gagatcatca gtgatactaa
3601 ggtggatgcc aaccagagaa gctgctaccc ctacatcatc tccaaccggt cagaagccgc
3661 ctccctcgct ccctgctcct ccaggaattc ccagcaggct ctctggtgtt cagggtcctt
3721 gtccctcctt tccctaagc agaaaactgg ccctgccctg ccctgcccc atttcctcct
3781 catctgatcc cccataggcg gctgagcatc ggagtggagt tcgtggggaa ctgcgtggtg
3841 ctctttgctg cactatttgc cgtcatcggg aggagcagcc tgaacccggg gctggtgggc
3901 ctttctgtgt cctactcctt gcaggtgaca tttgctctga actggatgat acgaatgatg
3961 tcagatttgg aatctaacat cgtggctgtg gagagggtca aggagtactc caagacagag
4021 acagaggcgc cctgggtggt ggaaggcagc cgccctcccg aaggttggcc cccacgtggg
4081 gaggtggagt tccggaatta ttctgtgcgc taccggccgg gcctagacct ggtgctgaga
4141 gacctgagtc tgcatgtgca cggtggcgag aaggtgggga tcgtgggccg cactggggct
4201 ggcaagtctt ccatgaccct ttgcctgttc cgcatcctgg aggcggcaaa gggtgaaatc
4261 cgcattgatg gcctcaatgt ggcagacatc ggcctccatg acctgcgctc tcagctgacc
4321 atcatcccgc aggaccccat cctgttctcg gggaccctgc gcatgaacct ggaccccttc
4381 ggcagctact cagaggagga catttggtgg gctttggagc tgtcccacct gcacgcgttt
4441 gtgagctccc agccggcagg cctggacttc cagtgctcag agggcgggga gaatctcagc
4501 gtgggccaga ggcagctcgt gtgcctggcc cgagccctgc tccgcaagag ccgcatcctg
4561 gttttagacg aggccacagc tgccatcgac ctggagactg acaacctcat ccaggctacc
4621 atccgcaccc agtttgatac ctgcactgtc ctgaccatcg cacaccggct taacactatc
4681 atggactaca ccagggtcct ggtcctggac aaaggagtag tagctgaatt tgattctcca
4741 gccaacctca ttgcagctag aggcatcttc tacgggatgg ccagagatgc tggacttgcc
4801 taaaatatat tcctgagatt tcctcctggc ctttcctggt tttcatcagg aaggaaatga
4861 caccaaatat gtccgcagaa tggacttgat agcaaacact gggggcacct taagattttg
4921 cacctgtaaa gtgccttaca gggtaactgt gctgaatgct ttagatgagg aaatgatccc
4981 caagtggtga atgacacgcc taaggtcaca gctagtttga gccagttaga ctagtccccc
5041 ggtctcccga ttcccaactg agtgttattt gcacactgca ctgttttcaa ataacgattt
5101 tatgaaatga cctctgtcct ccctctgatt tttcatattt tcctaaagtt tcgtttctgt
5161 tttttaataa aaagcttttt cctcctggaa cagaagacag ctgctgggtc aggccacccc
5221 taggaactca gtcctgtact ctggggtgct gcctgaatcc attaaaaatg ggagtactga
5281 tgaaataaaa ctacatggtc aacagtaaaa
```

| Gene Name | Gene Symbol | GenBank Accession # | SEQ ID NO |
|---|---|---|---|
| specifically androgen-regulated protein | SARG | NM_023938 | 3 |

```
  1 gtgggggcca ggcagcacag atgaagcatt tacctatcta ggtaagtcag gaggagctca
 61 aaaggagaag aaaacagtag gaggcagggg aagcagcctc tgtctccatc tctgcccttt
121 gaaacaaaag ggtatttctt ttctctcttc agccccccaac ccagtggagg cccggcttgg
```

APPENDIX-continued

Nucleotide Sequences for HDACi Compound Resistance Biomarker Genes

```
 181 gacattgttc acttccccto gcttccccto tagaagcccc ctttgccatc cctgcacctt
 241 gtttcgggtg atgcccgaga gggagctgtg gccagcgggg actggctcag aacccgtgac
 301 ccgtgtcggc agctgtgaca gcatgatgag cagcacctcc acccgctctg gatctagtga
 361 tagcagctac gacttcctgt ccactgaaga aaggagtgt ctgctcttcc tggaggagac
 421 cattggctca ctggacacgg aggctgacag cggactgtcc actgacgagt ctgagccagc
 481 cacaactccc agaggtttcc gagcactgcc cataacccaa cccactcccc ggggaggtcc
 541 agaggagacc atcactcagc aaggacgaac gccaaggaca gtaactgagt ccagctcatc
 601 ccaccctcct gagccccagg gcctaggcct caggtctggc tcctacagcc tccctaggaa
 661 tatccacatt gccagaagcc agaacttcag gaaaagcacc cccaggcta gcagtcacaa
 721 ccctggagaa ccggggaggc ttgcgccaga gcctgagaaa gaacaggtca gccagagcag
 781 ccaacccagg caggcacctg ccagccccca ggaggctgcc cttgacttgg acgtggtgct
 841 catccctccg ccagaagctt tccgggacac ccagccagag cagtgtaggg aagccagcct
 901 gcccgagggg ccaggacagc agggccacac accccagctc cacacaccat ccagctccca
 961 ggaaagagag cagactcctt cagaagccat gtcccaaaaa gccaaggaaa cagtctcaac
1021 caggtacaca caacccccagc ctcctcctgc agggttgcct cagaatgcaa gagctgaaga
1081 tgctcccctc tcatcagggg aggacccaaa cagccgacta gctcccctca caaccccctaa
1141 gccccggaag ctgccaccta atattgttct gaagagcagc cgaagcagtt ccacagtga
1201 cccccagcac tggctgtccc gccacactga ggctgcccct ggagattctg gcctgatctc
1261 ctgttcactg caagagcaga gaaaagcacg taaagaagct ctagagaagc tggggctacc
1321 ccaggatcaa gatgagcctg gactccactt aagtaagccc accagctcca tcagacccaa
1381 ggagacacgg gcccagcatc tgtccccagc tccaggtctg gctcagcctg cagctccagc
1441 ccaggcctca gcagctattc ctgctgctgg gaaggctctg gctcaagctc cggctccagc
1501 tccaggtcca gctcagggac ctttgccaat gaagtctcca gctccaggca atgttgcagc
1561 tagcaaatct atgccaattc ctatccctaa ggccccaagg gcaaacagtg ccctgactcc
1621 accgaagcca gagtcagggc tgactctcca ggagagcaac accccctggcc tgagacagat
1681 gaacttcaag tccaacactc tggagcgctc aggcgtggga ctgagcagct acctttcaac
1741 tgagaaagat gccagcccca aaaccagcac ttctctggga aagggctcct tcttggacaa
1801 gatctcgccc agtgtcttac gtaattctcg gccccgcccg gcctccctgg gcacggggaa
1861 agattttgca ggtatccagg taggcaagct ggctgacctg gagcaggagc agagctccaa
1921 gcgcctgtcc taccaaggac agagccgtga caagcttcct cgccccccct gtgtcagtgt
1981 caagatctcc ccaaagggtg tccccaatga acacagaagg gaggccctga gaagctggg
2041 actgttgaag gagtagactc tgcgaccagt acagaccctg tcctggctga acaagaagag
2101 acacatgctc cacttgggag cctttgccac cacgcaactc agggctcaag atgaatggga
2161 gggagagatt tgagtccaag catacattta tattcagtgt tgtgccattg agttcccatg
2221 tggatcattc tgaaggtgat ctccacaaga gggtgtgtgt gtgtgtgttt ggtgtgtgtg
2281 tggagggggg gccgctggat acatcactga agctattgat ataacacaat gagtcactgt
2341 tcagaatttt gctcttgtta gatgttttct tacattgggt agagtccagc ctagtgagag
2401 ctgagtgaag gggctggcca tgcctgagac aaaaagtcaa atgagacaat ggacgtgtca
```

APPENDIX-continued

Nucleotide Sequences for HDACi Compound Resistance Biomarker Genes

```
2461 atgacttgaa aaaaagtcac atccagcaaa tgcagggtca catgaaatat gggcctcctg
2521 gaatccctac agtggatgga gactggctca taccttgcca gatccctctc tcagttccag
2581 ccttctggac aaggcctggg ctaagaggag ctgattcgtt atctcttcac ccactgccct
2641 ctcagtatca ccagtcccaa agacaggata cgtccctgta acccaatctc tcggttgatt
2701 gatagcagaa cagctcttgt tggtctgaga aggcaggata agtgaccaca tatttatgcc
2761 actacctcca ccagggagag tccttctcca caggcttgat aaattcaatc accaactgtg
2821 ctgtcgtccc tgactctgct actcccgttc ttcctgcttt cctgctccgt atctcagtct
2881 gcactgaccc cagggctggg ctgacatcaa gatgggagcc cagcccacgg gctttataaa
2941 cacccaagaa ccgtttcaga tcttctctgt gctgatgcag gtagttttaa attttctca
3001 gttccagtga tagaaaaccc acacaataca tcctctgcca gtcttaatag aatatcagag
3061 gtaagagggg cctcagagaa gctctgacgc agtgctgctg gggaagggaa gtgactaacc
3121 ccgggtcagc ctgccattta gggaaagagc tgaggttctt acccttgttg catgctgcca
3181 cctctcctta gccagtgctc ttgtacatcc acacagcacc ctaaggagcc atagtcacca
3241 tcaaagactc aaccctaagg cccttcaaga tctcaaagtg ccttctgaag catcagagat
3301 taaatattgt tcaaactaat agttattgct gtggcttta attttatctt tggaagatag
3361 ctatatggta actcatcatt aaccagaaca cctctcccct caaattccgt gaccaagttg
3421 tgcagcttga gcaaatgccg aaagagggta ttatgggtgg gtggtgtggg cttgcaaata
3481 caagcttgga ggtgagacat ggccagacat gactcctgct tccccttagg aagtaaatct
3541 tacttatggt tgtgaactgc ttggagtcca ggatgcccag atgtgagggg cagatgaagg
3601 gaatgttgct ggaaaggtgc cttttaaggc tgctgagaat ttctggactg tgtcctgatg
3661 gacgcagcac catcaaagcc cagaatttct gaaaacggtg acaaggttaa cataaggaca
3721 acaaatactc caccctgtca tggtatgtga ggtgtgggtg tggcggtttc tgtgtacgtt
3781 tgctcataca cgcacatcca aaagcctgtg cctcattcct ggccatgggt gaggacttgg
3841 tctgtcacgg ctgatgagga ctcccacaac cggccaagtt atgtcttatt atacaccccc
3901 agaaagagag aaagctgcct tctggaggac tgattccaca tgctatattc agctgagttg
3961 atttctgtgt ctatttcaac ccataacctg aagaatgatc accttattcc ttattcatta
4021 attttcttga ttaataggga aacttgggaa tagctataaa gtaaaacttg ggtggaacct
4081 ggggccctgg catcacacaa gtgtgattag gatggtcaag gtcatcagga gtacagccta
4141 ttatattccc acatcctgag aaaggtcatt tctcccacac acgacaaagt cacagacatc
4201 ctgcacctgc cactaggcat cctcatccta ctgacatgcc catttctcca gttttcttaa
4261 tctgagactc ccttcccttg ttttttaaag ataccgtgct tctccacatc ctcatccttc
4321 aaggagcata ttttgctctt aggatggtct ttgggattca agaatagaat aataaatcca
4381 aacttggtca ttcccatttt gaagagatgc aagagggccc agtgaggaca tccgcctccc
4441 tgaaagtggt gctagacaga gctgaggtca ttgtatctgt gtatccacat aggatttctc
4501 ttaattcagc ttgaattgat ggggagggag gtaagagtag ggtcagagtt actcatccct
4561 tttcaaagaa ttgtgggtgg aagtttgtaa aggccattca tttgattttc aaaatcaaag
4621 cgacagctct acttccactt ggccttagat ctctgctata ccctgccata gccttgatgc
4681 cactgggcac aagccacctg ccaaatacag gagtggcctc tcccagcctg gcatgatagg
4741 ggggtctgtg ccctcagatg tgttgacagc tgctcttctg aattgccaca cctgtgctac
```

APPENDIX-continued

Nucleotide Sequences for HDACi Compound Resistance Biomarker Genes

```
4801 acttggaatt ctgtgctctg actctgcagg gtaggaccac gtgccatctc acacagaggt
4861 caaccgatga gcccactcac tcgtacatgc cttcttccac agtgggaagc atgatctggc
4921 aggggccgcc ctgtaggctg gggatgggct gctgtgtgaa tgttgacgtt cgtttcatgg
4981 agaaagggga ggtgaaagat tgaagagcag gttcctgtca atgttctgag ttcgagctgg
5041 aggtgtagat tgaatagtct acatggtctg tgagtgtgtg agatgaaccc ttccatcctt
5101 tgacacctgg ttgtatgtgt aggctaagaa ggaaggaccc tcctgtcagt gtgcaaagct
5161 gtaatctcat ggactagagg agaggggggcc aaggggatgg acaggagaag tcatgcagaa
5221 tctaagcagg aatgcagata gaacacatct aggctctttt ccccaggaga gtgatgatgg
5281 agcatataga tctggctcaa attcagcctc catcacttac cagtcaggaa ccctggcgat
5341 atcactttaa ctttctgaac ctcagagtct tcacctataa gacggggaaa ataataccac
5401 cctttcaaga ttgttgagat aaataagtga tataaaacat gtaaagctta gttctggcca
5461 cagtgtagct actcaataaa tgataatact
```

| Gene Name | Gene Symbol | GenBank Accession # | SEQ ID NO |
|---|---|---|---|
| phosphatidic acid phosphatase type 2C | PPAP2C | NM_177526 | 4 |

```
   1 ctcctctccg cgcggggcgg gctccgcgcc acgtgactcc gcggccgggc cgggacgcga
  61 cgggacgcgc tgggaccggc gtcgggggtc gcggggacca tgcagcggag cctccctgcc
 121 cttcgctatc ctgacgctgg tgaacgcccc gtacaagcga ggattttact gcggggatga
 181 ctccatccgg taccctacc gtccagatac catcacccac gggctcatgg ctggggtcac
 241 catcacggcc accgtcatcc ttgtctcggc cggggaagcc tacctggtgt acacagaccg
 301 gctctattct cgctcggact tcaacaacta cgtggctgct gtatacaagg tgctggggac
 361 cttcctgttt ggggctgccg tgagccagtc tctgacagac ctggccaagt acatgattgg
 421 gcgtctgagg cccaacttcc tagccgtctg cgaccccgac tggagccggg tcaactgctc
 481 ggtctatgtg cagctggaga aggtgtgcag gggaaaccct gctgatgtca ccgaggccag
 541 gttgtctttc tactcgggac actcttcctt tgggatgtac tgcatggtgt tcttggcgct
 601 gtatgtgcag gcacgactct gttggaagtg ggcacggctg ctgcgaccca cagtccagtt
 661 cttcctggtg gcctttgccc tctacgtggg ctacacccgc gtgtctgatt acaaacacca
 721 ctggagcgat gtccttgttg gcctcctgca ggggcactg gtggctgccc tcactgtctg
 781 ctacatctca gacttcttca aagcccgacc cccacagcac tgtctgaagg aggaggagct
 841 ggaacggaag cccagcctgt cactgacgtt gaccctgggc gaggctgacc acaaccacta
 901 tggatacccg cactcctcct cctgaggccg gaccccgccc aggcagggag ctgctgtgag
 961 tccagctgag gcccacccag gtggtccctc cagccctggt taggcactga gggctctgga
1021 cgggctccag gaaccctggg ctgatgggag cagtgagcgg gctccgctgc ccctgccct
1081 gcactgacc aggagtctgg agatgcctgg gtagccctca gcatttggag gggaacctgt
1141 tcccgtcggt ccccaaatat ccccttcttt ttatggggtt aaggaaggga ccgagagatc
1201 agatagttgc tgttttgtaa aatgtaatgt atatgtggtt tttagtaaaa tagggcacct
1261 gtttcacaaa
```

APPENDIX-continued

Nucleotide Sequences for HDACi Compound Resistance Biomarker Genes

| Gene Name | Gene Symbol | GenBank Accession # | SEQ ID NO |
|---|---|---|---|
| neural proliferation, differentiation and control, 1 | NPDC1 | NM_015392 | 5 |

```
   1 gcgcgcctcg ccggcgcctc catcccggat ccttgctgca cgtcagcgc cgccgcccgt
  61 gcctttcctc ttcctcctcc tcctccttgg catccgcctc ttcttcctcc tgcgtcctcc
 121 cccgctgcct ccgctgctcc cgacgcggag cccggagccc gcgccgagcc cctggcctcg
 181 cggtgccatg ctgccccggc ggcggcgctg aaggatggcg acgccgctgc ctccgccctc
 241 cccgcggcac ctgcggctgc tgcggctgct gctctccggc ctcgtcctcg gcgccgccct
 301 gcgtggagcc gccgccggcc acccggatgt agccgcctgt cccgggagcc tggactgtgc
 361 cctgaagagg cgggcaaggt gtcctcctgg tgcacatgcc tgtgggccct gccttcagcc
 421 cttccaggag gaccagcaag ggctctgtgt gcccaggatg cgccggcctc caggcggggg
 481 ccggccccag cccagactgg aagatgagat tgacttcctg gcccaggagc ttgcccggaa
 541 ggagtctgga cactcaactc cgcccctacc caaggaccga cagcggctcc cggagcctgc
 601 caccctgggc ttctcggcac gggggcaggg gctggagctg gcctcccct ccactccagg
 661 aaccccacg cccacgcccc acacctccat gggctcccct gtgtcatccg acccggtgca
 721 catgtcgccc ctggagcccc ggggagggca aggcgacggc ctcgcccttg tgctgatcct
 781 ggcgttctgt gtggccggtg cagccgccct ctccgtagcc tccctctgct ggtgcaggct
 841 gcatcgtgag atccgcctga ctcagaaggc cgactacgcc actgcgaagg cccctggctc
 901 acctgcagct ccccggatct cgcctgggga ccaacggctg gcacagagcg cggagatgta
 961 ccactaccag caccaacggc aacagatgct gtgcctggag cggcataaag agccacccaa
1021 ggagctggac acggcctcct cggatgagga gaatgaggac ggagacttca cggtgtacga
1081 gtgcccgggc ctggccccga ccggggaaat ggaggtgcgc aaccctctgt tcgaccacgc
1141 cgcactgtcc gcgcccctgc cggcccccag ctcaccgcct gcactgccat gacctggagg
1201 cagacagacg cccacctgct ccccgacctc gaggccccg gggagggca gggcctggag
1261 cttcccacta aaaacatgtt ttgatgctgt gtgcttttgg ctgggcctcg ggctccaggc
1321 cctgggaccc cttgccaggg agaccccga acctttgtgc caggacacct cctggtcccc
1381 tgcacctctc ctgttcggtt tagaccccca aactggaggg ggcatggaga accgtagagc
1441 gcaggaacgg gtgggtaatt ctagagacaa aagccaatta aagtccattt cagaaaaaaa
```

| Gene Name | Gene Symbol | GenBank Accession # | SEQ ID NO |
|---|---|---|---|
| C-terminal tensin-like | CTEN | NM_032865 | 6 |

```
   1 gggcaacagt ctgcccacct gtggacacca gatcctggga gctcctggtt agcaagtgag
  61 atctctggga tgtcagtgag gctggttgaa gaccagaggt aaactgcaga ggtcaccacc
 121 cccaccatgt cccaggtgat gtccagccca ctgctggcag gaggccatgc tgtcagcttg
 181 gcgccttgtg atgagcccag gaggaccctg cacccagcac ccagcccag cctgccaccc
 241 cagtgttctt actacaccac ggaaggctgg ggagcccagg ccctgatggc cccgtgccc
 301 tgcatggggc ccctggccg actccagcaa gccccacagg tggaggccaa agccacctgc
 361 ttcctgccgt ccctggtga gaaggccttg ggacccag aggaccttga ctcctacatt
```

APPENDIX-continued

Nucleotide Sequences for HDACi Compound Resistance Biomarker Genes

```
 421 gacttctcac tggagagcct caatcagatg atcctggaac tggaccccac cttccagctg
 481 cttcccccag ggactggggg ctcccaggct gagctggccc agagcaccat gtcaatgaga
 541 aagaaggagg aatctgaagc cttggacata aagtacatcg aggtgacctc cgccagatca
 601 aggtgccacg attggcccca gcactgctcc agccctctg tcaccccgcc cttcggctcc
 661 cctcgcagtg gtggcctcct cctttccaga gacgtccccc gagagacacg aagcagcagt
 721 gagagcctca tcttctctgg gaaccagggc aggggcacc agcgccctct gccccctca
 781 gagggtctct cccctcgacc cccaaattcc cccagcatct caatcccttg catggggagc
 841 aaggcctcga gcccccatgg tttgggctcc ccgctggtgg cttctccaag actggagaag
 901 cggctgggag gcctggcccc acagcggggc agcaggatct ctgtgctgtc agccagccca
 961 gtgtctgatg tcagctatat gtttggaagc agccagtccc tcctgcactc cagcaactcc
1021 agccatcagt catcttccag atccttggaa agtccagcca actcttcctc cagcctccac
1081 agccttggct cagtgtccct gtgtacaaga cccagtgact tccaggctcc cagaaacccc
1141 accctaacca tgggccaacc cagaacaccc cactctccac cactgccaa gaacatgcc
1201 agcatctgcc ccccatccat caccaactcc atggtggaca tacccattgt gctgatcaac
1261 ggctgcccag aaccagggtc ttctccaccc cagcggaccc caggacacca gaactccgtt
1321 caacctggag ctgcttctcc cagcaacccc tgtccagcca ccaggagcaa cagccagacc
1381 ctgtcagatg cccccttac cacatgccca gagggtcccg ccagggacat gcagcccacc
1441 atgaagttcg tgatggacac atctaaatac tggtttaagc caaacatcac ccgagagcaa
1501 gcaatcgagc tgctgaggaa ggaggagcca ggggcttttg tcataaggga cagctcttca
1561 taccgaggct ccttcggcct ggccctgaag gtgcaggagg ttcccgcgtc tgctcagaat
1621 cgaccaggtg aggacagcaa tgacctcatc cgacacttcc tcatcgagtc gtctgccaaa
1681 ggagtgcatc tcaaaggagc agatgaggag ccctactttg ggagcctctc tgccttcgtg
1741 tgccagcatt ccatcatggc cctggccctg ccctgcaaac tcaccatccc acagagagaa
1801 ctgggaggtg cagatggggc ctcggactct acagacagcc cagcctcctg ccagaagaaa
1861 tctgcgggct gccacaccct gtacctgagc tcagtgagcg tggagaccct gactggagcc
1921 ctggccgtgc agaaagccat ctccaccacc tttgagaggg acatcctccc cacgcccacc
1981 gtggtccact tcgaagtcac agagcagggc atcactctga ctgatgtcca gaggaaggtg
2041 tttttccggc gccattaccc actcaccacc ctccgcttct gtggtatgga ccctgagcaa
2101 cggaagtggc agaagtactg caaaccctcc tggatctttg ggtttgtggc caagagccag
2161 acagagcctc aggagaacgt atgccacctc tttgcggagt atgacatggt ccagccagcc
2221 tcgcaggtca tcggcctggt gactgctctg ctgcaggacg cagaaaggat gtaggggaga
2281 gactgcctgt gcacctaacc aacacctcca ggggctcgct aaggagcccc cctccacccc
2341 ctgaatgggt gtggcttgtg gccatattga cagaccaatc tatgggacta ggggattgg
2401 catcaagttg acacccttga acctgctatg gccttcagca gtcaccatca tccagacccc
2461 ccgggcctca gtttcctcaa tcatagaaga agaccaatag acaagatcag ctgttcttag
2521 atgctggtgg gcatttgaac atgctcctcc atgattctga agcatgcaca cctctgaaga
2581 cccctgcatg aaaataacct ccaaggaccc tctgacccca tcgacctggg ccctgcccac
2641 acaacagtct gagcaagaga cctgcagccc ctgtttcgtg gcagacagca ggtgcctggc
```

APPENDIX-continued

Nucleotide Sequences for HDACi Compound Resistance Biomarker Genes

```
2701 ggtgacccac ggggctcctg gcttgcagct ggtgatggtc aagaactgac tacaaaacag
2761 gaatggatag actctatttc cttccatatc tgttcctctg ttccttttcc cactttctgg
2821 gtggcttttt gggtccaccc agccaggatg ctgcaggcca agctgggtgt ggtatttagg
2881 gcagctcagc aggggaact  tgtccccatg gtcagaggag acccagctgt cctgcacccc
2941 cttgcagatg agtatcaccc catcttttct ttccacttgg tttttatttt tatttttttt
3001 gagacagagt ctcactgtca cccaggctga actgcagtgg tgtgatctag gctcactgca
3061 acctccacct cccaggttca agcaattatc ctgcctcagg ctcccgagta gctgggatta
3121 caggcatgtg caactcaccc agctaatttt gtattttag  tagagacagg gtttcaccat
3181 gttggccagg ctggtcttga actcctgacc gcaggtaatc cacctgcttc ggcctcccaa
3241 agtgctggga ttacaggcgc aagccaccca gcccagcttc tttccattcc ttgataggcg
3301 agtattccaa agctggtatc gtagctgccc taatgttgca tattaggcgg cgggggcaga
3361 gataagggcc atctctctgt gattctgcct cagctcctgt cttgctgagc cctcccccaa
3421 cccacgctcc aacacacaca cacacacaca cacacacaca cacacacaca cacacacaca
3481 cacgcccctc tactgctatg tggcttcaac cagcctcaca gccacacggg ggaagcagag
3541 agtcaagaat gcaaagaggc cgcttcccta agaggcttgg aggagctggg ctctatccca
3601 cacccacccc caccccaccc ccacccagcc tccagaagct ggaaccattt ctcccgcagg
3661 cctgagttcc taaggaaacc accctaccgg ggtggaaggg agggtcaggg aagaaaccca
3721 ctcttgctct acgaggagca agtgcctgcc ccctcccagc agccagccct gccaaagttg
3781 cattatcttt ggccaaggct gggcctgacg gttatgattt cagccctggg cctgcaggag
3841 aggctgagat cagcccaccc agccagtggt cgagcactgc cccgccgcca aagtctgcag
3901 aatgtgagat gaggttctca aggtcacagg ccccagtccc agcctggggg ctggcagagg
3961 cccccatata ctctgctaca gctcctatca tgaaaaataa aatgt
```

| Gene Name | Gene Symbol | GenBank Accession # | SEQ ID NO |
|---|---|---|---|
| RAB25, member RAS oncogene family | RAB25 | NM_020387 | 7 |

```
  1 ctctgcttcc ttacagcacc cccacctgcc agagctgatc ctccctaggc cctgcctaac
 61 cttgagttgg cccccaatcc ctctggctgc agaagtcccc ttaccccaa  tgagaggagg
121 ggcaggacca gatcttttga gagctgaggg ttgagggcat tgagccaaca cacagatttg
181 tcgcctctgt ccccgaagac acctgcaccc tccatgcgga gccaagatgg ggaatggaac
241 tgaggaagat tataactttg tcttcaaggt ggtgctgatc ggcgaatcag gtgtggggaa
301 gaccaatcta ctctcccgat tcacgcgcaa tgagttcagc cacgacagcc gcaccaccat
361 cggggttgag ttctccaccc gcactgtgat gttgggcacc gctgctgtca aggctcagat
421 ctggacacaa gctggcctgg agcggtaccg agccatcacc tcggcgtact atcgtggtgc
481 agtgggggcc ctcctggtgt ttgacctaac caagcaccag acctatgctg tggtggagcg
541 atggctgaag gagctctatg accatgctga agccacgatc gtcgtcatgc tcgtgggtaa
601 caaaagtgac ctcagccagg cccgggaagt gcccactgag gaggcccgaa tgttcgctga
661 aaacaatgga ctgctcttcc tggagaccct agccctggac tctaccaatg ttgagctagc
721 ctttgagact gtcctgaaag aaatctttgc gaaggtgtcc aagcagagac agaacagcat
```

APPENDIX-continued

Nucleotide Sequences for HDACi Compound Resistance Biomarker Genes

```
 781 ccggaccaat gccatcactc tgggcagtgc ccaggctgga caggagcctg gccctgggga
 841 gaagagggcc tgttgcatca gcctctgacc ttggccagca ccacctgccc ccactggctt
 901 tttggtgccc cttgtcccca cttcagcccc aggacctttc cttgcccttt ggttccagat
 961 atcagactgt tccctgttca cagcaccctc agggtcttaa ggtcttcatg ccctatcaca
1021 aatacctctt ttatctgtcc acccctcaca gactaggacc ctcaaataaa gctgttttat
1081 atcaaaaaaa
```

| Gene Name | Gene Symbol | GenBank Accession # | SEQ ID NO |
|---|---|---|---|
| hephaestin | HEPH | NM_138737 | 8 |

```
   1 gcccagcctg cctggagaaa agtgtctgct cctagccaag atctcctcat cacaaaagta
  61 atgtgggcca tggagtcagg ccacctcctc tgggctctgc tgttcatgca gtccttgtgg
 121 cctcaactga ctgatggagc cactcgagtc tactacctgg catccggga tgtgcagtgg
 181 aactatgctc ccaagggaag aaatgtcatc acgaaccagc ctctggacag tgacatagtg
 241 gcttccagct tcttaaagtc tgacaagaac cggatagggg gaacctacaa gaagaccatc
 301 tataaagaat acaaggatga ctcatacaca gatgaagtgg cccagcctgc ctggttgggc
 361 ttcctggggc cagtgttgca ggctgaagtg ggggatgtca ttcttattca cctgaagaat
 421 tttgccactc gtccctatac catccaccct catggtgtct tctacgagaa ggactctgaa
 481 ggttccctat acccagatgg ctcctctggg ccactgaaag ctgatgactc tgttcccccg
 541 gggggcagcc atatctacaa ctggaccatt ccagaaggcc atgcacccac cgatgctgac
 601 ccagcgtgcc tcacctggat ctaccattct catgtagatg ctccacgaga cattgcaact
 661 ggcctaattg ggcctctcat cacctgtaaa agaggagccc tggatgggaa ctcccctcct
 721 caacgccagg atgtagacca tgatttcttc ctcctcttca gtgtggtaga tgagaacctc
 781 agctggcatc tcaatgagaa cattgccact tactgctcag atcctgcttc agtggacaaa
 841 gaagatgaga catttcagga gagcaatagg atgcatgcaa tcaatggctt tgttttgggg
 901 aatttacctg agctgaacat gtgtgcacag aaacgtgtgg cctggcactt gtttggcatg
 961 ggcaatgaaa ttgatgtcca cacagcattt ttccatggac agatgctgac tacccgtgga
1021 caccacactg atgtggctaa catctttcca gccacctttg tgactgctga gatggtgccc
1081 tgggaacctg gtacctggtt aattagctgc caagtgaaca gtcactttcg agatggcatg
1141 caggcactct acaaggtcaa gtcttgctcc atggcccctc ctgtggacct gctcacaggc
1201 aaagttcgac agtacttcat tgaggcccat gagattcaat gggactatgg cccgatgggg
1261 catgatggga gtactgggaa gaatttgaga gagccaggca gtatctcaga taagttttc
1321 cagaagagct ccagccgaat tggggggcact tactggaaag tgcgatatga agcctttcaa
1381 gatgagacat tccaagagaa gatgcatttg gaggaagata ggcatcttgg aatcctgggg
1441 ccagtgatcc gggctgaggt gggtgacacc attcaggtgg tcttctacaa ccgtgcctcc
1501 cagccattca gcatgcagcc ccatgggtc ttttatgaga aagactatga aggcactgtg
1561 tacaatgatg gctcatctta ccctggcttg gttgccaagc cctttgagaa agtaacatac
1621 cgctggacag tccccctca tgccggtccc actgctcagg atcctgcttg tctcacttgg
1681 atgtacttct ctgctgcaga tcccataaga gacacaaatt ctggcctggt gggccccgctg
1741 ctggtgtgca gggctggtgc cttgggtgca gatggcaagc agaaaggggt ggataaagaa
```

APPENDIX-continued

Nucleotide Sequences for HDACi Compound Resistance Biomarker Genes

```
1801 ttctttcttc tcttcactgt gttggatgag aacaagagct ggtacagcaa tgccaatcaa
1861 gcagctgcta tgttggattt ccgactgctt tcagaggata ttgagggctt ccaagactcc
1921 aatcggatgc atgccattaa tgggtttctg ttctctaacc tgcccaggct ggacatgtgc
1981 aagggtgaca cagtggcctg gcacctgctc ggcctgggca cagagactga tgtgcatgga
2041 gtcatgttcc agggcaacac tgtgcagctt cagggcatga ggaagggtgc agctatgctc
2101 tttcctcata cctttgtcat ggccatcatg cagcctgaca accttgggac atttgagatt
2161 tattgccagg caggcagcca tcgagaagca gggatgaggg caatctataa tgtctcccag
2221 tgtcctggcc accaagccac ccctcgccaa cgctaccaag ctgcaagaat ctactatatc
2281 atggcagaag aagtagagtg ggactattgc cctgaccgga gctgggaacg ggaatggcac
2341 aaccagtctg agaaggacag ttatggttac attttcctga gcaacaagga tgggctcctg
2401 ggttccagat acaagaaagc tgtattcagg gaatacactg atggtacatt caggatccct
2461 cggccaagga ctggaccaga gaacacttg ggaatcttgg gtccacttat caaaggtgaa
2521 gttggtgata tcctgactgt ggtattcaag aataatgcca gccgcccta ctctgtgcat
2581 gctcatggag tgctagaatc tactactgtc tggccactgg ctgctgagcc tggtgaggtg
2641 gtcacttatc agtggaacat cccagagagg tctggccctg ggcccaatga ctctgcttgt
2701 gtttcctgga tctattattc tgcagtggat cccatcaagg acatgtatag tggcctggtg
2761 gggccctggg ctatctgcca aaagggcatc ctggagcccc atggaggacg gagtgacatg
2821 gatcgggaat ttgcattgtt gttcttgatt tttgatgaaa ataagtcttg gtatttggag
2881 gaaaatgtgg caacccatgg gtcccaggat ccaggcagta ttaacctaca ggatgaaact
2941 ttcttggaga gcaataaaat gcatgcaatc aatgggaaac tctatgccaa ccttagggt
3001 cttaccatgt accaaggaga acgagtggcc tggtacatgc tggccatggg ccaagatgtg
3061 gatctacaca ccatccactt tcatgcagag agcttcctct atcggaatgg cgagaactac
3121 cgggcagatg tggtggatct gttcccaggg acttttgagg ttgtggagat ggtggccagc
3181 aaccctggga catggctgat gcactgccat gtgactgacc atgtccatgc tggcatggag
3241 accctcttca ctgttttttc tcgaacagaa cacttaagcc ctctcaccgt catcaccaaa
3301 gagactgaaa aagcagtgcc ccccagagac attgaagaag gcaatgtgaa gatgctgggc
3361 atgcagatcc ccataaagaa tgttgagatg ctggcctctg ttttggttgc cattagtgtc
3421 acccttctgc tcgttgttct ggctcttggt ggagtggttt ggtaccaaca tcgacagaga
3481 aagctacgac gcaataggag gtccatcctg gatgacagct tcaagcttct gtctttcaaa
3541 cagtaacatc tggagcctgg agatatcctc aggaagcaca tctgtagtgc actcccagca
3601 ggccatggac tagtcactaa ccccacactc aaaggggcat gggtggtgga aagcagaag
3661 gagcaatcaa gcttatctgg atatttcttt ctttatttat tttacatgga ataatatga
3721 tttcactttt tctttagttt ctttgctcta cgtgggcacc tggcactaag ggagtacctt
3781 attatcctac atcgcaaatt tcaacagcta cattatattt ccttctgaca cttggaaggt
3841 attgaaattt ctagaaatgt atccttctca caaagtagag accaagagaa aaactcattg
3901 attgggtttc tacttctttc aaggactcag gaaatttcac tttgaactga ggccaagtga
3961 gctgttaaga taacccacac ttaaactaaa ggctaagaat ataggcttga tgggaaattg
4021 aaggtaggct gagtattggg aatccaaatt gaattttgat tctccttggc agtgaactac
4081 tttgaagaag tggtcaatgg gttgttgctg ccatgagcat gtacaacctc tggagctaga
```

APPENDIX-continued

Nucleotide Sequences for HDACi Compound Resistance Biomarker Genes

```
4141 agctcctcag gaaagccagt tctccaagtt cttaacctgt ggcactgaaa ggaatgttga
4201 gttacctctt catgttttag acagcaaacc ctatccatta aagtacttgt tagaacactg
```

| Gene Name | Gene Symbol | GenBank Accession # | SEQ ID NO |
|---|---|---|---|
| thiopurine S-methyl-transferase | TPMT | NM_000367 | 9 |

```
   1 gcgggcggag gcggggcgcg gagaagtggc ggaggtggaa gcggaggcgt acccgcccct
  61 ggggacgtca ttggtggcgg aggcaatggc cggcaaccag ctgtaagcga ggcacggaag
 121 acatatgctt gtgagacaaa ggtgtctctg aaactatgga tggtacaaga acttcacttg
 181 acattgaaga gtactcggat actgaggtac agaaaaacca agtactaact ctggaagaat
 241 ggcaagacaa gtgggtgaac ggcaagactg cttttcatca ggaacaagga catcagctat
 301 taaagaagca tttagatact ttccttaaag gcaagagtgg actgagggta ttttttcctc
 361 tttgcggaaa agcggttgag atgaaatggt ttgcagaccg gggacacagt gtagttggtg
 421 tggaaatcag tgaacttggg atacaagaat tttttacaga gcagaatctt tcttactcag
 481 aagaaccaat caccgaaatt cctggaacca aagtatttaa gagttcttcg gggaacattt
 541 cattgtactg ttgcagtatt tttgatcttc ccaggacaaa tattggcaaa tttgacatga
 601 tttgggatag aggagcatta gttgccatca atccaggtga tcgcaaatgc tatgcagata
 661 caatgttttc cctcctggga aagaagtttc agtatctcct gtgtgttctt tcttatgatc
 721 caactaaaca tccaggtcca ccattttatg ttccacatgc tgaaattgaa aggttgtttg
 781 gtaaaatatg caatatacgt tgtcttgaga aggttgatgc ttttgaagaa cgacataaaa
 841 gttggggaat tgactgtctt tttgaaaagt tatatctact tacagaaaag taaatgagac
 901 atagataaaa taaaatcaca ctgacatgtt tttgaggaat tgaaaattat gctaaagcct
 961 gaaaatgtaa tggatgaatt tttaaaattg tttataaatc atatgataga tctttactaa
1021 aaatggcttt ttagtaaagc catttacttt ttctaaaaaa gttttagaag aaaaagatgt
1081 aactaaactt ttaaagtagc tcctttggag aggagattat gatgtgaaag attatgccta
1141 tgtgtcttgc agattgcaag atattttacc aatcagcatg tgttacctgt acaattaaaa
1201 aaatatttca aaatgcaatg catattaaat ataatacaca cagaaaaact ggcatttatt
1261 ttgtttattt tttttgagat ggagtttcgt tcttgttgcc caacctggag tgcaatggtg
1321 caatctcagc tcactgcaac ctctgcctcc caggttcagg tgattctcct gcctcagcct
1381 cctgagtagc tgggattaca ggtgtgcgcc accacgccca gctaattttt tgtattttta
1441 gtagagacag ggtttcacca tgttggtcag gctgatctcg agctcctgac ctcaggtgat
1501 ctacccacct cggcctccca aagtgctggg attacaggcg tgagccactg cacctggcct
1561 gacattcttt atgaaattta gaattgttga agaactataa catttcagta gggttcaagg
1621 tggtcccaaa agttatataa aagattagtt tttactataa acccttgtct tttactcaga
1681 tcctagcatc ccttttcaca tggtttctcc atgtatataa cagaatcaag aaacaaattt
1741 taattaaaca atctgtaaca gaatcaagaa acaaatacat tttaattaaa caatctatat
1801 ggaacaaaca ttcccaaatt ctaagaataa attttttcttt aagttttctc tgagtttggc
1861 aattgttgtt ttttataatt taatctgttt aaatcatcag gtcttataaa atataatgta
1921 cttagagctg gattcatggc tgtttattat gaaaggttag atttctcagt tcttctttaa
```

APPENDIX-continued

Nucleotide Sequences for HDACi Compound Resistance Biomarker Genes

```
1981 ccacattttg ttatatcaga cagtcctcta taactctgta ctacccaaca actaaatggt
2041 ttagattgtt tagctcatgt taataggatg gttgtgtatt ataaaaaacg agttacgtgt
2101 gtgtgtgcac gcatgcacgc acatgtgctg gcttaaaggt tgttaatgca aggtttgggg
2161 tcccctttaa cactggtgaa agctacggta ctctccccag agatatgtct tgtcagcctc
2221 tctagttccc cttggcctgc atgtacaaac ttctacccta gaagctctct gccatcgatg
2281 tattctaata gatttgtaag gctattaatt tgaagcaact ccttgctcac agtgattctt
2341 gcttctctga gacctgctcc cagtcgatac tgtgggcttc agaagccatg actccccaac
2401 tctgcctgta tcaccggttg aatggacaac taacccgagc tggaccaaca caattctctc
2461 cagagacttt tgattttact tttatgtaga dacagggtct cactttgttg cccacgctga
2521 tgttgaactt gacgtgaggc ctcaagcagt cctcctgtct tggccaccca aagtgctagg
2581 attacaggta tgagccattg cgctggccct cttcataggc ttttggactt gggaatagaa
2641 aagcaacccc gtctctacta aaaatacaaa aaaattagcc aggcgtggtg gcacgtgcct
2701 gtaatcccag ctacttggga ggctgaggca ggagaatcac ttgaacctag gaggcggagg
2761 ttgcagtgag ctgagatcat gccactgcac gcaagcctgg gcaacagagc aagactctgt
2821 ctcaaaagaa agaaaaagaa aagaaaaaaa agaaaggcaa gttgactgct gaaaggggaa
2881 tctgtgtacg cctgggagct gtggggcagc cacattccag cacatggatc tgagaaacag
2941 aacgctgatc tgcagaaaga gatgagaacc aaagagaggc cacctgcgtc ctgggtccat
3001 tttcatcctc cctgaagccc agctgcccag ggtggggaga acaccctgt gtccatggga
3061 tagagtcctt tccgcttgca gttgtgccca aagaatctta aatacaaatg agatatcctt
3121 aggtagttga tcatttatgt aatatgtgtc ttcactgggg aatactgact tcctaaaatc
3181 tcaagatgga agatatacca catgtaaatt attttagagc aattaaattg ttttcaggat
3241 tttccaaaaa
```

| Gene Name | Gene Symbol | GenBank Accession # | SEQ ID NO |
|---|---|---|---|
| plakophilin 3 | PKP3 | NM_007183 | 10 |

```
   1 ggcctcgagg gacaggacgt gaagatagtt gggtttggag gcggccgcca ggcccaggcc
  61 cggtggacct gccgccatgc aggacggtaa cttcctgctg tcggccctgc agcctgaggc
 121 cggcgtgtgc tccctggcgc tgccctctga cctgcagctg gaccgccggg gcgccgaggg
 181 gccggaggcc gagcggctgc gggcagcccg cgtccaggag caggtccgcg cccgcctctt
 241 gcagctggga cagcagccgc ggcacaacgg ggccgctgag cccgagcctg aggccgagac
 301 tgccagaggc acatccaggg ggcagtacca caccctgcag gctggcttca gctctcgctc
 361 tcagggcctg agtggggaca agacctcggg cttccggccc atcgccaagc cggcctacag
 421 cccagcctcc tggtcctccc gctccgccgt ggatctgagc tgcagtcgga ggctgagttc
 481 agcccacaac gggggcagcg cctttgggcg gctgggtac ggggtgccc agcccacccc
 541 tcccatgccc accaggcccg tgtccttcca tgagcgcggt ggggttggga gccgggccga
 601 ctatgacaca ctctccctgc gctcgctgcg gctggggccc ggggcctgg acgaccgcta
 661 cagcctggtg tctgagcagc tggagcccgc ggccacctcc acctacaggg cctttgcgta
 721 cgagcgccag gccagctcca gctccagccg ggcagggggg ctggactggc ccgaggccac
 781 tgaggtttcc ccgagccgga ccatccgtgc ccctgccgtg cggaccctgc agcgattcca
```

APPENDIX-continued

Nucleotide Sequences for HDACi Compound Resistance Biomarker Genes

```
 841 gagcagccac cggagccgcg gggtaggcgg ggcagtgccg ggggccgtcc tggagccagt
 901 ggctcgagcg ccatctgtgc gcagcctcag cctcagcctg gctgactcgg gccacctgcc
 961 ggacgtgcat gggttcaaca gctacggtag ccaccgaacc ctgcagagac tcagcagcgg
1021 ttttgatgac attgacctgc cctcagcagt caagtacctc atggcttcag accccaacct
1081 gcaggtgctg ggagcggcct acatccagca caagtgctac agcgatgcag ccgccaagaa
1141 gcaggcccgc agccttcagg ccgtgcctag gctggtgaag ctcttcaacc acgccaacca
1201 ggaagtgcag cgccatgcca caggtgccat gcgcaacctc atctacgaca acgctgacaa
1261 caagctggcc ctggtggagg agaacgggat cttcgagctg ctgcggacac tgcgggagca
1321 ggatgatgag cttcgcaaaa atgtcacagg gatcctgtgg aacctttcat ccagcgacca
1381 cctgaaggac cgcctggcca gagacacgct ggagcagctc acagacctgg tgttgagccc
1441 cctgtcgggg gctgggggtc cccccctcat ccagcagaac gcctcggagg cggagatctt
1501 ctacaacgcc accggcttcc tcaggaacct cagctcagcc tctcaggcca ctcgccagaa
1561 gatgcgggag tgccacgggc tggtggacgc cctggtcacc tctatcaacc acgccctgga
1621 cgcgggcaaa tgcgaggaca agagcgtgga gaacgcggtg tgcgtcctgc ggaacctgtc
1681 ctaccgcctc tacgacgaga tgccgccgtc cgcgctgcag cggctggagg gtcgcggccg
1741 cagggacctg gcggggcgc cgccgggaga ggtcgtgggc tgcttcacgc cgcagagccg
1801 gcggctgcgc gagctgcccc tcgccgccga tgcgctcacc ttcgcggagg tgtccaagga
1861 ccccaagggc ctcgagtggc tgtggagccc ccagatcgtg gggctgtaca accggctgct
1921 gcagcgctgc gagctcaacc ggcacacgac ggaggcggcc gccggggcgc tgcagaacat
1981 cacggcaggc gaccgcaggt gggcgggggt gctgagccgc ctggccctgg agcaggagcg
2041 tattctgaac cccctgctag accgtgtcag gaccgccgac caccaccagc tgcgctcact
2101 gactggcctc atccgaaacc tgtctcggaa cgctaggaac aaggacgaga tgtccacgaa
2161 ggtggtgagc cacctgatcg agaagctgcc gggcagcgtg ggtgagaagt cgcccccagc
2221 cgaggtgctg gtcaacatca tagctgtgct caacaacctg gtggtggcca gccccatcgc
2281 tgcccgagac ctgctgtatt ttgacggact ccgaaagctc atcttcatca agaagaagcg
2341 ggacagcccc gacagtgaga agtcctcccg ggcagcatcc agcctcctgg ccaacctgtg
2401 gcagtacaac aagctccacc gtgacttccg ggcgaagggc tatcggaagg aggacttcct
2461 gggcccatag gtgaagcctt ctggaggaga aggtgacgtg gcccagcgtc aagggacag
2521 actcagctcc aggctgcttg gcagcccagc ctggaggaga aggctaatga cggaggggcc
2581 cctcgctggg gcccctgtgt gcatctttga gggtcctggg ccaccaggag gggcagggtc
2641 ttatagctgg ggacttggct tccgcagggc aggggtggg gcagggctca aggctgctct
2701 ggtgtatggg gtggtgaccc agtcacattg gcagaggtgg gggttggctg tggcctggca
2761 gtatcttggg atagccagca ctgggaataa agatggccat gaacagtcaa
```

APPENDIX-continued

Nucleotide Sequences for HDACi Compound Resistance Biomarker Genes

| Gene Name | Gene Symbol | GenBank Accession # | SEQ ID NO |
|---|---|---|---|
| UDP-N-acetyl-alpha-D-galactosamine:polypeptide N-acetylgalactosaminyltransferase 5 (GalNAc-T5) | GALNT5 | NM_014568 | 11 |

```
   1 agtgtttatc agaacttagc cagggccagc caagcaggca cagatgctct gctatgaaat
  61 gccacgcagg cagagactga caagcggtag gaactgagct ttcccttgg actgctgctt
 121 cctgctgtgt tcaggggagg gggtcacttt ctggcaactc tgctgctgct gctgctgctg
 181 ctgctacttc agcttcctct ccactcaagg taagcaggct aagggagggc aggctgctag
 241 ggaaagcttt gtaccatgaa caggatccga aagttttcc gaggaagtgg gcgagtcttg
 301 gcatttatct ttgtagcttc tgtcatctgg ctcctctttg acatggcagc tctccgcctc
 361 tcattcagtg agatcaacac tcgggtcatc aaggaagaca ttgtgaggag ggagcggata
 421 ggattcagag ttcagccaga ccaaggaaaa attttttaca gcagcataaa agagatgaaa
 481 cctcccctaa ggggacatgg gaaggggca tggggcaaag agaatgttag aaaaactgag
 541 gagagtgtgc tcaaggttga ggtggacttg gaccaaaccc agagggaaag aaaaatgcag
 601 aatgccctgg gaagggcaa ggttgtgccg ttgtggcatc ctgcacatct gcagaccctc
 661 cctgtgactc ctaacaagca gaagacagac gggagaggca ccaaacctga agcctcctct
 721 caccagggga caccaaagca aacgacagct caggggctc caaagacctc attcatagca
 781 gcaaaaggaa ctcaggtagt caaaatatca gtacacatgg gacgtgtcag tttaaaacag
 841 gagccccgga gagtcatag tcccagcagt gacacatcaa aactagcagc tgaaagggac
 901 ttgaatgtga ccatcagtct tagtactgat agaccaaagc agcgatcaca ggcagtagca
 961 aacgagaggg cacaccctgc cagcacagca gtgccgaagt ctggggaagc catggcctta
1021 aacaaaacta agactcagag caaagaagtc aatgcaaata acacaaagc caatacgagt
1081 cttccttttc ctaagttcac tgtcaattca aatcgcttaa ggaagcaatc tattaatgag
1141 acacctttgg gaagtttgtc aaaggatgat ggagctagag gggctcatgg gaagaaactc
1201 aatttctctg aaagccatct tgtgattata accaaagagg aagagcaaaa ggcagacccc
1261 aaagaggtct ctaattctaa aaccaaaaca atatttccta agtattggg taaaagccaa
1321 agtaaacaca tttccaggaa tagaagtgag atgtcttcct cttcacttgc tccacataga
1381 gtgccactgt cccaaactaa ccatgcttta actggagggc tagagccagc aaaaatcaac
1441 ataactgcca aagcccctc tacagaatac aaccagagtc atataaagc ccttttacct
1501 gaagacagtg gaacgcacca ggtgttaaga attgatgtga cactttctcc aagggacccc
1561 aaagctccag gcagtttgg gcgtcctgta gttgtccccc atggaaagga aaggaggca
1621 gaaagaagat ggaagaagg aaacttcaat gtctaccta gcgatttgat cccagtggat
1681 agagccattg aagacaccag acctgctgga tgtgcagagc agctagttca caataacctc
1741 ccaaccacca gtgtcatcat gtgctttgtg gatgaagtgt ggtccactct cctgagatct
1801 gttcacagtg tcatcaatcg ctctcctcca cacctcatca aggagattct gctggtagat
1861 gacttcagca ccaaagacta tctaaaagat aatttggata aatacatgtc ccagtttcca
1921 aaagttcgga ttcttcgcct caaagagaga catggcttaa taagggccag gctggcagga
1981 gcacagaatg caacaggtga tgtgttaca ttttagatt ctcatgtgga atgtaacgtt
2041 ggttggttgg aacctcttct ggaaagagtt tatttaagta gaaagaaagt ggcctgtcca
```

APPENDIX-continued

Nucleotide Sequences for HDACi Compound Resistance Biomarker Genes

```
2101 gtaatcgaag tcatcaatga taaggatatg agttacatga cagtggataa ctttcaaaga
2161 ggcatctttg tgtggcccat gaactttggt tggagaacaa ttcctccaga tgtcattgca
2221 aaaaacagaa ttaaagaaac tgatacaata aggtgccctg tcatggctgg tggattgttt
2281 tctattgaca aaagttactt ttttgaactt ggaacatacg accctggcct tgatgtttgg
2341 ggtggggaaa atatggagct ctcattcaag gtgtggatgt gtggtggtga aattgagatc
2401 attccctgct cccgagtggg ccatatattc agaaatgaca atccatattc cttccccaaa
2461 gaccggatga agacagtgga gcggaacttg gtgcgggttg ccgaggtctg gctggatgag
2521 tataaggagc tgttctatgg ccacggagac cacctcatcg accaagggct agatgttggc
2581 aacctcaccc agcaaaggga gctgcgaaag aaactgaagt gcaaaagttt caaatggtac
2641 ttggagaatg tctttcctga cttaagggct cccattgtga gagctagtgg tgtgcttatt
2701 aatgtggctt tgggtaaatg catttccatt gaaaacacta cagtcattct ggaagactgc
2761 gatgggagca aagagcttca acaatttaat tacacctggt taagacttat taaatgtgga
2821 gaatggtgta tagcccccat ccctgataaa ggagccgtaa ggctgcaccc ttgtgataac
2881 agaaacaaag gctaaaatg gctgcataaa tcaacatcag tctttcatcc agaactggtg
2941 aatcacattg tttttgaaaa caatcagcaa ttattatgct tggaaggaaa tttttctcaa
3001 aagatcctga agtagctgc ctgtgaccca gtgaagccat atcaaaagtg gaaatttgaa
3061 aaatattatg aagcctgaag tgtaactgat gttttttatat agtaaaccca ttaaatactg
3121 tgaaaataac a
```

| Gene Name | Gene Symbol | GenBank Accession # | SEQ ID NO |
|---|---|---|---|
| calmodulin-like 4 | CALML4 | NM_033429 | 12 |

```
   1 ggggctgagg gtggagagag gaagggaagg aagaaaaggg gagccttcct ggccagggta
  61 accggcacta agaggcctca ctccaagccc ccgaggagcc tgtggtgggg ctggagaccc
 121 ggctcaggcc cctccaccac ccttaaagtc ctcagaaggt gggaactgaa ctggcacagg
 181 atgggaaccg gctgtgcgct ggccacttga ttttgccagc tgccctgtaa ttcagctggt
 241 gaggaaactg aggcacagac tgaggtagaa tgattcgcca gtcactcagc aagtcagcag
 301 acggggagga ctgaatccca gcctgagagc accgaagctt gtatccctgc aataccgagc
 361 cccaagcctg cgagccccgg tgcccatctc tgagttaggc cgtcttggaa gggttccctt
 421 cctcctacaa gatggtgtgt gaggagcctt caatacgacc cggggtgtaa agtgtccaac
 481 tctagtaggg gcctgatggc atcccgccg agtcccagga gagagagaga agacccttc
 541 ctggagtcca gggctcccgg gaagaaacac tggcatttgt cctttgctt cggcttctgg
 601 aggcagagac tctgagccca gggagagcct tctgcagccc catttcctca aaaatccaac
 661 ctgcccaggt ggcgggtcat gagctgtgct caggaagctg gaatctgacc ctggtggcgt
 721 cgggcccagt ctccatggca gccgagcatt tattacccgg gcctccaccc agcttggcag
 781 actttagact tgaggctgga ggaaagggaa ctgaacgcgg ttctgggagc agcaagccca
 841 cgggtagcag ccgaggcccc agaatggcca agtttctttc ccaagaccaa attaatgagt
 901 acaaggaatg cttctcccctg tatgacaagc agcagagggg gaagataaaa gccaccgacc
 961 tcatggtggc catgaggtgc ctgggggcca gcccgacgcc aggggaggtg cagcggcacc
1021 tgcagaccca cgggatagac ggaaatggag agctggattt ctccactttt ctgaccatta
```

APPENDIX-continued

Nucleotide Sequences for HDACi Compound Resistance Biomarker Genes

```
1081 tgcacatgca aataaaacaa gaagacccaa agaaagaaat tcttctagcc atgttgatgg 1141 tggacaagga gaagaaaggt tacgtcatgg cgtccgacct gcggtcaaaa ctcacgagtc 1201 tgggggagaa gctcacccac aaggaagtgg atgatctctt cagggaagca gatatcgaac 1261 ccaatggcaa agtgaagtat gatgaattta tccacaagat cacccttcct ggacgggact 1321 attgaaggag gagaatggga gagcctcccc tgggcctgaa aacttggagc aattaatttt 1381 ttttaaaaag tgttcttttc acttgggaga gatggcaaac acagtggcaa gacaacatta 1441 cccaactata gaagagaggc taactagcaa caataataga tgatttcagc catggtatga 1501 gtagatcttt aataaaagat ttgtattgat tttattaact accgtgagtc cggcccttc 1561 aagcatggaa ggagcctgcg gtttggagtc tggcctgggt tccagtcctg gctctgctgc 1621 ttcccactgt gactttgggc aaatcatttc actcctcaaa gcccccccac acaagctgga 1681 ttcccacttc ttacctcatg gagcctgttg aggaaggatt gagctgatga cttaagggca 1741 atctaccaag agacttattc tgtatttggg ggctagaacc atcttccata tttccaagat 1801 tttccaagat gaagccagtg ctagctgaga agcagcaatg aacagaaagc tgtaacactt 1861 atgacaacaa ttcttgcagt gccagaggcc catttacaaa ttctcatttc catctcaaca 1921 gatatagtga catagctcag gctattcatt cataaacaca gagtgtagag tgaaaacact 1981 agagtgaaaa cacatgctac aatgaggcag catcagctga gagcaggaag agcgatctac 2041 tttacacccc acaccaaagg aaaccagatg tgagctgcta aattgactgg ccttgcagag 2101 ctcaagaagg gggcttccaa tgctgtgaga attccgagct gttccctggg ctctgttaac 2161 aggcagagag gttccgggat ggtctgctca agtggcccac actggtcatt gccttaagcc 2221 acctccccag gacttacgga gagaaataag gggatgtaac cagcaatggc cagggtacaa 2281 cagccctgga aaacagtagt aggagcacta ggctttctgg gagtccatcc agctggagtg 2341 gctttgagtg agttacacag ctagaaggtg ccaggttggt gctgccagag attcagaggt 2401 gccatacact tgtcaaatct ggatcattcg tagtgccagc acagtcctaa aagggctgga 2461 gtaccacacc aacacaggta ggggtgcagg gcttcaagta caaagatttg catccatgta 2521 tgtatcaaaa gtgggttctc tgggctgtgg ctttgtctag tagtaccaca gtggctaaag 2581 tagaagaaaa ccaaatcaaa tgggatgtgt cttttgggag gatgtacaag acacaaatct 2641 ttcactaggc accgggcaca gggaaaactg cagggaacaa gagttgtagt gttagtgcaa 2701 ctgtctcaac gatgctgtgt ggcttcagac ccaaacaagg ccctgaggaa ggagactctc 2761 atttccccaa gcataactgc aaggagagga ggaattccta ggagccaaag agttttgtgg 2821 ggtgagggta aataaatggc ccaaatgcca actaggtgaa gttgtgacca tctggctggg 2881 aagcccaggt ccacacagtg taggagcaga tgttttgtgg ggtctgaggt ttacgagatt 2941 tggctgcctt aagaatacaa aaacagaaat gcagaatttc tggggctgct cctaggacca 3001 gaacaagtga agggtcctgg tgcttaaact tcattacctt catggtaaat ccaccagagg 3061 gccggttaga tgctggcccc gccgagagaa ctgctgtcac tttcaggcaa agctcaaagg 3121 tcctaggccc acagttcttt tgagctccag tcatggacat taggaagtaa atcctgcaca 3181 gccaacctgg aataccaaag attagatggg agatagatac caatgattta gatggcacag 3241 gaagagcaag ttctggatat aataaatgag ggtactttcc gtcaaagctt ttctatgtct 3301 atatttatca ctgaatagtc ccagtatggt tttaaagcaa gttttatgaa tctcatttgc
```

APPENDIX-continued

Nucleotide Sequences for HDACi Compound Resistance Biomarker Genes

```
3361 ctaacaggaa tctgaaatat aacttgccaa aaacacacag ttggtgtgga atggtcatta 3421 gaacctgggg ctcctcttca cggactccct gctcattaag ggattcagtg gtccagagtc 3481 taagatccta ttaagtgttt gattcaaacc tctacccgag aagggctgt taccttactc 3541 ctggtcctgg tttcaagctc attcctgaaa ttccagctgg tttctctagc acctagtgtt 3601 gtttacaaga aggccacggt gctcttagca ttcaaactgc agatactaaa cagatgctgt 3661 gatttattaa agagttagcc atatttcaac aagaaaggga aatgatggct atattcatta 3721 cttacctcaa agcatgctgc aagaaaatta gttagttact tgtcatgctt tgaaatctct 3781 ggatgaaagg tgctttggaa gcacaaacca ttatcacttg tctcataggg attgtcccct 3841 tgaacatcca gcagtgttat tttacagaag acaaattaac tgaaggcttt tcttttatta 3901 catctaaaga gctctacata aacaggtaac attcaatagg taaacaattt ttttccaatg 3961 catgtaataa atattttcac ttggtacttt tatacaaact gacattgtct actatacatt 4021 tttaaaagcc attttactgg tttggcatgc ggtatggaaa ttctaagaga gaaagtttta 4081 aggcaatgaa tcacagattt aagttcatgg aatttatggt aactttatct gtttatgtac 4141 attttccct ttgttaaaca attaacagca gcacactctg ggaccaccag ctattttccc 4201 tctctttctg aaatctaagc tttgtattta attaaaaaac agaattcaac atctattgat 4261 aaaacaaaat tcttactaaa ataatttcaa atgtgcttta aaaagtcctg aagatcttga 4321 aagttttatg tgtttaaaat tgaaattgtc taaaaaaatg ctctttccac attaatttag 4381 ttaggatata ttttcactcc atttcagaca cttgactcaa aggaaaatct gccaaagaat 4441 ccgattttc agagcttacg tgaatctttc ctcagtaaag atacagaatt gtgatcatgt 4501 ctaaataatt agtaaagcaa ttttaatgct caaaatagtc aaccaagtat ggcatggttc 4561 tggttcagat ttttttttt taagatgtat ccaataacac tcacgaagta attaaaagcc 4621 actttaaccc tgctaaaaaa
```

| Gene Name | Gene Symbol | GenBank Accession # | SEQ ID NO |
|---|---|---|---|
| UDP-N-acetyl-alpha-D-galactosamine:polypeptide N-acetylgalactosaminyltransferase 12 (GalNAc-T12) | GALNT12 | AK024865 | 13 |

```
  1 cattttataa tgaagcctgg tcaactctcc ttcggacagt ttacagtgtc cttgagacat 61 ccccggatat cctgctagaa gaagtgatcc ttgtagatga ctacagtgat agagagcacc 121 tgaaggagcg cttggccaat gagctttcgg gactgcccaa ggtgcgcctg atccgcgcca 181 acaagagaga gggcctggtg cgagcccggc tgctgggggc gtctgcggcg aggggcgatg 241 ttctgacctt cctggactgt cactgtgagt gccacgaagg gtggctggag ccgctgctgc 301 agaggatcca tgaagaggag tcggcagtgg tgtgcccggt gattgatgtg atcgactgga 361 acaccttcga atacctgggg aactccgggg agccccagat cggcggtttc gactggaggc 421 tggtgttcac gtggcacaca gttcctgaga gggagaggat acggatgcaa tccccccgtcg 481 atgtcatcag gtctccaaca atggctggtg ggctgtttgc tgtgagtaag aaatattttg 541 aatatctggg gtcttatgat acaggaatgg aagtttgggg aggagaaaac ctcgaatttt 601 cctttaggat ctggcagtgt ggtggggttc tggaaacaca cccatgttcc catgttggcc 661 atgttttccc caagcaagct ccctactccc gcaacaaggc tctggccaac agtgttcgtg 721 cagctgaagt atggatggat gaatttaaag agctctacta ccatcgcaac ccccgtgccc
```

APPENDIX-continued

Nucleotide Sequences for HDACi Compound Resistance Biomarker Genes

```
 781 gcttggaacc ttttggggat gtgacagaga ggaagcagct ccgggacaag ctccagtgta
 841 aagacttcaa gtggttcttg gagactgtgt atccagaact gcatgtgcct gaggacaggc
 901 ctggcttctt cgggatgctc cagaacaaag gactaacaga ctactgcttt gactataacc
 961 ctcccgatga aaaccagatt gtgggacacc aggtcattct gtacctctgt catgggatgg
1021 gccagaatca gttttttcgag tacacgtccc agaaagaaat acgctataac acccaccagc
1081 ctgagggctg cattgctgtg gaagcaggaa tggatacccct tatcatgcat ctctgcgaag
1141 aaactgcccc agagaatcag aagttcatct tgcaggagga tggatcttta tttcacgaac
1201 agtccaagaa atgtgtccag gctgcgagga aggagtcgag tgacagtttc gttccactct
1261 tacgagactg caccaactcg gatcatcaga atggttcttt caaagagcgc atgttatgaa
1321 gcctcgtgta tcaaggagcc atcgaagga gactgtggag ccaggactct gcccaacaaa
1381 gacttagcta agcagtgacc agaacccacc aaaaactagg ctgcattgct ttgaagaggc
1441 aatcattttg ccatttgtga agttgtgtt ggatttagta aaaatgtgaa taagcttttgt
1501 acttattttg agaactttt aaatgttcca aaatacccta ttttcaaagg gtaatcgtaa
1561 gatgttaacc cttggtattt agaaaattaa aaccttataa tattttttcta tcaagatgta
1621 tattttacag tcgtgccttt tactctcatt agcaaaaaag ataaagattt tatttttggta
1681 tttacaagaa ttcccaggta cgaagatatc tgcatgggtg gaaatcaggt tcaagcaacg
1741 tactttgcat taactgataa tacctcagct gcggggttaa agttttccca gtatagagag
1801 actgtcacta ggaacattgt attgatttat tcaggtcatt gagatcttct agatgtattt
1861 taaaagaat gcttttttggt tatgtgttgc taccacagtt aacactccat aatgttcatg
1921 tcagccaaag aggactaacc aaagctgaaa tctcagagaa caatttgctt tactaagctg
1981 agtcaacttg agagcgaact tctaacaatg ccgcactgta gtgtggctgg ttctaccact
2041 atgactttaa acatgtttta tatcattttt aattttatg atacggtagt gtcagggaga
2101 aatgtaatgt tctatatgaa attccttttt caagtttgtt cattaataac agttattaat
2161 ttaaatcagc gttagagttt gtgctgctgc aactgctgtg aaaatttctc tgagtaattc
2221 tgatttgtga atgatcccag accaaccctg agatttttgtc aacctgatta agtcaatatg
2281 aatgattaaa aagatgtgag
```

| Gene Name | Gene Symbol | GenBank Accession # | SEQ ID NO |
|---|---|---|---|
| thiamin pyrophospho-kinase 1 | TPK1 | NM_022445 | 14 |

```
   1 aaggctcctc agccgagcgc cgagcggtcg atcgccgtag ctcccgcagc ctgcgatctc
  61 cagtctgtgg ctcctaccag ccattgtagg ccaataatcc gttatggagc atgcctttac
 121 cccgttggag cccctgcttt ccactgggaa tttgaagtac tgccttgtaa ttcttaatca
 181 gcctttggac aactatttc gtcatctttg gaacaaagtc cttttaagag cctgtgccga
 241 tggaggtgcc aaccgcttat atgatatcac cgaaggagag agagaaagct ttttgcctga
 301 attcatcaat ggagactttg attctattag gcctgaagtc agagaatact atgctactaa
 361 gggatgtgag ctcatttcaa ctcctgatca agaccacact gactttacta agtgccttaa
 421 aatgctccaa aagaagatag aagaaaaaga cttaaaggtt gatgtgatcg tgacactggg
 481 aggccttgct gggcgttttg accagattat ggcatctgtg aataccttgt tccaagcgac
```

APPENDIX-continued

Nucleotide Sequences for HDACi Compound Resistance Biomarker Genes

```
 541 tcacatcact cctttccaa ttataataat ccaagaggaa tcgctgatct acctgctcca
 601 accaggaaag cacaggttgc atgtagacac tggaatggag ggtgattggt gtggccttat
 661 tcctgttgga cagccttgta tgcaggttac aaccacaggc ctcaagtgga acctcacaaa
 721 tgatgtgctt gcttttggaa cattggtcag tacttccaat acctacgacg ggtctggtgt
 781 tgtgactgtg gaaactgacc acccactcct ctggaccatg gccatcaaaa gctaacctgt
 841 tgactggcat ccataagtgt gcctctgcct tatctcattt ctcaacagtt cattgctcaa
 901 caagaacgat tcacctgggt ttgcaagaat ctaaacctct ctaggggaag cccactgggt
 961 ttaaagatgt tagtgtttag ataatacagg taacattata aatgacagat ctcaatttta
1021 tagtagtggg aaagatacat gctaagaaag caaataagct ctattatatt cggttggaac
1081 ctaatgggaa tcattccact atacaattca gtactgatta ttcttcttac attattaatc
1141 attccattta tcctagaaaa ttgtttttaa tttgaatcag agaaaactgt tgaggttcct
1201 cttggagtct agaacatcct taatgtcta acaacaaggg ctacctctga gtaccttta
1261 gtattagttt tctgtatatg atatatatta tcttatactg aaaaaaaatt cctttcagat
1321 tggggtgtta gaagtgcacc aggtcactct gaccttatta ctgtctttgg tattgtctta
1381 aataaatcaa gaatcattga cctaattgtt aaatttaaaa ataggtagtt agcaataggt
1441 ggaaagagaa atgatgtgaa agataaatga tgattcgtgg agccctactc acacattaac
1501 ccccaaattc aaaagtaaga atgcaaaagt ctagagggg taacagtctg catcatcatc
1561 acaacctaaa tggagaaagc tgtgcagagg aaacttaagc ataaaaattg aattcgtttc
1621 tgacatacct tagactgaaa aactgttggt tcatccagaa gtgtattcat attaccagaa
1681 aatgagtttg tctatgggga tacatgaact tcatatacta aggagcctaa ctccaaagcc
1741 tgcgttctca tcccagtctg atattcacct aagtttccgg accctttcc ttagctgtaa
1801 aatggaagcg gttggactga tggtgtctga ggttctttcc cacactgaaa ttctaaatat
1861 tgacacttag cagtcatagg gctgataata cacacagtta ctgacttagc ctaaacaacc
1921 tggtgcatcg aaatgtattc acctttcttt tgtaaagaga ccatcttcta tcttctttcc
1981 accttctctct gttttatgaa accaactgtt gacatacaaa ccatgattga aggagaacct
2041 gtccaacatg ttttatgtac acaaatccct atgttgctat aagaaaagtg aaagtaactg
2101 ttttcttctt ggtgctatga cagtgtgaga ctcaggttgt ctgtagagaa tgaaaggagc
2161 agtggcccgc gtgattgtgg catttaagga gcagtggccc atgtgactgt ggcattttcg
2221 gcacttttca ttactttctg cttgaccgga agttgaggct tagctatgtt tccatcttca
2281 gtttctgaag actagttata tattccttac tagaaatata ttcataatat ataaaagaaa
2341 tatatctgtg attttaaaat tttgctacca aagaatgcat gttctgtgtg ccctgaaaat
2401 gttaccagtg ttaataaatg gatacttatc aaaaaagaaa
```

| Gene Name | Gene Symbol | GenBank Accession # | SEQ ID NO |
|---|---|---|---|
| defensin, alpha 6, Paneth cell-specific | DEFA6 | NM_001926 | 15 |

```
   1 acacatctgc tcctgctctc tctcctccag cgaccctagc catgagaacc ctcaccatcc
  61 tcactgctgt tctcctcgtg gccctccagg ccaaggctga ccactccaa gctgaggatg
 121 atccactgca ggcaaaagct tatgaggctg atgcccagga gcagcgtggg gcaaatgacc
```

APPENDIX-continued

Nucleotide Sequences for HDACi Compound Resistance Biomarker Genes

```
 181 aggactttgc cgtctccttt gcagaggatg caagctcaag tcttagagct tgggctcaa
 241 caagggcttt cacttgccat tgcagaaggt cctgttattc aacagaatat tcctatggga
 301 cctgcactgt catgggtatt aaccacagat tctgctgcct ctgagggatg agaacagaga
 361 gaaatatatt cataatttac tttatgacct agaaggaaac tgtcgtgtgt cccatacatt
 421 gccatcaact ttgtttcctc atctcaaata aagtcctttc agcaaaaaaa aaaaa
```

| Gene Name | Gene Symbol | GenBank Accession # | SEQ ID NO |
|---|---|---|---|
| epithelial protein lost in neoplasm beta | EPLIN | NM_016357 | 16 |

```
   1 gcgctaggta gagcgccggg acctgtgaca gggctggtag cagcgcagag gaaaggcggc
  61 ttttagccag gtatttcagt gtctgtagac aagatggaat catctccatt taatagacgg
 121 caatggacct cactatcatt gagggtaaca gccaagaaac tttctcttgt caacaagaac
 181 aagtcatcgg ctattgtgga aatattctcc aagtaccaga aagcagctga gaaacaaac
 241 atggagaaga agagaagtaa caccgaaaat ctctcccagc actttagaaa ggggaccctg
 301 actgtgttaa agaagaagtg ggagaaccca gggctgggag cagagtctca cacagactct
 361 ctacggaaca gcagcactga gattaggcac agagcagacc atcctcctgc tgaagtgaca
 421 agccacgctg cttctggagc caaagctgac caagaagaac aaatccaccc cagatctaga
 481 ctcaggtcac ctcctgaagc cctcgttcag ggtcgatatc cccacatcaa ggacggtgag
 541 gatcttaaag accactcaac agaaagtaaa aaaatggaaa attgtctagg agaatccagg
 601 catgaagtag aaaaatcaga atcagtgaa acacagatg cttcgggcaa aatagagaaa
 661 tataatgttc cgctgaacag gcttaagatg atgtttgaga aaggtgaacc aactcaaact
 721 aagattctcc gggcccaaag ccgaagtgca agtggaagga agatctctga aaacagctat
 781 tctctagatg acctggaaat aggcccaggt cagttgtcat cttctacatt tgactcggag
 841 aaaaatgaga gtagacgaaa tctggaactt ccacgcctct cagaaacctc tataaaggat
 901 cgaatggcca gtaccaggc agctgtgtcc aaacaaagca gctcaaccaa ctatacaaat
 961 gagctgaaag ccagtggtgg cgaaatcaaa attcataaaa tggagcaaaa ggagaatgtg
1021 cccccaggtc ctgaggtctg catcacccat caggaagggg aaaagatttc tgcaaatgag
1081 aatagcctgg cagtccgttc cacccctgcc gaagatgact cccgtgactc ccaggttaag
1141 agtgaggttc aacagcctgt ccatcccaag ccactaagtc cagattccag agcctccagt
1201 ctttctgaaa gttctcctcc caaagcaatg aagaagtttc aggcacctgc aagagagacc
1261 tgcgtggaat gtcagaagac agtctatcca atggagcgtc tcttggccaa ccagcaggtg
1321 tttcacatca gctgcttccg ttgctcctat tgcaacaaca actcagtct aggaacatat
1381 gcatctttac atggaagaat ctattgtaag cctcacttca atcaactctt taaatctaag
1441 ggcaactatg atgaaggctt tgggcacaga ccacacaagg atctatgggc aagcaaaaat
1501 gaaaacgaag agattttgga gagaccagcc cagcttgcaa atgcaaggga gacccctcac
1561 agcccagggg tagaagatgc ccctattgct aaggtgggtg tcctggctgc aagtatggaa
1621 gccaaggcct cctctcagca ggagaaggaa gacaagccag ctgaaaccaa gaagctgagg
1681 atcgcctggc acccccccac tgaacttgga agttcaggaa gtgccttgga ggaagggatc
1741 aaaatgtcaa agcccaaatg gcctcctgaa gacgaaatca gcaagcccga agttcctgag
```

APPENDIX-continued

Nucleotide Sequences for HDACi Compound Resistance Biomarker Genes

```
1801 gatgtcgatc tagatctgaa gaagctaaga cgatcttctt cactgaagga aagaagccgc
1861 ccattcactg tagcagcttc atttcaaagc acctctgtca agagcccaaa aactgtgtcc
1921 ccacctatca ggaaaggctg gagcatgtca gagcagagtg aagagtctgt gggtggaaga
1981 gttgcagaaa ggaaacaagt ggaaaatgcc aaggcttcta agaagaatgg gaatgtggga
2041 aaaacaacct ggcaaaacaa agaatctaaa ggagagacag ggaagagaag taaggaaggt
2101 catagtttgg agatggagaa tgagaatctt gtagaaaatg gtgcagactc cgatgaagat
2161 gataacagct tcctcaaaca acaatctcca caagaaccca agtctctgaa ttggtcgagt
2221 tttgtagaca cacctttgc tgaagaattc actactcaga atcagaaatc ccaggatgtg
2281 gaactctggg agggagaagt ggtcaaagag ctctctgtgg aagaacagat aaagagaaat
2341 cggtattatg atgaggatga ggatgaagag tgacaaattg caatgatgct gggccttaaa
2401 ttcatgttag tgttagcgag ccactgccct ttgtcaaaat gtgatgcaca taagcaggta
2461 tcccagcatg aaatgtaatt tacttggaag taactttgga aaagaattcc ttcttaaaat
2521 caaaaacaaa acaaaaaaac acaaaaaaca cattctaaat actagagata actttactta
2581 aattcttcat tttagcagtg atgatatgcg taagtgctgt aaggcttgta actggggaaa
2641 tattccacct gataatagcc cagattctac tgtattccca aaaggcaata ttaaggtaga
2701 tagatgatta gtagtatatt gttacacact attttggaat tagagaacat acagaaggaa
2761 tttaggggct taaacattac gactgaatgc actttagtat aaagggcaca gtttgtatat
2821 ttttaaatga ataccaattt aatttttag tatttacctg ttaagagatt atttagtctt
2881 taaatttttt aggttaattt tcttgctgtg atatatatga ggaatttact actttatgtc
2941 ctgctctcta aactacatcc tgaactcgac gtcctgaggt ataatacaac agagcacttt
3001 ttgaggcaat tgaaaaacca acctacactc ttcggtgctt agagagatct gctgtctccc
3061 aaataagctt ttgtatctgc cagtgaattt actgtactcc aaatgattgc tttctttct
3121 ggtgatatct gtgcttctca taattactga agctgcaat attttagtaa taccttcggg
3181 atcactgtcc cccatcttcc gtgttagagc aaagtgaaga gtttaaagga ggaagaagaa
3241 agaactgtct tacaccactt gagctcagac ctctaaaccc tgtatttccc ttatgatgtc
3301 cccttttga gacactaatt tttaaatact tactagctct gaaatatatt gatttttatc
3361 acagtattct cagggtgaaa ttaaaccaac tataggcctt tttcttggga tgattttcta
3421 gtcttaaggt ttggggacat tataaacttg agtacatttg ttgtacacag ttgatattcc
3481 aaattgtatg gatgggaggg agaggtgtct taagctgtag gcttttcttt gtactgcatt
3541 tatagagatt tagctttaat attttttaga gatgtaaaac attctgcttt cttagtctta
3601 cctagtctga aacatttta ttcaataaag attttaatta aaatttgaaa
```

| Gene Name | Gene Symbol | GenBank Accession # | SEQ ID NO |
|---|---|---|---|
| chloride intra-cellular channel 5 | CLIC5 | NM_016929 | 17 |

```
  1 gacagtcgcg gatcctgtga cacctccggg cagcccggca cttgttgctc ccacgacctg
 61 ttgtcattcc cttaacccgg cttccccgt ggccccccgc ctcctcccgg cttcgctcct
121 tttcatgtga gcatctggga cactgatctc tcagaccccg ctgctcgggc tggagaatag
181 atggttttgt gaaaaattaa acaccgccct gaagaggagc cccgctgggc agcggcagga
```

APPENDIX-continued

Nucleotide Sequences for HDACi Compound Resistance Biomarker Genes

```
 241 gcgcagagtg ctggcccagg tgctgcagag gtggcgcctc cccggcccgg gacggtagcc
 301 ccgggcgcca acggcatgac agactcggcg acagctaacg gggacgacag ggaccccgag
 361 atcgagctct tgtgaaggc tggaatcgat ggagaaagca tcggcaactg tcctttctct
 421 cagcgcctct tcatgatcct ctggctgaaa ggagtcgtgt tcaatgtcac cactgtggat
 481 ctgaaaagaa agccagctga cctgcacaac ctagcccccg gcacgcaccc gcccttcctg
 541 accttcaacg gggacgtgaa gacagacgtc aataagatcg aggagttcct ggaggagacc
 601 ttgacccctg aaaagtaccc caaactggct gcaaaacacc gggaatccaa cacagcgggc
 661 atcgacatct tttccaagtt ttctgcctac atcaaaaata ccaagcagca gaacaatgct
 721 gctcttgaaa gaggcctaac caaggctcta agaaattgg atgactacct gaacacccct
 781 ctaccagagg agattgacgc caacacttgt ggggaagaca aggggtcccg gcgcaagttc
 841 ctggatgggg atgagctgac cctggctgac tgcaatctgt tgcccaagct ccatgtggtc
 901 aagattgtgg ccaagaaata ccgcaactat gatatcccgg ctgagatgac aggcctgtgg
 961 cggtacctca agaacgccta tgcccgtgat gagttcacca cacctgtgc agctgacagt
1021 gagatcgagt tggcctacgc tgatgtcgcc aaacgcctca gccgatcctg agcacagcca
1081 ttttgcccca tccccgctgc agaaggactc aaccactccc ctaagactcc agcttcatag
1141 actcctctgt atcactgcct tgaggcgcac ttttttataat caagcctcat cttgctggta
1201 tcatgggaac tccagcctgc tatctttcat gaaggtcagc accatccctg gcctcctcac
1261 ataggaatct agcagaaatg atagacacag tccacctttc ggccggccag cctgatctgg
1321 gctcagcatg tttggggtca gtcagtgttg gagagcccac atatgggatt gccactagct
1381 tcttctgcca atatcaaaat accttctcag atgctttaga acatgcaac accaactcct
1441 tttctaccct cctctccgtc catacctaca aggccaagga caaacgccat cttcatcctt
1501 cttagaaaga gatctattac cccattaggg gagacagaga gagtgaatgg aggagtaccg
1561 agctggctat ggacttgggt gtctggcaaa cacagcttca gtctcactac ttctgacact
1621 ctggttattg gcactaagg gccagactgg aaagtcactt gagacacatt ctcagtttgt
1681 tgcagtgcca ggaatgctgc gctgctgctg ctgcgcacct ggcccatgct gtccctggct
1741 tccatgccgt ccaggccctg ccagaaaagg aaattggcat gcaattctaa actgcagtga
1801 ctgggatggg aggggagggg agcagtgttg atgccaaaat acccacgggg tctaccagcc
1861 atggggtttg cttcttagg agtagttgtt tcagaggtga ttacaggcct gggtttgact
1921 gtgcttacca atgagtggtt tttgagctat gagaaagtgg atgggagtgg gaggaggaga
1981 gatgggtgaa gacaaaagag ttctttatga gcctcgatgt tccctggtaa acttttaaaa
2041 aggccttctc tcatgatcta agtcttggac tggtggcatc atgtaactgc taaccttaca
2101 gtaaaaaccc aagaatgggt caaaaatgtc ttcccagttt ctccaagctg cttctggaat
2161 gcaggtctgt cggctgggtg ctctccagca gctgctcctg cctgattcaa ctgtagcctg
2221 taatgggtaa aagccacatt taggaggtgg tctgatcata gaacaccttg ggaagaaagt
2281 ccatgagact ttctgactag gaaaccatgt ggtttgaact tgaagaaaaa tgtagaccca
2341 tctgggttaa ttttcctaca atctgactca actgccaggt gaaaaaaaaa aggaaaaatt
2401 tttaagctaa tatttcactc ttttgtcatt ctccttaagt ttcatctcct aaaaagctta
2461 cccagcctga gcttggggac ctgtgcagag gaaactaaga aaaatgcact catcaactcc
```

APPENDIX-continued

Nucleotide Sequences for HDACi Compound Resistance Biomarker Genes

```
2521 ttctcccagt gaacgcccgg tgagaaaatc catttgccac aggcccttac cttcaacaat
2581 ccccttcta tagtgttcgc tggtaaaggg tgaggctccc aagtgctgga aagcccctgg
2641 acttggctca tttctcagca agggcaggat agcacgggtc ctttccatag aaatatcaac
2701 aaattctaac ccaagcaatc cctggaccta cctgcctcca gggatctctg aagaaaaaaa
2761 gtaacccatt gatcaaatca gaggagagga agcaggaggt ctcctagagc ccattgagga
2821 agaggaactt tctcagtagg acactttata agcctgagaa agctttgaaa aggcggaatg
2881 agttgattca tttccacctc aaaaggaacc tttccaggtc cccctggaaa ttgtgccctg
2941 gagatgttta acaaggagaa ctggtgagga aagagtcctt ttttactgta gggaaaagcc
3001 ccaaactggc ctcctgggggg atgagggctg aaatgatccc gaaggccttt taattagtgt
3061 gaaatcctgc tgtactcaga aatccttccc cgaatttaca gcacaggcag gatgacctaa
3121 gaggcagttt acttccctga gacccacagt tgggctgttc tggaaacaca tctgtgaatc
3181 atagccaatt gccacagaga aaacagaacc aagcctccgg tgaggccact ccaccccaga
3241 gaagtctgca gaattccaag gactcggatt ggatgttcag aattcagcaa ctggaaagtc
3301 cttaaaaaca aacaggccaa accaaatcaa tattgctgtt tctagatgtc ccttctgtgg
3361 ttgagctagt tttacagaga taaatatatt aagacaagga ggtgggggtg ttatatgatc
3421 aatgatagcc atttgaaaga gagggaggag tacagaagga aggcacttct gggtacttaa
3481 ttcagaaatt tctttatatt tcagcactgg attatcatat aatgcaagtg actatggact
3541 aagagttagt tatggtgtct tatgactaga tttattatgg tatattaaag taacaataat
3601 attaatatta ccttccttt tttttttgtt tcaaaagaga tctttctcca gatgcttcag
3661 cctgtctggc cttcttatca tatgtgcagc acatcatgtc tcagcaacag tgtggtgagg
3721 tccttaggtg tcccaagaac aactcaggga gcacgggagg gtctgcagtt gggaccccac
3781 aactatacag ctatagggta ggaggcttcc ttttcattgg tcctgaatga atacaaatcg
3841 ctcagaaagc attttggtgg cacagaaagg ggatgtattt tgttgagat cttattttat
3901 tttgtattta tttatcttct ttgacttgca cagcactatt gggggtgggg gaagcagggt
3961 agtgggagac gaaggcagaa gcaagagtca aactcagaat gactgagttg aattcactgt
4021 ctagtcagca atgcctgctt ctgagtttgg cccagagaga aggtattgag taagatttta
4081 ataactgtaa aaagtaagct ggataagtaa aatcatgatg gatccaaagc acagtttctt
4141 catctcctga taaagaaagt caaatgcttg ataaattcag agtcacagat gtgagcatag
4201 ctatattctt ttaaacgaga ggtagagtga cctagcacta agcaaatgag ctgaaatgtc
4261 ggaaacagag tccatcagct tatttggcca cacgatccca aactagtttt atcttgggaa
4321 atggccctgt cctcagcatt cccttcttgt gctggtgggg ccagtgaagt cttgatctta
4381 tcagaaaaag gccacaccaa gtgcgagttt tcccaggctg actttccagg cccttatcaa
4441 atgaaacaac agaagctctt cacagttctg tgccccatgg ccactccaca gacagacaat
4501 accaagcatc ttagaactgt cataagatag gtcatgcctg aaatagatct tgaccatatg
4561 agagtcccag aaatcagcaa ggcctggaca aatagaacta agagagaggc agaggcagga
4621 agctgcgggt ctatcttgta aagagtttag catcactgtg agagtgtgtg tctaaaatta
4681 aattaaacta gaagcagcag gtgagtattt ggtaagtact tctgtgactc gcctcaattc
4741 ccactggcca ggggccatct caactgcacg gtgaatcaag atgctggtgt catcctcctt
4801 ggaaaaagga aatgttaact catggttaaa actaagtaca atgattccca agggatcact
```

APPENDIX-continued

Nucleotide Sequences for HDACi Compound Resistance Biomarker Genes

```
4861 ttcttatttt tttaaatgac attaaggaga atcttaagaa agcatcagag aaagacatgt
4921 gcatgtgaag caccctgatt ctgatgttag gaaaacttaa gcgaacagga cctgctgcac
4981 acagccccat tgtcttctat ccatttctct ttatcattca aatcaagcaa catgtgccct
5041 cctcatcaac acacattctt cccctttgtc agtatgcatc tcccagctta gtgtcaggat
5101 actttcgatt cataattatg tatgatccaa agtgtgcata atttcattta acgttaaaga
5161 aatagatcca attcctttct tgcaaccaaa aataaataaa atacgttgcc tcaatataag
5221 gtttgggcta ttctgtgttt ctatagaagc aatctgtttt tggtaaaatg tacttttaag
5281 gatccagtca tctgaagtat tttatgtaga gttagagatt tcacaatatt gactatacat
5341 atatttaaaa tataaattat ccagctgatg tttgaatttg tcttactttc ctggccacct
5401 cgttgtccta tttataagc tggggagtta actagcttaa caaaagatgc ttagcttttg
5461 taaaagaaca agtgtttcat tttacaaaga cactccaaat gatagttact tgattttctc
5521 gagaccttta actatggtga tgaataacag gacttgcttt caagccttaa taaatgtaaa
5581 atgcctttta atgaagatac agctgagtgt tttcctcatg aatctgaacc aattaccaat
5641 ttgtgttcca gtcttgattg gtattgactg attcaaataa agttggttta ttttcaaata
5701 tta
```

| Gene Name | Gene Symbol | GenBank Accession # | SEQ ID NO |
|---|---|---|---|
| PERP, TP53 apoptosis effector | PERP | NM_022121 | 18 |

```
   1 gcttttgtgg cggcgcccgc gctcgcaggc cactctctgc tgtcgcccgt cccgcgcgct
  61 cctccgaccc gctccgctcc gctccgctcg gccccgcgcc gcccgtcaac atgatccgct
 121 gcggcctggc ctgcgagcgc tgccgctgga tcctgcccct gctcctactc agcgccatcg
 181 ccttcgacat catcgcgctg gccggccgcg gctggttgca gtctagcgac cacggccaga
 241 cgtcctcgct gtggtggaaa tgctcccaag agggcggcgg cagcgggtcc tacgaggagg
 301 gctgtcagag cctcatggag tacgcgtggg gtagagcagc ggctgccatg ctcttctgtg
 361 gcttcatcat cctggtgatc tgtttcatcc tctccttctt cgccctctgt ggaccccaga
 421 tgcttgtctt cctgagagtg attggaggtc tccttgcctt ggctgctgtg ttccagatca
 481 tctccctggt aatttacccc gtgaagtaca cccagaccct cacccttcat gccaaccctg
 541 ctgtcactta catctataac tgggcctacg gctttgggtg ggcagccacg attatcctga
 601 ttggctgtgc cttcttcttc tgctgcctcc ccaactacga agatgacctt ctgggcaatg
 661 ccaagcccag gtacttctac acatctgcct aacttgggaa tgaatgtggg agaaaatcgc
 721 tgctgctgag atggactcca gaagaagaaa ctgtttctcc aggcgacttt gaacccattt
 781 tttggcagtg ttcatattat taaactagtc aaaaatgcta aaataatttg ggagaaaata
 841 ttttttaagt agtgttatag tttcatgttt atcttttatt atgttttgtg aagttgtgtc
 901 ttttcactaa ttacctatac tatgccaata tttcctatct atccataaca tttatactac
 961 atttgtaaga gaatatgcac gtgaaactta acactttata aggtaaaaat gagggtttcca
1021 agatttaata atctgatcaa gttcttgtta tttccaaata gaatggactc ggtctgttaa
1081 gggctaagga gaagaggaag ataaggttaa aagttgttaa tgaccaaaca ttctaaaaga
1141 aatgcaaaaa aaaagtttat tttcaagcct tcgaactatt taaggaaagc aaaatcattt
```

APPENDIX-continued

Nucleotide Sequences for HDACi Compound Resistance Biomarker Genes

```
1201 cctaaatgca tatcatttgt gagaatttct cattaatatc ctgaatcatt cattttagct
1261 aaggcttcat gttgactcga tatgtcatct aggaaagtac tatttcatgg tccaaacctg
1321 ttgccatagt tggtaaggct ttcctttaag tgtgaaatat ttagatgaaa ttttctcttt
1381 taaagttctt tataggggtta gggtgtggga aaatgctata ttaataaatc tgtagtgttt
1441 tgtgtttata tgttcagaac cagagtagac tggattgaaa gatggactgg gtctaattta
1501 tcatgactga tagatctgtt aagttgtgta gtaaagcatt aggagggtca ttcttgtcac
1561 aaaagtgcca ctaaaacagc ctcaggagaa taaatgactt gcttttctaa atctcaggtt
1621 tatctgggct ctatcatata gacaggcttc tgatagtttg caactgtaag cagaaaccta
1681 catatagtta aaatcctggt ctttcttggt aaacagattt taaatgtctg atataaaaca
1741 tgccacagga gaattcgggg atttgagttt ctctgaatag catatatatg atgcatcgga
1801 taggtcatta tgattttta ccatttcgac ttacataatg aaaaccaatt cattttaaat
1861 atcagattat tattttgtaa gttgtggaaa aagctaattg tagttttcat tatgaagttt
1921 tcccaataaa ccaggtattc t
```

| Gene Name | Gene Symbol | GenBank Accession # | SEQ ID NO |
|---|---|---|---|
| spleen tyrosine kinase | SYK | NM_003177 | 19 |

```
  1 aggaagagcc gcgggcccgg cggctgaggc caccccggcg gcggctggag agcgaggagg
 61 agcgggtggc cccgcgctgc gcccgccctc gcctcacctg gcgcaggtgg acacctgcgc
121 aggtgtgtgc cctccggccc ctgaagcatg gccagcagcg gcatggctga cagcgccaac
181 cacctgccct tcttttttcgg caacatcacc cgggaggagg cagaagatta cctggtccag
241 gggggcatga gtgatgggct ttatttgctg cgccagagcc gcaactacct gggtggcttc
301 gccctgtccg tggcccacgg gaggaaggca caccactaca ccatcgagcg ggagctgaat
361 ggcacctacg ccatcgccgg tggcaggacc catgccagcc ccgccgacct ctgccactac
421 cactcccagg agtctgatgg cctggtctgc ctcctcaaga agcccttcaa ccggccccaa
481 ggggtgcagc ccaagactgg gcccttt gag gatttgaagg aaaacctcat cagggaatat
541 gtgaagcaga catggaacct gcagggtcag gctctggagc aggccatcat cagtcagaag
601 cctcagctgg agaagctgat cgctaccaca gcccatgaaa aaatgccttg gttccatgga
661 aaaatctctc gggaagaatc tgagcaaatt gtcctgatag gatcaaagac aaatggaaag
721 ttcctgatcc gagccagaga caacaacggc tcctacgccc tgtgcctgct gcacgaaggg
781 aaggtgctgc actatcgcat cgacaaagac aagacaggga agctctccat ccccgaggga
841 aagaagttcg acacgctctg gcagctagtc gagcattatt cttataaagc agatggtttg
901 ttaagagttc ttactgtccc atgtcaaaaa atcggcacac agggaaatgt aattttgga
961 ggccgtccac aacttccagg ttcccatcct gcgacttggt cagcgggtgg aataatctca
1021 agaatcaaat catactcctt cccaaagcct ggccacagaa agtcctcccc tgcccaaggg
1081 aaccggcaag agagtactgt gtcattcaat ccgtatgagc cagaacttgc acctgggct
1141 gcagacaaag gccccagag agaagcccta cccatggaca cagaggtgta cgagagcccc
1201 tacgcggacc ctgaggagat caggcccaag gaggtttacc tggaccgaaa gctgctgacg
1261 ctggaagaca aagaactggg ctctggtaat tttggaactg tgaaaaaggg ctactaccaa
```

APPENDIX-continued

Nucleotide Sequences for HDACi Compound Resistance Biomarker Genes

```
1321 atgaaaaaag ttgtgaaaac cgtggctgtg aaaatactga aaaacgaggc caatgacccc
1381 gctcttaaag atgagttatt agcagaagca aatgtcatgc agcagctgga caacccgtac
1441 atcgtgcgca tgatcgggat atgcgaggcc gagtcctgga tgctagttat ggagatggca
1501 gaacttggtc ccctcaataa gtatttgcag cagaacagac atgtcaagga taagaacatc
1561 atagaactgg ttcatcaggt ttccatgggc atgaagtact tggaggagag caattttgtg
1621 cacagagatc tggctgcaag aaatgtgttg ctagttaccc aacattatgc caagatcagt
1681 gatttcggac tctccaaagc actgcgtgct gatgaaaact actacaaggc ccagacccat
1741 ggaaagtggc ctgtcaagtg gtacgctccg gaatgcatca actactacaa gttctccagc
1801 aaaagcgatg tctggagctt tggagtgttg atgtgggaag cattctccta tgggcagaag
1861 ccatatcgag ggatgaaagg aagtgaagtc accgctatgt tagagaaagg agagcggatg
1921 gggtgccctg cagggtgtcc aagagagatg tacgatctca tgaatctgtg ctggacatac
1981 gatgtggaaa acaggcccgg attcgcagca gtggaactgc ggctgcgcaa ttactactat
2041 gacgtggtga actaaccgct cccgcacctg tcggtggctg cctttgatca caggagcaat
2101 cacaggaaaa tgtatccaga ggaattgatt gtcagccacc tccctctgcc agtcgggaga
2161 gccaggcttg gatggaacat gcccacaact tgtcacccaa agcctgtccc aggactcacc
2221 ctccacaaag caaaggcagt cccgggagaa aagacggatg gcaggatcca aggggctagc
2281 tggatttgtt tgttttcttg tctgtgtgat tttcatacag gttattttta cgatctgttt
2341 ccaaatccct ttcatgtctt tccacttctc tgggtcccgg ggtgcatttg ttactcatcg
2401 ggcccaggga cattgcagag tggcctagag cactctcacc ccaagcggcc ttttccaaat
2461 gcccaaggat gccttagcat gtgactcctg aagggaaggc aaaggcagag gaatttggct
2521 gcttctacgg ccatgagact gatccctggc cactgaaaag ctttcctgac aataaaaatg
2581 ttttgaggct taaaaagaa atcaagttt gaccagtgca gtttctaagc atgtagccag
2641 ttaaggaaag aaagaaaaaa
```

| Gene Name | Gene Symbol | GenBank Accession # | SEQ ID NO |
|---|---|---|---|
| solute carrier family 12 (sodium/potassium/chloride transporters), member 2 | SLC12A2 | NM_001046 | 20 |

```
   1 ggtggcctct gtggccgtcc aggctagcgg cggcccgcag gcggcgggga gaaagactct
  61 ctcacctggt cttgcggctg tggccaccgc cggccagggg tgtggagggc gtgctgccgg
 121 agacgtccgc cgggctctgc agttccgccg ggggtcgggc agctatggag ccgcggccca
 181 cggcgccctc ctccggcgcc ccgggactgg ccggggtcgg ggagacgccg tcagccgctg
 241 cgctggccga agccagggtg gaactgcccg gcacggctgt gccctcggtg ccggaggatg
 301 ctgcgcccgc gagccgggac ggcggcgggg tccgcgatga gggccccgcg gcggccgggg
 361 acgggctggg cagacccttg gggcccaccc cgagccagag ccgtttccag gtggacctgg
 421 tttccgagaa cgccgggcgg gccgctgctg cggcggcggc ggcggcggcg gcagcggcgg
 481 cggctggtgc tggggcgggg gccaagcaga ccccgcgcga cggggaagcc agcggcgaga
 541 gcgagccggc taaaggcagc gaggaagcca agggccgctt ccgcgtgaac ttcgtggacc
 601 cagctgcctc ctcgtcggct gaagacagcc tgtcagatgc tgccggggtc ggagtcgacg
 661 ggccccaacgt gagcttccag aacggcgggg acacggtgct gagcgagggc agcagcctgc
```

APPENDIX-continued

Nucleotide Sequences for HDACi Compound Resistance Biomarker Genes

```
 721 actccggcgg cggcggcggc agtgggcacc accagcacta ctattatgat acccacacca
 781 acacctacta cctgcgcacc ttcggccaca acaccatgga cgctgtgccc aggatcgatc
 841 actaccggca cacagccgcg cagctgggcg agaagctgct ccggcctagc ctggcggagc
 901 tccacgacga gctggaaaag gaacctttg aggatggctt tgcaaatggg gaagaaagta
 961 ctccaaccag agatgctgtg gtcacgtata ctgcagaaag taaaggagtc gtgaagtttg
1021 gctggatcaa gggtgtatta gtacgttgta tgttaaacat ttggggtgtg atgcttttca
1081 ttagattgtc atggattgtg ggtcaagctg aataggtct atcagtcctt gtaataatga
1141 tggccactgt tgtgacaact atcacaggat tgtctacttc agcaatagca actaatggat
1201 ttgtaagagg aggaggagca tattatttaa tatctagaag tctagggcca gaatttggtg
1261 gtgcaattgg tctaatcttc gcctttgcca acgctgttgc agttgctatg tatgtggttg
1321 gatttgcaga aaccgtggtg gagttgctta aggaacattc catacttatg atagatgaaa
1381 tcaatgatat ccgaattatt ggagccatta cagtcgtgat tcttttaggt atctcagtag
1441 ctggaatgga gtgggaagca aaagctcaga ttgttctttt ggtgatccta cttcttgcta
1501 ttggtgattt cgtcatagga acatttatcc cactggagag caagaagcca aaagggtttt
1561 ttggttataa atctgaaata tttaatgaga actttgggcc cgattttcga gaggaagaga
1621 ctttcttttc tgtatttgcc atctttttc ctgctgcaac tggtattctg gctggagcaa
1681 atatctcagg tgatcttgca gatcctcagt cagccatacc caaaggaaca ctcctagcca
1741 ttttaattac tacattggtt tacgtaggaa ttgcagtatc tgtaggttct tgtgttgttc
1801 gagatgccac tggaaacgtt aatgacacta tcgtaacaga gctaacaaac tgtacttctg
1861 cagcctgcaa attaaacttt gattttcat cttgtgaaag cagtccttgt tcctatggcc
1921 taatgaacaa cttccaggta atgagtatgg tgtcaggatt tacaccacta atttctgcag
1981 gtatattttc agccactctt tcttcagcat tagcatccct agtgagtgct cccaaaatat
2041 ttcaggctct atgtaaggac aacatctacc cagctttcca gatgtttgct aaaggttatg
2101 ggaaaaataa tgaacctctt cgtggctaca tcttaacatt cttaattgca cttggattca
2161 tcttaattgc tgaactgaat gttattgcac caattatctc aaacttcttc cttgcatcat
2221 atgcattgat caattttttca gtattccatg catcacttgc aaaatctcca ggatggcgtc
2281 ctgcattcaa atactacaac atgtggatat cacttcttgg agcaattctt tgttgcatag
2341 taatgttcgt cattaactgg tgggctgcat tgctaacata tgtgatagtc cttgggctgt
2401 atatttatgt tacctacaaa aaaccagatg tgaattgggg atcctctaca caagccctga
2461 cttacctgaa tgcactgcag cattcaattc gtctttctgg agtggaagac cacgtgaaaa
2521 actttaggcc acagtgtctt gttatgacag gtgctccaaa ctcacgtcca gctttacttc
2581 atcttgttca tgatttcaca aaaaatgttg gtttgatgat ctgtggccat gtacatatgg
2641 gtcctcgaag acaagccatg aaagagatgt ccatcgatca agccaaatat cagcgatggc
2701 ttattaagaa caaaatgaag gcattttatg ctccagtaca tgcagatgac ttgagagaag
2761 gtgcacagta tttgatgcag gctgctggtc ttggtcgtat gaagccaaac acacttgtcc
2821 ttggatttaa gaaagattgg ttgcaagcag atatgaggga tgtggatatg tatataaact
2881 tatttcatga tgcttttgac atacaatatg gagtagtggt tattcgccta aaagaaggtc
2941 tggatatatc tcatcttcaa ggacaagaag aattattgtc atcacaagag aaatctcctg
3001 gcaccaagga tgtggtagta agtgtggaat atagtaaaaa gtccgattta gatacttcca
```

APPENDIX-continued

Nucleotide Sequences for HDACi Compound Resistance Biomarker Genes

```
3061 aaccactcag tgaaaaacca attacacaca aagttgagga agaggatggc aagactgcaa
3121 ctcaaccact gttgaaaaaa gaatccaaag gccctattgt gcctttaaat gtagctgacc
3181 aaaagcttct tgaagctagt acacagtttc agaaaaaaca aggaaagaat actattgatg
3241 tctggtggct ttttgatgat ggaggtttga ccttattgat accttacctt ctgacgacca
3301 agaaaaaatg gaaagactgt aagatcagag tattcattgg tggaaagata aacagaatag
3361 accatgaccg gagagcgatg gctactttgc ttagcaagtt ccggatagac ttttctgata
3421 tcatggttct aggagatatc aataccaaac caaagaaaga aatattata gcttttgagg
3481 aaatcattga gccatacaga cttcatgaag atgataaaga gcaagatatt gcagataaaa
3541 tgaaagaaga tgaaccatgg cgaataacag ataatgagct tgaactttat aagaccaaga
3601 cataccggca gatcaggtta aatgagttat taaggaaca ttcaagcaca gctaatatta
3661 ttgtcatgag tctcccagtt gcacgaaaag gtgctgtgtc tagtgctctc tacatggcat
3721 ggttagaagc tctatctaag gacctaccac caatcctcct agttcgtggg aatcatcaga
3781 gtgtccttac cttctattca taaatgttct atacagtgga cagccctcca gaatggtact
3841 tcagtgccta gtgtagtaac tgaaatcttc aatgacacat taacatcaca atggcgaatg
3901 gtgacttttc tttcacgatt tcattaattt gaaagcacac aggaaagttg ctccattgat
3961 aacgtgtatg gagacttcgg ttttagtcaa ttccatatct caatcttaat ggtgattctt
4021 ctctgttgaa ctgaagtttg tgagagtagt tttcctttgc tacttgaata gcaataaaag
4081 cgtgttaact ttttgattga tgaaagaagt acaaaaagcc tttagccttg aggtgccttc
4141 tgaaattaac caaatttcat ccatatatcc tcttttataa acttatagaa tgtcaaactt
4201 tgccttcaac tgttttttatt tctagtctct tccactttaa aacaaaatga acactgcttg
4261 tcttcttcca ttgaccattt agtgttgagt actgtatgtg ttttgttaat tctataaagg
4321 tatctgttag atattaaagg tgagaattag ggcaggttaa tcaaaaatgg ggaaggggaa
4381 atggtaacca aaaagtaacc ccatggtaag gtttatatga gtatatgtga atatagagct
4441 aggaaaaaaa gcccccccaa ataccttttt aaccctctg attggctatt attactatat
4501 ttattattat ttattgaaac cttagggaag attgaagatt catcccatac ttctatatac
4561 catgcttaaa aatcacgtca ttcttttaaac aaaaatactc aagatcattt atatttattt
4621 ggagagaaaa ctgtcctaat ttagaatttc cctcaaatct gagggacttt taagaaatgc
4681 taacagattt ttctggagga aatttagaca aaacaatgtc atttagtaga atatttcagt
4741 atttaagtgg aatttcagta tactgtacta tccttttataa gtcattaaaa taatgtttca
4801 tcaaatggtt aaatggacca ctggtttctt agagaaatgt ttttaggctt aattcattca
4861 attgtcaagt acacttagtc ttaatacact caggtttgaa cagattattc tgaatattaa
4921 aatttaatcc attcttaata ttttaaaact tttgttaaga aaaactgcca gtttgtgctt
4981 ttgaaatgtc tgttttgaca tcatagtcta gtaaaatttt gacagtgcat atgtactgtt
5041 actaaaagct ttatatgaaa ttattaatgt gaagtttttc atttataatt caaggaagga
5101 tttcctgaaa acatttcaag ggatttatgt ctacatattt gtgtgtgtgt gtgtatatat
5161 atgtaatatg catacacaga tgcatatgtg tatatataat gaaatttatg ttgctggtat
5221 tttgcatttt aaagtgatca agattcatta ggcaaacttt ggtttaagta aacatatgtt
5281 caaaatcaga ttaacagata caggtttcat agagaacaaa ggtgatcatt tgaagggcat
```

APPENDIX-continued

Nucleotide Sequences for HDACi Compound Resistance Biomarker Genes

```
5341 gctgtaattt cacacaattt tccagttcaa aaatggagaa tacttcgcct aaaatactgt
5401 taagtgggtt aattgataca agtttctgtg gtggaaaatt tatgcaggtt ttcacgaatc
5461 cttttttttt tttttttttt ttttgagac ggagtcttgc tctgttgcca cgctggaatg
5521 cagtaacgtg atcttggctc actgcgacct ccacctcccc agttcaagcg attctcctgc
5581 ctcagcctcc ctagtagctg ggactacggg tgcacgccac catgcccagc taattttgt
5641 attttgagta gagacagggt ttcaccgtgt tggctaggat ggtgtctatc tcttgacctt
5701 gtgatccacc cgcctcagcc tcccagagtg ctgggattac aggtgcgagc cactgcgcct
5761 ggctggtttt catgaatctt gatagacatc tataacgtta ttattttcag tggtgtgcag
5821 cattttttgct tcatgagtat gacctaggta tagagatctg ataacttgaa ttcagaatat
5881 taagaaaatg aagtaactga ttttctaaaa aaaaaaaaaa aaaaaatttc tacattataa
5941 ctcacagcat tgttccattg caggttttgc aatgtttggg ggtaaagaca gtagaaatat
6001 tattcagtaa acaataatgt gtgaactttt aagatggata atagggcatg gactgagtgc
6061 tgctatcttg aaatgtgcac aggtacactt accttttttt tttttttttt taagtttttc
6121 ccattcagga aaacaacatt gtgatctgta ctacaggaac caaatgtcat gcgtcataca
6181 tgtgggtata aagtacataa aatatatcta actattcata atgtgggggtg ggtaatactg
6241 tctgtgaaat aatgtaagaa gcttttcact taaaaaaaat gcattacttt cacttaacac
6301 tagacaccag gtcgaaaatt ttcaaggtta tagtacttat ttcaacaatt cttagagatg
6361 ctagctagtg ttgaagctaa aaatagcttt atttatgctg aattgtgatt tttttatgcc
6421 aaatttttttt tagttctaat cattgatgat agcttggaaa taaataatta tgccatggca
6481 tttgacagtt cattattcct ataagaatta aattgagttt agagagaatg gtggtgttga
6541 gctgattatt aacagttact gaaatcaaat atttatttgt tacattattc catttgtatt
6601 ttaggtttcc ttttacattc tttttatatg cattctgaca ttacatattt tttaagacta
6661 tggaaataat ttaagatttt aagctctggt ggatgattat ctgctaagta agtctgaaaa
6721 tgtaatattt tgataatact gtaatatacc tgtcacacaa atgcttttct aatgttttaa
6781 ccttgagtat tgcagttgct gctttgtaca gaggttactg caataaagga agtggattca
6841 ttaaacctat ttaatgtcca
```

| Gene Name | Gene Symbol | GenBank Accession # | SEQ ID NO |
|---|---|---|---|
| guanylate cyclase 2C (heat stable entero-toxin receptor) | GUCY2C | NM_004963 | 21 |

```
  1 cgcaaagcaa gtgggcacaa ggagtatggt tctaacgtga ttggggtcat gaagacgttg
 61 ctgttggact tggctttgtg gtcactgctc ttccagcccg ggtggctgtc ctttagttcc
121 caggtgagtc agaactgcca caatggcagc tatgaaatca gcgtcctgat gatgggcaac
181 tcagcctttg cagagcccct gaaaaacttg gaagatgcgg tgaatgaggg gctgaaaata
241 gtgagaggac gtctgcaaaa tgctggccta aatgtgactg tgaacgctac tttcatgtat
301 tcggatggtc tgattcataa ctcaggcgac tgccggagta gcacctgtga aggcctcgac
361 ctactcagga aaatttcaaa tgcacaacgg atgggctgtg tcctcatagg ccctcatgt
421 acatactcca ccttccagat gtaccttgac acagaattga gctacccat gatctcagct
481 ggaagttttg gattgtcatg tgactataaa gaaacccttaa ccaggctgat gtctccagct
```

APPENDIX-continued

Nucleotide Sequences for HDACi Compound Resistance Biomarker Genes

```
 541 agaaagttga tgtacttctt ggttaacttt tggaaaacca acgatctgcc cttcaaaact
 601 tattcctgga gcacttcgta tgtttacaag aatggtacag aaactgagga ctgtttctgg
 661 taccttaatg ctctggaggc tagcgtttcc tatttctccc acgaactcgg ctttaaggtg
 721 gtgttaagac aagataagga gtttcaggat atcttaatgg accacaacag gaaaagcaat
 781 gtgattatta tgtgtggtgg tccagagttc ctctacaagc tgaagggtga ccgagcagtg
 841 gctgaagaca ttgtcattat tctagtggat cttttcaatg accagtactt ggaggacaat
 901 gtcacagccc ctgactatat gaaaaatgtc cttgttctga cgctgtctcc tgggaattcc
 961 cttctaaata gctctttctc caggaatcta tcaccaacaa aacgagactt tgctcttgcc
1021 tatttgaatg gaatcctgct ctttggacat atgctgaaga tatttcttga aaatggagaa
1081 aatattacca cccccaaatt tgctcatgct ttcaggaatc tcacttttga agggtatgac
1141 ggtccagtga ccttggatga ctgggggat gttgacagta ccatggtgct tctgtatacc
1201 tctgtggaca ccaagaaata caaggttctt ttgacctatg atacccacgt aaataagacc
1261 tatcctgtgg atatgagccc cacattcact ggaagaact ctaaacttcc taatgatatt
1321 acaggccggg ccctcagat cctgatgatt gcagtcttca ccctcactgg agctgtggtg
1381 ctgctcctgc tcgtcgctct cctgatgctc agaaaatata gaaaagatta tgaacttcgt
1441 cagaaaaaat ggtcccacat tcctcctgaa aatatctttc ctctggagac caatgagacc
1501 aatcatgtta gcctcaagat cgatgatgac aaaagacgag atacaatcca gagactacga
1561 cagtgcaaat acgacaaaaa gcgagtgatt ctcaaagatc tcaagcacaa tgatggtaat
1621 ttcactgaaa aacagaagat agaattgaac aagttgcttc agattgacta ttacaacctg
1681 accaagttct acggcacagt gaaacttgat accatgatct tcggggtgat agaatactgt
1741 gagagaggat ccctccggga agttttaaat gacacaattt cctaccctga tggcacattc
1801 atggattggg agtttaagat ctctgtcttg tatgacattg ctaagggaat gtcatatctg
1861 cactccagta agacagaagt ccatggtcgt ctgaaatcta ccaactgcgt agtggacagt
1921 agaatggtgg tgaagatcac tgattttggc tgcaattcca ttttacctcc aaaaaaggac
1981 ctgtggacag ctccagagca cctccgccaa gccaacatct ctcagaaagg agatgtgtac
2041 agctatggga tcatcgcaca ggagatcatt ctgcggaaag aaaccttcta cactttgagc
2101 tgtcggacc ggaatgagaa gattttcaga gtggaaaatt ccaatggaat gaaacccttc
2161 cgcccagatt tattcttgga aacagcagag gaaaagagc tagaagtgta cctacttgta
2221 aaaaactgtt gggaggaaga tccagaaaag agaccagatt tcaaaaaaat tgagactaca
2281 cttgccaaga tatttggact ttttcatgac caaaaaatg aaagctatat ggatacctg
2341 atccgacgtc tacagctata ttctcgaaac ctggaacatc tggtagagga aaggacacag
2401 ctgtacaagg cagagaggga cagggctgac agacttaact ttatgttgct tccaaggcta
2461 gtggtaaagt ctctgaagga gaaaggcttt gtggagccgg aactatatga ggaagttaca
2521 atctacttca gtgacattgt aggtttcact actatctgca aatacagcac ccccatggaa
2581 gtggtggaca tgcttaatga catctataag agttttgacc acattgttga tcatcatgat
2641 gtctacaagg tggaaaccat cggtgatgcg tacatggtgg ctagtggttt gcctaagaga
2701 aatggcaatc ggcatgcaat agacattgcc aagatggcct tggaaatcct cagcttcatg
2761 gggacctttg agctggagca tcttcctggc ctcccaatat ggattcgcat ggagttcac
2821 tctggtccct gtgctgctgg agttgtggga atcaagatgc ctcgttattg tctatttgga
```

APPENDIX-continued

Nucleotide Sequences for HDACi Compound Resistance Biomarker Genes

```
2881 gatacggtca acacagcctc taggatggaa tccactggcc tcccttgag aattcacgtg
2941 agtggctcca ccatagccat cctgaagaga actgagtgcc agttcctta tgaagtgaga
3001 ggagaaacat acttaaaggg aagaggaaat gagactacct actggctgac tgggatgaag
3061 gaccagaaat tcaacctgcc aaccctcct actgtggaga atcaacagcg tttgcaagca
3121 gaattttcag acatgattgc caactcttta cagaaaagac aggcagcagg gataagaagc
3181 caaaaaccca gacgggtagc cagctataaa aaaggcactc tggaatactt gcagctgaat
3241 accacagaca aggagagcac ctattttaa acctaaatga ggtataagga ctcacacaaa
3301 ttaaaataca gctgcactga ggcagcgacc tcaagtgtcc tgaaagctta cattttcctg
3361 agacctcaat gaagcagaaa tgtacttagg cttggctgcc ctgtctggaa catggacttt
3421 cttgcatgaa tcagatgtgt gttctcagtg aaataactac cttccactct ggaaccttat
3481 tccagcagtt gttccaggga gcttctacct ggaaaagaaa agaaatgaat agactatcta
3541 gaacttgaga agattttatt cttatttcat ttatttttg tttgtttatt tttatcgttt
3601 ttgtttactg gctttccttc tgtattcata agattttta aattgtcata attatatttt
3661 aaatacccat cttcattaaa gtatatttaa ctcataattt ttgcagaaaa tatgctatat
3721 attaggcaag aataaaagct aaagg
```

| Gene Name | Gene Symbol | GenBank Accession # | SEQ ID NO |
|---|---|---|---|
| transmembrane 4 superfamily member 4 | TM4SF4 | NM_004617 | 22 |

```
   1 cttcaggtca gggagaatgt ataaatgtcc attgccatcg aggttctgct attttgaga
  61 agctgaagca actccaagga cacagttcac agaaatttgg ttctcagccc caaaatactg
 121 attgaattgg agacaattac aaggactctc tggccaaaaa cccttgaaga ggccccgtga
 181 aggaggcagt gaggagcttt tgattgctga cctgtgtcgt accacccag aatgtgcact
 241 gggggctgtg ccagatgcct ggggggggacc ctcattcccc ttgctttttt tggcttcctg
 301 gctaacatcc tgttattttt tcctggagga aaagtgatag atgacaacga ccacctttcc
 361 caagagatct ggttttcgg aggaatatta ggaagcggtg tcttgatgat cttccctgcg
 421 ctggtgttct tgggcctgaa gaacaatgac tgctgtgggt gctgcggcaa cgagggctgt
 481 gggaagcgat tgcgatgtt cacctccacg atatttgctg tggttggatt cttgggagct
 541 ggatactcgt ttatcatctc agccatttca atcaacaagg gtcctaaatg cctcatggcc
 601 aatagtacat ggggctaccc cttccacgac ggggattatc tcaatgatga ggccttatgg
 661 aacaagtgcc gagagcctct caatgtggtt ccctggaatc tgaccctctt ctccatcctg
 721 ctggtcgtag gaggaatcca gatggttctc tgcgccatcc aggtggtcaa tggcctcctg
 781 gggaccctct gtggggactg ccagtgttgt ggctgctgtg ggggagatgg acccgtttaa
 841 acctccgaga tgagctgctc agactctaca gcatgacgac tacaatttct tttcataaaa
 901 cttcttctct tcttggaatt attaattcct atctgcttcc tagctgataa agcttagaaa
 961 aggcagttat tccttctttc caaccagctt tgctcgagtt agaattttgt tatttcaaa
1021 taaaaaatag tttggccact taacaaattt gatttataaa tctttcaaat tagttccttt
1081 ttagaattta ccaacaggtt caaagcatac ttttcatgat tttttatta caaatgtaaa
1141 atgtataaag tcacatgtac tgccatacta cttctttgta tataaagatg tttatatctt
```

APPENDIX-continued

Nucleotide Sequences for HDACi Compound Resistance Biomarker Genes

```
1201 tggaagtttt acataaatca aggaagaaa gcacatttaa aatgagaaac taagaccaat
1261 ttctgttttt aagaggaaaa agaatgattg atgtatccta agtattgtta tttgttgtct
1321 ttttttgctg ccttgcttga gttgcttgtg actgatcttt tgaggctgtc atcatggcta
1381 gggttctttt atgtatgtta aattaaaacc tgaattcaga ggtaacgt
```

| Gene Name | Gene Symbol | GenBank Accession # | SEQ ID NO |
|---|---|---|---|
| transforming growth factor, alpha | TGFA | NM_003236 | 23 |

```
   1 ctggagagcc tgctgccgc ccgcccgtaa aatggtcccc tcggctggac agctcgccct
  61 gttcgctctg ggtattgtgt tggctgcgtg ccaggccttg gagaacagca cgtccccgct
 121 gagtgcagac ccgcccgtgg ctgcagcagt ggtgtcccat tttaatgact gcccagattc
 181 ccacactcag ttctgcttcc atggaacctg caggtttttg gtgcaggagg acaagccagc
 241 atgtgtctgc cattctgggt acgttggtgc acgctgtgag catgcggacc tcctggccgt
 301 ggtggctgcc agccagaaga agcaggccat caccgccttg gtggtggtct ccatcgtggc
 361 cctggctgtc cttatcatca catgtgtgct gatacactgc tgccaggtcc gaaaacactg
 421 tgagtggtgc cgggccctca tctgccggca cgagaagccc agcgccctcc tgaagggaag
 481 aaccgcttgc tgccactcag aaacagtggt ctgaagagcc cagaggagga gtttggccag
 541 gtggactgtg gcagatcaat aaagaaaggc ttcttcagga cagcactgcc agagatgcct
 601 gggtgtgcca cagaccttcc tacttggcct gtaatcacct gtgcagcctt ttgtgggcct
 661 tcaaaactct gtcaagaact ccgtctgctt ggggttattc agtgtgacct agagaagaaa
 721 tcagcggacc acgatttcaa gacttgttaa aaaagaactg caaagagacg gactcctgtt
 781 cacctaggtg aagtgtgtgc agcagttggt gtctgagtcc acatgtgtgc agttgtcttc
 841 tgccagccat ggattccagg ctatatattt cttttttaatg ggccacctcc ccacaacaga
 901 attctgccca acacaggaga tttctatagt tattgttttc tgtcatttgc ctactgggga
 961 agaaagtgaa ggaggggaaa ctgtttaata tcacatgaag accctagctt taagagaagc
1021 tgtatcctct aaccacgaga ctctcaacca gcccaacatc ttccatggac acatgacatt
1081 gaagaccatc ccaagctatc gccacccttg gagatgatgt cttatttatt agatggataa
1141 tggttttatt tttaatctct taagtcaatg taaaagtat aaaacccctt cagacttcta
1201 cattaatgat gtatgtgttg ctgactgaaa agctatactg attagaaatg tctggcctct
1261 tcaagacagc taaggcttgg gaaaagtctt ccagggtgcg gagatggaac cagaggctgg
1321 gttactggta ggaataaagg taggggttca gaaatggtgc cattgaagcc acaaagccgg
1381 taaatgcctc aatacgttct gggagaaaac ttagcaaatc catcagcagg gatctgtccc
1441 ctctgttggg gagagaggaa gagtgtgtgt gtctacacag gataaaccca atacatattg
1501 tactgctcag tgattaaatg ggttcacttc ctcgtgagcc ctcggtaagt atgtttagaa
1561 atagaacatt agccacgagc cataggcatt tcaggccaaa tccatgaaag ggggaccagt
1621 catttatttt ccatttttgtt gcttggttgg tttgttgctt tattttttaaa aggagaagtt
1681 taactttgct atttatttc gagcactagg aaaactattc cagtaatttt tttttcctca
1741 tttccattca ggatgccggc tttattaaca aaaactctaa caagtcacct ccactatgtg
1801 ggtcttcctt tccctcaag agaaggagca attgttcccc tgacatctgg gtccatctga
```

APPENDIX-continued

Nucleotide Sequences for HDACi Compound Resistance Biomarker Genes

```
1861 cccatggggc ctgcctgtga gaaacagtgg gtcccttcaa atacatagtg gatagctcat
1921 ccctaggaat tttcattaaa atttggaaac agagtaatga agaaataata tataaactcc
1981 ttatgtgagg aaatgctact aatatctgaa aagtgaaaga tttctatgta ttaactctta
2041 agtgcaccta gcttattaca tcgtgaaagg tacatttaaa atatgttaaa ttggcttgaa
2101 attttcagag aattttgtct tcccctaatt cttcttcctt ggtctggaag aacaatttct
2161 atgaattttc tctttatttt ttttttataa ttcagacaat tctatgaccc gtgtcttcat
2221 ttttggcact cttatttaac aatgccacac ctgaagcact tggatctgtt cagagctgac
2281 cccctagcaa cgtagttgac acagctccag gttttttaaat tactaaaata agttcaagtt
2341 tacatccctt gggccagata tgtgggttga ggcttgactg tagcatcctg cttagagacc
2401 aatcaatgga cactggtttt tagacctcta tcaatcagta gttagcatcc aagagacttt
2461 gcagaggcgt aggaatgagg ctggacagat ggcggaacga gaggttccct gcgaagactt
2521 gagatttagt gtctgtgaat gttctagttc ctaggtccag caagtcacac ctgccagtgc
2581 cctcatcctt atgcctgtaa cacacatgca gtgagaggcc tcacatatac gcctccctag
2641 aagtgccttc caagtcagtc ctttggaaac cagcaggtct gaaaagagg ctgcatcaat
2701 gcaagcctgg ttggaccatt gtccatgcct caggatagaa cagcctggct tatttgggga
2761 ttttcttct agaaatcaaa tgactgataa gcattggctc cctctgccat ttaatggcaa
2821 tggtagtctt tggttagctg caaaaatact ccatttcaag ttaaaaatgc atcttctaat
2881 ccatctctgc aagctccctg tgtttccttg ccctttagaa aatgaattgt tcactacaat
2941 tagagaatca tttaacatcc tgacctggta agctgccaca cacctggcag tggggagcat
3001 cgctgtttcc aatggctcag gagacaatga aaagccccca tttaaaaaa taacaaacat
3061 tttttaaaag gcctccaata ctcttatgga gcctggattt ttcccactgc tctacaggct
3121 gtgactttt ttaagcatcc tgacaggaaa tgttttcttc tacatggaaa gatagacagc
3181 agccaaccct gatctggaag acagggcccc ggctggacac acgtggaacc aagccaggga
3241 tgggctggcc attgtgtccc cgcaggagag atgggcagaa tggccctaga gttctttcc
3301 ctgagaaagg agaaaaagat gggattgcca ctcacccacc cacactggta agggaggaga
3361 atttgtgctt ctggagcttc tcaagggatt gtgttttgca ggtacagaaa actgcctgtt
3421 atcttcaagc caggttttcg agggcacatg ggtcaccagt tgcttttttca gtcaatttgg
3481 ccgggatgga ctaatgaggc tctaacactg ctcaggagac ccctgccctc tagttggttc
3541 tgggctttga tctcttccaa cctgcccagt cacagaagga ggaatgactc aaatgcccaa
3601 aaccaagaac acattgcaga agtaagacaa acatgtatat ttttaaatgt tctaacataa
3661 gacctgttct ctctagccat tgatttacca ggctttctga aagatctagt ggttcacaca
3721 gagagagaga gagtactgaa aaagcaactc ctccttcttag tcttaataat ttactaaaat
3781 ggtcaacttt tcattatctt tattataata aacctgatgc ttttttttag aactccttac
3841 tctgatgtct gtatatgttg cactgaaaag gttaatattt aatgttttaa tttattttgt
3901 gtggtaagtt aattttgatt tctgtaatgt gttaatgtga ttagcagtta ttttccttaa
3961 tatctgaatt atacttaaag agtagtgagc aatataagac gcaattgtgt ttttcagtaa
4021 tgtgcattgt tattgagttg tactgtacct tatttggaag gatgaaggaa tgaacctttt
4081 tttcctaaaa
```

APPENDIX-continued

Nucleotide Sequences for HDACi Compound Resistance Biomarker Genes

| Gene Name | Gene Symbol | GenBank Accession # | SEQ ID NO |
|---|---|---|---|
| fibroblast growth factor binding protein 1 | FGFBP1 | NM_005130 | 24 |

```
   1 gaatagtcta ccccccttgc actctacctg acacagctgc agcctgcaat tcactcgcac
  61 tgcctgggat tgcactggat ccgtgtgctc agaacaaggt gaacgcccag ctgcagccat
 121 gaagatctgt agcctcaccc tgctctcctt cctcctactg gctgtcagg tgctcctggt
 181 ggagggaaa aaaaaagtga agaatggact tcacagcaaa gtggtctcag aacaaaagga
 241 cactctgggc aacacccaga ttaagcagaa aagcaggccc gggaacaaag gcaagtttgt
 301 caccaaagac caagccaact gcagatgggc tgctactgag caggaggagg gcatctctct
 361 caaggttgag tgcactcaat tggaccatga attttcctgt gtctttgctg caatccaac
 421 ctcatgccta aagctcaagg atgagagagt ctattggaaa caagttgccc ggaatctgcg
 481 ctcacagaaa gacatctgta gatattccaa gacagctgtg aaaaccagag tgtgcagaaa
 541 ggattttcca gaatccagtc ttaagctagt cagctccact ctatttggga acacaaagcc
 601 caggaaggag aaaacagaga tgtcccccag ggagcacatc aaaggcaaag agaccacccc
 661 ctctagccta gcagtgaccc agaccatggc caccaaagct cccgagtgtg tggaggaccc
 721 agatatggca aaccagagga agactgccct ggagttctgt ggagagactt ggagctctct
 781 ctgcacattc ttcctcagca tagtgcagga cacgtcatgc taatgaggtc aaaagagaac
 841 gggttccctt aagagatgtc atgtcgtaag tccctctgta tactttaaag ctctctacag
 901 tccccccaaa atatgaactt ttgtgcttag tgagtgcaac gaaatattta aacaagtttt
 961 gtatttttg cttttgtgtt ttggaatttg ccttattttt cttggatgcg atgttcagag
1021 gctgtttcct gcagcatgta tttccatggc ccacacagct atgtgtttga gcagcgaaga
1081 gtctttgagc tgaatgagcc agagtgataa tttcagtgca acgaactttc tgctgaatta
1141 atggtaataa aactctgggt gttttcaga aatacattca
```

| Gene Name | Gene Symbol | GenBank Accession # | SEQ ID NO |
|---|---|---|---|
| PTK6 protein tyrosine kinase 6 | PTK6 | NM_005975 | 25 |

```
   1 gctgggccac agcctggtcc tgccgctgcg cccgcccgcc atggtgtccc gggaccaggc
  61 tcacctgggc cccaagtatg tgggcctctg ggacttcaag tcccggacgg acgaggagct
 121 gagcttccgc gcggggacg tcttccacgt ggccaggaag gaggagcagt ggtggtgggc
 181 cacgctgctg gacgaggcgg gtgggccgt ggcccagggc tatgtgcccc acaactacct
 241 ggccgagagg gagacggtgg agtcggaacc gtggttcttt ggctgcatct cccgctcgga
 301 agctgtgcgt cggctgcagg ccgagggcaa cgccacgggc gccttcctga tcagggtcag
 361 cgagaagccg agtgccgact acgtcctgtc ggtgcgggac acgcaggctg tgcggcacta
 421 caagatctgg cggcgtgccg ggggccggct gcacctgaac gaggcggtgt ccttcctcag
 481 cctgcccgag cttgtgaact accacaggg ccagagcctg tcccacgcc tgcggctggc
 541 cgcgcccctgc cggaagcacg agcctgagcc cctgcccat tgggatgact gggagaggcc
 601 gagggaggag ttcacgctct gcaggaagct ggggtccggc tacttggggg aggtcttcga
 661 ggggctctgg aaagaccggg tccaggtggc cattaaggtg atttctcgag acaacctcct
```

APPENDIX-continued

Nucleotide Sequences for HDACi Compound Resistance Biomarker Genes

```
 721 gcaccagcag atgctgcagt cggagatcca ggccatgaag aagctgcggc acaaacacat
 781 cctggcgctg tacgccgtgg tgtccgtggg ggacccgtg tacatcatca cggagctcat
 841 ggccaagggc agcctgctgg agctgctccg cgactctgat gagaaagtcc tgcccgtttc
 901 ggagctgctg acatcgcct ggcaggtggc tgagggcatg tgttacctgg agtcgcagaa
 961 ttacatccac cgggacctgg ccgccaggaa catcctcgtc ggggaaaaca ccctctgcaa
1021 agttggggac ttcgggttag ccaggcttat caaggaggac gtctacctct cccatgacca
1081 caatatcccc tacaagtgga cggcccctga agcgctctcc cgaggccatt actccaccaa
1141 atccgacgtc tggtcctttg ggattctcct gcatgagatg ttcagcaggg gtcaggtgcc
1201 ctacccaggc atgtccaacc atgaggcctt cctgagggtg gacgccggct accgcatgcc
1261 ctgccctctg gagtgcccgc ccagcgtgca aagctgatg ctgacatgct ggtgcaggga
1321 ccccgagcag agaccctgct tcaaggccct gcgggagagg ctctccagct tcaccagcta
1381 cgagaacccg acctgagctg ctgtggagcg ggcatggccg ggccctgctg aggaggggcc
1441 tgggcagagg gcctggacct gggatcaagg cccacgcgct tccctggggt ttactgaggt
1501 gatgggtgca ggaaaggttc acaaatgtgg agtgtctgcg tccaatacac gcgtgtgctc
1561 ctctccttac tccatcgtgt gtgccttggg tctcagctgc tgacacgcag cctgctctgg
1621 agcctgcaga tgagatccgg gagactgaca cgaagccagc agaggtcaga ggggactctg
1681 accacagccc gctctctggc tgtctgtctg cagtgcccgg ctgagggtgg gaggcaaaca
1741 cgccttgttc ctgctcttcc cagttcagct tggtgggaga aagtcattcg cgtggctcgg
1801 gacgctcatg taaatttggt tttggtgctc aagggttctt tcctcccagg ggcaggtgtt
1861 tctttcctgt ttgtcttgtg tcttgagagc ttggccttat gaccagtgag aactctctcc
1921 ctggtctctg ccagcccaag catcactgcc cgaggcgcca gctcagtttc accgtccacg
1981 tccacaaggg gcttttccca ccttcaccct tgtcgctggg tcagtgctgg aaagcgcccc
2041 tcactcctgc gctgacaagg gcccttctct actgtctgtg gggtggttcc gggctggggg
2101 ggctgcctcc tttgcacctg attttgaagg tgtctctttc atccatggtt aagtcataaa
2161 aagcttattg gttttggttt tgactcacct gaaagttttt ttggtttaaa agaagaatag
2221 gcggggcacg gtggctcatg cctgtaatcc cagcactttg ggaggctgag gcaggtggat
2281 cacgaggtca ggagatcgac accatcctgg ctaacacggt gaaaccccgt ctctactaaa
2341 aaatacaaaa aattagctgg gtgtggtggt gggggtgggc gcctgtagtc ccagctacgt
2401 gggaggctga ggcagcagac tggtgtgaac ccgggaggtg gagcttgcag tgagccgaga
2461 tcgcgccact gcactccagc ctgggcgaca gagcgagact ccatctcaaa
```

| Gene Name | Gene Symbol | GenBank Accession # | SEQ ID NO |
|---|---|---|---|
| epithelial V-like antigen 1 | EVA1 | NM_005797 | 26 |

```
  1 acaggcacag gtgaggaact caactcaaac tcctctctct gggaaaacgc ggtgcttgct
 61 cctcccggag tggccttggc agggtgttgg agccctcggt ctgccccgtc cggtctctgg
121 ggccaaggct gggtttccct catgtatggc aagagctcta ctcgtgcggt gcttcttctc
181 cttggcatac agctcacagc tctttggcct atagcagctg tggaaattta tacctcccgg
241 gtgctggagg ctgttaatgg gacagatgct cggttaaaat gcactttctc cagctttgcc
```

APPENDIX-continued

Nucleotide Sequences for HDACi Compound Resistance Biomarker Genes

```
 301 cctgtgggtg atgctctaac agtgacctgg aattttcgtc ctctagacgg gggacctgag
 361 cagtttgtat tctactacca catagatccc ttccaaccca tgagtgggcg gtttaaggac
 421 cgggtgtctt gggatgggaa tcctgagcgg tacgatgcct ccatccttct ctggaaactg
 481 cagttcgacg acaatgggac atacacctgc caggtgaaga acccacctga tgttgatggg
 541 gtgatagggg agatccggct cagcgtcgtg cacactgtac gcttctctga gatccacttc
 601 ctggctctgg ccattggctc tgcctgtgca ctgatgatca taatagtaat tgtagtggtc
 661 ctcttccagc attaccggaa aaagcgatgg gccgaaagag ctcataaagt ggtgagata
 721 aaatcaaaag aagaggaaag gctcaaccaa gagaaaaagg tctctgttta tttagaagac
 781 acagactaac aattttagat ggaagctgag atgatttcca agaacaagaa ccctagtatt
 841 tcttgaagtt aatggaaact tttctttggc ttttccagtt gtgacccgtt ttccaaccag
 901 ttctgcagca tattagattc tagacaagca acacccctct ggagccagca cagtgctcct
 961 ccatatcacc agtcatacac agcctcatta ttaaggtctt atttaatttc agagtgtaaa
1021 tttttttcaag tgctcattag gttttataaa caagaagcta cattttttgcc cttaagacac
1081 tacttacagt gttatgactt gtatacacat atattggtat caaaagggat aaaagccaat
1141 ttgtctgtta catttccttt cacgtatttc ttttagcagc acttctgcta ctaaagttaa
1201 tgtgtttact ctctttcctt cccacattct caattaaaag gtgagctaag cctcctcggt
1261 gtttctgatt aacagtaaat cctaaattca aactgttaaa tgacattttt atttttatgt
1321 ctctccttaa ctatgagaca catcttgttt tactgaattt ctttcaatat tccaggtgat
1381 agatttttgt tgttttgtta attaatccaa gatttacaat agcacaacgc taaatcacac
1441 agtaactaca aaaggttaca tagatatgaa aagattggca gaggccattg caggatgaat
1501 cacttgtcac ttttcttctg tgctgggaaa ataatcaac aatgtgggtc tttcatgagc
1561 agtgacggat agtttagctt actatgtttc cccccaatt caatgatcta taacaacaga
1621 gcaaagtcta tgctcatttg cagactggaa tcattaagta atttaataaa aaaattgtga
1681 aacagcatat tacaagtttg aaaattcagg gctggtgaaa aaaatcaact ctaaatgatg
1741 ataatttttgt acagttttat ataaaactct gagaactaga agaaattatt aacttttttt
1801 cttttttaat tctaattcac ttgtttattt tggggaggga agactttggt atggagcaaa
1861 gaaataccaa aactacttta aatggaataa aaccaacttt attcttttttt tcccccatac
1921 tggtagataa agcaaacttt ataagtgggc tattgaaaga aaagttacaa gcttaagata
1981 cagaagcatt tgttcaaagg atagaaagca tctaaaagtt taggctcaag atcaatcttt
2041 acagattgat attttcagtt tttaatcgac tggactgcag atgttttttc ttttaacaaa
2101 ctggaatttt caaacagatt atctgtattt aaatgtatag accttgatat ttttccaata
2161 ctattttta aaaaattgta tgatttacat atgaacctca gttctgaaat tcattacata
2221 tctgtctcat tctgccttt atactgtcta aaaaagcaaa gttttaaagt gcaattttaa
2281 aactgtaaat tacatctgaa ggctatatat cctttaatca catttttatat ttttcttca
2341 caattctaac ctttgaaaat attataactg gatatttctt caaacagatg tcctggatga
2401 tggtccataa gaataatgaa gaagtagtta aaaatgtatg gacagttttt ccggcaaaat
2461 ttgtagctta tgtcttggct aaatagtcaa ggggtaatat gggcctgttg tttagtgtct
```

APPENDIX-continued

Nucleotide Sequences for HDACi Compound Resistance Biomarker Genes

```
2521 ccttcctaaa gagcactttt gtattgtaat ttattttta ttatgcttta aacactatgt
2581 aaataaacct ttagtaataa agaattatca gttataaaaa
```

| Gene Name | Gene Symbol | GenBank Accession # | SEQ ID NO |
|---|---|---|---|
| EPH receptor A2 | EPHA2 | NM_004431 | 27 |

```
   1 attaaggact cggggcagga ggggcagaag ttgcgcgcag gccggcgggc gggagcggac
  61 accgaggccg gcgtgcaggc gtgcgggtgt gcgggagccg ggctcggggg gatcggaccg
 121 agagcgagaa gcgcggcatg gagctccagg cagcccgcgc ctgcttcgcc ctgctgtggg
 181 gctgtgcgct ggccgcggcc gcggcggcgc agggcaagga agtggtactg ctggactttg
 241 ctgcagctgg aggggagctc ggctggctca cacaccgta tggcaaaggg tgggacctga
 301 tgcagaacat catgaatgac atgccgatct acatgtactc cgtgtgcaac gtgatgtctg
 361 gcgaccagga caactggctc cgcaccaact gggtgtaccg aggagaggct gagcgtatct
 421 tcattgagct caagtttact gtacgtgact gcaacagctt ccctggtggc gccagctcct
 481 gcaaggagac tttcaacctc tactatgccg agtcggacct ggactacggc accaacttcc
 541 agaagcgcct gttcaccaag attgacacca ttgcgcccga tgagatcacc gtcagcagcg
 601 acttcgaggc acgccacgtg aagctgaacg tggaggagcg ctccgtgggg ccgctcaccc
 661 gcaaaggctt ctacctggcc ttccaggata tcggtgcctg tgtggcgctg ctctccgtcc
 721 gtgtctacta caagaagtgc cccgagctgc tgcagggcct ggcccacttc cctgagacca
 781 tcgccggctc tgatgcacct tccctggcca ctgtggccgg cacctgtgtg accatgccg
 841 tggtgccacc gggggggtgaa gagccccgta tgcactgtgc agtggatggc gagtggctgg
 901 tgcccattgg gcagtgcctg tgccaggcag gctacgagaa ggtggaggat gcctgccagg
 961 cctgctcgcc tggatttttt aagtttgagg catctgagag ccctgcttg gagtgccctg
1021 agcacacgct gccatcccct gagggtgcca cctcctgcga gtgtgaggaa ggcttcttcc
1081 gggcacctca ggacccagcg tcgatgcctt gcacacgacc cccctccgcc ccacactacc
1141 tcacagccgt gggcatgggt gccaaggtgg agctgcgctg gacgcccct caggacagcg
1201 ggggccgcga ggacattgtc tacagcgtca cctgcgaaca gtgctggccc gagtctgggg
1261 aatgcgggcc gtgtgaggcc agtgtgcgct actcggagcc tcctcacgga ctgacccgca
1321 ccagtgtgac agtgagcgac ctggagcccc acatgaacta caccttcacc gtggaggccc
1381 gcaatggcgt ctcaggcctg gtaaccagcc gcagcttccg tactgccagt gtcagcatca
1441 accagacaga gccccccaag gtgaggctgg agggccgcag caccacctcg cttagcgtct
1501 cctggagcat ccccccgccg cagcagagcc gagtgtggaa gtacgaggtc acttaccgca
1561 agaagggaga ctccaacagc tacaatgtgc gccgcaccga gggtttctcc gtgaccctgg
1621 acgacctggc cccagacacc acctacctgg tccaggtgca ggcactgacg caggagggcc
1681 agggggccgg cagcaaggtg cacgaattcc agacgctgtc cccggaggga tctggcaact
1741 tggcggtgat tggcggcgtg gctgtcggtg tggtcctgct tctggtgctg gcaggagttg
1801 gcttctttat ccaccgcagg aggaagaacc agcgtgcccg ccagtccccg gaggacgttt
1861 acttctccaa gtcagaacaa ctgaagcccc tgaagacata cgtggacccc cacacatatg
1921 aggaccccaa ccaggctgtg ttgaagttca ctaccgagat ccatccatcc tgtgtcactc
1981 ggcagaaggt gatcggagca ggagagtttg gggaggtgta caagggcatg ctgaagacat
```

APPENDIX-continued

Nucleotide Sequences for HDACi Compound Resistance Biomarker Genes

```
2041 cctcggggaa gaaggaggtg ccggtggcca tcaagacgct gaaagccggc tacacagaga
2101 agcagcgagt ggacttcctc ggcgaggccg gcatcatggg ccagttcagc caccacaaca
2161 tcatccgcct agagggcgtc atctccaaat acaagcccat gatgatcatc actgagtaca
2221 tggagaatgg ggccctggac aagttccttc gggagaagga tggcgagttc agcgtgctgc
2281 agctggtggg catgctgcgg ggcatcgcag ctggcatgaa gtacctggcc aacatgaact
2341 atgtgcaccg tgacctggct gcccgcaaca tcctcgtcaa cagcaacctg gtctgcaagg
2401 tgtctgactt tggcctgtcc cgcgtgctgg aggacgaccc cgaggccacc tacaccacca
2461 gtggcggcaa gatccccatc cgctggaccg ccccggaggc catttcctac cggaagttca
2521 cctctgccag cgacgtgtgg agctttggca ttgtcatgtg ggaggtgatg acctatggcg
2581 agcggcccta ctgggagttg tccaaccacg aggtgatgaa agccatcaat gatggcttcc
2641 ggctccccac acccatggac tgcccctccg ccatctacca gctcatgatg cagtgctggc
2701 agcaggagcg tgcccgccgc cccaagttcg ctgacatcgt cagcatcctg gacaagctca
2761 ttcgtgcccc tgactccctc aagaccctgg ctgactttga ccccgcgtg tctatccggc
2821 tccccagcac gagcggctcg gagggggtgc ccttccgcac ggtgtccgag tggctggagt
2881 ccatcaagat gcagcagtat acggagcact tcatggcggc cggctacact gccatcgaga
2941 aggtggtgca gatgaccaac gacgacatca gaggattgg ggtgcggctg cccggccacc
3001 agaagcgcat cgcctacagc ctgctgggac tcaaggacca ggtgaacact gtggggatcc
3061 ccatctgagc ctcgacaggg cctggagccc catcggccaa gaatacttga agaaacagag
3121 tggcctccct gctgtgccat gctgggccac tggggacttt atttatttct agttctttcc
3181 tccccctgca acttccgctg aggggtctcg gatgacaccc tggcctgaac tgaggagatg
3241 accagggatg ctgggctggg ccctctttcc ctgcgagacg cacacagctg agcacttagc
3301 aggcaccgcc acgtcccagc atccctggag caggagcccc gccacagcct cggacagac
3361 atataggata ttcccaagcc gaccttccct ccgccttctc ccacatgagg ccatctcagg
3421 agatggaggg cttggcccag cgccaagtaa acagggtacc tcaagcccca tttcctcaca
3481 ctaagagggc agactgtgaa cttgactggg tgagacccaa agcggtccct gtccctctag
3541 tgccttcttt agaccctcgg gccccatcct catccctgac tggccaaacc cttgctttcc
3601 tgggcctttg caagatgctt ggttgtgttg aggttttaa atatatattt tgtactttgt
3661 ggagagaatg tgtgtgtgtg gcaggggcc ccgccagggc tggggacaga gggtgtcaaa
3721 cattcgtgag ctggggactc agggaccggt gctgcaggag tgtcctgccc atgccccagt
3781 cggccccatc tctcatcctt ttggataagt ttctattctg tcagtgttaa agattttgtt
3841 ttgttggaca ttttttttcga atcttaattt attatttttt ttatatttat tgttagaaaa
3901 tgacttattt ctgctctgga ataaagttgc agatgattca aaccgaaaaa
```

| Gene Name | Gene Symbol | GenBank Accession # | SEQ ID NO |
|---|---|---|---|
| integrin, alpha 6 | ITGA6 | NM_000210 | 28 |

```
   1 aacgggctca ttcagcggtc gcgagctgcc cgcgaggggg agcggccgga cggagagcgc
  61 gacccgtccc gggggtgggg ccgggcgcag cggcgagagg aggcgaaggt ggctgcggta
 121 gcagcagcgc ggcagcctcg gacccagccc ggagcgcagg gcggccgctg caggtccccg
 181 ctcccctccc cgtgcgtccg cccatggccg ccgccgggca gctgtgcttg ctctacctgt
```

APPENDIX-continued

Nucleotide Sequences for HDACi Compound Resistance Biomarker Genes

```
 241 cggcggggct cctgtcccgg ctcggcgcag ccttcaactt ggacactcgg gaggacaacg
 301 tgatccggaa atatggagac cccgggagcc tcttcggctt ctcgctggcc atgcactggc
 361 aactgcagcc cgaggacaag cggctgttgc tcgtgggggc cccgcgggca gaagcgcttc
 421 cactgcagag agccaacaga acgggagggc tgtacagctg cgacatcacc gcccgggggc
 481 catgcacgcg gatcgagttt gataacgatg ctgaccccac gtcagaaagc aaggaagatc
 541 agtggatggg ggtcaccgtc cagagccaag gtccaggggg caaggtcgtg acatgtgctc
 601 accgatatga aaaaggcag catgttaata cgaagcagga atcccgagac atctttgggc
 661 ggtgttatgt cctgagtcag aatctcagga ttgaagacga tatggatggg ggagattgga
 721 gcttttgtga tgggcgattg agaggccatg agaaatttgg ctcttgccag caaggtgtag
 781 cagctacttt tactaaagac tttcattaca ttgtatttgg agcccgggt acttataact
 841 ggaaagggat tgttcgtgta gagcaaaaga ataacacttt ttttgacatg aacatctttg
 901 aagatgggcc ttatgaagtt ggtggagaga ctgagcatga tgaaagtctc gttcctgttc
 961 ctgctaacag ttacttaggt ttttctttgg actcagggaa aggtattgtt tctaaagatg
1021 agatcacttt tgtatctggt gctcccagag ccaatcacag tggagccgtg gttttgctga
1081 agagagacat gaagtctgca catctcctcc ctgagcacat attcgatgga gaaggtctgg
1141 cctcttcatt tggctatgat gtggcggtgg tggacctcaa caaggatggg tggcaagata
1201 tagttattgg agcccacag tattttgata gagatggaga agttggaggt gcagtgtatg
1261 tctacatgaa ccagcaaggc agatggaata atgtgaagcc aattcgtctt aatggaacca
1321 aagattctat gtttggcatt gcagtaaaaa atattggaga tattaatcaa gatggctacc
1381 cagatattgc agttggagct ccgtatgatg acttgggaaa ggttttatc tatcatggat
1441 ctgcaaatgg aataaatacc aaaccaacac aggttctcaa gggtatatca ccttatttg
1501 gatattcaat tgctggaaac atggaccttg atcgaaattc ctaccctgat gttgctgttg
1561 gttccctctc agattcagta actattttca gatcccggcc tgtgattaat attcagaaaa
1621 ccatcacagt aactcctaac agaattgacc tccgccagaa acagcgtgt ggggcgccta
1681 gtgggatatg cctccaggtt aaatcctgtt ttgaatatac tgctaacccc gctggttata
1741 atccttcaat atcaattgtg ggcacacttg aagctgaaaa agaaagaaga aaatctgggc
1801 tatcctcaag agttcagttt cgaaaccaag gttctgagcc caaatatact caagaactaa
1861 ctctgaagag gcagaaacag aaagtgtgca tggaggaaac cctgtggcta caggataata
1921 tcagagataa actgcgtccc attcccataa ctgcctcagt ggagatccaa gagccaagct
1981 ctcgtaggcg agtgaattca cttccagaag ttcttccaat tctgaattca gatgaaccca
2041 agacagctca tattgatgtt cacttcttaa aagagggatg tggagacgac aatgtatgta
2101 acagcaacct taaactagaa tataaatttt gcacccgaga aggaaatcaa gacaaatttt
2161 cttatttacc aattcaaaaa ggtgtaccag aactagttct aaaagatcag aaggatattg
2221 ctttagaaat aacagtgaca aacagcccct tccaacccaag gaatcccaca aaagatggcg
2281 atgacgccca tgaggctaaa ctgattgcaa cgtttccaga cactttaacc tattctgcat
2341 atagagaact gagggctttc cctgagaaac agttgagttg tgttgccaac cagaatggct
2401 cgcaagctga ctgtgagctc ggaaatcctt ttaaaagaaa ttcaaatgtc acttttatt
2461 tggtttaag tacaactgaa gtcacccttg acaccccaga tctggatatt aatctgaagt
```

APPENDIX-continued

Nucleotide Sequences for HDACi Compound Resistance Biomarker Genes

```
2521 tagaaacaac aagcaatcaa gataatttgg ctccaattac agctaaagca aaagtggtta
2581 ttgaactgct tttatcggtc tcgggagttg ctaaaccttc ccaggtgtat tttggaggta
2641 cagttgttgg cgagcaagct atgaaatctg aagatgaagt gggaagttta atagagtatg
2701 aattcagggt aataaactta ggtaaacctc ttacaaacct cggcacagca accttgaaca
2761 ttcagtggcc aaaagaaatt agcaatggga atggttgct ttatttggtg aaagtagaat
2821 ccaaaggatt ggaaaggta acttgtgagc cacaaaagga gataaactcc ctgaacctaa
2881 cggagtctca caactcaaga aagaaacggg aaattactga aaaacagata gatgataaca
2941 gaaaattttc tttatttgct gaaagaaaat accagactct taactgtagc gtgaacgtga
3001 actgtgtgaa catcagatgc ccgctgcggg ggctggacag caaggcgtct cttattttgc
3061 gctcgaggtt atggaacagc acatttctag aggaatattc caaactgaac tacttggaca
3121 ttctcatgcg agccttcatt gatgtgactg ctgctgccga aaatatcagg ctgccaaatg
3181 caggcactca ggttcgagtg actgtgtttc cctcaaagac tgtagctcag tattcgggag
3241 taccttggtg gatcatccta gtggctattc tcgctgggat cttgatgctt gctttattag
3301 tgtttatact atggaagtgt ggtttcttca agagaaataa gaaagatcat tatgatgcca
3361 catatcacaa ggctgagatc catgctcagc catctgataa agagaggctt acttctgatg
3421 catagtattg atctacttct gtaattgtgt ggattcttta aacgctctag gtacgatgac
3481 agtgttcccc gataccatgc tgtaaggatc cggaaagaag agcgagagat caaagatgaa
3541 aagtatattg ataaccttga aaaaaaacag tggatcacaa agtggaacga aaatgaaagc
3601 tactcatagc gggggcctaa aaaaaaaaag cttcacagta cccaaactgc tttttccaac
3661 tcagaaattc aatttggatt taaaagcctg ctcaatccct gaggactgat ttcagagtga
3721 ctacacacag tacgaaccta cagtttaac tgtggatatt gttacgtagc ctaaggctcc
3781 tgttttgcac agccaaattt aaaactgttg gaatggattt ttctttaact gccgtaattt
3841 aactttctgg gttgccttta tttttggcgt ggctgactta catcatgtgt tgggaaggg
3901 cctgcccagt tgcactcagg tgacatcctc cagatagtgt agctgaggag gcacctacac
3961 tcacctgcac taacagagtg gccgtcctaa cctcgggcct gctgcgcaga cgtccatcac
4021 gttagctgtc ccacatcaca agactatgcc attggggtag ttgtgtttca acggaaagtg
4081 ctgtcttaaa ctaaatgtgc aatagaaggt gatgttgcca tcctaccgtc ttttcctgtt
4141 tcctagctgt gtgaatacct gctcacgtca aatgcataca agtttcattc tcccttcac
4201 taaaacacac aggtgcaaca gacttgaatg ctagttatac ttatttgtat atggtattta
4261 ttttttcttt tctttacaaa ccattttgtt attgactaac aggccaaaga gtctccagtt
4321 taccctccag gttggtttaa tcaatcagaa ttagagcatg ggaggtcatc actttgacct
4381 aaattattta ctgcaaaaag aaaatcttta taaatgtacc agagagagtt gttttaataa
4441 cttatctata aactataacc tctccttcat gacagcctcc accccacaac ccaaaaggtt
4501 taagaaatag aattataact gtaaagatgt ttatttcagg cattggatat ttttttacttt
4561 agaagcctgc ataatgtttc tggatttcat actgtaacat tcaggaattc ttggagaaaa
4621 tgggtttatt cactgaactc tagtgcggtt tactcactgc tgcaaatact gtatattcag
4681 gacttgaaag aaatggtgaa tgcctatggt ggatccaaac tgatccagta taagactact
4741 gaatctgcta ccaaaacagt taatcagtga gtcgatgttc tatttttttgt tttgtttcct
4801 cccctatctg tattcccaaa aattactttg gggctaattt aacaagaact ttaaattgtg
```

APPENDIX-continued

Nucleotide Sequences for HDACi Compound Resistance Biomarker Genes

```
4861 ttttaattgt aaaaatggca gggggtggaa ttattactct atacattcaa cagagactga
4921 atagatatga aagctgattt tttttaatta ccatgcttca caatgttaag ttatatgggg
4981 agcaacagca aacaggtgct aatttgtttt ggatatagta taagcagtgt ctgtgttttg
5041 aaagaataga acacagtttg tagtgccact gttgttttgg gggggctttt ttcttttcgg
5101 aaatcttaaa ccttaagata ctaaggacgt tgttttggtt gtactttgga attcttagtc
5161 acaaaatata ttttgtttac aaaaatttct gtaaaacagg ttataacagt gtttaaagtc
5221 tcagtttctt gcttggggaa cttgtgtccc taatgtgttt agattgctag attgctaagg
5281 agctgatact ttgacagtgt ttttagacct gtgttactaa aaaaaagatg aatgtcctga
5341 aaagggtgtt gggagggtgg ttcaacaaag aaacaaagat gttatggtgt ttagatttat
5401 ggttgttaaa aatgtcatct caagtcaagt cactggtctg tttgcatttg atacattttt
5461 gtactaacta gcattgtaaa attatttcat gattagaaat tacctgtgga tatttgtata
5521 aaagtgtgaa ataaattttt tataaaagtg ttcattgttt cgtaacacag cattgtatat
5581 gtgaagcaaa ctctaaaatt ataaatgaca acctgaatta tctatttcat caaaccaaag
5641 ttcagtgttt ttattttggg tgtctcatgt aatctcagat cagccaaaga tactagtgcc
5701 aaagcaatgg gattcggggt ttttttctgt tttcgctcta tgtaggtgat cctcaagtct
5761 ttcatttttcc ttctttatga ttaaaagaaa cctacaggta tttaacaacc
```

| Gene Name | Gene Symbol | GenBank Accession # | SEQ ID NO |
|---|---|---|---|
| tumor necrosis factor receptor superfamily, member 21 | TNFRSF21 | NM_014452 | 29 |

```
   1 gccaccacgt gtgtccctgc gcccggtggc caccgactca gtccctcgcc gaccagtctg
  61 ggcagcggag gagggtggtt ggcagtggct ggaagcttcg ctatgggaag ttgttccttt
 121 gctctctcgc gcccagtcct cctccctggt tctcctcagc cgctgtcgga ggagagcacc
 181 cggagacgcg ggctgcagtc gcggcggctt ctccccgcct gggcggccgc gccgctgggc
 241 aggtgctgag cgcccctaga gcctcccttg ccgcctccct cctctgcccg gccgcagcag
 301 tgcacatggg gtgttggagg tagatgggct cccggcccgg gaggcggcgg tggatgcggc
 361 gctgggcaga agcagccgcc gattccagct gccccgcgcg ccccgggcgc ccctgcgagt
 421 ccccggttca gccatgggga cctctccgag cagcagcacc gccctcgcct cctgcagccg
 481 catcgcccgc cgagccacag ccacgatgat cgcgggctcc cttctcctgc ttggattcct
 541 tagcaccacc acagctcagc cagaacagaa ggcctcgaat tcattggca catatccgcca
 601 tgttgaccgt gccaccggcc aggtgctaac ctgtgacaag tgtccagcag gaacctatgt
 661 ctctgagcat tgtaccaaca caagcctgcg cgtctgcagc agttgccctg tggggaccct
 721 taccaggcat gagaatggca tagagaaatg ccatgactgt agtcagccat gcccatggcc
 781 aatgattgag aaaattacctt gtgctgcctt gactgaccga gaatgcactt gcccacctgg
 841 catgttccag tctaacgcta cctgtgcccc ccatacggtg tgtcctgtgg gttggggtgt
 901 gcggaagaaa gggacagaga ctgaggatgt gcggtgtaag cagtgtgctc ggggtacctt
 961 ctcagatgtg ccttctagtg tgatgaaatg caaagcatac acagactgtc tgagtcagaa
1021 cctggtggtg atcaagccgg ggaccaagga gacagacaac gtctgtggca cactcccgtc
1081 cttctccagc tccacctcac cttccccctgg cacagccatc tttccacgcc ctgagcacat
```

APPENDIX-continued

Nucleotide Sequences for HDACi Compound Resistance Biomarker Genes

```
1141 ggaaacccat gaagtccctt cctccactta tgttcccaaa ggcatgaact caacagaatc
1201 caactcttct gcctctgtta gaccaaaggt actgagtagc atccaggaag ggacagtccc
1261 tgacaacaca agctcagcaa gggggaagga agacgtgaac aagaccctcc caaaccttca
1321 ggtagtcaac caccagcaag gcccccacca cagacacatc ctgaagctgc tgccgtccat
1381 ggaggccact gggggcgaga agtccagcac gcccatcaag ggccccaaga ggggacatcc
1441 tagacagaac ctacacaagc attttgacat caatgagcat ttgccctgga tgattgtgct
1501 tttcctgctg ctggtgcttg tggtgattgt ggtgtgcagt atccggaaaa gctcgaggac
1561 tctgaaaaag gggccccggc aggatcccag tgccattgtg gaaaaggcag ggctgaagaa
1621 atccatgact ccaacccaga accgggagaa atggatctac tactgcaatg ccatggtat
1681 cgatatcctg aagcttgtag cagcccaagt gggaagccag tggaaagata tctatcagtt
1741 tctttgcaat gccagtgaga gggaggttgc tgctttctcc aatgggtaca cagccgacca
1801 cgagcgggcc tacgcagctc tgcagcactg gaccatccgg ggccccgagg ccagcctcgc
1861 ccagctaatt agcgccctgc gccagcaccg gagaaacgat gttgtggaga agattcgtgg
1921 gctgatggaa gacaccaccc agctggaaac tgacaaacta gctctcccga tgagccccag
1981 cccgcttagc ccgagcccca tccccagccc caacgcgaaa cttgagaatt ccgctctcct
2041 gacggtggag ccttccccac aggacaagaa caagggcttc ttcgtggatg agtcggagcc
2101 ccttctccgc tgtgactcta catccagcgg ctcctccgcg ctgagcagga acggttcctt
2161 tattaccaaa gaaaagaagg acacagtgtt gcggcaggta cgcctggacc cctgtgactt
2221 gcagcctatc tttgatgaca tgctccactt tctaaatcct gaggagctgc gggtgattga
2281 agagattccc caggctgagg acaaactaga ccggctattc gaaattattg gagtcaagag
2341 ccaggaagcc agccagaccc tcctggactc tgtttatagc catcttcctg acctgctgta
2401 gaacataggg atactgcatt ctggaaatta ctcaatttag tggcagggtg gttttttaat
2461 tttcttctgt ttctgatttt tgttgtttgg ggtgtgtgtg tgtgtttgtg tgtgtgtgtg
2521 tgtgtgtgtg tgtgtgtgtg tttaacagag aatatggcca gtgcttgagt tctttctcct
2581 tctctctctc tcttttttttt ttaaataact cttctgggaa gttggtttat aagcctttgc
2641 caggtgtaac tgttgtgaaa tacccaccac taaagttttt taagttccat attttctcca
2701 ttttgccttc ttatgtattt tcaagattat tctgtgcact ttaaatttac ttaacttacc
2761 ataaatgcag tgtgactttt cccacacact ggattgtgag gctcttaact tcttaaaagt
2821 ataatggcat cttgtgaatc ctataagcag tcttttatgtc tcttaacatt cacacctact
2881 ttttaaaaac aaatattatt actattttta ttattgtttg tcctttataa attttcttaa
2941 agattaagaa aatttaagac cccattgagt tactgtaatg caattcaact ttgagttatc
3001 ttttaaatat gtcttgtata gttcatattc atggctgaaa cttgaccaca ctattgctga
3061 ttgtatggtt ttcacctgga caccgtgtag aatgcttgat tacttgtact cttcttatgc
3121 taatatgctc tgggctggag aaatgaaatc ctcaagccat caggatttgc tatttaagtg
3181 gcttgacaac tgggccacca agaacttgaa acttcacctt ttaggatttg agctgttctg
3241 gaacacattg ctgcactttg gaaagtcaaa atcaagtgcc agtggcgccc tttccataga
3301 gaatttgccc agctttgctt taaaagatgt cttgtttttt atatacacat aatcaatagg
3361 tccaatctgc tctcaaggcc ttggtcctgg tgggattcct tcaccaatta ctttaattaa
```

APPENDIX-continued

Nucleotide Sequences for HDACi Compound Resistance Biomarker Genes

```
3421 aaatggctgc aactgtaaga acccttgtct gatatatttg caactatgct cccatttaca
3481 aatgtacctt ctaatgctca gttgccaggt tccaatgcaa aggtggcgtg gactcccttt
3541 gtgtgggtgg ggtttgtggg tagtggtgaa ggaccgatat cagaaaaatg ccttcaagtg
3601 tactaattta ttaataaaca ttaggtgttt gttaaaaaaa
```

| Gene Name | Gene Symbol | GenBank Accession # | SEQ ID NO |
|---|---|---|---|
| transmembrane 4 superfamily member 3 | TM4SF3 | NM_004616 | 30 |

```
   1 agtgccccag gagctatgac aagcaaagga acatacttgc ctggagatag cctttgcgat
  61 atttaaatgt ccgtggatac agaaatctct gcaggcaagt tgctccagag catattgcag
 121 gacaagcctg taacgaatag ttaaattcac ggcatctgga ttcctaatcc ttttccgaaa
 181 tggcaggtgt gagtgcctgt ataaaatatt ctatgtttac cttcaacttc ttgttctggc
 241 tatgtggtat cttgatccta gcattagcaa tatgggtacg agtaagcaat gactctcaag
 301 caattttttgg ttctgaagat gtaggctcta gctcctacgt tgctgtggac atattgattg
 361 ctgtaggtgc catcatcatg attctgggct tcctgggatg ctgcggtgct ataaaagaaa
 421 gtcgctgcat gcttctgttg ttttttcatag gcttgcttct gatcctgctc ctgcaggtgg
 481 cgacaggtat cctaggagct gttttcaaat ctaagtctga tcgcattgtg aatgaaactc
 541 tctatgaaaa cacaaagctt ttgagcgcca caggggaaag tgaaaaacaa ttccaggaag
 601 ccataattgt gtttcaagaa gagtttaaat gctgcggttt ggtcaatgga gctgctgatt
 661 ggggaaataa ttttcaacac tatcctgaat tatgtgcctg tctagataag cagagaccat
 721 gccaaagcta taatggaaaa caagtttaca aagagacctg tatttctttc ataaaagact
 781 tcttggcaaa aaatttgatt atagttattg gaatatcatt tggactggca gttattgaga
 841 tactgggttt ggtgttttct atggtcctgt attgccagat cgggaacaaa tgaatctgtg
 901 gatgcatcaa cctatcgtca gtcaaacccc tttaaaatgt tgctttggct ttgtaaattt
 961 aaatatgtaa gtgctatata agtcaggagc agctgtcttt ttaaaatgtc tcggctagct
1021 agaccacaga tatcttctag acatattgaa cacatttaag atttgaggga tataagggaa
1081 aatgatatga atgtgtattt ttactcaaaa taaagtaac tgtttacgtt
```

| Gene Name | Gene Symbol | GenBank Accession # | SEQ ID NO |
|---|---|---|---|
| interleukin 18 (interferon-gamma-inducing factor) | IL18 | NM_001562 | 31 |

```
   1 attctctccc cagcttgctg agccctttgc tcccctggcg actgcctgga cagtcagcaa
  61 ggaattgtct cccagtgcat tttgccctcc tggctgccaa ctctggctgc taaagcggct
 121 gccacctgct gcagtctaca cagcttcggg aagaggaaag gaacctcaga ccttccagat
 181 cgcttcctct cgcaacaaac tatttgtcgc aggaataaag atggctgctg aaccagtaga
 241 agacaattgc atcaactttg tggcaatgaa atttattgac aatacgcttt actttatagc
 301 tgaagatgat gaaaacctgg aatcagatta ctttggcaag cttgaatcta aattatcagt
 361 cataagaaat ttgaatgacc aagttctctt cattgaccaa ggaaatcggc ctctatttga
 421 agatatgact gattctgact gtagagataa tgcaccccgg accatatttta ttataagtat
 481 gtataaagat agccagccta gaggtatggc tgtaactatc tctgtgaagt gtgagaaaat
```

APPENDIX-continued

Nucleotide Sequences for HDACi Compound Resistance Biomarker Genes

```
 541 ttcaactctc tcctgtgaga acaaaattat ttcctttaag gaaatgaatc ctcctgataa
 601 catcaaggat acaaaaagtg acatcatatt ctttcagaga agtgtcccag gacatgataa
 661 taagatgcaa tttgaatctt catcatacga aggatacttt ctagcttgtg aaaaagagag
 721 agaccttttt aaactcattt tgaaaaaaga ggatgaattg ggggatagat ctataatgtt
 781 cactgttcaa aacgaagact agctattaaa atttcatgcc gggcgcagtg gctcacgcct
 841 gtaatcccag ccctttggga ggctgaggcg ggcagatcac cagaggtcag gtgttcaaga
 901 ccagcctgac caacatggtg aaacctcatc tctactaaaa atacaaaaaa ttagctgagt
 961 gtagtgacgc atgccctcaa tcccagctac tcaagaggct gaggcaggag aatcacttgc
1021 actccggagg tagaggttgt ggtgagccga gattgcacca ttgcgctcta gcctgggcaa
1081 caacagcaaa actccatctc aaaaaataaa ataaataaat aaacaaataa aaaattcata
1141 atgtg
```

| Gene Name | Gene Symbol | GenBank Accession # | SEQ ID NO |
|---|---|---|---|
| bone morphogenetic protein 4 | BMP4 | NM_130850 | 32 |

```
   1 gagggagggg ccgccgggga agaggaggag gaaggaaaga aagaaagcga gggagggaaa
  61 gaggaggaag gaagatgcga gaaggcagag gaggagggag ggagggaagg agcgcggagc
 121 ccggcccgga agctaggagc cattccgtag tgccatcccg agcaacgcac tgctgcagct
 181 tccctgagcc tttccagcaa gtttgttcaa gattggctgt caagaatcat ggactgttat
 241 tatatgcctt gttttctgtc aagacaccat gattcctggt aaccgaatgc tgatggtcgt
 301 tttattatgc caagtcctgc taggaggcgc gagccatgct agtttgatac ctgagacggg
 361 gaagaaaaaa gtcgccgaga ttcagggcca cgcggggagga cgccgctcag ggcagagcca
 421 tgagctcctg cgggacttcg aggcgacact tctgcagatg tttgggctgc gccgccgccc
 481 gcagcctagc aagagtgccg tcattccgga ctacatgcgg gatctttacc ggcttcagtc
 541 tgggggaggag gaggaagagc agatccacag cactggtctt gagtatcctg agcgcccggc
 601 cagccgggcc aacaccgtga ggagcttcca ccacgaagaa catctggaga acatcccagg
 661 gaccagtgaa aactctgctt ttcgtttcct cttttaacctc agcagcatcc ctgagaacga
 721 ggcgatctcc tctgcagagc ttcggctctt ccgggagcag gtggaccagg gccctgattg
 781 ggaaaggggc ttccaccgta taaacattta tgaggttatg aagcccccag cagaagtggt
 841 gcctgggcac ctcatcacac gactactgga cacgagactg gtccaccaca atgtgacacg
 901 gtgggaaact tttgatgtga gccctgcggt ccttcgctgg acccgggaga agcagccaaa
 961 ctatgggcta gccattgagg tgactcacct ccatcagact cggacccacc agggccagca
1021 tgtcaggatt agccgatcgt tacctcaagg gagtgggaat tgggcccagc tccggccccct
1081 cctggtcacc tttggccatg atggccgggg ccatgccttg acccgacgcc ggagggccaa
1141 gcgtagccct aagcatcact cacagcgggc caggaagaag aataagaact gccggcgcca
1201 ctcgctctat gtggacttca gcgatgtggg ctggaatgac tggattgtgg ccccaccagg
1261 ctaccaggcc ttctactgcc atggggactg cccctttcca ctggctgacc acctcaactc
1321 aaccaaccat gccattgtgc agaccctggt caattctgtc aattccagta tccccaaagc
1381 ctgttgtgtg cccactgaac tgagtgccat ctccatgctg tacctggatg agtatgataa
```

APPENDIX-continued

Nucleotide Sequences for HDACi Compound Resistance Biomarker Genes

```
1441 ggtggtactg aaaaattatc aggagatggt agtagaggga tgtgggtgcc gctgagatca
1501 ggcagtcctt gaggatagac agatatacac accacacaca cacaccacat acaccacaca
1561 cacacgttcc catccactca cccacacact acacagactg cttccttata gctggacttt
1621 tatttaaaaa aaaaaaaaa aaatggaaa aatccctaa acattcacct tgaccttatt
1681 tatgacttta cgtgcaaatg ttttgaccat attgatcata tattttgaca aaatatattt
1741 ataactacgt attaaaagaa aaaataaaa tgagtcatta ttttaaaggt
```

| Gene Name | Gene Symbol | GenBank Accession # | SEQ ID NO |
|---|---|---|---|
| sphingomyelin phosphodiesterase, acid-like 3B | SMPDL3B | NM_014474 | 33 |

```
   1 ccagatcata ccctgctggg caaaggagga agagccagag gatccagacg ccttggagga
  61 cttggaacac ctgtaacagg acaaggagtt ctgctcaggc acgtggccac agaaaactac
 121 ttaggaagcc tgtggtgaga acaacaacag tgcctgagaa tcccacgcgt ctggggaagt
 181 gagccccgag gatgaggctg ctcgcctggc tgattttcct ggctaactgg ggaggtgcca
 241 gggctgaacc agggaagttc tggcacatcg ctgacctgca ccttgaccct gactacaagg
 301 tatccaaaga cccttccag gtgtgcccat cagctggatc ccagccagtg cccgacgcag
 361 gcccctgggg tgactacctc tgtgattctc cctgggccct catcaactcc tccatctatg
 421 ccatgaagga gattgagcca gagccagact tcattctctg gactggtgat gacacgcctc
 481 atgtgcccga tgagaaactg ggagaggcag ctgtactgga aattgtggaa cgcctgacca
 541 agctcatcag agaggtcttt ccagatacta agtctatgc tgctttggga aatcatgatt
 601 ttcaccccaa aaaccagttc ccagctggaa gtaacaacat ctacaatcag atagcagaac
 661 tatggaaacc ctggcttagt aatgagtcca tcgctctctt caaaaaaggt gccttctact
 721 gtgagaagct gccgggtccc agcggggctg ggcgaattgt ggtcctcaac accaatctgt
 781 actataccag caatgcgctg acagcagaca tggcggaccc tggccagcag ttccagtggc
 841 tggaagatgt gctgaccgat gcatccaaag ctggggacat ggtgtacatt gtcggccacg
 901 tgccccgggg gttctttgag aagacgcaaa acaaggcatg gttccgggag ggcttcaatg
 961 aaaaatacct gaaggtggtc cggaagcatc atcgcgtcat agcagggcag ttcttcgggc
1021 accaccacac cgacagcttt cggatgctct atgatgatgc aggtgtcccc ataagcgcca
1081 tgttcatcac acctggagtc accccatgga aaaccacatt acctggagtg gtcaatgggg
1141 ccaacaatcc agccatccgg gtgttcgaat atgaccgagc cacactgagc ctgaaggaca
1201 tggtgaccta cttcatgaac ctgagccagg cgaatgctca ggggacgccg cgctgggagc
1261 tcgagtacca gctgaccgag gcctatgggg tgccggacgc cagcgcccac tccatgcaca
1321 cagtgctgga ccgcatcgct ggcgaccaga gcacactgca gcgctactac gtctataact
1381 cagtcagcta ctctgctggg gtctgcgacg aggcctgcag catgcagcac gtgtgtgcca
1441 tgcgccaggt ggacattgac gcttacacca cctgtctgta tgcctctggc accacgcccg
1501 tgccccagct cccgctgctg ctgatggccc tgctgggcct tgcacgctc gtgctgtgac
1561 ctgccaggct caccttcttc ctggtaacgg gtaacggggg cagcgcccag gatcacccag
1621 agctgggcct tccaccattt cctccgcgcc tgaggagtga actgaaatag gacaaccgaa
1681 tcaggaagcg aagccccagg agctgcagcc atccgtgatc gcgccactgc actccagcct
```

APPENDIX-continued
Nucleotide Sequences for HDACi Compound Resistance Biomarker Genes

```
1741 gggcgacaaa gccagactct ctccaaaaac aaaccagaaa cagaaaagaa atgacgaccc
1801 aagaccccc tacaagcata cttcttttgc gtattatgtt ttactcacaa aacaaagctc
1861 atcatgcgtt tgaaaaaaaa
```

| Gene Name | Gene Symbol | GenBank Accession # | SEQ ID NO |
|---|---|---|---|
| transmembrane protease, serine 2 | TMPRSS2 | NM_005656 | 34 |

```
   1 cgcgagctaa gcaggaggcg gaggcggagg cggagggcga ggggcgggga gcgccgcctg
  61 gagcgcggca ggtcatattg aacattccag atacctatca ttactcgatg ctgttgataa
 121 cagcaagatg gctttgaact cagggtcacc accagctatt ggaccttact atgaaaacca
 181 tggataccaa ccggaaaacc cctatcccgc acagcccact gtggtcccca ctgtctacga
 241 ggtgcatccg gctcagtact acccgtcccc cgtgccccag tacgcccga gggtcctgac
 301 gcaggcttcc aaccccgtcg tctgcacgca gcccaaatcc catccgggaa cagtgtgcac
 361 ctcaaagact aagaaagcac tgtgcatcac cttgaccctg ggaccttcc tcgtgggagc
 421 tgcgctggcc gctggcctac tctggaagtt catgggcagc aagtgctcca actctgggat
 481 agagtgcgac tcctcaggta cctgcatcaa cccctctaac tggtgtgatg gcgtgtcaca
 541 ctgccccggc ggggaggacg agaatcggtg tgttcgcctc tacggaccaa acttcatcct
 601 tcagatgtac tcatctcaga ggaagtcctg gcaccctgtg tgccaagacg actggaacga
 661 gaactacggg cgggcggcct gcagggacat gggctataag aataattttt actctagcca
 721 aggaatagtg gatgacagcg gatccaccag ctttatgaaa ctgaacacaa gtgccggcaa
 781 tgtcgatatc tataaaaaac tgtaccacag tgatgcctgt tcttcaaaag cagtggtttc
 841 tttacgctgt atagcctgcg gggtcaactt gaactcaagc cgccagagca ggatcgtggg
 901 cggtgagagc gcgctcccgg gggcctggcc ctggcaggtc agcctgcacg tccagaacgt
 961 ccacgtgtgc ggaggctcca tcatcacccc cgagtggatc gtgacagccg cccactgcgt
1021 ggaaaaacct cttaacaatc catggcattg gacggcattt gcggggattt tgagacaatc
1081 tttcatgttc tatggagccg ataccaagt agaaaaagtg atttctcatc caaattatga
1141 ctccaagacc aagaacaatg acattgcgct gatgaagctg cagaagcctc tgactttcaa
1201 cgacctagtg aaaccagtgt gtctgcccaa cccaggcatg atgctgcagc agaacagct
1261 ctgctggatt tccgggtggg gggccaccga ggagaaaggg aagacctcag aagtgctgaa
1321 cgctgccaag gtgcttctca ttgagacaca gagatgcaac agcagatatg tctatgacaa
1381 cctgatcaca ccagccatga tctgtgccgg cttcctgcag gggaacgtcg attcttgcca
1441 gggtgacagt ggagggcctc tggtcacttc gaagaacaat atctggtggc tgataggga
1501 tacaagctgg ggttctggct gtgccaaagc ttacagacca ggagtgtacg ggaatgtgat
1561 ggtattcacg gactggattt atcgacaaat gagggcagac ggctaatcca catggtcttc
1621 gtccttgacg tcgttttaca agaaaacaat ggggctggtt ttgcttcccc gtgcatgatt
1681 tactcttaga gatgattcag aggtcacttc attttatta aacagtgaac ttgtctggct
1741 ttggcactct ctgccattct gtgcaggctg cagtggctcc cctgcccagc tgctctccc
1801 taacccttg tccgcaaggg gtgatggccg gctggttgtg ggcactggcg gtcaagtgtg
1861 gaggagaggg gtgaggctg ccccattgag atcttcctgc tgagtccttt ccaggggcca
1921 attttggatg agcatggagc tgtcaccctct cagctgctgg atgacttgag atgaaaaagg
```

APPENDIX-continued

Nucleotide Sequences for HDACi Compound Resistance Biomarker Genes

```
1981 agagacatgg aaagggagac agccaggtgg cacctgcagc ggctgccctc tggggccact
2041 tggtagtgtc cccagcctac ctctccacaa ggggattttg ctgatgggtt cttagagcct
2101 tagcagccct ggatggtggc cagaaataaa gggaccagcc cttcatgggt ggtgacgtgg
2161 tagtcacttg taaggggaac agaaacattt ttgttcttat ggggtgagaa tatagacagt
2221 gcccttggtg cgagggaagc aattgaaaag gaacttgccc tgagcactcc tggtgcaggt
2281 ctccacctgc acattgggtg gggctcctgg gagggagact cagccttcct cctcatcctc
2341 cctgaccctg ctcctagcac cctggagagt gcacatgccc cttggtcctg gcagggcgcc
2401 aagtctggca ccatgttggc ctcttcaggc ctgctagtca ctggaaattg aggtccatgg
2461 gggaaatcaa ggatgctcag tttaaggtac actgtttcca tgttatgttt ctacacattg
2521 ctacctcagt gctcctggaa acttagcttt tgatgtctcc aagtagtcca ccttcattta
2581 actctttgaa actgtatcac ctttgccaag taagagtggt ggcctatttc agctgctttg
2641 acaaaatgac tggctcctga cttaacgttc tataaatgaa tgtgctgaag caaagtgccc
2701 atggtggcgg cgaagaagag aaagatgtgt tttgttttgg actctctgtg gtcccttcca
2761 atgctgtggg tttccaacca ggggaagggt ccctttttgca ttgccaagtg ccataaccat
2821 gagcactact ctaccatggt tctgcctcct ggccaagcag gctggtttgc aagaatgaaa
2881 tgaatgattc tacagctagg acttaacctt gaaatggaaa gtcttgcaat cccatttgca
2941 ggatccgtct gtgcacatgc ctctgtagag agcagcattc ccagggacct tggaaacagt
3001 tggcactgta aggtgcttgc tccccaagac acatcctaaa aggtgttgta atggtgaaaa
3061 cgtcttcctt ctttattgcc ccttcttatt tatgtgaaca actgtttgtc ttttttttgta
3121 tcttttttaa actgtaaagt tcaattgtga aaatgaatat catgcaaata aattatgcga
3181 ttttttttttc aaagcaaaaa
```

| Gene Name | Gene Symbol | GenBank Accession # | SEQ ID NO |
|---|---|---|---|
| guanine deaminase | GDA | NM_004293 | 35 |

```
  1 gtagggagcc agcccctggg cgcggcctgc agggtaccgg caaccgcccg ggtaagcggg
 61 ggcaggacaa ggccggagcc tgtgtccgcc cggcagccgc ccgcagctgc agagagtccc
121 gctgcgtctc cgccgcgtgc gccctcctcg accagcagac ccgcgctgcg ctccgccgct
181 gacatgtgtg ccgctcagat gccgcccctg gcgcacatct tccgagggac gttcgtccac
241 tccacctgga cctgccccat ggaggtgctg cgggatcacc tcctcggcgt gagcgacagc
301 ggcaaaatag tgttttttaga agaagcatct caacaggaaa aactggccaa agaatggtgc
361 ttcaagccgt gtgaaataag agaactgagc caccatgagt tcttcatgcc tgggctggtt
421 gatacacaca tccatgcctc tcagtattcc tttgctggaa gtagcataga cctgccactc
481 ttggagtggc tgaccaagta cacatttcct gcagaacaca gattccagaa catcgacttt
541 gcagaagaag tatataccag agttgtcagg agaaacactaa agaatggaac aaccacagct
601 tgttactttg caacaattca cactgactca tctctgctcc ttgccgacat tacagataaa
661 tttggacagc gggcatttgt gggcaaagtt tgcatggatt tgaatgacac ttttccagaa
721 tacaaggaga ccactgagga atcgatcaag gaaactgaga gatttgtgtc agaaatgctc
781 caaaagaact attctagagt gaagcccata gtgacaccac gttttttccct ctcctgctct
841 gagactttga tgggtgaact gggcaacatt gctaaaaccc gtgatttgca cattcagagc
```

APPENDIX-continued

Nucleotide Sequences for HDACi Compound Resistance Biomarker Genes

```
 901 catataagtg aaaatcgtga tgaagttgaa gctgtgaaaa acttataccc cagttataaa
 961 aactacacat ctgtgtatga taaaaacaat cttttgacaa ataagacagt gatggcacac
1021 ggctgctacc tctctgcaga agaactgaac gtattccatg aacgaggagc atccatcgca
1081 cactgtccca attctaattt atcgctcagc agtggatttc taaatgtgct agaagtcctg
1141 aaacatgaag tcaagatagg gctgggtaca gacgtggctg gtggctattc atattccatg
1201 cttgatgcaa tcagaagagc agtgatggtt tccaatatcc ttttaattaa taaggtaaat
1261 gagaaaagcc tcaccctcaa agaagtcttc agactagcta ctcttggagg aagccaagcc
1321 ctggggctgg atggtgagat tggaaacttt gaagtgggca aggaatttga tgccatcctg
1381 atcaacccca aagcatccga ctctcccatt gacctgtttt atggggactt ttttggtgat
1441 atttctgagg ctgttatcca gaagttcctc tatctaggag atgatcgaaa tattgaagag
1501 gtttatgtgg gcggaaagca ggtggttccg ttttccagct cagtgtaaga ccctcgggcg
1561 tctacaaagt tctcctggga ttagcgtggt tctgcatctc ccttgtgccc aggtggagtt
1621 agaaagtcaa aaaatagtac cttgttcttg ggatgactat ccctttctgt gtctagttac
1681 agtattcact tgacaaatag ttcgaaggaa gttgcactaa ttctcaactc tggttgagag
1741 ggttcataaa tttcatgaaa atatctccct ttggagctgc tcagacttac tttaagctca
1801 aacagaaggg aatgctatta ctggtggtgt tcctacggta agacttaagc aaagcctttt
1861 tcatatttga aaatgtggaa agaaaagatg ttcctaaaag gttagatatt ttgagctaat
1921 aattgcaaaa attagaagac tgaaaatgga cccatgagag tatattttta tgagggagca
1981 aaagttagac tgagaacaaa cgttagaaaa tcacttcaga ttgtgtttga aaattatata
2041 ctgagcatac taatttaaaa agagaacttg ttgaaattta aaacgtgttt ctaggttgac
2101 cttgtgtttt agaaatttgc acttaatgga atttgcattt cagagatgtg ttagtgttgt
2161 gctttgcctt ctttggcgat gaatgtcaga aattgaatgc cacatgcttt cataatatag
2221 ttttgtgctt caaagtgttt gacagaagtt gggtattaaa gatttaaagt ctcttaggaa
2281 tattattcat gtaactccat ggcataaata gttgtatttt tgtgtacttt aaaatcaact
2341 tataactgtg agatgttatt gcttccattt tattagaaga gaaacaaatt ccatgcttta
2401 tggaatttat gtagactgga gtcttcgtga actggggcaa atgctggcat ccaggagccg
2461 ccaatactaa caggacaggt tccattgcca tggcctattc cacccaaaca atatgttgta
2521 gtttctggaa attccatact cagatatcag tctgctagaa ctttaaaatg aaggacaaat
2581 cctgttaaag aaatattgtt aaaaatcttt aaaccctgtg tattgaaagc actctatttt
2641 ctaattttat ccagttttct gtttaactcc ttataatgtt taggatatta aaattttagg
2701 ataatgaaga gtacataatg tcctacttaa tatttatgtt aataggactt aattcttact
2761 agacatctag gaacattaca aagcaaagac tatttttatg cttccataac ctagaattaa
2821 aaccaaatta tgaccttatg ataaatcttt aagtattggt gtgaatgtta tttaaattct
2881 atatttttct tatttaatta caaatactat aaatgagcaa ggaaaaggaa tagactttct
2941 taatatatta taacactcat tcctagagct taggggtgac tctttaatat taccttatag
3001 tagaaacttt atgtaatata gctaactccg tatttacaga acaaaaaaac acagttcccc
3061 ctcctgtagt ataaattttta ttttcacata cttagctaat ttagcagtaa ttggcccagt
3121 ttttttcccta atagaaatac ttttagattt gattatgtat acatgacacc taaagaggga
```

APPENDIX-continued

Nucleotide Sequences for HDACi Compound Resistance Biomarker Genes

```
3181 acaaaagtta gttttatttt tttaataaac aacagagttt gttttgtgag ataagtatct
3241 tagtaaaccc aatttccagt cttagtctgt atttccaata tttctaattc ctgagccacg
3301 tcaaagatgc cttgccaaat ttctccccat ttctctacgg ggctagcaaa aatcttcagc
3361 tttatcactc aacccctgcc aaaggaactt gattacatgg tgtctaacca aatgagcagg
3421 cttaggaatt tagatgagat gtgtaagatt cacttacagg cagtagctgc ttctagcatt
3481 tgcaagatcc tacacttttta ccttctttaa gggtgtacat tttgatgttg aacatcagtt
3541 ttcatgtaga cttaggactc atgtgcagta aatataaata agtgtagcat cagaagcagt
3601 aggaatggcc gtatacaacc atcctgttaa acatttaaat ttagctctga tagtgtgtta
3661 agacctgaat atctttccta gtaaaaatag gatgtgttga aatatttata tgtactttga
3721 tctctccaca tcacttataa cttatgtgtt ttatttctcc aagtgcggtg ttcctgaatg
3781 ttatgtatgc ttttttttct gtaccacagg cattatctat acctggggcc agattttctg
3841 cactttgaaa tgttgccttt gcctaatgta ggttgacttt ctgaattgtg gagaggcact
3901 tttccaagcc aatcttattt gtcacttttt gttttaatat cttgctctct gacaggaaag
3961 aaacaattca cttaccagcc tcctcacccc atcctccacc atttccttaa tgttccatgg
4021 tattttcaac ggaatacact ttgaaaggta aaaacaattc aaaagtatcg attatcataa
4081 attcacaaaa tatttttgca accagaacac aaaagcaggc tagtcagcta aggtaaattt
4141 cattttcaaa cgagagggaa acatgggaag taaaagatta ggatgtgaaa ggttgtccta
4201 aacagaccaa ggagactgtt ccctaattta ttctcttggc tggttctctc attgaattat
4261 cagaccccaa gaggagatat tggaacaggc tcccttcatg ccaagggtct ttctaagtta
4321 atactgtgag cattgagccc ccattaaaac tctttttttac ttcagaaaga attttacagg
4381 ttaaagggaa agaaatggtg ggaaactctc cccgtaatgc ttagccaact ttaaagtgta
4441 cccttcaata tccccattgg caactgcagc tgagatctta gagaggaaat ataaccggtg
4501 tgagatctag caatgcattt tgaatcttca ctccctacca ggctcttcct atttttaatc
4561 tcttcacctc agaactagac atatggagag ctttaaaggc aagctggaag gcacattgta
4621 tcaattctac cttgtgctat acgtaggaga gatccaaaat ttggatgctt ctggagactc
4681 ttagacatct tttcattgtt gtccatttttt aaagttgatg attgctggaa acattcacac
4741 gcttaaaagc aatggtgtga gttattaatg ggtaaactaa gaagtgttat aggcaatgac
4801 ttgaaatggt ttttaaattg tatggattgt taagaattgt tgaaaaaaaa tttttttttt
4861 ttggacagct tcaaggagat gttagcaatt tcagatatac tagccagttt aggtatgact
4921 ttggaagtgc agaaacagaa ggatactgtt agaaaatcct aacattggtc tccgtgcatg
4981 tgttcacacc tggtctcact gcctttcctt cccacagacc tgagtgtgaa agactgagag
5041 ttgaggagtt actttgtgga tcttgtccaa atttagtgaa atgtggaagt caaccagacc
5101 aatgatggaa ttaaatgtaa attccaagag ggctttcaca gtccacaggg ttcaaatgac
5161 ttgggtaaca gaagttattc ttagcttacc tgttatgtga cagtgattta cctgtccatt
5221 tccaacccaa aagcctgtca gaaagcattc tttagagaaa accactttac atttgttgtt
5281 aaactcctga tcgctactct taagaatata catgtatgta ttcataggaa catttttttct
5341 caatatttgt atgattcgct tactgttatt gtgctgagtg agctcctgtg tgcttcagac
5401 aaaaataaat gagactttgt gtttacgtta
```

APPENDIX-continued

Nucleotide Sequences for HDACi Compound Resistance Biomarker Genes

| Gene Name | Gene Symbol | GenBank Accession # | SEQ ID NO |
|---|---|---|---|
| macrophage stimulating 1 receptor (c-met-related tyrosine kinase) | MST1R | NM_002447 | 36 |

```
   1 ggatcctcta gggtcccagc tcgcctcgat ggagctcctc ccgccgctgc ctcagtcctt
  61 cctgttgctg ctgctgttgc ctgccaagcc cgcggcgggc gaggactggc agtgcccgcg
 121 caccccctac gcggcctctc gcgactttga cgtgaagtac gtggtgccca gcttctccgc
 181 cggaggcctg gtacaggcca tggtgaccta cgagggcgac agaaatgaga gtgctgtgtt
 241 tgtagccata cgcaatcgcc tgcatgtgct tgggcctgac ctgaagtctg tccagagcct
 301 ggccacgggc cctgctggag accctggctg ccagacgtgt gcagcctgtg cccaggacc
 361 ccacggccct cccggtgaca cagacacaaa ggtgctggtg ctggatcccg cgctgcctgc
 421 gctggtcagt tgtggctcca gcctgcaggg ccgctgcttc ctgcatgacc tagagcccca
 481 agggacagcc gtgcatctgg cagcgccagc ctgcctcttc tcagcccacc ataaccggcc
 541 cgatgactgc cccgactgtg tggccagccc attgggcacc cgtgtaactg tggttgagca
 601 aggccaggcc tcctatttct acgtggcatc ctcactggac gcagccgtgg ctggcagctt
 661 cagcccacgc tcagtgtcta tcaggcgtct caaggctgac gcctcgggat tcgcaccggg
 721 ctttgtggcg ttgtcagtgc tgcccaagca tcttgtctcc tacagtattg aatacgtgca
 781 cagcttccac acgggagcct tcgtatactt cctgactgta cagccggcca gcgtgacaga
 841 tgatcctagt gccctgcaca cacgcctggc acggcttagc gccactgagc cagagttggg
 901 tgactatcgg gagctggtcc tcgactgcag atttgctcca aaacgcaggc gccgggggc
 961 cccagaaggc ggacagccct accctgtgct gcaggtggcc cactccgctc cagtgggtgc
1021 ccaacttgcc actgagctga gcatcgccga gggccaggaa gtactatttg gggtctttgt
1081 gactggcaag gatggtggtc ctggcgtggg ccccaactct gtcgtctgtg ccttccccat
1141 tgacctgctg gacacactaa ttgatgaggg tgtggagcgc tgttgtgaat ccccagtcca
1201 tccaggcctc cggcgaggcc tcgacttctt ccagtcgccc agtttttgcc ccaacccgcc
1261 tggcctggaa gccctcagcc caacaccag ctgccgccac ttccctctgc tggtcagtag
1321 cagcttctca cgtgtggacc tattcaatgg gctgttggga ccagtacagg tcactgcatt
1381 gtatgtgaca cgccttgaca acgtcacagt ggcacacatg ggcacaatgg atgggcgtat
1441 cctgcaggtg gagctggtca ggtcactaaa ctacttgctg tatgtgtcca acttctcact
1501 gggtgacagt gggcagcccg tgcagcggga tgtcagtcgt cttggggacc acctactctt
1561 tgcctctggg gaccaggttt tccaggtacc tatccgaggc cctggctgcc gccacttcct
1621 gacctgtggg cgttgcctaa gggcatgca tttcatgggc tgtggctggt gtgggaacat
1681 gtgcggccag cagaaggagt gtcctggctc ctggcaacag gaccactgcc cacctaagct
1741 tactgagttc caccccaca gtggacctct aaggggcagt acaaggctga ccctgtgtgg
1801 ctccaacttc taccttcacc cttctggtct ggtgcctgag ggaacccatc aggtcactgt
1861 gggccaaagt ccctgccggc cactgcccaa ggacagctca aaactcagac cagtgccccg
1921 gaaagacttt gtagaggagt ttgagtgtga actggagccc ttgggcaccc aggcagtggg
1981 gcctaccaac gtcagcctca ccgtgactaa catgccaccg ggcaagcact tccgggtaga
2041 cggcacctcc gtgctgagag cttctctttt catggagcca gtgctgatag cagtgcaacc
```

APPENDIX-continued

Nucleotide Sequences for HDACi Compound Resistance Biomarker Genes

```
2101 cctctttggc ccacgggcag gaggcacctg tctcactctt gaaggccaga gtctgtctgt
2161 aggcaccagc cgggctgtgc tggtcaatgg gactgagtgt ctgctagcac gggtcagtga
2221 ggggcagctt ttatgtgcca cacccctgg ggccacggtg gccagtgtcc cccttagcct
2281 gcaggtgggg ggtgcccagg tacctggttc ctggaccttc cagtacagag aagaccctgt
2341 cgtgctaagc atcagcccca actgtggcta catcaactcc cacatcacca tctgtggcca
2401 gcatctaact tcagcatggc acttagtgct gtcattccat gacgggctta gggcagtgga
2461 aagcaggtgt gagaggcagc ttccagagca gcagctgtgc cgccttcctg aatatgtggt
2521 ccgagacccc cagggatggg tggcagggaa tctgagtgcc cgaggggatg gagctgctgg
2581 ctttacactg cctggctttc gcttcctacc cccacccat ccacccagtg ccaacctagt
2641 tccactgaag cctgaggagc atgccattaa gtttgagtat attgggctgg gcgctgtggc
2701 tgactgtgtg ggtatcaacg tgaccgtggg tggtgagagc tgccagcacg agttccgggg
2761 ggacatggtt gtctgccccc tgccccatc cctgcagctt ggccaggatg gtgccccatt
2821 gcaggtctgc gtagatggtg aatgtcatat cctgggtaga gtggtgcggc cagggccaga
2881 tggggtccca cagagcacgc tccttggtat cctgctgcct ttgctgctgc ttgtggctgc
2941 actggcgact gcactggtct tcagctactg gtggcggagg aagcagctag ttcttcctcc
3001 caacctgaat gacctggcat ccctggacca gactgctgga gccacacccc tgcctattct
3061 gtactcgggc tctgactaca gaagtggcct tgcactccct gccattgatg gtctggattc
3121 caccacttgt gtccatggag catccttctc cgatagtgaa gatgaatcct gtgtgccact
3181 gctgcggaaa gagtccatcc agctaaggga cctggactct gcgctcttgg ctgaggtcaa
3241 ggatgtgctg attccccatg agcgggtggt cacccacagt gaccgagtca ttggcaaagg
3301 ccactttgga gttgtctacc acggagaata catagaccag gcccagaatc gaatccaatg
3361 tgccatcaag tcactaagtc gcatcacaga gatgcagcag gtggaggcct tcctgcgaga
3421 ggggctgctc atgcgtggcc tgaaccaccc gaatgtgctg gctctcattg gtatcatgtt
3481 gccacctgag ggcctgcccc atgtgctgct gccctatatg tgccacggtg acctgctcca
3541 gttcatccgc tcacctcagc ggaacccac cgtgaaggac ctcatcagct ttggcctgca
3601 ggtagcccgc ggcatggagt acctggcaga gcagaagttt gtgcacaggg acctggctgc
3661 gcggaactgc atgctggacg agtcattcac agtcaaggtg gctgactttg gtttggcccg
3721 cgacatcctg gacagggagt actatagtgt tcaacagcat cgccacgctc gcctacctgt
3781 gaagtggatg gcgctggaga gcctgcagac ctatagattt accaccaagt ctgatgtgtg
3841 gtcatttggt gtgctgctgt gggaactgct gacacgggt gccccaccat accgccacat
3901 tgaccctttt gaccttaccc acttcctggc ccagggtcgg cgcctgcccc agcctgagta
3961 ttgccctgat tctctgtacc aagtgatgca gcaatgctgg gaggcagacc cagcagtgcg
4021 acccaccttc agagtactag tggggaggt ggagcagata gtgtctgcac tgcttgggga
4081 ccattatgtg cagctgccag caacctacat gaacttgggc cccagcacct cgcatgagat
4141 gaatgtgcgt ccagaacagc cgcagttctc acccatgcca gggaatgtac gccggccccg
4201 gccactctca gagcctcctc ggcccacttg acttagttct tgggctggac ctgcttagct
4261 gccttgagct aaccccaagg ctgcctctgg gccatgccag gccagagcag tggccctcca
4321 ccttgttcct gcccttaac tttcagaggc aataggtaaa tgggcccatt aggtccctca
```

APPENDIX-continued

Nucleotide Sequences for HDACi Compound Resistance Biomarker Genes

```
4381 ctccacagag tgagccagtg agggcagtcc tgcaacatgt atttatggag tgcctgctgt
4441 ggaccctgtc ttctgggcac agtggactga gcagtgacca caccaacact gacccttgaa
4501 ccaataaagg aacaaatgac tattaaagca caaaaaaaaa a
```

| Gene Name | Gene Symbol | GenBank Accession # | SEQ ID NO |
|---|---|---|---|
| integrin, beta 4 | ITGB4 | NM_000213 | 37 |

```
   1 gcgctgcccg cctcgtcccc acccccccaa ccccgcgcc cgccctcgga cagtccctgc
  61 tcgcccgcgc gctgcagccc catctcctag cggcagccca ggcgcggagg gagcgagtcc
 121 gccccgaggt aggtccagga cgggcgcaca gcagcagccg aggctggccg ggagagggag
 181 gaagaggatg gcagggccac gccccagccc atgggccagg ctgctcctgg cagccttgat
 241 cagcgtcagc ctctctggga ccttggcaaa ccgctgcaag aaggccccag tgaagagctg
 301 cacggagtgt gtccgtgtgg ataaggactg cgcctactgc acagacgaga tgttcaggga
 361 ccggcgctgc aacacccagg cggagctgct ggccgcgggc tgccagcggg agagcatcgt
 421 ggtcatggag agcagcttcc aaatcacaga ggagacccag attgacacca ccctgcggcg
 481 cagccagatg tccccccaag gcctgcgggt ccgtctgcgg cccggtgagg agcggcattt
 541 tgagctggag gtgtttgagc cactggagag ccccgtggac ctgtacatcc tcatggactt
 601 ctccaactcc atgtccgatg atctggacaa cctcaagaag atggggcaga acctggctcg
 661 ggtcctgagc cagctcacca gcgactacac tattggattt ggcaagtttg tggacaaagt
 721 cagcgtcccg cagacggaca tgaggcctga aagctgaag gagccctggc caacagtga
 781 cccccccttc tccttcaaga acgtcatcag cctgacagaa gatgtggatg agttccggaa
 841 taaactgcag ggagagcgga tctcaggcaa cctggatgct cctgagggcg gcttcgatgc
 901 catcctgcag acagctgtgt gcacgaggga cattggctgg cgcccggaca gcacccacct
 961 gctggtcttc tccaccgagt cagccttcca ctatgaggct gatggcgcca acgtgctggc
1021 tggcatcatg agccgcaacg atgaacggtg ccacctggac accacgggca cctacaccca
1081 gtacaggaca caggactacc cgtcggtgcc cacccttggtg cgcctgctcg ccaagcacaa
1141 catcatcccc atctttgctg tcaccaacta ctcctatagc tactacgaga agcttcacac
1201 ctatttccct gtctcctcac tgggggtgct gcaggaggac tcgtccaaca tcgtggagct
1261 gctggaggag gccttcaatc ggatccgctc caacctggac atccgggccc tagacagccc
1321 ccgaggcctt cggacagagg tcacctccaa gatgttccag aagacgagga ctgggtcctt
1381 tcacatccgg cggggggaag tgggtatata ccaggtgcag ctgcgggccc ttgagcacgt
1441 ggatgggacg cacgtgtgcc agctgccgga ggaccagaag ggcaacatcc atctgaaacc
1501 ttccttctcc gacggcctca agatggacgc gggcatcatc tgtgatgtgt gcacctgcga
1561 gctgcaaaaa gaggtgcggt cagctcgctg cagcttcaac ggagacttcg tgtgcggaca
1621 gtgtgtgtgc agcgagggct ggagtggcca gacctgcaac tgctccaccg gctctctgag
1681 tgacattcag cctgcctgc ggagggcga ggacaagccg tgctccggcc gtggggagtg
1741 ccagtgcggg cactgtgtgt gctacggcga aggccgctac gagggtcagt tctgcgagta
1801 tgacaacttc cagtgtcccc gcacttccgg gttcctctgc aatgaccgag gacgctgctc
1861 catgggccca tgtgtgtgtg agcctggttg gacaggccca agctgtgact gtcccctcag
1921 caatgccacc tgcatcgaca gcaatggggg catctgtaat ggacgtggcc actgtgagtg
```

APPENDIX-continued

Nucleotide Sequences for HDACi Compound Resistance Biomarker Genes

```
1981 tggccgctgc cactgccacc agcagtcgct ctacacggac accatctgcg agatcaacta
2041 ctcggcgatc cacccgggcc tctgcgagga cctacgctcc tgcgtgcagt gccaggcgtg
2101 gggcaccggc gagaagaagg ggcgcacgtg tgaggaatgc aacttcaagg tcaagatggt
2161 ggacgagctt aagagagccg aggaggtggt ggtgcgctgc tccttccggg acgaggatga
2221 cgactgcacc tacagctaca ccatggaagg tgacggcgcc cctgggccca acagcactgt
2281 cctggtgcac aagaagaagg actgccctcc gggctccttc tggtggctca tccccctgct
2341 cctcctcctc ctgccgctcc tggccctgct actgctgcta tgctggaagt actgtgcctg
2401 ctgcaaggcc tgcctggcac ttctcccgtg ctgcaaccga ggtcacatgg tgggctttaa
2461 ggaagaccac tacatgctgc gggagaacct gatggcctct gaccacttgg acacgcccat
2521 gctgcgcagc gggaacctca agggccgtga cgtggtccgc tggaaggtca ccaacaacat
2581 gcagcggcct ggctttgcca ctcatgccgc cagcatcaac cccacagagc tggtgcccta
2641 cgggctgtcc ttgcgcctgg cccgcctttg caccgagaac ctgctgaagc ctgacactcg
2701 ggagtgcgcc cagctgcgcc aggaggtgga ggagaacctg aacgaggtct acaggcagat
2761 ctccggtgta cacaagctcc agcagaccaa gttccggcag cagcccaatg ccgggaaaaa
2821 gcaagaccac accattgtgg acacagtgct gatggcgccc cgctcggcca agccggccct
2881 gctgaagctt acagagaagc aggtggaaca gagggccttc cacgacctca aggtggcccc
2941 cggctactac accctcactg cagaccagga cgcccggggc atggtggagt tccaggaggg
3001 cgtggagctg gtggacgtac gggtgccccT ctTtatccgg cctgaggatg acgacgagaa
3061 gcagctgctg gtggaggcca tcgacgtgcc cgcaggcact gccaccctcg gccgccgcct
3121 ggtaaacatc accatcatca aggagcaagc cagagacgtg gtgtcctttg agcagcctga
3181 gttctcggtc agccgcgggg accaggtggc ccgcatccct gtcatccggc gtgtcctgga
3241 cggcgggaag tcccaggtct cctaccgcac acaggatggc accgcgcagg caaccgggga
3301 ctacatcccc gtggagggtg agctgctgtt ccagcctggg gaggcctgga agagctgca
3361 ggtgaagctc ctggagctgc aagaagttga ctccctcctg cggggccgcc aggtccgccg
3421 tttccacgtc cagctcagca accctaagtt tggggcccac ctgggccagc cccactccac
3481 caccatcatc atcagggacc cagatgaact ggaccggagc ttcacgagtc agatgttgtc
3541 atcacagcca cccctcacg gcgacctggg cgccccgcag aaccccaatg ctaaggccgc
3601 tgggtccagg aagatccatt tcaactggct gccccttct ggcaagccaa tggggtacag
3661 ggtaaagtac tggattcagg gtgactccga atccgaagcc cacctgctcg acagcaaggt
3721 gccctcagtg gagctcacca acctgtaccc gtattgcgac tatgagatga aggtgtgcgc
3781 ctacggggct cagggcgagg gaccctacag ctccctggtg tcctgccgca cccaccagga
3841 agtgccagc gagccagggc gtctggcctt caatgtcgtc tcctccacgg tgacccagct
3901 gagctgggct gagccggctg agaccaacgg tgagatcaca gcctacgagg tctgctatgg
3961 cctggtcaac gatgacaacc gacctattgg gcccatgaag aaagtgctgg ttgacaaccc
4021 taagaaccgg atgctgctta ttgagaacct tcgggagtcc cagccctacc gctacacggt
4081 gaaggcgcgc aacggggccg gctggggcc tgagcgggag gccatcatca acctggccac
4141 ccagccaag aggcccatgt ccatccccat catccctgac atccctatcg tggacgccca
4201 gagcggggag gactacgaca gcttccttat gtacagcgat gacgttctac gctctccatc
4261 gggcagccag aggcccagcg tctccgatga cactggctgc ggctggaagt tcgagcccct
```

APPENDIX-continued

Nucleotide Sequences for HDACi Compound Resistance Biomarker Genes

```
4321  gctgggggag gagctggacc tgcggcgcgt cacgtggcgg ctgccccgg agctcatccc
4381  gcgcctgtcg gccagcagcg ggcgctcctc cgacgccgag gcgccccacg ggcccccgga
4441  cgacggcggc gcgggcggga agggcggcag cctgccccgc agtgcgacac ccgggccccc
4501  cggagagcac ctggtgaatg gccggatgga ctttgccttc ccgggcagca ccaactccct
4561  gcacaggatg accacgacca gtgctgctgc ctatggcacc cacctgagcc cacacgtgcc
4621  ccaccgcgtg ctaagcacat cctccaccct cacacgggac tacaactcac tgacccgctc
4681  agaacactca cactcgacca cactgcccag ggactactcc accctcacct ccgtctcctc
4741  ccacgactct cgcctgactg ctggtgtgcc cgacacgccc accgcctgg tgttctctgc
4801  cctggggccc acatctctca gagtgagctg gcaggagccg cggtgcgagc ggccgctgca
4861  gggctacagt gtggagtacc agctgctgaa cggcggtgag ctgcatcggc tcaacatccc
4921  caaccctgcc cagacctcgg tggtggtgga agacctcctg cccaaccact cctacgtgtt
4981  ccgcgtgcgg gcccagagcc aggaaggctg gggccgagag cgtgagggtg tcatcaccat
5041  tgaatcccag gtgcacccgc agagcccact gtgtcccctg ccaggctccg ccttcacttt
5101  gagcactccc agtgcccag gcccgctggt gttcactgcc ctgagcccag actcgctgca
5161  gctgagctgg gagcggccac ggaggcccaa tggggatatc gtcggctacc tggtgacctg
5221  tgagatggcc caaggaggag ggccagccac cgcattccgg gtggatggag acagccccga
5281  gagccggctg accgtgccgg gcctcagcga gaacgtgccc tacaagttca aggtgcaggc
5341  caggaccact gagggcttcg ggccagagcg cgagggcatc atcaccatag agtcccagga
5401  tggaggaccc ttcccgcagc tgggcagccg tgccgggctc ttccagcacc cgctgcaaag
5461  cgagtacagc agcatcacca ccacccacac cagcgccacc gagcccttcc tagtggatgg
5521  gctgaccctg ggggcccagc acctggaggc aggcggctcc ctcacccggc atgtgaccca
5581  ggagtttgtg agccggacac tgaccaccag cggaaccctt agcacccaca tggaccaaca
5641  gttcttccaa acttgaccgc accctgcccc accccgcca cgtcccacta ggcgtcctcc
5701  cgactcctct cccggagcct cctcagctac tccatccttg caccctggg ggcccagccc
5761  acccgcatgc acagagcagg ggctaggtgt ctcctgggag gcatgaaggg ggcaaggtcc
5821  gtcctctgtg ggcccaaacc tatttgtaac caaagagctg ggagcagcac aaggacccag
5881  cctttgttct gcacttaata aatggttttg ctactgctaa
```

| Gene Name | Gene Symbol | GenBank Accession # | SEQ ID NO |
|---|---|---|---|
| annexin A3 | ANXA3 | NM_005139 | 38 |

```
  1  gggtggggaa gcttagagac cggtgaggga gcagagctgg ggcgcctgtg tacagggata
 61  gagcccggcg gcagcagggc gcggcttccc tttcccgggg cctggggccg caatcaggtg
121  gagtcgagag gccggaggag gggcaggagg aaggggtgcg gtcgcgatcc ggacccggag
181  ccagcgcgga gcacctgcgc ccgcggctga caccttcgct cgcagtttgt tcgcagttta
241  ctcgcacacc agtttccccc accgcgcttt ggattagtgt gatctcagct caaggcaaag
301  gtgggatatc atggcatcta tctggttggg acaccgagga acagtaagag attatccaga
361  ctttagccca tcagtggatg ctgaagctat tcagaaagca atcagaggaa ttggaactga
421  tgagaaaatg ctcatcagca ttctgactga gaggtcaaat gcacagcggc agctgattgt
481  taaggaatat caagcagcat atggaaagga gctgaaagat gacttgaagg gtgatctctc
```

APPENDIX-continued

Nucleotide Sequences for HDACi Compound Resistance Biomarker Genes

```
 541 tggccacttt gagcatctca tggtggccct agtgactcca ccagcagtct ttgatgcaaa
 601 gcagctaaag aaatccatga agggcgcggg aacaaacgaa gatgccttga ttgaaatctt
 661 aactaccagg acaagcaggc aaatgaagga tatctctcaa gcctattata cagtatacaa
 721 gaagagtctt ggagatgaca ttagttccga aacatctggt gacttccgga aagctctgtt
 781 gactttggca gatggcagaa gagatgaaag tctgaaagtg gatgagcatc tggccaaaca
 841 agatgcccag attctctata aagctggtga aacagatgg ggcacggatg aagacaaatt
 901 cactgagatc ctgtgtttaa ggagcttttcc tcaattaaaa ctaacatttg atgaatacag
 961 aaatatcagc caaaaggaca ttgtggacag cataaaagga gaattatctg gcattttga
1021 agacttactg ttggccatag ttaattgtgt gaggaacacg ccggccttt tagccgaaag
1081 actgcatcga gccttgaagg gtattggaac tgatgagttt actctgaacc gaataatggt
1141 gtccagatca gaaattgacc ttttggacat tcgaacagag ttcaagaagc attatggcta
1201 ttccctatat tcagcaatta aatcggatac ttctggagac tatgaaatca cactcttaaa
1261 aatctgtggt ggagatgact gaaccaagaa gataatctcc aaaggtccac gatgggcttt
1321 cccaacagct ccaccttact tcttctcata ctatttaaga gaacaagcaa atataaacag
1381 caacttgtgt tcctaacagg aattttcatt gttctataac aacaacaaca aaagcgatta
1441 ttattttaga gcatctcatt tataatgtag cagctcataa atgaaattga aaatggtatt
1501 aaagatctgc aactactatc caacttatat ttctgctttc aaagttaaga atctttatag
1561 ttctactcca ttaaatataa agcaagataa taaaaattgt tgcttttgtt aaaagtaaaa
```

| Gene Name | Gene Symbol | GenBank Accession # | SEQ ID NO |
|---|---|---|---|
| chemokine (C-C motif) ligand 15 | CCL15 | NM_032965 | 39 |

```
   1 tgcagactga tatggattca ccactgctaa cacctcctgg ttggaactac aggaatagaa
  61 ctggaaaggg aaaaaaggca gcattcacca catcccaatc ctgaatccaa gagtctaaga
 121 tagtccccca ctcctatctc aggcttagag gattagatta atctcctgga gggaagactc
 181 ttccttgaaa cattttttt tatctgcctg tagctattgg gataattcgg gaaatccaca
 241 gggacagttc aagtcatctt tgtcctctac tttctgttgc actctcagcc ttgttctctt
 301 tttagaaact gcatggtaac tattatatag ctaaagaaga gcattctgac ctctgccctg
 361 ggacttcctg gatcctcctc ttcttataaa tacaagggca gagctggtat cccggggagc
 421 caggaagcag tgagcccagg agtcctcggc cagccctgcc tgcccaccag gaggatgaag
 481 gtctccgtgg ctgccctctc ctgcctcatg cttgttgctg tccttggatc ccaggcccag
 541 ttcataaatg atgcagagac agagttaatg atgtcaaagc ttccactgga aaatccagta
 601 gttctgaaca gctttcactt tgctgctgac tgctgcacct cctacatctc acaaagcatc
 661 ccgtgttcac tcatgaaaag ttatttttgaa acgagcagcg agtgctccaa gccaggtgtc
 721 atattcctca ccaagaaggg gcggcaagtc tgtgccaaac ccagtggtcc gggagttcag
 781 gattgcatga aaaagctgaa gccctactca atataataat aaagagacaa aagaggccag
 841 ccacccacct ccaacacctc ctgtgagttt cttggtctga aatacttaaa aaatatatat
 901 attgttgtgt ctggtaatga agtaatgca tctaataaag agtattcaat ttttt
```

APPENDIX-continued

Nucleotide Sequences for HDACi Compound Resistance Biomarker Genes

| Gene Name | Gene Symbol | GenBank Accession # | SEQ ID NO |
|---|---|---|---|
| dipeptidase 1 (renal) | DPEP1 | NM_004413 | 40 |

```
   1 cggggggta ctgtgcgagc cctcaaggag gtggctgttc tgtagctgga gagctccgtg
  61 ggtggcagga ctgaacttga acaccagaaa caaccccccaa gccttgtgac ctgggaggca
 121 ggaggcgggt ctgtctccct gggacttggg tggctgagcc gaggtactcg ggaccctgtc
 181 ccgcgcatgg cagagtggct cctcacagcc tgaagctcat ccttctgcac gggccagcca
 241 ggccagcaca gaggcaccag ggcagcagtg cacacaggtc cccggggacc ccaccatgtg
 301 gagcggatgg tggctgtggc cccttgtggc cgtctgcact gcagacttct ttcgggacga
 361 ggcagagagg atcatgaggg actcccctgt cattgatggg cacaatgacc tccccctggca
 421 gctgctggat atgttcaaca accggctgca ggacgagagg gccaacctga ccaccttggc
 481 cggcacacac accaacatcc ccaagctgag ggccggcttt gtgggaggcc agttctggtc
 541 cgtgtacacg ccctgcgaca cccagaacaa agacgccgtg cggaggacgc tggagcagat
 601 ggacgtggtc caccgcatgt gccggatgta cccggagacc ttcctgtatg tcaccagcag
 661 tgcaggcatt cggcaggcct tccgggaagg gaaggtggcc agcctgatcg gcgtggaggg
 721 cggccactcc attgacagca gtttggggcgt cctgcgggca ctctatcagc tgggcatgcg
 781 gtacctgacc ctcacccaca gctgcaacac gccctgggct gacaactggc tggtggacac
 841 gggagacagc gagccccaga gccaaggctt gtcacccttt gggcagcgtg tggtgaagga
 901 gctgaaccgt ctggggggtcc tcatcgactt ggctcacgtg tctgtggcca ccatgaaggc
 961 caccctgcag ctgtccagag ccccggtcat cttcagccac tcctcggcct acagcgtgtg
1021 cgcaagccgg cgcaacgtgc ctgacgacgt cctgaggctg gtgaaacaga cagacagcct
1081 ggtgatggtg aacttctaca acaattacat ttcctgcacc aacaaggcca acctgtccca
1141 agtggccgac catctggatc acatcaagga ggtggcagga gccagagccg tgggtttttgg
1201 tggggacttt gatggtgttc caagggtccc tgagggggctg gaggacgtct ccaagtatcc
1261 agacctgatc gctgagctgc tcaggaggaa ctggacgagg gcggaggtca agggcgcact
1321 ggctgacaac ctgctgaggg tcttcgaggc tgtggaacag gccagcaacc tcacacaggc
1381 tcccgaggag gagcccatcc cgctggacca gctgggtggc tcctgcagga cccattacgg
1441 ctactcctct gggggcttcca gcctccatcg ccactggggg ctcctgctgg cctccctcgc
1501 tccccctggtc ctctgtctgt ctctcctgtg aaacctggga gaccagagtc ccctttaggg
1561 ttcccggagc tccggaaga cccgcccatc ccaggactcc agatgccagg agccctgctg
1621 cccacatgca aggaccagca tctcctgaga ggacgcctgg gcttacctgg ggggcaggat
1681 gcctggggac agttcaggac acacacacag taggcccgca ataaaagcaa cacccctt
```

| Gene Name | Gene Symbol | GenBank Accession # | SEQ ID NO |
|---|---|---|---|
| NADPH oxidase organizer 1 | NOXO1 | NM_172167 | 41 |

```
   1 agccatggca ggccccccgat acccagtttc agtgcaaggg gcagccctgg tgcagatcaa
  61 gaggctccaa acgtttgcct tctctgtgcg ctggtcagac ggcagcgaca ccttcgtgcg
 121 caggagttgg gacgaattca ggcagctcaa gaagacccttc aaggagacct tcccggtgga
 181 ggcgggcctg ctgcggagat ctgaccgcgt tctcccaaag cttctcgatg caccactgtt
```

APPENDIX-continued

Nucleotide Sequences for HDACi Compound Resistance Biomarker Genes

```
 241 gggacgcgtg gggcgcacga gccgcggcct ggcgcgcctg cagctgttgg aaacctattc
 301 tcggaggctg ctggcgactg cagagcgcgt ggcacggagc ccgacgatca ctggcttctt
 361 cgcaccgcaa cccctggacc tggagcccgc gctgccaccc ggcagccggg tgatcctgcc
 421 caccccagag gagcagcctc tttctcgcgc tgcgggccgc ctctccatcc acagtctgga
 481 ggctcagagc ctgcgctgcc tgcagccctt ctgtacccag gacacgcggg ataggccttt
 541 tcaggcgcag gcccaggaga gcctggacgt gctgctgcgg cacccctcag gctggtggct
 601 ggtggagaac gaagaccggc agaccgcctg gtttccagcg ccctacctgg aggaggcggc
 661 cccgggccaa ggccgggagg gaggcccgtc cctagggagc agcggtcccc agttctgtgc
 721 ttcccgcgcc tacgagagca gccgcgcaga tgagctgtcc gtgcccgcgg gggcgcgcgt
 781 gcgcgtgttg gaaacgtcag accgcggctg gtggctatgc aggtacggcg accgggcggg
 841 cctactcccc gcggtgctgc tgcggccgga agggctgggc gctctcctga gcgggacggg
 901 gttccgtgga ggagacgacc cggcgggtga ggcccggggc ttccctgaac cctcccaggc
 961 caccgcccct cccccaccg tgcccacccg accttcgccg ggcgccatcc agagccgctg
1021 ctgcaccgtc acacgcaggg ccctggagcg gcgcccacgg cgccagggcc gccctcgagg
1081 gtgcgtggac tctgtgccgc accccacgac ggagcagtga gcgcgaggat cc
```

| Gene Name | Gene Symbol | GenBank Accession # | SEQ ID NO |
|---|---|---|---|
| interferon, alpha-inducible protein 27 | IFI27 | NM_005532 | 42 |

```
   1 gggaacacat ccaagcttaa gacggtgagg tcagcttcac attctcagga actctccttc
  61 tttgggtctg gctgaagttg aggatctctt actctctagg ccacggaatt aacccgagca
 121 ggcatggagg cctctgctct cacctcatca gcagtgacca gtgtggccaa agtggtcagg
 181 gtggcctctg gctctgccgt agttttgccc ctggccagga ttgctacagt tgtgattgga
 241 ggagttgtgg ctgtgcccat ggtgctcagt gccatgggct tcactgcggc gggaatcgcc
 301 tcgtcctcca tagcagccaa gatgatgtcc gcggcggcca ttgccaatgg gggtggagtt
 361 gcctcgggca gccttgtggc tactctgcag tcactgggag caactggact ctccggattg
 421 accaagttca tcctgggctc cattgggtct gccattgcgg ctgtcattgc gaggttctac
 481 tagctccctg cccctcgccc tgcagagaag agaaccatgc caggggagaa ggcacccagc
 541 catcctgacc cagcgaggag ccaactatcc caaatatacc tggggtgaaa tataccaaat
 601 tctgcatctc cagaggaaaa taagaaataa agatgaattg ttgcaactct tcaaaa
```

| Gene Name | Gene Symbol | GenBank Accession # | SEQ ID NO |
|---|---|---|---|
| cytochrome P450, family 3, subfamily A, polypeptide 43 | CYP3A43 | NM_057095 | 43 |

```
   1 acctctgggc agagaaacaa agctctatat gcacagccca gcaaagagca gcacacagct
  61 gaaagaaaaa ctcagaagac agagctgaaa aagaaaactg gtgatggatc tcattccaaa
 121 ctttgccatg gaaacatggg ttcttgtggc taccagcctg gtactcctct atatttatgg
 181 gacccattca cataaacttt ttaagaagct gggaattcct gggccaaccc ctctgccttt
 241 tctgggaact attttgttct accttagggg tctttggaat tttgacagag aatgtaatga
 301 aaaatacgga gaaatgtggg ggctgtatga gggcaacag cccatgctgg tcatcatgga
```

APPENDIX-continued

Nucleotide Sequences for HDACi Compound Resistance Biomarker Genes

```
 361 tcccgacatg atcaaaacag tgttagtgaa agaatgttac tctgtcttca caaaccagat
 421 gcctttaggt ccaatgggat ttctgaaaag tgccttaagt tttgctgaag atgaagaatg
 481 gaagagaata cgaacattgc tatctccagc tttcaccagt gtaaaattca aggaaatggt
 541 ccccatcatt tcccaatgtg gagatatgtt ggtgagaagc ctgaggcagg aagcagagaa
 601 cagcaagtcc atcaacttga agatttctt tggggcctac accatggatg taatcactgg
 661 cacattattt ggagtgaact tggattctct caacaatcca caagatccct ttctgaaaaa
 721 tatgaagaag cttttaaaat tggatttttt ggatcccttt ttactcttaa tatcactctt
 781 tccatttctt accccagttt ttgaagccct aaatatcggt ttgtttccaa agatgttac
 841 ccatttttta aaaaattcca ttgaaaggat gaaagaaagt cgcctcaaag ataaacaaaa
 901 gcatcgagta gatttcttc aacagatgat cgactcccag aattccaaag aaacaaagtc
 961 ccataaagct ctgtctgatc tggagcttgt ggcccagtca attatcatca ttttgctgc
1021 ctatgacaca actagcacca ctctcccctt cattatgtat gaactggcca ctcaccctga
1081 tgtccagcag aaactgcagg aggagattga cgcagtttta cccaataagg cacctgtcac
1141 ctacgatgcc ctggtacaga tggagtacct tgacatggtg gtgaatgaaa cgctcagatt
1201 attcccagtt gttagtagag ttacgagagt ctgcaagaaa gatattgaaa tcaatggagt
1261 gttcattccc aaagggttag cagtgatggt tccaatctat gctcttcacc atgacccaaa
1321 gtactggaca gagcctgaga agttctgccc tgaaaggttc agtaagaaga caaggacag
1381 catagatctt tacagataca tacctttttgg agctggaccc cgaaactgca ttggcatgag
1441 gtttgctctc acaaacataa aacttgctgt cattagagca ctgcagaact tctccttcaa
1501 accttgtaaa gagactcaga tcccactgaa attagacaat ctaccaattc ttcaaccaga
1561 aaaacctatt gttctaaaag tgcacttaag agatgggatt acaagtggac cctgactttc
1621 cctaaggact tccactttgt tcaagaaagc tgtatcccag aacactagac acttcaaatt
1681 gttttgtgaa taaaactcag aaatgaagat gagcttaatt aacctagtat actgggtgaa
1741 taattagaaa ttctctacat tcattgagct ctcattgtct gggtagagta ttacacgttg
1801 catactacaa agcaggtgac aaatcaatgc caaataagta cagtcatctt ctctagttct
1861 cataagacta tctccccgcc acctatagtt agtaccctca agtcctcctg agctgtgatc
1921 agagaataaa catttctcaa caattttacc aacaattttt aatgaaaagg aaaattatac
1981 ttgtgattct cgtagtgaca tttatattac atgttccatt tgtgatattc tataataagt
2041 attatattga gaaagtcaac aagcacctct ttacaaaact gttatctgat gtcttcctgc
2101 atattaagga tgaatctaca gaattagatc aataaggatc aacaaataaa tatttttggt
2161 catt
```

| Gene Name | Gene Symbol | GenBank Accession # | SEQ ID NO |
|---|---|---|---|
| plakophilin 2 | PKP2 | NM_004572 | 44 |

```
   1 gtggcggctt cgcccgcgag tccagaggca ggcgagcagc tcggtcgccc ccaccggccc
  61 catggcagcc cccggcgccc cagctgagta cggctacatc cggaccgtcc tgggccagca
 121 gatcctggga caactggaca gctccagcct ggcgctgccc tccgaggcca agctgaagct
 181 ggcggggagc agcggccgcg gcggccgac agtcaagagc ctgcggatcc aggagcaggt
 241 gcagcagacc ctcgcccgga agggccgcag ctccgtgggc aacggaaatc ttcaccgaac
```

APPENDIX-continued

Nucleotide Sequences for HDACi Compound Resistance Biomarker Genes

```
 301 cagcagtgtt cctgagtatg tctacaacct acacttggtt gaaaatgatt ttgttggagg
 361 ccgttcccct gttcctaaaa cctatgacat gctaaaggct ggcacaactg ccacttatga
 421 aggtcgctgg ggaagaggaa cagcacagta cagctcccag aagtccgtgg aagaaaggtc
 481 cttgaggcat cctctgagga gactggagat ttctcctgac agcagcccgg agagggctca
 541 ctacacgcac agcgattacc agtacagcca gagaagccag gctgggcaca ccctgcacca
 601 ccaagaaagc aggcgggccg ccctcctagt gccaccgaga tatgctcgtt ccgagatcgt
 661 gggggtcagc cgtgctggca ccacaagcag gcagcgccac tttgacacat accacagaca
 721 gtaccagcat ggctctgtta gcgacaccgt ttttgacagc atccctgcca acccggccct
 781 gctcacgtac cccaggccag gaccagccg cagcatgggc aacctcttgg agaaggagaa
 841 ctacctgacg gcagggctca ctgtcgggca ggtcaggccg ctggtgcccc tgcagcccgt
 901 cactcagaac agggcttcca ggtcctcctg gcatcagagc tccttccaca gcacccgcac
 961 gctgagggaa gctgggccca gtgtcgccgt ggattccagc gggaggagag cgcacttgac
1021 tgtcggccag gcggccgcag ggggaagtgg gaatctgctc actgagagaa gcactttcac
1081 tgactcccag ctggggaatg cagacatgga gatgactctg gagcgagcag tgagtatgct
1141 cgaggcagac cacatgccgc catccaggat ttctgctgca gctactttca tacagcacga
1201 gtgcttccag aaatctgaag ctcggaagag ggttaaccag cttcgtggca tcctcaagct
1261 tctgcagctc ctaaaagttc agaatgaaga cgttcagcga gctgtgtgtg gggccttgag
1321 aaacttagta tttgaagaca atgacaacaa attggaggtg gctgaactaa atggggtacc
1381 tcggctgctc caggtgctga agcaaaccag agacttggag actaaaaaac aaataacaga
1441 ccatacagtc aatttaagaa gtaggaatgg ctggccgggc gcggtggctc acgcctgtaa
1501 tcccagcact ttgggaggcc aaggcgggcg gatcacgagg tcaggagttc gagaccagcc
1561 tgaccaacat ggtttgctgt ggaatttgtc atctaatgac aaactcaaga atctcatgat
1621 aacagaagca ttgcttacgc tgacggagaa tatcatcatc ccctttctg ggtggcctga
1681 aggagactac ccaaaagcaa atggtttgct cgattttgac atattctaca acgtcactgg
1741 atgcctaaga aacatgagtt ctgctggcgc tgatgggaga aaagcgatga gaagatgtga
1801 cggactcatt gactcactgg tccattatgt cagaggaacc attgcagatt accagccaga
1861 tgacaaggcc acggagaatt gtgtgtgcat tcttcataac ctctcctacc agctggaggc
1921 agagctccca gagaaatatt cccagaatat ctatattcaa aaccggaata tccagactga
1981 caacaacaaa agtattggat gttttggcag tcgaagcagg aaagtaaaag agcaatacca
2041 ggacgtgccg atgccggagg aaaagagcaa ccccaagggc gtggagtggc tgtggcattc
2101 cattgttata aggatgtatc tgtccttgat cgccaaaagt gtccgcaact acacacaaga
2161 agcatcctta ggagctctgc agaacctcac ggccggaagt ggaccaatgc cgacatcagt
2221 ggctcagaca gttgtccaga aggaaagtgg cctgcagcac acccgaaaga tgctgcatgt
2281 tggtgaccca agtgtgaaaa agacagccat ctcgctgctg aggaatctgt cccggaatct
2341 ttctctgcag aatgaaattg ccaaagaaac tctccctgat ttggtttcca tcattcctga
2401 cacagtcccg agtactgacc ttctcattga aactacagcc tctgcctgtt acacattgaa
2461 caacataatc caaacagtt accagaatgc acgcgacctt ctaaacaccg ggggcatcca
2521 gaaaattatg gccattagtg caggcgatgc ctatgcctcc aacaaagcaa gtaaagctgc
2581 ttccgtcctt ctgtattctc tgtgggcaca cacggaactg catcatgcct acaagaaggc
```

APPENDIX-continued

Nucleotide Sequences for HDACi Compound Resistance Biomarker Genes

```
2641 tcagtttaag aagacagatt ttgtcaacag ccggactgcc aaagcctacc actcccttaa
2701 agactgagga aaatgacaaa gtattctcgg ctgcaaaaat ccccaaagga aaacacctat
2761 ttttctacta cccagcccaa gaaacctcaa aagcatgcct tgtttctatc cttctctatt
2821 tccgtggtcc cctgaatcca gaaaacaaat agaacataat tttatgagtc ttccagaaga
2881 cctttgcaag tttgccacca gtagataccg gccacaggct cgacaaatag tggtctttgt
2941 tattagggct tatggtacat ggcttcctgg aatcaaaatg tgaattcatg tggaagggac
3001 attaatccaa taaataagga aagaagctgt tgcattactg ggattttaaa agtttgattt
3061 acatttatat tccttttctg gttcccatgt tttgtcactc atgtgcacat tgcttcgcca
3121 ttgggcctcc agtgtattgt tctgcagtgt tgaaacagaa tggaaatgac aagaaatatc
3181 tgcagttatc caggagaaag tataatggca aaattattgg tttctttctt tactttgtgc
3241 ttgttttat ccccttgggt tgttttctc tgattttaa ataaacttaa gaaatttaga
3301 ttacagagta tgcatgactg taagaaaaag aaattgagag gaagtgatca tagcaaatta
3361 aagaagtctt ttcctcccag aacttaaagt aaaataaaaa ataaataaat aaataaaatc
3421 ttttccacag agaaaggcaa ctgtgatgat aaaatttaac gttcccccaa acactgagtc
3481 aatgagattt ttctcaggag atactttacc tataacaacg ccgttaaatc caaatctctt
3541 ctaaacgatg gcattctatg taatgccttt cctggacttt tttggccact gccctggact
3601 agtgaaagaa tggactctat ctttatctgc aagaggaact aaggccttct atcagactgc
3661 ctggccagcc tggggcactg aaaatacggc tcatgttaat gagttacatt atcagccagc
3721 ccagccttgc ccaccattta agaaatatca cagagccact agatctcata tgatcttctt
3781 caagccatta ttttaactca agaaaactct agagaagaaa agtgaagaag tcatgttgaa
3841 gaagatgtaa gaatgtgtca agaccatcca gaaatgatat gagaaatact gatattttaa
3901 atggttgaca tcatccagcg aaatgaatct acattaaatg ttgttttaac tgcgctatga
3961 ttaaaaccat tcatatagag ttagtcttta caactactat tctgttattt ttttttttaa
4021 tctgacaaca tttgtcctaa gtaagataag caaaaaaatt cttcaactcc ttttggcaag
4081 aaaactgtaa cagaaaataa attttgaatg tgtacttaag tctttattat atttgaagca
4141 attttttttc aattttaaaa gctgaatgaa gacaacttag gttgctaacc tagttcaaaa
4201 tgaaattatt tagataccaa ttttaaaat actggagaga atttatatgt ctttttccag
4261 agttctgatg ataagcattt ggagtgcatt tattcctcca gataataaat gtgtgttcag
4321 aacttttgt gttttttaag gcattaataa agccttcgat aatattaaat acaaaatgaa
```

What is claimed is:

1. A method for classifying a cancer in a patient, comprising comparing the expression levels of each gene in a set of biomarker genes that are expressed in cancerous cells to a first set or second set of previously established threshold values for each gene in the set of biomarker genes, and indicating that the cancer is sensitive to a HDAC inhibitor if the expression levels of each gene in the set of biomarker genes are lower than the first set of threshold values for each gene in the set of biomarker genes, or indicating that the cancer is resistant to a HDAC inhibitor if the expression levels of each gene in the set of biomarker genes is greater than the second set of threshold values for each gene in the set of biomarker genes, wherein the set of biomarker genes comprises DEFA6, ITGB4, TM4SF3, SYK, PPAP2C, RAB25, and IL18.

2. The method of claim 1, wherein the set of biomarker genes further comprises at least one biomarker gene selected from HEPH, NOXO1, TM4SF4, PTPN3, EPHA2, FGFBP1, ABCC3, TPMT, and DPEP1.

3. The method of claim 1, wherein the expression levels comprises the mRNA expression level, the polypeptide expression level, or a combination thereof.

4. The method of claim 1, further comprising determining the expression levels of each gene in the set of biomarker genes in the cancer prior to performing the comparing step.

5. The method of claim 1, further comprising prescribing or administering an HDAC inhibitor to the patient based on the comparison.

6. The method of claim 1, further comprising at least one biomarker gene selected from PTPN3, ABCC3, SARG, NPDC1, CTEN, HEPH, TPMT, PKP3, GALNT5, CALML4, GALNT12, TPK1, EPLIN, CLIC5, PERP, SLC12A2, GUCY2C, TM4SF4, TGFA, FGFBP1, PTK6, EVA1, EPHA2, ITGA6, TNFRSF21, BMP4, SMPDL3B, TMPRSS2, GDA, MST1R, ANXA3, CCL15, DPEP1, NOXO1, IFI27, CYP3A43, and PKP2.

7. A method for increasing the likelihood of therapeutically effective treatment of a cancer with an HDAC inhibitor, comprising providing an indication that a cancer in a patient is sensitive to treatment with an HDAC inhibitor if the expression levels of each gene in the set of biomarker genes in a sample of cancerous cells obtained from the patient is lower than a first previously established threshold values for each gene in the set of biomarker genes, or providing an indication that the cancer is resistant to treatment with the HDAC inhibitor if the expression levels of each gene in the set of biomarker genes is higher than a second previously established threshold value for each gene in the set of biomarker genes, wherein the set of biomarker genes comprises DEFA6, ITGB4, TM4SF3, SYK, PPAP2C, RAB25, and IL18 whereby the likelihood of therapeutically effective treatment of the cancer with the HDAC inhibitor is increased.

8. The method of claim 7, further comprising at least one biomarker gene selected from PTPN3, ABCC3, SARG, NPDC1, CTEN, HEPH, TPMT, PKP3, GALNT5, CALML4, GALNT12, TPK1, EPLIN, CLIC5, PERP, SLC12A2, GUCY2C, TM4SF4, TGFA, FGFBP1, PTK6, EVA1, EPHA2, ITGA6, TNFRSF21, BMP4, SMPDL3B, TMPRSS2, GDA, MST1R, ANXA3, CCL15, DPEP1, NOXO1, IFI27, CYP3A43, and PKP2.

9. A method for optimizing selection of an anti-cancer agent for treating a cancer in combination with an HDAC inhibitor compound, the method comprising:

(a) comparing a first set of biomarker genes the expression of which is correlated to resistance or sensitivity of the cancer to the anti-cancer agent to a second set of biomarker genes the expression of which is correlated with resistance to the HDAC inhibitor compound; and (b) selecting the anti-cancer agent for treatment of the cancer in combination with the HDAC inhibitor if the biomarker genes in the first set are different from the biomarker genes in the second set, wherein the second set of biomarker genes comprises DEFA6, ITGB4, TM4SF3, SYK, PPAP2C, RAB25, and IL18.

10. The method of claim 9, further comprising at least one biomarker gene selected from HEPH, NOXO1, TM4SF4, PTPN3, EPHA2, FGFBP1, ABCC3, TPMT, and DPEP1.

11. A method for determining the likelihood of effectively treating a cancer in a patient with an HDAC inhibitor compound, comprising
(i) determining in the cancer the expression levels of biomarker genes, wherein the biomarker genes comprise DEFA6, ITGB4, TM4SF3, SYK, PPAP2C, RAB25, and IL18; and
(ii) comparing the expression levels of the biomarker genes in the cancer to expression levels of the biomarker genes in an expression level reference sample derived from cancer cells previously determined to be resistant to the HDAC inhibitor compound, wherein the likelihood of effectively treating the cancer is higher if the expression level of the biomarkers in the cancer from the patient is lower than the expression levels of the biomarker genes in the expression level reference sample.

12. The method of claim 11, further comprising selecting an anti-cancer agent other than an HDAC inhibitor compound for treating the cancer.

13. The method of claim 11, further comprising at least one biomarker gene selected from HEPH, NOXO1, TM4SF4, PTPN3, EPHA2, FGFBP1, ABCC3, TPMT, and DPEP.

14. A method for classifying a cancer in a patient, comprising comparing the expression levels of biomarker genes in the cancer to a first or second set of expression level values for the biomarker genes, and for each comparison assigning a probability to the biomarker gene expression level that the cancer in the patient is resistant to a histone deacetylase inhibitor compound, wherein
(i) the first set of expression level values were measured in cancer cells determined to be resistant to the histone deacetylase inhibitor compound;
(ii) the second set of expression level values were measured in cancer cells determined to be sensitive to the histone deacetylase inhibitor compound;
(iii) the assigned probability is inversely proportional to a negative deviation of the biomarker gene expression level from the first set of expression level values and directly proportional to a positive deviation of the biomarker gene expression level from the second set of expression level values; and
(iv) the biomarker genes comprise DEFA6, ITGB4, TM4SF3, SYK, PPAP2C, RAB25, and IL18.

15. The method of claim 14, further comprising at least one biomarker gene selected from PTPN3, ABCC3, SARG, NPDC1, CTEN, HEPH, TPMT, PKP3, GALNT5, CALML4, GALNT12, TPK1, EPLIN, CLIC5, PERP, SLC12A2, GUCY2C, TM4SF4, TGFA, FGFBP1, PTK6, EVA1, EPHA2, ITGA6, TNFRSF21, BMP4, SMPDL3B, TMPRSS2, GDA, MST1R, ANXA3, CCL15, DPEP1, NOXO1, IFI27, CYP3A43, and PKP2.

16. A method for determining HDAC inhibition in vivo, comprising determining the expression level of each gene in a set of HDAC inhibitor-responsive biomarker genes in a biological sample obtained from a subject after the subject had been administered an HDAC inhibitor compound, wherein the set of HDAC inhibitor-responsive biomarker genes comprises DEFA6, ITGB4, TM4SF3, SYK, PPAP2C, RAB25, and IL18.

17. The method of claim 16, further comprising at least one biomarker gene selected from PTPN3, ABCC3, SARG, NPDC1, CTEN, HEPH, TPMT, PKP3, GALNT5, CALML4, GALNT12, TPK1, EPLIN, CLIC5, PERP, SLC12A2, GUCY2C, TM4SF4, TGFA, FGFBP1, PTK6, EVA1, EPHA2, ITGA6, TNFRSF21, BMP4, SMPDL3B, TMPRSS2, GDA, MST1R, ANXA3, CCL15, DPEP1, NOXO1, IFI27, CYP3A43, and PKP2.

* * * * *

SEQUENCE LISTING

<160> NUMBER OF SEQ ID NOS: 44

<210> SEQ ID NO 1
<211> LENGTH: 2376
<212> TYPE: DNA
<213> ORGANISM: Homo sapiens

<400> SEQUENCE: 1
tgaatagttt gctggtagca agacggatga agacctatat gggagattct ttatctctag    60

```
agctagcata tttacttgca tactttgttt cttttccaca tggatatttt actgctaaat    120
ggcagaggtg ggagggagat gtcacacagt accataaccc catattgaaa acaagaaacc    180
accagaaagt ttgcagctaa ggggcagggg attcagttcc tacgcccact cagcactaac    240
tacttgcggg cctggttgct tagaagctct acctctcttt cattatctgt aaaatagaaa    300
caatacttag gactttagtt ggaacatgag gattgaataa gatcacgcta ttcatgtgac    360
tttttatcgg ctagaacagc aacagacact gctgtgggtg agttacttag aaaagtttag    420
ttatcagtga ttagcccaaa aacacatcag tcaaaaatag aatccactgg atttttgtct    480 ctcttttag agacagggtc tcactgtcgc ccaggctgga gtacagtggc atgatcattg    540
ttcactgcag cctcaaattc ctgggctcaa gcaatcctcg cacctcagcc tcctgagtag    600
ccgggactat aggcacatgc cacctcacct ggcttgtgtg tgtgtgtgtg tgtgtgtgtg    660
tgtgtgtgtg tgtgtgtgta gagacaggat cttgatgtgt cgcctaggct ggtctcaaac    720
tcctggcctc aagtgatctt cccacctcag cctccaaaac tgttgggatt ataggcgtga    780
gccactgtgc ccagcctaac tgggttttta tgagaggaaa atagaaaatg ctcttctaga    840
agagagagaa caagagcaca aaataatctg gactcacaaa aattcagcaa gctccaagaa    900 aggggatgg agggaacgct ggcaaaaatt taaatgccat taggatatt agcaagttat    960 tactgtttgg taaaaatgca tcatcaccct gtgtgcaaaa tgcttgcaaa gtagtctaaa    1020
tgtctttgga gatgggtgtt ttactgcttt tttccaaaaa caaattgttt attatggttg    1080
cagaaatgca gccattacgg tcacataaat ttctaaaaag cctaccaaag gttgcaagca    1140
gtcttctgcc actgggcagg ccagcagttc agcccagcg aggttgccag gaacaaatcc    1200
aggaaatact gggaagaaca agacaagaga attacctaaa agagcaaaca attcaagtaa    1260
atcctgtagc tattaccact taaaatccgt agctcaagat tcctgtttca ccaccttata    1320
cacttaagca attatactta agcctttttt tagtcctaag tgaagaacta catcagaatc    1380
aggataagta ttttgcctgg gaaatttggc tgcatatgaa tggagaagac atttacatcc    1440
tatgttctgg cactttctga aagatctaat taaacatgtt gatgtgccaa tttaatcaag    1500
atgagagatc cctgctggtg tcaccctcta gaacctgcac ttggtgtttt gactttccag    1560
aagaaaaaaa tgcaactttg gttagggggc agtggttgga tcacacagtt gtctttcgtt    1620
tcctaccaca gtaattcata tttaaatatg cttttagatt agtgtggata ctattgctgc    1680
tgtgttgcta cctgaccttt ttctgggggg ggtacctcag aaatgagcat ttgagggcaa    1740
gcgaaaaagc cctcttcatc ctccagaggc aacaagagg cagcagaaat ggggaaagat    1800
tgtgagaggc agggcttggg tctagacctg gacttaggca agatatgttg ccctcaaccc    1860
tgagttttct tatatgtaaa aagggaaggt tgggctggac tagatgaggt caagatttgc    1920
cattctggga ggctgatatt ccagagaatc aaaattaatc ctaaaccaaa gctttatggc    1980
tgctacagag acatgtcaca tttctgagac ttgtcaccaa gagtttgtcc ctcagacttt    2040
ggcgctgttg aatgcaaaga caaggatggc caccttctgg ttcttgcctg ttgtcctcag    2100
ctgagagcag tctcggtaaa ggtggcaaag attctgtgac ctcagaccgg ggaccaaatg    2160
cttgggagtc tgatgccgg gctgggccac cattctcata gctctcattc tgtttggagc    2220
aaccaaagga tttgtgtgaa gttatttgga aaaggacctt aactgagcag taatctttt    2280 tctgtatatt tggaatgttt ttcattctga cctgttctgt cagtgattct actgaaaaac    2340
aatttaatca atataaaaat gttcaagcta tgcaac                             2376
```

<210> SEQ ID NO 2
<211> LENGTH: 5310
<212> TYPE: DNA
<213> ORGANISM: Homo sapiens

<400> SEQUENCE: 2

| | | | | | | |
|---|---|---|---|---|---|---|
| ctccggcgcc | cgctctgccc | gccgctgggt | ccgaccgcgc | tcgccttcct | tgcagccgcg | 60 |
| cctcggcccc | atggacgccc | tgtgcggttc | cggggagctc | ggctccaagt | tctgggactc | 120 |
| caacctgtct | gtgcacacag | aaaacccgga | cctcactccc | tgcttccaga | actccctgct | 180 |
| ggcctgggtg | ccctgcatct | acctgtgggt | cgccctgccc | tgctacttgc | tctacctgcg | 240 |
| gcaccattgt | cgtggctaca | tcatcctctc | ccacctgtcc | aagctcaaga | tggtcctggg | 300 |
| tgtcctgctg | tggtgcgtct | cctgggcgga | ccttttttac | tccttccatg | gcctggtcca | 360 |
| tggccgggcc | cctgcccctg | ttttctttgt | caccccttg | gtggtggggg | tcaccatgct | 420 |
| gctggccacc | ctgctgatac | agtatgagcg | gctgcagggc | gtacagtctt | cggggtcct | 480 |
| cattatcttc | tggttcctgt | gtgtggtctg | cgccatcgtc | ccattccgct | ccaagatcct | 540 |
| tttagccaag | gcagagggtg | agatctcaga | ccccttccgc | ttcaccacct | tctacatcca | 600 |
| ctttgccctg | gtactctcta | ccctcatctt | ggcctgcttc | agggagaaac | ctccattttt | 660 |
| ctccgcaaag | aatgtcgacc | ctaacccta | ccctgagacc | agcgctggct | ttctctcccg | 720 |
| cctgtttttc | tggtggttca | caagatggc | catctatggc | taccggcatc | cctggagga | 780 |
| gaaggaccte | tggtccctaa | aggaagagga | cagatcccag | atggtggtgc | agcagctgct | 840 |
| ggaggcatgg | aggaagcagg | aaaagcagac | ggcacgacac | aaggcttcag | cagcacctgg | 900 |
| gaaaaatgcc | tccggcgagg | acgaggtgct | gctgggtgcc | cggcccaggc | ccggaagcc | 960 |
| ctccttcctg | aaggccctgc | tggccacctt | cggctccagc | ttcctcatca | gtgcctgctt | 1020 |
| caagcttatc | caggacctgc | tctccttcat | caatccacag | ctgctcagca | tcctgatcag | 1080 |
| gtttatctcc | aaccccatgg | cccctcctg | gtggggcttc | ctggtggctg | ggctgatgtt | 1140 |
| cctgtgctcc | atgatgcagt | cgctgatctt | acaacactat | taccactaca | tctttgtgac | 1200 |
| tgggggtgaag | tttcgtactg | ggatcatggg | tgtcatctac | aggaaggctc | tggttatcac | 1260 |
| caactcagtc | aaacgtgcgt | ccactgtggg | ggaaattgtc | aacctcatgt | cagtggatgc | 1320 |
| ccagcgcttc | atggaccttg | ccccttcct | caatctgctg | tggtcagcac | ccctgcagat | 1380 |
| catcctggcg | atctacttcc | tctggcagaa | cctaggtccc | tctgtcctgg | ctggagtcgc | 1440 |
| tttcatggtc | ttgctgattc | cactcaacgg | agctgtggcc | gtgaagatgc | gcgccttcca | 1500 |
| ggtaaagcaa | atgaaattga | aggactcgcg | catcaagctg | atgagtgaga | tcctgaacgg | 1560 |
| catcaaggtg | ctgaagctgt | acgctggga | gcccagcttc | tgaagcagg | tggagggcat | 1620 |
| caggcagggt | gagctccagc | tgctgcgcac | ggcggcctac | ctccacacca | caaccacctt | 1680 |
| cacctggatg | tgcagcccct | tcctggtgac | cctgatcacc | ctctgggtgt | acgtgtacgt | 1740 |
| ggacccaaac | aatgtgctgg | acgccgagaa | ggcctttgtg | tctgtgtcct | tgtttaatat | 1800 |
| cttaagactt | ccctcaaca | tgctgcccca | gttaatcagc | aacctgactc | aggccagtgt | 1860 |
| gtctctgaaa | cggatccagc | aattcctgag | ccaagaggaa | cttgaccccc | agagtgtgga | 1920 |
| aagaaagacc | atctccccag | gctatgccat | caccatacac | agtggcacct | tcacctgggc | 1980 |
| ccaggacctg | cccccactc | tgcacagcct | agacatccag | gtcccgaaag | ggcactggt | 2040 |
| ggccgtggtg | gggcctgtgg | gctgtgggaa | gtcctccctg | gtgtctgccc | tgctgggaga | 2100 |
| gatggagaag | ctagaaggca | aagtgcacat | gaagggctcc | gtggcctatg | tgccccagca | 2160 |

```
ggcatggatc cagaactgca ctcttcagga aaacgtgctt ttcggcaaag ccctgaaccc    2220
caagcgctac cagcagactc tggaggcctg tgccttgcta gctgacctgg agatgctgcc    2280
tggtggggat cagacagaga ttggagagaa gggcattaac ctgtctgggg ccagcggca    2340 gcgggtcagt ctggctcgag ctgtttacag tgatgccgat attttcttgc tggatgaccc    2400
actgtccgcg gtggactctc atgtggccaa gcacatcttt gaccacgtca tcgggccaga    2460
aggcgtgctg gcaggcaaga cgcgagtgct ggtgacgcac ggcattagct tcctgcccca    2520
gacagacttc atcattgtgc tagctgatgg acaggtgtct gagatgggcc cgtacccagc    2580
cctgctgcag cgcaacggct cctttgccaa ctttctctgc aactatgccc ccgatgagga    2640
ccaagggcac ctggaggaca gctggaccgc gttggaaggt gcagaggata aggaggcact    2700
gctgattgaa gacacactca gcaaccacac ggatctgaca gacaatgatc cagtcaccta    2760
tgtggtccag aagcagttta tgagacagct gagtgccctg tcctcagatg ggagaggaca    2820
gggtcggcct gtaccccgga ggcacctggg tccatcagag aaggtgcagg tgacagaggc    2880
gaaggcagat ggggcactga cccaggagga gaaagcagcc attggcactg tggagctcag    2940
tgtgttctgg gattatgcca aggccgtggg gctctgtacc acgctggcca tctgtctcct    3000
gtatgtgggt caaagtgcgg ctgccattgg agccaatgtg tggctcagtg cctggacaaa    3060
tgatgccatg cagacagta gacagaacaa cacttccctg aggctgggcg tctatgctgc    3120
tttaggaatt ctgcaagggt tcttggtgat gctggcagcc atggccatgg cagcgggtgg    3180
catccaggct gcccgtgtgt tgcaccaggc actgctgcac aacaagatac gctcgccaca    3240
gtccttcttt gacaccacac catcaggccg catcctgaac tgcttctcca aggacatcta    3300
tgtcgttgat gaggttctgg ccccctgtcat cctcatgctg ctcaattcct tcttcaacgc    3360
catctccact cttgtggtca tcatggccag cacgccgctc ttcactgtgg tcatcctgcc    3420
cctggctgtg ctctacacct tagtgcagcg cttctatgca gccacatcac ggcaactgaa    3480
gcggctggaa tcagtcagcc gctcaccta t ctactcccac ttttcggaga cagtgactgg    3540
tgccagtgtc atccgggcct acaaccgcag ccgggatttt gagatcatca gtgatactaa    3600
ggtggatgcc aaccagagaa gctgctaccc ctacatcatc tccaaccggt cagaagccgc    3660
ctccctcgct ccctgctcct ccaggaattc ccagcaggct ctctggtgtt cagggtcctt    3720
gtccctcctt tcccctaagc agaaaactgg ccctgccctg cccctgcccc atttcctcct    3780
catctgatcc cccataggcg gctgagcatc ggagtggagt tcgtggggaa ctgcgtggtg    3840
ctctttgctg cactatttgc cgtcatcggg aggagcagcc tgaacccggg gctggtgggc    3900
cttcctgtgt cctactcctt gcaggtgaca tttgctctga actggatgat acgaatgatg    3960
tcagatttgg aatctaacat cgtggctgtg agagggtca aggagtactc caagacagag    4020
acagaggcgc cctgggtggt ggaaggcagc cgccctcccg aaggttggcc cccacgtggg    4080
gaggtggagt tccggaatta ttctgtgcgc taccggccgg gcctagacct ggtgctgaga    4140
gacctgagtc tgcatgtgca cggtggcgag aaggtgggga tcgtgggccg cactgggggct    4200 ggcaagtctt ccatgaccct ttgcctgttc cgcatcctgg aggcggcaaa gggtgaaatc    4260
cgcattgatg gcctcaatgt ggcagacatc ggcctccatg acctgcgctc tcagctgacc    4320
atcatcccgc aggaccccat cctgttctcg ggaccctgc gcatgaacct ggacccttc    4380 ggcagctact cagaggagga catttggtgg gcttttgagc tgtcccacct gcacacgttt    4440
gtgagctccc agccggcagg cctggacttc cagtgctcag agggcgggga gaatctcagc    4500
```

```
gtgggccaga ggcagctcgt gtgcctggcc cgagccctgc tccgcaagag ccgcatcctg   4560
gttttagacg aggccacagc tgccatcgac ctggagactg acaacctcat ccaggctacc   4620
atccgcaccc agtttgatac ctgcactgtc ctgaccatcg cacaccggct taacactatc   4680
atggactaca ccagggtcct ggtcctggac aaaggagtag tagctgaatt tgattctcca   4740
gccaacctca ttgcagctag aggcatcttc tacgggatgg ccagagatgc tggacttgcc   4800
taaaatatat tcctgagatt tcctcctggc ctttcctggt tttcatcagg aaggaaatga   4860
caccaaatat gtccgcagaa tggacttgat agcaaacact gggggcacct taagattttg   4920
cacctgtaaa gtgccttaca gggtaactgt gctgaatgct ttagatgagg aaatgatccc   4980
caagtggtga atgacacgcc taaggtcaca gctagtttga gccagttaga ctagtccccc   5040
ggtctcccga ttcccaactg agtgttattt gcacactgca ctgttttcaa ataacgattt   5100
tatgaaatga cctctgtcct ccctctgatt tttcatattt tcctaaagtt tcgtttctgt   5160
tttttaataa aaagcttttt cctcctggaa cagaagacag ctgctgggtc aggccacccc   5220
taggaactca gtcctgtact ctggggtgct gcctgaatcc attaaaaatg ggagtactga   5280
tgaaataaaa ctacatggtc aacagtaaaa                                    5310

<210> SEQ ID NO 3
<211> LENGTH: 5490
<212> TYPE: DNA
<213> ORGANISM: Homo sapiens

<400> SEQUENCE: 3
gtgggggcca ggcagcacag atgaagcatt tacctatcta ggtaagtcag gaggagctca     60
aaaggagaag aaaacagtag gaggcagggg aagcagcctc tgtctccatc tctgcccttt    120
gaaacaaaag ggtatttctt ttctctcttc agcccccaac ccagtggagg cccggcttgg    180
gacattgttc acttcccctc gcttcccctc tagaagcccc cttttgccat cctgcacctt    240
gtttcgggtg atgcccgaga gggagctgtg gccagcgggg actggctcag aacccgtgac    300
ccgtgtcggc agctgtgaca gcatgatgag cagcacctcc acccgctctg gatctagtga    360
tagcagctac gacttcctgt ccactgaaga gaaggagtgt ctgctcttcc tggaggagac    420
cattggctca ctggacacgg aggctgacag cggactgtcc actgacgagt ctgagccagc    480
cacaactccc agaggtttcc gagcactgcc cataacccaa cccactcccc ggggaggtcc    540
agaggagacc atcactcagc aaggacgaac gccaaggaca gtaactgagt ccagctcatc    600
ccaccctcct gagcccagg gcctaggcct caggtctggc tcctacagcc tccctaggaa    660
tatccacatt gccagaagcc agaacttcag gaaaagcacc acccaggcta gcagtcacaa    720
ccctggagaa ccggggaggc ttgcgccaga gcctgagaaa gaacaggtca gccagagcag    780
ccaacccagg caggcacctg ccagccccca ggaggctgcc cttgacttgg acgtggtgct    840
catccctccg ccagaagctt tccgggacac ccagccagag cagtgtaggg aagccagcct    900
gcccgagggg ccaggacagc agggccacac accccagctc cacacaccat ccagctccca    960
ggaaagagag cagactcctt cagaagccat gtcccaaaaa gccaaggaaa cagtctcaac   1020
caggtacaca caaccccagc ctcctcctgc agggttgcct cagaatgcaa gagctgaaga   1080 tgctccctc tcatcagggg aggacccaaa cagccgacta gctccctca caaccccta    1140 gccccggaag ctgccaccta atattgttct gaagagcagc cgaagcagtt ccacagtga    1200 cccccagcac tggctgtccc gccacactga ggctgcccct ggagattctg gcctgatctc   1260
ctgttcactg caagagcaga gaaaagcacg taaagaagct ctagagaagc tggggctacc   1320
```

```
ccaggatcaa gatgagcctg gactccactt aagtaagccc accagctcca tcagacccaa    1380
ggagacacgg gcccagcatc tgtccccagc tccaggtctg gctcagcctg cagctccagc    1440
ccaggcctca gcagctattc ctgctgctgg gaaggctctg gctcaagctc cggctccagc    1500
tccaggtcca gctcagggac cttttgccaat gaagtctcca gctccaggca atgttgcagc   1560
tagcaaatct atgccaattc ctatccctaa ggccccaagg gcaaacagtg ccctgactcc    1620
accgaagcca gagtcagggc tgactctcca ggagagcaac cccctggcc tgagacagat     1680
gaacttcaag tccaacactc tggagcgctc aggcgtggga ctgagcagct acctttcaac    1740
tgagaaagat gccagcccca aaccagcac ttctctggga aagggctcct tcttggacaa     1800
gatctcgccc agtgtcttac gtaattctcg gccccgcccg gcctccctgg gcacggggaa    1860
agattttgca ggtatccagg taggcaagct ggctgacctg gagcaggagc agagctccaa    1920
gcgcctgtcc taccaaggac agagccgtga caagcttcct cgcccccccct gtgtcagtgt   1980
caagatctcc ccaaagggtg tccccaatga acacagaagg gaggccctga gaagctggg    2040
actgttgaag gagtagactc tgcgaccagt acagaccctg tcctggctga caagaagag    2100
acacatgctc cacttgggag cctttgccac cacgcaactc agggctcaag atgaatggga   2160
gggagagatt tgagtccaag catacatttta tattcagtgt tgtgccattg agttcccatg  2220
tggatcattc tgaaggtgat ctccacaaga gggtgtgtgt gtgtgtgttt ggtgtgtgtg   2280
tggaggggg gccgctggat acatcactga agctattgat ataacacaat gagtcactgt    2340
tcagaattt gctcttgtta gatgttttct tacattgggt agagtccagc ctagtgagag    2400
ctgagtgaag gggctggcca tgcctgagac aaaaagtcaa atgagacaat ggacgtgtca   2460
atgacttgaa aaaagtcac atccagcaaa tgcagggtca catgaaatat gggcctcctg    2520
gaatccctac agtggatgga gactggctca taccttgcca gatccctctc tcagttccag   2580
ccttctggac aaggcctggg ctaagaggag ctgattcgtt atctcttcac ccactgccct   2640
ctcagtatca ccagtcccaa agacaggata cgtccctgta acccaatctc tcggttgatt   2700
gatagcagaa cagctcttgt tggtctgaga aggcaggata agtgaccaca tatttatgcc   2760
actacctcca ccagggagag tccttctcca caggcttgat aaattcaatc accaactgtg   2820
ctgtcgtccc tgactctgct actcccgttc ttcctgcttt cctgctccgt atctcagtct   2880
gcactgaccc cagggctggg ctgacatcaa gatgggagcc cagcccacgg gctttataaa    2940
cacccaagaa ccgtttcaga tcttctctgt gctgatgcag gtagttttaa attttttctca  3000
gttccagtga tagaaaaccc acacaataca tcctctgcca gtcttaatag aatatcagag    3060
gtaagagggg cctcagagaa gctctgacgc agtgctgctg gggaagggaa gtgactaacc   3120
ccgggtcagc ctgccatttta gggaaagagc tgaggttctt accccttgttg catgctgcca  3180
cctctcctta gccagtgctc ttgtacatcc acacagcacc ctaaggagcc atagtcacca   3240
tcaaagactc aaccctaagg cccttcaaga tctcaaagtg ccttctgaag catcagagat   3300
taaatattgt tcaaactaat agttattgct gtggctttta attttatctt tggaagatag   3360
ctatatggta actcatcatt aaccagaaca cctctcccct caaattccgt gaccaagttg   3420
tgcagcttga gcaaatgccg aaagagggta ttatgggtgg gtggtgtggg cttgcaaata   3480
caagcttgga ggtgagacat ggccagacat gactcctgct tccccttagg aagtaaatct   3540
tacttatggt tgtgaactgc ttggagtcca ggatgcccag atgtgagggg cagatgaagg   3600
gaatgttgct ggaaaggtgc cttttaaggc tgctgagaat ttctggactg tgtcctgatg   3660
```

-continued

| | |
|---|---|
| gacgcagcac catcaaagcc cagaatttct gaaaacggtg acaaggttaa cataaggaca | 3720 |
| acaaatactc caccctgtca tggtatgtga ggtgtgggtg tggcggtttc tgtgtacgtt | 3780 |
| tgctcataca cgcacatcca aaagcctgtg cctcattcct ggccatgggt gaggacttgg | 3840 |
| tctgtcacgg ctgatgagga ctcccacaac cggccaagtt atgtcttatt atacacccc | 3900 |
| agaaagagag aaagctgcct tctggaggac tgattccaca tgctatattc agctgagttg | 3960 |
| atttctgtgt ctatttcaac ccataacctg aagaatgatc accttattcc ttattcatta | 4020 |
| attttcttga ttaatagga aacttgggaa tagctataaa gtaaaacttg ggtggaacct | 4080 |
| ggggccctgg catcacacaa gtgtgattag gatggtcaag gtcatcagga gtacagccta | 4140 |
| ttatattccc acatcctgag aaaggtcatt tctcccacac acgacaaagt cacagacatc | 4200 |
| ctgcacctgc cactaggcat cctcatccta ctgacatgcc catttctcca gttttcttaa | 4260 |
| tctgagactc ccttcccttg ttttttaaag ataccgtgct tctccacatc ctcatccttc | 4320 |
| aaggagcata ttttgctctt aggatggtct ttgggattca agaatagaat aataaatcca | 4380 |
| aacttggtca ttcccatttt gaagagatgc aagagggccc agtgaggaca tccgcctccc | 4440 |
| tgaaagtggt gctagacaga gctgaggtca ttgtatctgt gtatccacat aggatttctc | 4500 |
| ttaattcagc ttgaattgat ggggagggag gtaagagtag ggtcagagtt actcatccct | 4560 |
| tttcaaagaa ttgtgggtgg aagtttgtaa aggccattca tttgattttc aaaatcaaag | 4620 |
| cgacagctct acttccactt ggccttagat ctctgctata ccctgccata gccttgatgc | 4680 |
| cactgggcac aagccacctg ccaaatacag gagtggcctc tcccagcctg gcatgatagg | 4740 |
| ggggtctgtg ccctcagatg tgttgacagc tgctcttctg aattgccaca cctgtgctac | 4800 |
| acttggaatt ctgtgctctg actctgcagg gtaggaccac gtgccatctc acacagaggt | 4860 |
| caaccgatga gcccactcac tcgtacatgc cttcttccac agtgggaagc atgatctggc | 4920 |
| aggggccgcc ctgtaggctg gggatgggct gctgtgtgaa tgttgacgtt cgtttcatgg | 4980 |
| agaaagggga ggtgaaagat tgaagagcag gttcctgtca atgttctgag ttcgagctgg | 5040 |
| aggtgtagat tgaatagtct acatggtctg tgagtgtgtg agatgaaccc ttccatcctt | 5100 |
| tgacacctgg ttgtatgtgt aggctaagaa ggaaggaccc tcctgtcagt gtgcaaagct | 5160 |
| gtaatctcat ggactagagg agaggggggcc aaggggatgg acaggagaag tcatgcagaa | 5220 |
| tctaagcagg aatgcagata gaacacatct aggctctttt ccccaggaga gtgatgatgg | 5280 |
| agcatataga tctggctcaa attcagcctc catcacttac cagtcaggaa ccctggcgat | 5340 |
| atcactttaa ctttctgaac ctcagagtct tcacctataa gacggggaaa ataataccac | 5400 |
| cctttcaaga ttgttgagat aaataagtga tataaaacat gtaaagctta gttctggcca | 5460 |
| cagtgtagct actcaataaa tgataatact | 5490 |

<210> SEQ ID NO 4
<211> LENGTH: 1270
<212> TYPE: DNA
<213> ORGANISM: Homo sapiens

<400> SEQUENCE: 4

| | |
|---|---|
| ctcctctccg cgcggggcgg gctccgcgcc acgtgactcc gcggccgggc cgggacgcga | 60 |
| cgggacgcgc tgggaccggc gtcggggtc gcggggacca tgcagcggag cctccctgcc | 120 |
| cttcgctatc ctgacgctgg tgaacgcccc gtacaagcga ggattttact gcggggatga | 180 |
| ctccatccgg taccctacc gtccagatac catcacccac gggctcatgg ctgggggtcac | 240 |
| catcacggcc accgtcatcc ttgtctcggc cggggaagcc tacctggtgt acacagaccg | 300 |

| | |
|---|---|
| gctctattct cgctcggact tcaacaacta cgtggctgct gtatacaagg tgctggggac | 360 |
| cttcctgttt ggggctgccg tgagccagtc tctgacagac ctggccaagt acatgattgg | 420 |
| gcgtctgagg cccaacttcc tagccgtctg cgaccccgac tggagccggg tcaactgctc | 480 |
| ggtctatgtg cagctggaga aggtgtgcag gggaaaccct gctgatgtca ccgaggccag | 540 |
| gttgtctttc tactcgggac actcttcctt tgggatgtac tgcatggtgt tcttggcgct | 600 |
| gtatgtgcag gcacgactct gttggaagtg gcacggctg ctgcgaccca cagtccagtt | 660 |
| cttcctggtg gcctttgccc tctacgtggg ctacacccgc gtgtctgatt acaaacacca | 720 |
| ctggagcgat gtccttgttg gcctcctgca ggggcactg gtggctgccc tcactgtctg | 780 |
| ctacatctca gacttcttca aagcccgacc cccacagcac tgtctgaagg aggaggagct | 840 |
| ggaacggaag cccagcctgt cactgacgtt gaccctgggc gaggctgacc acaaccacta | 900 |
| tggatacccg cactcctcct cctgaggccg accccgccc aggcagggag ctgctgtgag | 960 |
| tccagctgag gcccacccag gtggtccctc cagccctggt taggcactga gggctctgga | 1020 |
| cgggctccag gaaccctggg ctgatggag cagtgagcgg gctccgctgc ccctgccct | 1080 |
| gcactggacc aggagtctgg agatgcctgg gtagccctca gcatttggag gggaacctgt | 1140 |
| tcccgtcggt ccccaaatat cccttcttt ttatggggtt aaggaaggga ccgagagatc | 1200 |
| agatagttgc tgttttgtaa aatgtaatgt atatgtggtt tttagtaaaa tagggcacct | 1260 |
| gtttcacaaa | 1270 |

<210> SEQ ID NO 5
<211> LENGTH: 1500
<212> TYPE: DNA
<213> ORGANISM: Homo sapiens

<400> SEQUENCE: 5

| | |
|---|---|
| gcgcgcctcg ccggcgcctc catcccggat ccttgctgca gcgtcagcgc cgccgcccgt | 60 |
| gcctttcctc ttcctcctcc tcctccttgg catccgcctc ttcttcctcc tgcgtcctcc | 120 |
| cccgctgcct ccgctgctcc cgacgcggag cccggagccc gcgccgagcc cctggctcg | 180 |
| cggtgccatg ctgccccggc ggcggcgctg aaggatggcg acgccgctgc ctccgccctc | 240 |
| cccgcggcac ctgcggctgc tgcggctgct gctctccggc ctcgtcctcg gcgccgcct | 300 |
| gcgtggagcc gccgccggcc accggatgt agccgcctgt cccgggagcc tggactgtgc | 360 |
| cctgaagagg cgggcaaggt gtcctcctgg tgcacatgcc tgtgggccct gccttcagcc | 420 |
| cttccaggag gaccagcaag ggctctgtgt gcccaggatg cgccggcctc caggcggggg | 480 |
| ccggccccag cccagactgg aagatgagat tgacttcctg gcccaggagc ttgcccggaa | 540 |
| ggagtctgga cactcaactc cgcccctacc caaggaccga cagcggctcc cggagcctgc | 600 |
| caccctgggc ttctcggcac gggggcaggg gctggagctg gcctcccct ccactccagg | 660 |
| aaccccacg cccacgcccc acacctccat gggctcccct gtgtcatccg accggtgca | 720 |
| catgtcgccc ctggagcccc ggggagggca aggcgacggc ctcgcccttg tgctgatcct | 780 |
| ggcgttctgt gtggccggtg cagccgccct ctccgtagcc tccctctgct ggtgcaggct | 840 |
| gcatcgtgag atccgcctga ctcagaaggc cgactacgcc actgcgaagg cccctggctc | 900 |
| acctgcagct cccccggatct cgcctgggga ccaacggctg gcacagagcg cggagatgta | 960 |
| ccactaccag caccaacggc aacagatgct gtgcctggag cggcataaag agccacccaa | 1020 |
| ggagctggac acggcctcct cggatgagga gaatgaggac ggagacttca cggtgtacga | 1080 |

-continued

| | |
|---|---|
| gtgcccgggc ctggccccga ccggggaaat ggaggtgcgc aaccctctgt tcgaccacgc | 1140 |
| cgcactgtcc gcgcccctgc cggccccag ctcaccgcct gcactgccat gacctggagg | 1200 |
| cagacagacg cccacctgct ccccgacctc gaggcccccg ggagggca gggcctggag | 1260 |
| cttcccacta aaaacatgtt ttgatgctgt gtgcttttgg ctgggcctcg ggctccaggc | 1320 |
| cctgggaccc cttgccaggg agaccccga acctttgtgc caggacacct cctggtcccc | 1380 |
| tgcacctctc ctgttcggtt tagaccccca aactggaggg gcatggaga accgtagagc | 1440 |
| gcaggaacgg gtgggtaatt ctagagacaa agccaatta aagtccattt cagaaaaaaa | 1500 |

<210> SEQ ID NO 6
<211> LENGTH: 4005
<212> TYPE: DNA
<213> ORGANISM: Homo sapiens

<400> SEQUENCE: 6

| | |
|---|---|
| gggcaacagt ctgcccacct gtggacacca gatcctggga gctcctggtt agcaagtgag | 60 |
| atctctggga tgtcagtgag gctggttgaa gaccagaggt aaactgcaga ggtcaccacc | 120 |
| cccaccatgt cccaggtgat gtccagccca ctgctggcag gaggccatgc tgtcagcttg | 180 |
| gcgccttgtg atgagcccag gaggaccctg cacccagcac ccagcccag cctgccaccc | 240 |
| cagtgttctt actacaccac ggaaggctgg ggagcccagg ccctgatggc ccccgtgccc | 300 |
| tgcatggggc cccctggccg actccagcaa gccccacagg tggaggccaa agccacctgc | 360 |
| ttcctgccgt cccctggtga aaggcccttg ggaccccag aggaccttga ctcctacatt | 420 |
| gacttctcac tggagagcct caatcagatg atcctggaac tggaccccac cttccagctg | 480 |
| cttccccag ggactggggg ctcccaggct gagctggccc agagcaccat gtcaatgaga | 540 |
| aagaaggagg aatctgaagc cttggacata aagtacatcg aggtgacctc cgccagatca | 600 |
| aggtgccacg attggcccca gcactgctcc agccctctg tcaccccgcc cttcggctcc | 660 |
| cctcgcagtg gtggcctcct cctttccaga gacgtccccc gagagacacg aagcagcagt | 720 |
| gagagcctca tcttctctgg gaaccagggc agggggcacc agcgccctct gccccccta | 780 |
| gagggtctct cccctcgacc cccaaattcc cccagcatct caatcccttg catggggagc | 840 |
| aaggcctcga gccccatgg tttgggctcc ccgctggtgg cttctccaag actggagaag | 900 |
| cggctgggag gcctggcccc acagcggggc agcaggatct ctgtgctgtc agccagccca | 960 |
| gtgtctgatg tcagctatat gtttggaagc agccagtccc tcctgcactc cagcaactcc | 1020 |
| agccatcagt catcttccag atccttggaa agtccagcca actcttcctc cagcctccac | 1080 |
| agccttggct cagtgtccct gtgtacaaga cccagtgact tccaggctcc cagaaacccc | 1140 |
| accctaacca tgggccaacc cagaacaccc cactctccac cactggccaa agaacatgcc | 1200 |
| agcatctgcc ccccatccat caccaactcc atggtggaca tacccattgt gctgatcaac | 1260 |
| ggctgcccag aaccagggtc ttctccaccc cagcggaccc caggacacca gaactccgtt | 1320 |
| caacctggag ctgcttctcc cagcaacccc tgtccagcca ccaggagcaa cagccagacc | 1380 |
| ctgtcagatg ccccctttac cacatgccca gagggtcccg ccaggacat gcagcccacc | 1440 |
| atgaagttcg tgatggacac atctaaatac tggtttaagc caaacatcac ccgagagcaa | 1500 |
| gcaatcgagc tgctgaggaa ggaggagcca ggggcttttg tcataaggga cagctcttca | 1560 |
| taccgaggct ccttcggcct ggccctgaag gtgcaggagg ttcccgcgtc tgctcagaat | 1620 |
| cgaccaggtg aggacagcaa tgacctcatc cgacacttcc tcatcgagtc gtctgccaaa | 1680 |
| ggagtgcatc tcaaaggagc agatgaggag ccctactttg ggagcctctc tgccttcgtg | 1740 |

-continued

```
tgccagcatt ccatcatggc cctggccctg ccctgcaaac tcaccatccc acagagagaa    1800
ctgggaggtg cagatggggc ctcggactct acagacagcc cagcctcctg ccagaagaaa    1860
tctgcgggct gccacaccct gtacctgagc tcagtgagcg tggagaccct gactggagcc    1920
ctggccgtgc agaaagccat ctccaccacc tttgagaggg acatcctccc cacgcccacc    1980
gtggtccact tcgaagtcac agagcagggc atcactctga ctgatgtcca gaggaaggtg    2040
tttttccggc gccattaccc actcaccacc ctccgcttct gtggtatgga ccctgagcaa    2100
cggaagtggc agaagtactg caaaccctcc tggatctttg ggtttgtggc caagagccag    2160
acagagcctc aggagaacgt atgccacctc tttgcggagt atgacatggt ccagccagcc    2220
tcgcaggtca tcggcctggt gactgctctg ctgcaggacg cagaaaggat gtaggggaga    2280
gactgcctgt gcacctaacc aacacctcca ggggctcgct aaggagcccc cctccacccc    2340
ctgaatgggt gtggcttgtg ccatattga cagaccaatc tatgggacta gggggattgg    2400
catcaagttg acacccttga acctgctatg gccttcagca gtcaccatca tccagacccc    2460
ccgggcctca gtttcctcaa tcatagaaga agaccaatag acaagatcag ctgttcttag    2520
atgctggtgg gcatttgaac atgctcctcc atgattctga agcatgcaca cctctgaaga    2580
cccctgcatg aaaataaccct ccaaggaccc tctgaccccca tcgacctggg ccctgcccac    2640
acaacagtct gagcaagaga cctgcagccc ctgtttcgtg gcagacagca ggtgcctggc    2700
ggtgacccac ggggctcctg gcttgcagct ggtgatggtc aagaactgac tacaaaacag    2760
gaatggatag actctatttc cttccatatc tgttcctctg ttccttttcc cactttctgg    2820
gtggcttttt gggtccaccc agccaggatg ctgcaggcca agctgggtgt ggtatttagg    2880
gcagctcagc aggggggaact tgtccccatg gtcagaggag acccagctgt cctgcacccc    2940
cttgcagatg agtatcaccc catctttttct ttccacttgg ttttatttt tatttttttt    3000
gagacagagt ctcactgtca cccaggctga actgcagtgg tgtgatctag ctcactgca    3060
acctccacct cccaggttca agcaattatc ctgcctcagg ctcccgagta gctgggatta    3120
caggcatgtg caactcaccc agctaatttt gtatttttag tagagacagg gtttcaccat    3180
gttggccagg ctggtcttga actcctgacc gcaggtaatc cacctgcttc ggcctcccaa    3240
agtgctggga ttacaggcgc aagccaccca gcccagcttc tttccattcc ttgataggcg    3300
agtattccaa agctggtatc gtagctgccc taatgttgca tattaggcgg cggggggcaga    3360
gataagggcc atctctctgt gattctgcct cagctcctgt cttgctgagc cctcccccaa    3420
cccacgctcc aacacacaca cacacacaca cacacacaca cacacacaca cacacacaca    3480
cacgcccctc tactgctatg tggcttcaac cagcctcaca gccacacggg ggaagcagag    3540
agtcaagaat gcaaagaggc cgcttcccta agaggcttgg aggagctggg ctctatccca    3600
cacccacccc cacccccaccc ccacccagcc tccagaagct ggaaccattt ctcccgcagg    3660
cctgagttcc taaggaaacc accctaccgg ggtggaaggg agggtcaggg aagaaaccca    3720
ctcttgctct acgaggagca agtgcctgcc cctcccagc agccagccct gccaaagttg    3780
cattatcttt ggccaaggct gggcctgacg gttatgattt cagccctggg cctgcaggag    3840
aggctgagat cagcccaccc agccagtggt cgagcactgc cccgccgcca aagtctgcag    3900
aatgtgagat gaggttctca aggtcacagg ccccagtccc agcctggggg ctggcagagg    3960
cccccatata ctctgctaca gctcctatca tgaaaaataa aatgt                    4005
```

<210> SEQ ID NO 7

-continued

```
<211> LENGTH: 1090
<212> TYPE: DNA
<213> ORGANISM: Homo sapiens

<400> SEQUENCE: 7
ctctgcttcc ttacagcacc cccacctgcc agagctgatc ctccctaggc cctgcctaac      60
cttgagttgg cccccaatcc ctctggctgc agaagtcccc ttaccccaa tgagaggagg     120 ggcaggacca gatcttttga gagctgaggg ttgagggcat tgagccaaca cacagatttg    180
tcgcctctgt ccccgaagac acctgcaccc tccatgcgga gccaagatgg ggaatggaac    240
tgaggaagat tataactttg tcttcaaggt ggtgctgatc ggcgaatcag gtgtggggaa    300
gaccaatcta ctctcccgat tcacgcgcaa tgagttcagc cacgacagcc gcaccaccat    360
cggggttgag ttctccaccc gcactgtgat gttgggcacc gctgctgtca aggctcagat    420
ctgggacaca gctggcctgg agcggtaccg agccatcacc tcggcgtact atcgtggtgc    480
agtgggggcc ctcctggtgt ttgacctaac caagcaccag acctatgctg tggtggagcg    540
atggctgaag gagctctatg accatgctga agccacgatc gtcgtcatgc tcgtgggtaa    600
caaaagtgac ctcagccagg cccgggaagt gcccactgag gaggcccgaa tgttcgctga    660
aaacaatgga ctgctcttcc tggagacctc agccctggac tctaccaatg ttgagctagc    720
ctttgagact gtcctgaaag aaatctttgc gaaggtgtcc aagcagagac agaacagcat    780
ccggaccaat gccatcactc tgggcagtgc ccaggctgga caggagcctg ccctgggga     840 gaagagggcc tgttgcatca gcctctgacc ttggccagca ccacctgccc ccactggctt    900
tttggtgccc cttgtcccca cttcagcccc aggacctttc cttgcccttt ggttccagat    960
atcagactgt tccctgttca cagcaccctc agggtcttaa ggtcttcatg ccctatcaca   1020
aatacctctt ttatctgtcc accctcaca gactaggacc ctcaaataaa gctgttttat    1080
atcaaaaaaa                                                          1090

<210> SEQ ID NO 8
<211> LENGTH: 4260
<212> TYPE: DNA
<213> ORGANISM: Homo sapiens

<400> SEQUENCE: 8
gcccagcctg cctggagaaa agtgtctgct cctagccaag atctcctcat cacaaaagta     60
atgtgggcca tggagtcagg ccacctcctc tgggctctgc tgttcatgca gtccttgtgg    120
cctcaactga ctgatggagc cactcgagtc tactacctgg gcatccggga tgtgcagtgg    180
aactatgctc ccaagggaag aaatgtcatc acgaaccagc ctctggacag tgacatagtg    240
gcttccagct tcttaaagtc tgacaagaac cggataggg gaacctacaa gaagaccatc    300
tataaagaat acaaggatga ctcatacaca gatgaagtgg cccagcctgc ctggttgggc    360 ttcctgggc cagtgttgca ggctgaagtg ggggatgtca ttcttattca cctgaagaat    420
tttgccactc gtccctatac catccaccct catggtgtct ctacgagaa ggactctgaa    480 ggttccctat acccagatgg ctcctctggg ccactgaaag ctgatgactc tgttcccccg    540
gggggcagcc atatctacaa ctggaccatt ccagaaggcc atgcacccac cgatgctgac    600
ccagcgtgcc tcacctggat ctaccattct catgtagatg ctccacgaga cattgcaact    660
ggcctaattg ggcctctcat cacctgtaaa agaggagccc tggatgggaa ctcccctcct    720
caacgccagg atgtagacca tgatttcttc tcctcttca gtgtggtaga tgagaacctc    780
agctggcatc tcaatgagaa cattgccact tactgctcag atcctgcttc agtggacaaa    840
```

```
gaagatgaga catttcagga gagcaatagg atgcatgcaa tcaatggctt tgttttgggg      900
aatttacctg agctgaacat gtgtgcacag aaacgtgtgg cctggcactt gtttggcatg      960
ggcaatgaaa ttgatgtcca cacagcattt ttccatggac agatgctgac tacccgtgga     1020
caccacactg atgtggctaa catctttcca gccacctttg tgactgctga tggtgccc       1080
tgggaacctg gtacctggtt aattagctgc aagtgaaca gtcactttcg agatggcatg      1140
caggcactct acaaggtcaa gtcttgctcc atggcccctc ctgtggacct gctcacaggc     1200
aaagttcgac agtacttcat tgaggcccat gagattcaat gggactatgg cccgatgggg     1260
catgatggga gtactgggaa gaatttgaga gagccaggca gtatctcaga taagttttc      1320
cagaagagct ccagccgaat tgggggcact tactggaaag tgcgatatga agcctttcaa     1380
gatgagacat tccaagagaa gatgcatttg gaggaagata ggcatcttgg aatcctgggg     1440
ccagtgatcc gggctgaggt gggtgacacc attcaggtgg tcttctacaa ccgtgcctcc     1500
cagccattca gcatgcagcc ccatggggtc ttttatgaga aagactatga aggcactgtg     1560
tacaatgatg gctcatctta ccctggcttg gttgccaagc cctttgagaa agtaacatac     1620
cgctggacag tcccccctca tgccggtccc actgctcagg atcctgcttg tctcacttgg     1680
atgtacttct ctgctgcaga tcccataaga gacacaaatt ctggcctggt gggcccgctg     1740
ctggtgtgca gggctggtgc cttgggtgca gatggcaagc agaaagggt ggataaagaa      1800
ttctttcttc tcttcactgt gttggatgag aacaagagct ggtacagcaa tgccaatcaa     1860
gcagctgcta tgttggattt ccgactgctt cagaggata ttgagggctt ccaagactcc      1920
aatcggatgc atgccattaa tgggtttctg ttctctaacc tgcccaggct ggacatgtgc     1980
aagggtgaca cagtggcctg gcacctgctc ggcctgggca cagagactga tgtgcatgga     2040
gtcatgttcc agggcaacac tgtgcagctt cagggcatga ggaagggtgc agctatgctc     2100
tttcctcata cctttgtcat ggccatcatg cagcctgaca accttgggac atttgagatt     2160
tattgccagg caggcagcca tcgagaagca gggatgaggg caatctataa tgtctcccag     2220
tgtcctggcc accaagccac ccctcgccaa cgctaccaag ctgcaagaat ctactatatc     2280
atggcagaag aagtagagtg ggactattgc cctgaccgga gctgggaacg ggaatggcac     2340
aaccagtctg agaaggacag ttatggttac attttcctga gcaacaagga tgggctcctg     2400
ggttccagat acaagaaagc tgtattcagg gaatacactg atggtacatt caggatccct     2460
cggccaagga ctggaccaga gaacacttg ggaatcttgg gtccacttat caaaggtgaa      2520
gttggtgata tcctgactgt ggtattcaag aataatgcca gccgccccta ctctgtgcat     2580
gctcatggag tgctagaatc tactactgtc tggccactgg ctgctgagcc tggtgaggtg     2640
gtcacttatc agtggaacat cccagagagg tctggccctg ggcccaatga ctctgcttgt     2700
gtttcctgga tctattattc tgcagtggat cccatcaagg acatgtatag tggcctggtg     2760
gggcccttgg ctatctgcca aaagggcatc ctggagcccc atggaggacg gagtgacatg     2820
gatcgggaat ttgcattgtt gttccttgatt tttgatgaaa ataagtcttg gtatttggag     2880
gaaaatgtgg caacccatgg gtcccaggat ccaggcagta ttaacctaca ggatgaaact     2940
ttcttggaga gcaataaaat gcatgcaatc aatgggaaac tctatgccaa ccttagggt      3000
cttaccatgt accaaggaga acgagtggcc tggtacatgc tggccatggg ccaagatgtg     3060
gatctacaca ccatccactt tcatgcagag agcttcctct atcggaatgg cgagaactac     3120
cgggcagatg tggtggatct gttcccaggg acttttgagg ttgtggagat ggtggccagc     3180
```

```
aaccctggga catggctgat gcactgccat gtgactgacc atgtccatgc tggcatggag    3240
accctcttca ctgtttttc tcgaacagaa cacttaagcc ctctcaccgt catcaccaaa    3300
gagactgaaa aagcagtgcc ccccagagac attgaagaag gcaatgtgaa gatgctgggc    3360
atgcagatcc ccataaagaa tgttgagatg ctggcctctg ttttggttgc cattagtgtc    3420
acccttctgc tcgttgttct ggctcttggt ggagtggttt ggtaccaaca tcgacagaga    3480
aagctacgac gcaataggag gtccatcctg gatgacagct tcaagcttct gtctttcaaa    3540
cagtaacatc tggagcctgg agatatcctc aggaagcaca tctgtagtgc actcccagca    3600
ggccatggac tagtcactaa ccccacactc aaggggcat gggtggtgga aagcagaag    3660 gagcaatcaa gcttatctgg atatttcttt ctttatttat tttacatgga aataatatga    3720
tttcactttt tctttagttt ctttgctcta cgtgggcacc tggcactaag ggagtacctt    3780
attatcctac atcgcaaatt tcaacagcta cattatattt ccttctgaca cttggaaggt    3840
attgaaattt ctagaaatgt atccttctca caaagtagag accaagagaa aaactcattg    3900
attgggtttc tacttctttc aaggactcag gaaatttcac tttgaactga ggccaagtga    3960
gctgttaaga taacccacac ttaaactaaa ggctaagaat ataggcttga tgggaaattg    4020
aaggtaggct gagtattggg aatccaaatt gaattttgat tctccttggc agtgaactac    4080
tttgaagaag tggtcaatgg gttgttgctg ccatgagcat gtacaacctc tggagctaga    4140
agctcctcag gaaagccagt tctccaagtt cttaacctgt ggcactgaaa ggaatgttga    4200
gttacctctt catgttttag acagcaaacc ctatccatta aagtacttgt tagaacactg    4260
```

```
<210> SEQ ID NO 9
<211> LENGTH: 3250
<212> TYPE: DNA
<213> ORGANISM: Homo sapiens

<400> SEQUENCE: 9
```

```
gcgggcggag gcggggcgcg gagaagtggc ggaggtggaa gcggaggcgt accgcccct      60 ggggacgtca ttggtggcgg aggcaatggc cggcaaccag ctgtaagcga ggcacggaag    120
acatatgctt gtgagacaaa ggtgtctctg aaactatgga tggtacaaga acttcacttg    180
acattgaaga gtactcggat actgaggtac agaaaaacca agtactaact ctggaagaat    240
ggcaagacaa gtgggtgaac ggcaagactg cttttcatca ggaacaagga catcagctat    300
taaagaagca tttagatact ttccttaaag gcaagagtgg actgagggta ttttttcctc    360
tttgcggaaa agcggttgag atgaaatggt ttgcagaccg gggacacagt gtagttggtg    420
tggaaatcag tgaacttggg atacaagaat tttttacaga gcagaatctt tcttactcag    480
aagaaccaat caccgaaatt cctggaacca agtatttaa gagttcttcg gggaacattt    540
cattgtactg ttgcagtatt tttgatcttc ccaggacaaa tattggcaaa tttgacatga    600
tttgggatag aggagcatta gttgccatca atccaggtga tcgcaaatgc tatgcagata    660
caatgttttc cctcctggga aagaagtttc agtatctcct gtgtgttctt tcttatgatc    720
caactaaaca tccaggtcca ccattttatg ttccacatgc tgaaattgaa aggttgtttg    780
gtaaaatatg caatatacgt tgtcttgaga aggttgatgc ttttgaagaa cgacataaaa    840
gttggggaat tgactgtctt tttgaaaagt tatatctact tacagaaaag taatgagac     900 atagataaaa taaaatcaca ctgacatgtt tttgaggaat tgaaaattat gctaaagcct    960
gaaaatgtaa tggatgaatt tttaaaattg tttataaatc atatgataga tctttactaa    1020
aaatggcttt ttagtaaagc catttacttt ttctaaaaaa gttttagaag aaaaagatgt    1080
```

```
aactaaactt ttaaagtagc tcctttggag aggagattat gatgtgaaag attatgccta    1140
tgtgtcttgc agattgcaag atatttacc aatcagcatg tgttacctgt acaattaaaa    1200
aaatatttca aaatgcaatg catattaaat ataatacaca cagaaaaact ggcatttatt    1260
ttgttttatt tttttgagat ggagtttcgt tcttgttgcc caacctggag tgcaatggtg    1320
caatctcagc tcactgcaac ctctgcctcc caggttcagg tgattctcct gcctcagcct    1380
cctgagtagc tgggattaca ggtgtgcgcc accacgccca gctaattttt tgtatttta    1440 gtagagacag ggtttcacca tgttggtcag gctgatctcg agctcctgac ctcaggtgat    1500
ctacccacct cggcctccca agtgctggg attacaggcg tgagccactg cacctggcct    1560
gacattcttt atgaaattta gaattgttga agaactataa catttcagta gggttcaagg    1620
tggtcccaaa agttatataa aagattagtt tttactataa acccttgtct tttactcaga    1680
tcctagcatc ccttttcaca tggtttctcc atgtatataa cagaatcaag aaacaaattt    1740
taattaaaca atctgtaaca gaatcaagaa acaaatacat tttaattaaa caatctatat    1800
ggaacaaaca ttcccaaatt ctaagaataa attttctttt aagttttctc tgagtttggc    1860
aattgttgtt tttataatt taatctgttt aaatcatcag gtcttataaa atataatgta    1920
cttagagctg gattcatggc tgtttattat gaaaggttag atttctcagt tcttctttaa    1980
ccacattttg ttatatcaga cagtcctcta taactctgta ctacccaaca actaaatggt    2040
ttagattgtt tagctcatgt taataggatg gttgtgtatt ataaaaaacg agttacgtgt    2100
gtgtgtgcac gcatgcacgc acatgtgctg gcttaaaggt tgttaatgca aggtttgggg    2160
tcccctttaa cactggtgaa agctacggta ctctccccag agatatgtct tgtcagcctc    2220
tctagttccc cttggcctgc atgtacaaac ttctacccta gaagctctct gccatcgatg    2280
tattctaata gatttgtaag gctattaatt tgaagcaact ccttgctcac agtgattctt    2340
gcttctctga gacctgctcc cagtcgatac tgtgggcttc agaagccatg actcccaac    2400 tctgcctgta tcaccggttg aatggacaac taacccgagc tggaccaaca caattctctc    2460
cagagacttt tgattttact tttatgtaga gacagggtct cactttgttg cccacgctga    2520
tgttgaactt gacgtgaggc tcaagcagt cctcctgtct tggccaccca agtgctagg    2580 attacaggta tgagccattg cgctggccct cttcataggc ttttggactt gggaatagaa    2640
aagcaacccc gtctctacta aaaatacaaa aaaattagcc aggcgtggtg gcacgtgcct    2700
gtaatcccag ctacttggga ggctgaggca ggagaatcac ttgaacctag gaggcggagg    2760
ttgcagtgag ctgagatcat gccactgcac gcaagcctgg gcaacagagc aagactctgt    2820
ctcaaaagaa agaaaagaa aagaaaaaaa agaaaggcaa gttgactgct gaaggggaa    2880 tctgtgtacg cctgggagct gtggggcagc acattccag cacatggatc tgagaaacag    2940
aacgctgatc tgcagaaaga gatgagaacc aagagaggc cacctgcgtc ctgggtccat    3000
tttcatcctc cctgaagccc agctgcccag ggtggggaga acaccctgt gtccatggga    3060 tagagtcctt tccgcttgca gttgtgccca aagaatctta aatacaaatg agatatcctt    3120
aggtagttga tcatttatgt aatatgtgtc ttcactgggg aatactgact tcctaaaatc    3180
tcaagatgga agatatacca catgtaaatt attttagagc aattaaattg ttttcaggat    3240
tttccaaaaa                                                          3250

<210> SEQ ID NO 10
<211> LENGTH: 2810
<212> TYPE: DNA
```

<213> ORGANISM: Homo sapiens

<400> SEQUENCE: 10

```
ggcctcgagg gacaggacgt gaagatagtt gggtttggag gcggccgcca ggcccaggcc     60
cggtggacct gccgccatgc aggacggtaa cttcctgctg tcggccctgc agcctgaggc    120
cggcgtgtgc tccctggcgc tgccctctga cctgcagctg gaccgccggg gcgccgaggg    180
gccggaggcc gagcggctgc gggcagcccg cgtccaggag caggtccgcg cccgcctctt    240
gcagctggga cagcagccgc ggcacaacgg ggccgctgag cccgagcctg aggccgagac    300
tgccagaggc acatccaggg ggcagtacca caccctgcag gctggcttca gctctcgctc    360
tcagggcctg agtggggaca agacctcggg cttccggccc atcgccaagc cggcctacag    420
cccagcctcc tggtcctccc gctccgccgt ggatctgagc tgcagtcgga ggctgagttc    480
agcccacaac gggggcagcg cctttggggc cgctgggtac gggggtgccc agcccacccc    540
tcccatgccc accaggcccg tgtccttcca tgagcgcggt ggggttggga gccgggccga    600
ctatgacaca ctctccctgc gctcgctgcg gctggggccc gggggcctgg acgaccgcta    660
cagcctggtg tctgagcagc tggagcccgc ggccacctcc acctacaggg cctttgcgta    720
cgagcgccag gccagctcca gctccagccg ggcagggggg ctggactggc ccgaggccac    780
tgaggtttcc ccgagccgga ccatccgtgc ccctgccgtg cggaccctgc agcgattcca    840
gagcagccac cggagccgcg gggtaggcgg ggcagtgccg ggggccgtcc tggagccagt    900
ggctcgagcg ccatctgtgc gcagcctcag cctcagcctg gctgactcgg gccacctgcc    960
ggacgtgcat gggttcaaca gctacggtag ccaccgaacc ctgcagagac tcagcagcgg   1020
ttttgatgac attgacctgc cctcagcagt caagtacctc atggcttcag accccaacct   1080
gcaggtgctg ggagcggcct acatccagca caagtgctac agcgatgcag ccgccaagaa   1140
gcaggcccgc agccttcagg ccgtgcctag gctggtgaag ctcttcaacc acgccaacca   1200
ggaagtgcag cgccatgcca caggtgccat gcgcaacctc atctacgaca cgctgacaa    1260
caagctggcc ctggtggagg agaacgggat cttcgagctg ctgcggacac tgcgggagca   1320
ggatgatgag cttcgcaaaa atgtcacagg gatcctgtgg aacctttcat ccagcgacca   1380
cctgaaggac cgcctggcca gagacacgct ggagcagctc acagacctgg tgttgagccc   1440
cctgtcgggg gctggggtc cccccctcat ccagcagaac gcctcggagg cggagatctt   1500
ctacaacgcc accggcttcc tcaggaacct cagctcagcc tctcaggcca ctcgccagaa   1560
gatgcgggag tgccacgggc tggtggacgc cctggtcacc tctatcaacc acgccctgga   1620
cgcgggcaaa tgcgaggaca gagcgtggaa gaacgcggtg tgcgtcctgc ggaacctgtc   1680
ctaccgcctc tacgacgaga tgccgccgtc cgcgctgcag cggctggagg tcgcggccg    1740
cagggacctg gcgggggcgc cgccgggaga ggtcgtgggc tgcttcacgc gcagagccg    1800
gcggctgcgc gagctgcccc tcgccgccga tgcgctcacc ttcgcggagg tgtccaagga   1860
ccccaagggc ctcgagtggc tgtggagccc ccagatcgtg gggctgtaca accggctgct   1920
gcagcgctgc gagctcaacc ggcacacgac ggaggcggcc gccggggcgc tgcagaacat   1980
cacggcaggc gaccgcaggt gggcggggt gctgagccgc ctggccctgg agcaggagcg   2040
tattctgaac cccctgctag accgtgtcag gaccgccgac caccaccagc tgcgctcact   2100
gactggccctc atccgaaacc tgtctcggaa cgctaggaac aaggacgaga tgtccacgaa   2160
ggtggtgagc cacctgatcg agaagctgcc gggcagcgtg gtgagaagt cgcccccagc   2220
cgaggtgctg gtcaacatca tagctgtgct caacaacctg gtggtggcca gcccatcgc    2280
```

```
tgcccgagac ctgctgtatt ttgacggact ccgaaagctc atcttcatca agaagaagcg    2340
ggacagcccc gacagtgaga agtcctcccg ggcagcatcc agcctcctgg ccaacctgtg    2400
gcagtacaac aagctccacc gtgacttccg ggcgaagggc tatcggaagg aggacttcct    2460
gggcccatag gtgaagcctt ctggaggaga aggtgacgtg gcccagcgtc aagggacag     2520 actcagctcc aggctgcttg gcagcccagc ctggaggaga aggctaatga cggaggggcc    2580
cctcgctggg gcccctgtgt gcatctttga gggtcctggg ccaccaggag gggcagggtc    2640
ttatagctgg ggacttggct ccgcagggc  aggggtggg  gcagggctca aggctgctct    2700
ggtgtatggg gtggtgaccc agtcacattg gcagaggtgg gggttggctg tggcctggca    2760
gtatcttggg atagccagca ctgggaataa agatggccat gaacagtcaa                2810

<210> SEQ ID NO 11
<211> LENGTH: 3131
<212> TYPE: DNA
<213> ORGANISM: Homo sapiens

<400> SEQUENCE: 11
agtgtttatc agaacttagc cagggccagc caagcaggca cagatgctct gctatgaaat      60
gccacgcagg cagagactga caagcggtag gaactgagct ttccccttgg actgctgctt     120
cctgctgtgt tcaggggagg gggtcacttt ctggcaactc tgctgctgct gctgctgctg     180
ctgctacttc agcttcctct ccactcaagg taagcaggct aagggagggc aggctgctag     240
ggaaagcttt gtaccatgaa caggatccga agttttttcc gaggaagtgg gcgagtcttg     300
gcatttatct ttgtagcttc tgtcatctgg ctcctctttg acatggcagc tctccgcctc     360
tcattcagtg agatcaacac tcgggtcatc aaggaagaca ttgtgaggag ggagcggata     420
ggattcagag ttcagccaga ccaaggaaaa atttttaca gcagcataaa agagatgaaa       480
cctcccctaa ggggacatgg gaaagggca tgggcaaag agaatgttag aaaaactgag       540
gagagtgtgc tcaaggttga ggtggacttg gaccaaaccc agagggaaag aaaaatgcag     600
aatgccctgg gaaggggcaa ggttgtgccg ttgtggcatc ctgcacatct gcagaccctc     660
cctgtgactc ctaacaagca gaagacagac gggagaggca ccaaacctga gcctcctct      720 caccaggga caccaaagca aacgacagct caggggctc caaagacctc attcatagca       780
gcaaaaggaa ctcaggtagt caaaatatca gtacacatgg gacgtgtcag tttaaaacag     840 gagcccgga agagtcatag tcccagcagt gacacatcaa aactagcagc tgaaagggac     900
ttgaatgtga ccatcagtct tagtactgat agaccaaagc agcgatcaca ggcagtagca     960
aacgagaggg cacaccctgc cagcacagca gtgccgaagt ctggggaagc catggcctta    1020
aacaaaacta agactcagag caaagaagtc aatgcaaata acacaaaagc caatacgagt    1080 cttcctttc ctaagttcac tgtcaattca aatcgcttaa ggaagcaatc tattaatgag     1140
acacctttgg gaagtttgtc aaaggatgat ggagctagag ggctcatgg gaagaaactc     1200 aatttctctg aaagccatct tgtgattata accaaagagg aagagcaaaa ggcagacccc    1260
aaagaggtct ctaattctaa aaccaaaaca atatttccta agtattggg taaaagccaa     1320 agtaaacaca tttccaggaa tagaagtgag atgtcttcct cttcacttgc tccacataga    1380
gtgccactgt cccaaactaa ccatgcttta actggagggc tagagccagc aaaaatcaac    1440
ataactgcca aagccccctc tacagaatac aaccagagtc atataaaagc ccttttacct    1500
gaagacagtg gaacgcacca ggtgttaaga attgatgtga cactttctcc aagggacccc    1560
```

-continued

```
aaagctccag ggcagtttgg gcgtcctgta gttgtccccc atggaaagga gaaggaggca   1620
gaaagaagat ggaaagaagg aaacttcaat gtctaccttta gcgatttgat cccagtggat   1680
agagccattg aagacaccag acctgctgga tgtgcagagc agctagttca caataacctc   1740
ccaaccacca gtgtcatcat gtgctttgtg atgaagtgt  ggtccactct cctgagatct   1800
gttcacagtg tcatcaatcg ctctcctcca cacctcatca aggagattct gctggtagat   1860
gacttcagca ccaaagacta tctaaaagat aatttggata aatacatgtc ccagtttcca   1920
aaagttcgga ttcttcgcct caaagagaga catggcttaa taagggccag gctggcagga   1980
gcacagaatg caacaggtga tgtgttgaca ttttttagatt ctcatgtgga atgtaacgtt   2040
ggttggttgg aacctcttct ggaaagagtt tatttaagta gaaagaaagt ggcctgtcca   2100
gtaatcgaag tcatcaatga taaggatatg agttacatga cagtggataa ctttcaaaga   2160
ggcatctttg tgtggcccat gaactttggt tggagaacaa ttcctccaga tgtcattgca   2220
aaaaacagaa ttaaagaaac tgatacaata aggtgccctg tcatggctgg tggattgttt   2280
tctattgaca aagttacttt ttttgaactt ggaacatacg accctggcct tgatgtttgg   2340
ggtggggaaa atatggagct ctcattcaag gtgtggatgt gtggtggtga aattgagatc   2400
attccctgct cccgagtggg ccatatattc agaaatgaca atccatattc cttccccaaa   2460
gaccggatga agacagtgga gcggaacttg gtgcgggttg ccgaggtctg gctggatgag   2520
tataaggagc tgttctatgg ccacggagac cacctcatcg accaagggct agatgttggc   2580
aacctcaccc agcaagggga gctgcgaaag aaactgaagt gcaaaagttt caaatggtac   2640
ttggagaatg tctttcctga cttaagggct cccattgtga gagctagtgg tgtgcttatt   2700
aatgtggctt tgggtaaatg catttccatt gaaaacacta cagtcattct ggaagactgc   2760
gatgggagca aagagcttca acaatttaat tacacctggt taagacttat taaatgtgga   2820
gaatggtgta tagcccccat ccctgataaa ggagccgtaa ggctgcaccc ttgtgataac   2880
agaaacaaag ggctaaaatg gctgcataaa tcaacatcag tctttcatcc agaactggtg   2940
aatcacattg tttttgaaaa caatcagcaa ttattatgct tggaaggaaa ttttctcaa    3000
aagatcctga agtagctgc ctgtgaccca gtgaagccat atcaaaagtg gaaatttgaa    3060
aaatattatg aagcctgaag tgtaactgat gttttttatat agtaaaccca ttaaatactg   3120
tgaaaataac a                                                        3131
```

<210> SEQ ID NO 12
<211> LENGTH: 4640
<212> TYPE: DNA
<213> ORGANISM: Homo sapiens

<400> SEQUENCE: 12

```
ggggctgagg gtggagagag gaagggaagg aagaaaaggg gagccttcct ggccagggta     60
accggcacta agaggcctca ctccaagccc ccgaggagcc tgtggtgggg ctggagaccc    120
ggctcaggcc cctccaccac ccttaaagtc ctcagaaggt gggaactgaa ctggcacagg    180
atgggaaccg gctgtgcgct ggccacttga ttttgccagc tgccctgtaa ttcagctggt    240
gaggaaactg aggcacagac tgaggtagaa tgattcgcca gtcactcagc aagtcagcag    300
acggggagga ctgaatccca gcctgagagc accgaagctt gtatccctgc aataccgagc    360
cccaagcctg cgagccccgg tgcccatctc tgagttaggc cgtcttggaa gggttccctt    420
cctcctacaa gatggtgtgt gaggagcctt caatacgacc cggggtgtaa agtgtccaac    480
tctagtaggg gcctgatggc atccccgccg agtcccagga gagagagaga agacccttc    540
```

```
ctggagtcca gggctcccgg gaagaaacac tggcatttgt cccttttgctt cggcttctgg    600
aggcagagac tctgagccca gggagagcct tctgcagccc catttcctca aaaatccaac    660
ctgcccaggt ggcgggtcat gagctgtgct caggaagctg gaatctgacc ctggtggcgt    720
cgggcccagt ctccatggca gccgagcatt tattacccgg gcctccaccc agcttggcag    780
actttagact tgaggctgga ggaaagggaa ctgaacgcgg ttctgggagc agcaagccca    840
cgggtagcag ccgaggcccc agaatggcca gtttctttc ccaagaccaa attaatgagt    900
acaaggaatg cttctccctg tatgacaagc agcagagggg gaagataaaa gccaccgacc    960
tcatggtggc catgaggtgc ctgggggcca gcccgacgcc aggggaggtg cagcggcacc   1020
tgcagaccca cggatagac ggaaatggag agctggattt ctccactttt ctgaccatta   1080
tgcacatgca aataaaacaa gaagacccaa agaaagaaat tcttctagcc atgttgatgg   1140
tggacaagga gaagaaggt tacgtcatgg cgtccgacct gcggtcaaaa ctcacgagtc   1200
tgggggagaa gctcacccac aaggaagtgg atgatctctt cagggaagca gatatcgaac   1260
ccaatggcaa agtgaagtat gatgaattta tccacaagat cacccttcct ggacgggact   1320
attgaaggag gagaatggga gagcctcccc tgggcctgaa aacttggagc aattaatttt   1380
ttttaaaaag tgttctttc acttgggaga gatggcaaac acagtggcaa gacaacatta   1440
cccaactata gaagagaggc taactagcaa caataataga tgatttcagc catggtatga   1500
gtagatcttt aataaaagat ttgtattgat tttattaact accgtgagtc cggccctttc   1560
aagcatggaa ggagcctgcg gtttggagtc tggcctgggt tccagtcctg gctctgctgc   1620
ttcccactgt gactttgggc aaatcatttc actcctcaaa gcccccccac acaagctgga   1680
ttcccacttc ttacctcatg gagcctgttg aggaaggatt gagctgatga cttaagggca   1740
atctaccaag agacttattc tgtatttggg ggctagaacc atcttccata tttccaagat   1800
tttccaagat gaagccagtg ctagctgaga agcagcaatg aacagaaagc tgtaacactt   1860
atgacaacaa ttcttgcagt gccagaggcc catttacaaa ttctcatttc catctcaaca   1920
gatatagtga catagctcag gctattcatt cataaacaca gagtgtagag tgaaaacact   1980
agagtgaaaa cacatgctac aatgaggcag catcagctga gagcaggaag agcgatctac   2040
tttacccccc acaccaaagg aaaccagatg tgagctgcta aattgactgg ccttgcagag   2100
ctcaagaagg gggcttccaa tgctgtgaga attccgagct gttccctggg ctctgttaac   2160
aggcagagag gttccgggat ggtctgctca agtggcccac actggtcatt gccttaagcc   2220
acctccccag gacttacgga gagaaataag gggatgtaac cagcaatggc cagggtacaa   2280
cagccctgga aaacagtagt aggagcacta ggctttctgg gagtccatcc agctggagtg   2340
gctttgagtg agttacacag ctagaaggtg ccaggttggt gctgccagag attcagaggt   2400
gccatacact tgtcaaatct ggatcattcg tagtgccagc acagtcctaa aagggctgga   2460
gtaccacacc aacacaggta ggggtgcagg gcttcaagta caaagatttg catccatgta   2520
tgtatcaaaa gtgggttctc tgggctgtgg cttttgtctag tagtaccaca gtggctaaag   2580
tagaagaaaa ccaaatcaaa tgggatgtgt cttttgggag gatgtacaag acacaaatct   2640
ttcactaggc accgggcaca gggaaaactg caggaacaa gagttgtagt gttagtgcaa   2700
ctgtctcaac gatgctgtgt ggcttcagac ccaaacaagg ccctgaggaa ggagactctc   2760
atttccccaa gcataactgc aaggagagga ggaattccta ggagccaaag agttttgtgg   2820
ggtgagggta aataaatggc ccaaatgcca actaggtgaa gttgtgacca tctggctggg   2880
```

```
aagcccaggt ccacacagtg taggagcaga tgttttgtgg ggtctgaggt ttacgagatt    2940
tggctgcctt aagaatacaa aaacagaaat gcagaatttc tggggctgct cctaggacca    3000
gaacaagtga agggtcctgg tgcttaaact tcattacctt catggtaaat ccaccgagg     3060 gccggttaga tgctggcccc gccgagagaa ctgctgtcac tttcaggcaa agctcaaagg    3120
tcctaggccc acagttcttt tgagctccag tcatggacat taggaagtaa atcctgcaca    3180
gccaacctgg aataccaaag attagatggg agatagatac caatgattta gatggcacag    3240
gaagagcaag ttctggatat aataaatgag ggtactttcc gtcaaagctt ttctatgtct    3300
atatttatca ctgaatagtc ccagtatggt tttaaagcaa gttttatgaa tctcatttgc    3360
ctaacaggaa tctgaaatat aacttgccaa aaacacacag ttggtgtgga atggtcatta    3420
gaacctgggg ctcctcttca cggactccct gctcattaag ggattcagtg gtccagagtc    3480
taagatccta ttaagtgttt gattcaaacc tctacccgag gaagggctgt taccttactc    3540
ctggtcctgg tttcaagctc attcctgaaa ttccagctgg tttctctagc acctagtgtt    3600
gtttacaaga aggccacggt gctcttagca ttcaaactgc agatactaaa cagatgctgt    3660
gatttattaa agagttagcc atatttcaac aagaaaggga aatgatggct atattcatta    3720
cttacctcaa agcatgctgc aagaaaatta gttagttact tgtcatgctt tgaaatctct    3780
ggatgaaagg tgctttggaa gcacaaacca ttatcacttg tctcataggg attgtcccct    3840
tgaacatcca gcagtgttat tttacagaag acaaattaac tgaaggcttt tcttttatta    3900
catctaaaga gctctacata aacaggtaac attcaatagg taaacaattt tttttccaatg   3960 catgtaataa atattttcac ttggtacttt tatacaaact gacattgtct actatacatt    4020
tttaaaagcc attttactgg tttggcatgc ggtatggaaa ttctaagaga gaaagtttta    4080
aggcaatgaa tcacagattt aagttcatgg aatttatggt aactttatct gtttatgtac    4140
attttcccct ttgttaaaca attaacagca gcacactctg ggaccaccag ctattttccc    4200
tctctttctg aaatctaagc tttgtattta attaaaaaac agaattcaac atctattgat    4260
aaaacaaaat tcttactaaa ataatttcaa atgtgcttta aaaagtcctg aagatcttga    4320
aagttttatg tgtttaaaat tgaaattgtc taaaaaaatg ctctttccac attaatttag    4380
ttaggatata ttttcactcc atttcagaca cttgactcaa aggaaaatct gccaaagaat    4440
ccgatttttc agagcttacg tgaatctttc ctcagtaaag atacagaatt gtgatcatgt    4500
ctaaataatt agtaaagcaa ttttaatgct caaaatagtc aaccaagtat ggcatggttc    4560
tggttcagat ttttttttttt taagatgtat ccaataacac tcacgaagta attaaaagcc    4620
actttaaccc tgctaaaaaa                                                 4640
```

<210> SEQ ID NO 13
<211> LENGTH: 2300
<212> TYPE: DNA
<213> ORGANISM: Homo sapiens

<400> SEQUENCE: 13

```
cattttataa tgaagcctgg tcaactctcc ttcggacagt ttacagtgtc cttgagacat      60
ccccggatat cctgctagaa gaagtgatcc ttgtagatga ctacagtgat agagagcacc     120
tgaaggagcg cttggccaat gagctttcgg gactgcccaa ggtgcgcctg atccgcgcca     180
acaagagaga gggcctggtg cgagcccggc tgctgggggc gtctgcggcg agggcgatg     240 ttctgacctt cctggactgt cactgtgagt gccacgaagg gtggctggag ccgctgctgc    300
agaggatcca tgaagaggag tcggcagtgg tgtgcccggt gattgatgtg atcgactgga    360
```

| | |
|---|---|
| acaccttcga ataccctgggg aactccgggg agccccagat cggcggtttc gactggaggc | 420 |
| tggtgttcac gtggcacaca gttcctgaga gggagaggat acggatgcaa tcccccgtcg | 480 |
| atgtcatcag gtctccaaca atggctggtg ggctgtttgc tgtgagtaag aaatattttg | 540 |
| aatatctggg gtcttatgat acaggaatgg aagtttgggg aggagaaaac ctcgaatttt | 600 |
| cctttaggat ctgcagtgt ggtggggttc tggaaacaca cccatgttcc catgttggcc | 660 |
| atgttttccc caagcaagct ccctactccc gcaacaaggc tctggccaac agtgttcgtg | 720 |
| cagctgaagt atggatggat gaatttaaag agctctacta ccatcgcaac ccccgtgccc | 780 |
| gcttggaacc ttttggggat gtgacagaga ggaagcagct ccgggacaag ctccagtgta | 840 |
| aagacttcaa gtggttcttg gagactgtgt atccagaact gcatgtgcct gaggacaggc | 900 |
| ctggcttctt cgggatgctc cagaacaaag gactaacaga ctactgcttt gactataacc | 960 |
| ctcccgatga aaaccagatt gtgggacacc aggtcattct gtacctctgt catgggatgg | 1020 |
| gccagaatca gttttttcgag tacacgtccc agaaagaaat acgctataac acccaccagc | 1080 |
| ctgagggctg cattgctgtg gaagcaggaa tggataccct tatcatgcat ctctgcgaag | 1140 |
| aaactgcccc agagaatcag aagttcatct tgcaggagga tggatctta tttcacgaac | 1200 |
| agtccaagaa atgtgtccag gctgcgagga aggagtcgag tgacagtttc gttccactct | 1260 |
| tacgagactg caccaactcg gatcatcaga aatggttctt caaagagcgc atgttatgaa | 1320 |
| gcctcgtgta tcaaggagcc catcgaagga gactgtggag ccaggactct gcccaacaaa | 1380 |
| gacttagcta agcagtgacc agaacccacc aaaaactagg ctgcattgct ttgaagaggc | 1440 |
| aatcattttg ccatttgtga agttgtgtt ggatttagta aaaatgtgaa taagctttgt | 1500 |
| acttattttg agaacttttt aaatgttcca aaatacccta ttttcaaagg gtaatcgtaa | 1560 |
| gatgttaacc cttggtattt agaaaattaa aaccttataa tattttcta tcaagatgta | 1620 |
| tatttttacag tcgtgccttt tactctcatt agcaaaaaag ataaagattt tattttggta | 1680 |
| tttacaagaa ttcccaggta cgaagatatc tgcatgggtg gaaatcaggt tcaagcaacg | 1740 |
| tactttgcat taactgataa tacctcagct gcggggttaa agttttccca gtatagagag | 1800 |
| actgtcacta ggaacattgt attgatttat tcaggtcatt gagatcttct agatgtattt | 1860 |
| taaaaagaat gcttttttggt tatgtgttgc taccacagtt aacactccat aatgttcatg | 1920 |
| tcagccaaag aggactaacc aaagctgaaa tctcagagaa caatttgctt tactaagctg | 1980 |
| agtcaacttg agacgaact tctaacaatg ccgcactgta gtgtggctgg ttctaccact | 2040 |
| atgactttaa acatgttta tatcattttt aattttatg atacggtagt gtcagggaga | 2100 |
| aatgtaatgt tctatatgaa attccttttt caagtttgtt cattaataac agttattaat | 2160 |
| ttaaatcagc gttagagttt tgctgctgc aactgctgtg aaaatttctc tgagtaattc | 2220 |
| tgatttgtga atgatcccag accaaccctg agattttgtc aacctgatta agtcaatatg | 2280 |
| aatgattaaa aagatgtgag | 2300 |

<210> SEQ ID NO 14
<211> LENGTH: 2440
<212> TYPE: DNA
<213> ORGANISM: Homo sapiens

<400> SEQUENCE: 14

| | |
|---|---|
| aaggctcctc agccgagcgc cgagcggtcg atcgccgtag ctcccgcagc ctgcgatctc | 60 |
| cagtctgtgg ctcctaccag ccattgtagg ccaataatcc gttatggagc atgcctttac | 120 |

-continued

```
cccgttggag cccctgcttt ccactgggaa tttgaagtac tgccttgtaa ttcttaatca      180
gcctttggac aactattttc gtcatctttg gaacaaagct cttttaagag cctgtgccga      240
tggaggtgcc aaccgcttat atgatatcac cgaaggagag agagaaagct ttttgcctga      300
attcatcaat ggagactttg attctattag gcctgaagtc agagaatact atgctactaa      360
gggatgtgag ctcatttcaa ctcctgatca agaccacact gactttacta agtgccttaa      420
aatgctccaa aagaagatag aagaaaaaga cttaaaggtt gatgtgatcg tgacactggg      480
aggccttgct gggcgttttg accagattat ggcatctgtg aatacctttgt tccaagcgac      540
tcacatcact cctttttccaa ttataataat ccaagaggaa tcgctgatct acctgctcca      600
accaggaaag cacaggttgc atgtagacac tggaatggag ggtgattggt gtggccttat      660
tcctgttgga cagccttgta tgcaggttac aaccacaggc ctcaagtgga acctcacaaa      720
tgatgtgctt gcttttggaa cattggtcag tacttccaat acctacgacg gtctggtgt       780
tgtgactgtg gaaactgacc acccactcct ctggaccatg gccatcaaaa gctaacctgt      840
tgactggcat ccataagtgt gcctctgcct tatctcattt ctcaacagtt cattgctcaa      900
caagaacgat tcacctgggt ttgcaagaat ctaaacctct ctaggggaag cccactgggt      960
ttaaagatgt tagtgtttag ataatacagg taacattata aatgacagat ctcaattttta    1020
tagtagtggg aaagatacat gctaagaaag caaataagct ctattatatt cggttggaac    1080
ctaatgggaa tcattccact atacaattca gtactgatta ttcttcttac attattaatc    1140
attccattta tcctagaaaa ttgttttttaa tttgaatcag agaaaactgt tgaggttcct    1200
cttggagtct agaacatcct taaatgtcta acaacaaggg ctacctctga gtaccttta     1260
gtattagttt tctgtatatg atatatatta tcttatactg aaaaaaaatt cctttcagat    1320
tggggtgtta aagtgcacc aggtcactct gaccttatta ctgtctttgg tattgtctta     1380
aataaatcaa gaatcattga cctaattgtt aaatttaaaa ataggtagtt agcaataggt    1440
ggaaagagaa atgatgtgaa agataaatga tgattcgtgg agccctactc acacattaac    1500
ccccaaattc aaaagtaaga atgcaaaagt ctagaggggg taacagtctg catcatcatc    1560
acaacctaaa tggagaaagc tgtgcagagg aaacttaagc ataaaaattg aattcgtttc    1620
tgacatacct tagactgaaa aactgttggt tcatccagaa gtgtattcat attaccagaa    1680
aatgagtttg tctatgggga tacatgaact tcatatacta aggagcctaa ctccaaagcc    1740
tgcgttctca tcccagtctg atattcacct aagtttccgg acccttttcc ttagctgtaa    1800
aatggaagcg gttggactga tggtgtctga ggttctttcc cacactgaaa ttctaaatat    1860
tgacacttag cagtcatagg gctgataata cacacagtta ctgacttagc ctaaacaacc    1920
tggtgcatcg aaatgtattc acctttcttt tgtaaagaga ccatcttcta tcttctttcc    1980
acctttctct gttttatgaa accaactgtt gacatacaaa ccatgattga aggagaacct    2040
gtccaacatg ttttatgtac acaaatccct atgttgctat aagaaaagtg aaagtaactg    2100
ttttcttctt ggtgctatga cagtgtgaga ctcaggttgt ctgtagagaa tgaaaggagc    2160
agtggcccgc gtgattgtgg catttaagga gcagtggccc atgtgactgt ggcattttcg    2220
gcacttttca ttactttctg cttgaccgga agttgaggct tagctatgtt tccatcttca    2280
gtttctgaag actagttata tattccttac tagaaatata ttcataatat ataaagaaa     2340
tatatctgtg attttaaaat tttgctacca agaatgcat gttctgtgtg ccctgaaaat     2400
gttaccagtg ttaataaatg gatacttatc aaaaaagaaa                           2440
```

<210> SEQ ID NO 15
<211> LENGTH: 475
<212> TYPE: DNA
<213> ORGANISM: Homo sapiens

<400> SEQUENCE: 15

```
acacatctgc tcctgctctc tctcctccag cgaccctagc catgagaacc ctcaccatcc      60
tcactgctgt tctcctcgtg gccctccagg ccaaggctga gccactccaa gctgaggatg     120
atccactgca ggcaaaagct tatgaggctg atgcccagga gcagcgtggg gcaaatgacc     180
aggactttgc cgtctccttt gcagaggatg caagctcaag tcttagagct ttgggctcaa     240
caagggcttt cacttgccat tgcagaaggt cctgttattc aacagaatat tcctatggga     300
cctgcactgt catgggtatt aaccacagat tctgctgcct ctgagggatg agaacagaga     360
gaaatatatt cataatttac tttatgacct agaaggaaac tgtcgtgtgt cccatacatt     420
gccatcaact ttgtttcctc atctcaaata aagtcctttc agcaaaaaaa aaaaa          475
```

<210> SEQ ID NO 16
<211> LENGTH: 3650
<212> TYPE: DNA
<213> ORGANISM: Homo sapiens

<400> SEQUENCE: 16

```
gcgctaggta gagcgccggg acctgtgaca gggctggtag cagcgcagag gaaaggcggc      60
ttttagccag gtatttcagt gtctgtagac aagatggaat catctccatt taatagacgg     120
caatggacct cactatcatt gagggtaaca gccaaagaac tttctcttgt caacaagaac     180
aagtcatcgg ctattgtgga atattctcc aagtaccaga agcagctga gaaacaaac       240
atggagaaga gagaagtaa caccgaaaat ctctcccagc actttagaaa ggggacctg      300
actgtgttaa agaagaagtg ggagaaccca gggctgggag cagagtctca cacagactct     360
ctacggaaca gcagcactga gattaggcac agagcagacc atcctcctgc tgaagtgaca     420
agccacgctg cttctggagc caaagctgac caagaagaac aaatccaccc cagatctaga     480
ctcaggtcac ctcctgaagc cctcgttcag ggtcgatatc cccacatcaa ggacggtgag     540
gatcttaaag accactcaac agaaagtaaa aaatggaaa attgtctagg agaatccagg      600
catgaagtag aaaaatcaga aatcagtgaa acacagatg cttcgggcaa aatagagaaa      660
tataatgttc cgctgaacag gcttaagatg atgtttgaga aggtgaacc aactcaaact      720
aagattctcc gggcccaaag ccgaagtgca agtggaagga agatctctga aaacagctat     780
tctctagatg acctggaaat aggcccaggt cagttgtcat cttctacatt tgactcggag     840
aaaaatgaga gtagcgaaa tctggaactt ccacgcctct cagaaacctc tataaaggat      900
cgaatggcca agtaccaggc agctgtgtcc aaacaaagca gctcaaccaa ctatacaaat     960
gagctgaaag ccagtggtgg cgaaatcaaa attcataaaa tggagcaaaa ggagaatgtg    1020
cccccaggtc ctgaggtctg catcacccat caggaagggg aaaagatttc tgcaaatgag    1080
aatagcctgg cagtccgttc cacccctgcc gaagatgact cccgtgactc ccaggttaag    1140
agtgaggttc aacagcctgt ccatcccaag ccactaagtc cagattccag agcctccagt    1200
cttctctgaaa gttctcctcc caaagcaatg aagaagtttc aggcacctgc aagagagacc    1260
tgcgtggaat gtcagaagac agtctatcca atggagcgtc tcttggccaa ccagcaggtg    1320
tttcacatca gctgcttccg ttgctcctat tgcaacaaca aactcagtct aggaacatat    1380
gcatctttac atgaagaat ctattgtaag cctcacttca atcaactctt taaatctaag    1440
```

```
ggcaactatg atgaaggctt tgggcacaga ccacacaagg atctatgggc aagcaaaaat    1500
gaaaacgaag agattttgga gagaccagcc cagcttgcaa atgcaaggga gacccctcac    1560
agcccagggg tagaagatgc ccctattgct aaggtgggtg tcctggctgc aagtatggaa    1620
gccaaggcct cctctcagca ggagaaggaa gacaagccag ctgaaaccaa gaagctgagg    1680
atcgcctggc cacccccac tgaacttgga agttcaggaa gtgccttgga ggaagggatc     1740
aaaatgtcaa agcccaaatg gcctcctgaa gacgaaatca gcaagcccga agttcctgag    1800
gatgtcgatc tagatctgaa gaagctaaga cgatcttctt cactgaagga aagaagccgc    1860
ccattcactg tagcagcttc atttcaaagc acctctgtca agagcccaaa aactgtgtcc    1920
ccacctatca ggaaaggctg gagcatgtca gagcagagtg aagagtctgt gggtggaaga    1980
gttgcagaaa ggaaacaagt ggaaaatgcc aaggcttcta agaagaatgg gaatgtggga    2040
aaaacaacct ggcaaaacaa agaatctaaa ggagagacag ggaagagaag taaggaaggt    2100
catagtttgg agatggagaa tgagaatctt gtagaaaatg gtgcagactc cgatgaagat    2160
gataacagct tcctcaaaca acaatctcca caagaaccca gtctctgaa ttggtcgagt      2220 tttgtagaca acacctttgc tgaagaattc actactcaga atcagaaatc ccaggatgtg    2280
gaactctggg agggagaagt ggtcaaagag ctctctgtgg aagaacagat aaagagaaat    2340
cggtattatg atgaggatga ggatgaagag tgacaaattg caatgatgct gggccttaaa    2400
ttcatgttag tgttagcgag ccactgccct ttgtcaaaat gtgatgcaca taagcaggta    2460
tcccagcatg aaatgtaatt tacttggaag taactttgga aaagaattcc ttcttaaaat    2520
caaaaacaaa acaaaaaaac acaaaaaaca cattctaaat actagagata actttactta    2580
aattcttcat tttagcagtg atgatatgcg taagtgctgt aaggcttgta actggggaaa    2640
tattccacct gataatagcc cagattctac tgtattccca aaaggcaata ttaaggtaga    2700
tagatgatta gtagtatatt gttacacact attttggaat tagagaacat acagaaggaa    2760
tttaggggct taaacattac gactgaatgc actttagtat aaagggcaca gtttgtatat    2820
ttttaaatga ataccaattt aatttttttag tatttacctg ttaagagatt atttagtctt    2880 taaattttt aggttaattt tcttgctgtg atatatatga ggaatttact actttatgtc      2940
ctgctctcta aactcatcc tgaactcgac gtcctgaggt ataatacaac agagcacttt     3000
ttgaggcaat tgaaaaacca acctacactc ttcggtgctt agagagatct gctgtctccc    3060
aaataagctt ttgtatctgc cagtgaattt actgtactcc aaatgattgc tttcttttct    3120
ggtgatatct gtgcttctca taattactga agctgcaat attttagtaa taccttcggg     3180
atcactgtcc cccatcttcc gtgttagagc aaagtgaaga gtttaaagga ggaagaagaa    3240
agaactgtct tacaccactt gagctcagac ctctaaaccc tgtatttccc ttatgatgtc    3300 cccttttga gacactaatt tttaaatact tactagctct gaaatatatt gattttatc      3360 acagtattct cagggtgaaa ttaaaccaac tataggcctt tttcttggga tgattttcta    3420
gtcttaaggt ttggggacat tataaacttg agtacatttg ttgtacacag ttgatattcc    3480
aaattgtatg gatgggaggg agaggtgtct taagctgtag gcttttcttt gtactgcatt    3540
tatagagatt tagcttttaat attttttaga gatgtaaaac attctgctttt cttagtctta   3600 cctagtctga aacattttta ttcaataaag attttaatta aatttgaaa                3650
```

<210> SEQ ID NO 17
<211> LENGTH: 5703
<212> TYPE: DNA
<213> ORGANISM: Homo sapiens

<400> SEQUENCE: 17

```
gacagtcgcg gatcctgtga cacctccggg cagcccggca cttgttgctc ccacgacctg      60
ttgtcattcc cttaacccgg ctttccccgt ggcccccgc ctcctcccgg cttcgctcct      120
tttcatgtga gcatctggga cactgatctc tcagaccccg ctgctcgggc tggagaatag      180
atggttttgt gaaaaattaa acaccgccct gaagaggagc cccgctgggc agcggcagga      240
gcgcagagtg ctggcccagg tgctgcagag gtggcgcctc cccggcccgg gacggtagcc      300
ccgggcgcca acggcatgac agactcggcg acagctaacg gggacgacag ggaccccgag      360
atcgagctct tgtgaaggc tggaatcgat ggagaaagca tcggcaactg tccttctct      420
cagcgcctct tcatgatcct ctggctgaaa ggagtcgtgt tcaatgtcac cactgtggat      480
ctgaaaagaa agccagctga cctgcacaac ctagcccccg gcacgcaccc gcccttcctg      540
accttcaacg gggacgtgaa gacagacgtc aataagatcg aggagttcct ggaggagacc      600
ttgaccctg aaaagtaccc caaactggct gcaaacacc gggaatccaa cacagcgggc      660
atcgacatct tttccaagtt ttctgcctac atcaaaaata ccaagcagca gaacaatgct      720
gctcttgaaa gaggcctaac caaggctcta agaaattgg atgactacct gaacacccct      780
ctaccagagg agattgacgc caacacttgt ggggaagaca aggggtcccg gcgcaagttc      840
ctggatgggg atgagctgac cctggctgac tgcaatctgt tgcccaagct ccatgtggtc      900
aagattgtgg ccaagaaata ccgcaactat gatatcccgg ctgagatgac aggcctgtgg      960
cggtacctca gaacgccta tgcccgtgat gagttcacca cacctgtgc agctgacagt     1020
gagatcgagt tggcctacgc tgatgtcgcc aaacgcctca gccgatcctg agcacagcca     1080
ttttgccccca tcccgctgc agaaggactc aaccactccc ctaagactcc agcttcatag     1140
actcctctgt atcactgcct tgaggcgcac tttttataat caagcctcat cttgctggta     1200
tcatgggaac tccagcctgc tatctttcat gaaggtcagc accatccctg gcctcctcac     1260
ataggaatct agcagaaatg atagacacag tccaccttt ggccggccag cctgatctgg     1320
gctcagcatg tttggggtca gtcagtgttg gagagcccac atatgggatt gccactagct     1380
tcttctgcca atatcaaaat accttctcag atgctttaga acatgcaac accaactcct     1440
tttctacct cctctccgtc catacctaca aggccaagga caaacgccat cttcatcctt     1500
cttagaaaga gatctattac cccattaggg gagacagaga gagtgaatgg aggagtaccg     1560
agctggctat ggacttgggt gtctggcaaa cacagcttca gtctcactac ttctgacact     1620
ctggttattg ggcactaagg gccagactgg aaagtcactt gagacacatt ctcagtttgt     1680
tgcagtgcca ggaatgctgc gctgctgctg ctgcgcacct ggcccatgct gtccctggct     1740
tccatgccgt ccaggccctg ccagaaaagg aaattggcat gcaattctaa actgcagtga     1800
ctgggatggg aggggagggg agcagtgttg atgccaaaat acccacgggg tctaccagcc     1860
atgggtttg cttgcttagg agtagttgtt tcagaggtga ttacaggcct gggtttgact     1920
gtgcttacca atgagtggtt tttgagctat gagaaagtgg atgggagtgg gaggaggaga     1980
gatgggtgaa gacaaaagag ttctttatga gcctcgatgt tccctggtaa acttttaaaa     2040
aggccttctc tcatgatcta agtcttggac tggtggcatc atgtaactgc taaccttaca     2100
gtaaaaaccc aagaatgggt caaaaatgtc ttcccagttt ctccaagctg cttctggaat     2160
gcaggtctgt cggctgggtg ctctccagca gctgctcctg cctgattcaa ctgtagcctg     2220
taatgggtaa aagccacatt taggaggtgg tctgatcata gaacacctta ggaagaaagt     2280
```

```
ccatgagact ttctgactag gaaaccatgt ggtttgaact tgaagaaaaa tgtagaccca    2340
tctgggttaa ttttcctaca atctgactca actgccaggt gaaaaaaaaa aggaaaaatt    2400
tttaagctaa tatttcactc ttttgtcatt ctccttaagt ttcatctcct aaaaagctta    2460
cccagcctga gcttggggac ctgtgcagag gaaactaaga aaaatgcact catcaactcc    2520
ttctcccagt gaacgcccgg tgagaaaatc catttgccac aggcccttac cttcaacaat    2580
cccccttcta tagtgttcgc tggtaaaggg tgaggctccc aagtgctgga aagcccctgg    2640
acttggctca tttctcagca agggcaggat agcacgggtc ctttccatag aaatatcaac    2700
aaattctaac ccaagcaatc cctggaccta cctgcctcca gggatctctg aagaaaaaaa    2760
gtaacccatt gatcaaatca gaggagagga agcaggaggt ctcctagagc ccattgagga    2820
agaggaactt tctcagtagg acactttata agcctgagaa agctttgaaa aggcggaatg    2880
agttgattca tttccacctc aaaaggaacc tttccaggtc ccctggaaa ttgtgccctg     2940
gagatgttta acaaggagaa ctggtgagga aagagtcctt ttttactgta gggaaaagcc    3000
ccaaactggc ctcctggggg atgagggctg aaatgatccc gaaggccttt taattagtgt    3060
gaaatcctgc tgtactcaga atccttccc cgaatttaca gcacaggcag gatgacctaa     3120
gaggcagttt acttccctga gacccacagt tgggctgttc tggaaacaca tctgtgaatc    3180
atagccaatt gccacagaga aaacagaacc aagcctccgg tgaggccact ccaccccaga    3240
gaagtctgca gaattccaag gactcggatt ggatgttcag aattcagcaa ctggaaagtc    3300
cttaaaaaca aacaggccaa accaaatcaa tattgctgtt ctagatgtc ccttctgtgg     3360
ttgagctagt tttacagaga taaatatatt aagacaagga ggtgggggtg ttatatgatc    3420
aatgatagcc atttgaaaga gagggaggag tacagaagga aggcacttct gggtacttaa    3480
ttcagaaatt tctttatatt tcagcactgg attatcatat aatgcaagtg actatggact    3540
aagagttagt tatggtgtct tatgactaga tttattatgg tatattaaag taacaataat    3600
attaatatta ccttcctttt tttttttgtt tcaaaagaga tctttctcca gatgcttcag    3660
cctgtctggc cttcttatca tatgtgcagc acatcatgtc tcagcaacag tgtggtgagg    3720
tccttaggtg tcccaagaac aactcaggga gcacgggagg gtctgcagtt gggaccccac    3780
aactatacag ctatagggta ggaggcttcc ttttcattgg tcctgaatga atacaaatcg    3840
ctcagaaagc atttttggtgg cacagaaagg ggatgtattt gtgttgagat cttattttat    3900
tttgtattta tttatcttct ttgacttgca cagcactatt gggggtgggg gaagcagggt    3960
agtgggagac gaaggcagaa gcaagagtca aactcagaat gactgagttg aattcactgt    4020
ctagtcagca atgcctgctt ctgagtttgg cccagagaga aggtattgag taagatttta    4080
ataactgtaa aaagtaagct ggataagtaa aatcatgatg gatccaaagc acagtttctt    4140
catctcctga taaagaaagt caaatgcttg ataaattcag agtcacagat gtgagcatag    4200
ctatattctt ttaaacgaga ggtagagtga cctagcacta agcaaatgag ctgaaatgtc    4260
ggaaacagag tccatcagct tatttggcca cacgatccca aactagtttt atcttgggaa    4320
atggccctgt cctcagcatt ccttcttgt gctggtgggg ccagtgaagt cttgatctta     4380
tcagaaaaag gccacaccaa gtgcgagttt tcccaggctg actttccagg cccttatcaa    4440
atgaaacaac agaagctctt cacagttctg tgccccatgg ccactccaca gacagacaat    4500
accaagcatc ttagaactgt cataagatag gtcatgcctg aaatagatct tgaccatatg    4560
agagtcccag aaatcagcaa ggcctggaca aatagaacta agagagaggc agaggcagga    4620
agctgcgggt ctatcttgta aagagtttag catcactgtg agagtgtgtg tctaaaatta    4680
```

```
aattaaacta gaagcagcag gtgagtattt ggtaagtact tctgtgactc gcctcaattc    4740
ccactggcca ggggccatct caactgcacg gtgaatcaag atgctggtgt catcctcctt    4800
ggaaaaagga aatgttaact catggttaaa actaagtaca atgattccca agggatcact    4860
ttcttatttt tttaaatgac attaaggaga atcttaagaa agcatcagag aaagacatgt    4920
gcatgtgaag caccctgatt ctgatgttag gaaaacttaa gcgaacagga cctgctgcac    4980
acagccccat tgtcttctat ccatttctct ttatcattca aatcaagcaa catgtgccct    5040
cctcatcaac acacattctt cccctttgtc agtatgcatc tcccagctta gtgtcaggat    5100
actttcgatt cataattatg tatgatccaa agtgtgcata atttcattta acgttaaaga    5160
aatagatcca attcctttct tgcaaccaaa aataaataaa atacgttgcc tcaatataag    5220
gtttgggcta ttctgtgttt ctatagaagc aatctgtttt tggtaaaatg tacttttaag    5280
gatccagtca tctgaagtat tttatgtaga gttagagatt tcacaatatt gactatacat    5340
atatttaaaa tataaattat ccagctgatg tttgaatttg tcttactttc ctggccacct    5400
cgttgtccta ttttataagc tggggagtta actagcttaa caaaagatgc ttagcttttg    5460
taaaagaaca agtgtttcat tttacaaaga cactccaaat gatagttact tgattttctc    5520 gagacccttta actatggtga tgaataacag gacttgcttt caagccttaa taaatgtaaa    5580 atgccttta atgaagatac agctgagtgt tttcctcatg aatctgaacc aattaccaat    5640
ttgtgttcca gtcttgattg gtattgactg attcaaataa agttggttta ttttcaaata    5700
tta                                                                  5703

<210> SEQ ID NO 18
<211> LENGTH: 1941
<212> TYPE: DNA
<213> ORGANISM: Homo sapiens

<400> SEQUENCE: 18
gcttttgtgg cggcgcccgc gctcgcaggc cactctctgc tgtcgcccgt cccgcgcgct      60
cctccgaccc gctccgctcc gctccgctcg gcccgcgcc gcccgtcaac atgatccgct     120
gcggcctggc ctgcgagcgc tgccgctgga tcctgcccct gctcctactc agcgccatcg     180
ccttcgacat catccgcgctg gccggccgcg gctggttgca gtctagcgac cacgccaga     240 cgtcctcgct gtggtggaaa tgctcccaag agggcggcgg cagcgggtcc tacgaggagg     300
gctgtcagag cctcatggag tacgcgtggg gtagagcagc ggctgccatg ctcttctgtg     360
gcttcatcat cctggtgatc tgtttcatcc tctccttctt cgccctctgt ggaccccaga     420
tgcttgtctt cctgagagtg attggaggtc tccttgcctt ggctgctgtg ttccagatca     480
tctccctggt aatttacccc gtgaagtaca cccagacctt caccttcat gccaaccctg     540 ctgtcactta catctataac tgggcctacg gctttgggtg ggcagccacg attatcctga     600
ttggctgtgc cttcttcttc tgctgcctcc ccaactacga agatgacctt ctgggcaatg     660
ccaagcccag gtacttctac acatctgcct aacttgggaa tgaatgtggg agaaaatcgc     720
tgctgctgag atggactcca gaagaagaaa ctgtttctcc aggcgacttt gaacccattt     780
tttggcagtg ttcatattat taaactagtc aaaaatgcta aaataatttg ggagaaaata     840
ttttttaagt agtgttatag tttcatgttt atcttttatt atgttttgtg aagttgtgtc     900
ttttcactaa ttacctatac tatgccaata tttcctatct atccataaca tttatactac     960
atttgtaaga gaatatgcac gtgaaactta acactttata aggtaaaaat gaggtttcca    1020
```

-continued

| | |
|---|---|
| agatttaata atctgatcaa gttcttgtta ttttccaaata gaatggactc ggtctgttaa | 1080 |
| gggctaagga gaagaggaag ataaggttaa aagttgttaa tgaccaaaca ttctaaaaga | 1140 |
| aatgcaaaaa aaaagtttat tttcaagcct tcgaactatt taaggaaagc aaaatcattt | 1200 |
| cctaaatgca tatcatttgt gagaatttct cattaatatc ctgaatcatt cattttagct | 1260 |
| aaggcttcat gttgactcga tatgtcatct aggaaagtac tatttcatgg tccaaacctg | 1320 |
| ttgccatagt tggtaaggct ttcctttaag tgtgaaatat ttagatgaaa ttttctcttt | 1380 |
| taaagttctt tatagggtta gggtgtggga aaatgctata ttaataaatc tgtagtgttt | 1440 |
| tgtgtttata tgttcagaac cagagtagac tggattgaaa gatggactgg gtctaattta | 1500 |
| tcatgactga tagatctgtt aagttgtgta gtaaagcatt aggagggtca ttcttgtcac | 1560 |
| aaaagtgcca ctaaaacagc ctcaggagaa taaatgactt gcttttctaa atctcaggtt | 1620 |
| tatctgggct ctatcatata gacaggcttc tgatagtttg caactgtaag cagaaaccta | 1680 |
| catatagtta aaatcctggt ctttcttggt aaacagattt taaatgtctg atataaaaca | 1740 |
| tgccacagga gaattcgggg atttgagttt ctctgaatag catatatatg atgcatcgga | 1800 |
| taggtcatta tgattttta ccatttcgac ttacataatg aaaaccaatt cattttaaat | 1860 |
| atcagattat tattttgtaa gttgtggaaa aagctaattg tagttttcat tatgaagttt | 1920 |
| tcccaataaa ccaggtattc t | 1941 |

<210> SEQ ID NO 19
<211> LENGTH: 2660
<212> TYPE: DNA
<213> ORGANISM: Homo sapiens

<400> SEQUENCE: 19

| | |
|---|---|
| aggaagagcc gcgggcccgg cggctgaggc caccccggcg gcggctggag agcgaggagg | 60 |
| agcgggtggc cccgcgctgc gcccgccctc gcctcacctg gcgcaggtgg acacctgcgc | 120 |
| aggtgtgtgc cctccggccc ctgaagcatg gccagcagcg gcatggctga cagcgccaac | 180 |
| cacctgccct tcttttttcgg caacatcacc cgggaggagg cagaagatta cctggtccag | 240 |
| gggggcatga gtgatgggct ttatttgctg cgccagagcc gcaactacct gggtggcttc | 300 |
| gccctgtccg tggcccacgg gaggaaggca caccactaca ccatcgagcg ggagctgaat | 360 |
| ggcacctacg ccatcgccgg tggcaggacc catgccagcc ccgccgacct ctgccactac | 420 |
| cactcccagg agtctgatgg cctggtctgc ctcctcaaga agcccttcaa ccggccccaa | 480 |
| ggggtgcagc ccaagactgg gccctttgag gatttgaagg aaaacctcat cagggaatat | 540 |
| gtgaagcaga catggaacct gcagggtcag gctctggagc aggccatcat cagtcagaag | 600 |
| cctcagctgg agagctgat cgctaccaca gcccatgaaa aaatgccttg gttccatgga | 660 |
| aaaatctctc gggaagaatc tgagcaaatt gtcctgatag gatcaaagac aaatggaaag | 720 |
| ttcctgatcc gagccagaga caacaacggc tcctacgccc tgtgcctgct gcacgaaggg | 780 |
| aaggtgctgc actatcgcat cgacaaagac aagacaggga agctctccat ccccgaggga | 840 |
| aagaagttcg acacgctctg gcagctagtc gagcattatt cttataaagc agatggtttg | 900 |
| ttaagagttc ttactgtccc atgtcaaaaa atcggcacac agggaaatgt taattttgga | 960 |
| ggccgtccac aacttccagg ttcccatcct gcgacttggt cagcgggtgg aataatctca | 1020 |
| agaatcaaat catactcctt cccaaagcct ggccacagaa agtcctcccc tgcccaaggg | 1080 |
| aaccggcaag agagtactgt gtcattcaat ccgtatgagc cagaacttgc accctgggct | 1140 |
| gcagacaaag gccccagag agaagcccta cccatggaca cagaggtgta cgagagcccc | 1200 |

```
tacgcggacc ctgaggagat caggcccaag gaggtttacc tggaccgaaa gctgctgacg    1260
ctggaagaca aagaactggg ctctggtaat tttggaactg tgaaaaaggg ctactaccaa    1320
atgaaaaaag ttgtgaaaac cgtggctgtg aaaatactga aaacgaggc caatgacccc     1380 gctcttaaag atgagttatt agcagaagca atgtcatgc agcagctgga caacccgtac     1440
atcgtgcgca tgatcgggat atgcgaggcc gagtcctgga tgctagttat ggagatggca    1500
gaacttggtc ccctcaataa gtatttgcag cagaacagac atgtcaagga taagaacatc    1560
atagaactgg ttcatcaggt ttccatgggc atgaagtact tggaggagag caattttgtg    1620
cacagagatc tggctgcaag aaatgtgttg ctagttaccc aacattatgc caagatcagt    1680
gatttcggac tctccaaagc actgcgtgct gatgaaaact actacaaggc ccagacccat    1740
ggaaagtggc ctgtcaagtg gtacgctccg gaatgcatca actactacaa gttctccagc    1800
aaaagcgatg tctggagctt tggagtgttg atgtgggaag cattctccta tgggcagaag    1860
ccatatcgag ggatgaaagg aagtgaagtc accgctatgt tagagaaagg agagcggatg    1920
gggtgccctg cagggtgtcc aagagagatg tacgatctca tgaatctgtg ctggacatac    1980
gatgtggaaa acaggcccgg attcgcagca gtggaactgc ggctgcgcaa ttactactat    2040
gacgtggtga actaaccgct cccgcacctg tcggtggctg cctttgatca caggagcaat    2100
cacaggaaaa tgtatccaga ggaattgatt gtcagccacc tccctctgcc agtcgggaga    2160
gccaggcttg gatggaacat gcccacaact tgtcacccaa agcctgtccc aggactcacc    2220
ctccacaaag caaaggcagt cccggagaa aagacggatg caggatcca aggggctagc      2280 tggatttgtt tgttttcttg tctgtgtgat tttcatacag gttattttta cgatctgttt    2340
ccaaatccct ttcatgtctt tccacttctc tgggtcccgg ggtgcatttg ttactcatcg    2400
ggcccaggga cattgcagag tggcctagag cactctcacc ccaagcggcc ttttccaaat    2460
gcccaaggat gccttagcat gtgactcctg aagggaaggc aaaggcagag gaatttggct    2520
gcttctacgg ccatgagact gatccctggc cactgaaaag ctttcctgac aataaaaatg    2580
ttttgaggct ttaaaaagaa aatcaagttt gaccagtgca gtttctaagc atgtagccag    2640
ttaaggaaag aaagaaaaaa                                                2660
```

<210> SEQ ID NO 20
<211> LENGTH: 6860
<212> TYPE: DNA
<213> ORGANISM: Homo sapiens

<400> SEQUENCE: 20

```
ggtggcctct gtggccgtcc aggctagcgg cggcccgcag gcggcgggga gaaagactct     60
ctcacctggt cttgcggctg tggccaccgc cggccagggg tgtggagggc gtgctgccgg    120
agacgtccgc cgggctctgc agttccgccg ggggtcgggc agctatggag ccgcggccca    180
cggcgccctc ctccggcgcc ccgggactgg ccggggtcgg ggagacgccg tcagccgctg    240
cgctggccgc agccagggtg gaactgcccg gcacggctgt gccctcggtg ccggaggatg    300
ctgcgcccgc gagccgggac ggcggcgggg tccgcgatga gggccccgcg gcggccgggg    360
acgggctggg cagaccccttg gggcccaccc cgagccagag ccgtttccag gtggacctgg    420
tttccgagaa cgccgggcgg gccgctgctg cggcggcgg ggcggcggcg cagcggcgg     480 cggctggtgc tggggcgggg gccaagcaga ccccgcgga cggggaagcc agcggcgaga    540
gcgagccggc taaaggcagc gaggaagcca agggccgctt ccgcgtgaac ttcgtggacc    600
```

```
cagctgcctc ctcgtcggct gaagacagcc tgtcagatgc tgccggggtc ggagtcgacg      660
ggcccaacgt gagcttccag aacggcgggg acacggtgct gagcgagggc agcagcctgc      720
actccggcgg cggcggcggc agtgggcacc accagcacta ctattatgat acccacacca      780
acacctacta cctgcgcacc ttcggccaca acaccatgga cgctgtgccc aggatcgatc      840
actaccggca cacagccgcg cagctgggcg agaagctgct ccggcctagc ctggcggagc      900
tccacgacga gctggaaaag gaacctttg aggatggctt tgcaaatggg aagaaagta       960 ctccaaccag agatgctgtg gtcacgtata ctgcagaaag taaaggagtc gtgaagtttg     1020
gctggatcaa gggtgtatta gtacgttgta tgttaaacat ttggggtgtg atgcttttca     1080
ttagattgtc atggattgtg ggtcaagctg aataggtct atcagtcctt gtaataatga      1140
tggccactgt tgtgacaact atcacaggat tgtctacttc agcaatagca actaatggat     1200
ttgtaagagg aggaggagca tattatttaa tatctagaag tctagggcca gaatttggtg     1260
gtgcaattgg tctaatcttc gcctttgcca acgctgttgc agttgctatg tatgtggttg     1320
gatttgcaga aaccgtggtg gagttgctta aggaacattc catacttatg atagatgaaa     1380
tcaatgatat ccgaattatt ggagccatta cagtcgtgat tcttttaggt atctcagtag     1440
ctggaatgga gtgggaagca aaagctcaga ttgttctttt ggtgatccta cttcttgcta     1500
ttggtgattt cgtcatagga acatttatcc cactggagag caagaagcca aagggttt       1560 ttggttataa atctgaaata tttaatgaga actttgggcc cgattttcga gaggaagaga     1620
cttctttttc tgtatttgcc atctttttc ctgctgcaac tggtattctg gctggagcaa      1680
atatctcagg tgatcttgca gatcctcagt cagccatacc caaggaaca ctcctagcca      1740 ttttaattac tacattggtt tacgtaggaa ttgcagtatc tgtaggttct tgtgttgttc     1800
gagatgccac tggaaacgtt aatgacacta tcgtaacaga gctaacaaac tgtacttctg     1860
cagcctgcaa attaaacttt gattttcat cttgtgaaag cagtccttgt tcctatggcc      1920
taatgaacaa cttccaggta atgagtatgg tgtcaggatt tacaccacta atttctgcag     1980
gtatattttc agccactctt tcttcagcat tagcatccct agtgagtgct cccaaaatat     2040
ttcaggctct atgtaaggac aacatctacc cagctttcca gatgtttgct aaaggttatg     2100
ggaaaaataa tgaaccctct cgtggctaca tcttaacatt cttaattgca cttggattca     2160
tcttaattgc tgaactgaat gttattgcac caattatctc aaacttcttc cttgcatcat     2220
atgcattgat caattttca gtattccatg catcacttgc aaaatctcca ggatggcgtc      2280
ctgcattcaa atactacaac atgtggatat cacttcttgg agcaattctt tgttgcatag     2340
taatgttcgt cattaactgg tgggctgcat tgctaacata tgtgatagtc cttgggctgt     2400
atatttatgt tacctacaaa aaaccagatg tgaattgggg atcctctaca caagccctga     2460
cttacctgaa tgcactgcag cattcaattc gtctttctgg agtggaagac cacgtgaaaa     2520
actttaggcc acagtgtctt gttatgacag gtgctccaaa ctcacgtcca gctttacttc     2580
atcttgttca tgatttcaca aaaaatgttg gtttgatgat ctgtggccat gtacatatgg     2640
gtcctcgaag acaagccatg aaagagatgt ccatcgatca agccaaatat cagcgatggc     2700
ttattaagaa caaatgaag gcattttatg ctccagtaca tgcagatgac ttgagagaag      2760
gtgcacagta tttgatgcag gctgctggtc ttggtcgtat gaagccaaac acacttgtcc     2820
ttggatttaa gaaagattgg ttgcaagcag atatgaggga tgtggatatg tatataaact     2880
tatttcatga tgcttttgac atacaatatg gagtagtggt tattcgccta aaagaaggtc     2940
tggatatatc tcatcttcaa ggacaagaag aattattgtc atcacaagag aaatctcctg     3000
```

```
gcaccaagga tgtggtagta agtgtggaat atagtaaaaa gtccgattta gatacttcca    3060
aaccactcag tgaaaaacca attacacaca aagttgagga agaggatggc aagactgcaa    3120
ctcaaccact gttgaaaaaa gaatccaaag gccctattgt gcctttaaat gtagctgacc    3180
aaaagcttct tgaagctagt acacagtttc agaaaaaaca aggaaagaat actattgatg    3240
tctggtggct ttttgatgat ggaggtttga ccttattgat accttacctt ctgacgacca    3300
agaaaaaatg gaaagactgt aagatcagag tattcattgg tggaaagata aacagaatag    3360
accatgaccg gagagcgatg gctactttgc ttagcaagtt ccggatagac ttttctgata    3420
tcatggttct aggagatatc aataccaaac caaagaaaga aaatattata gcttttgagg    3480
aaatcattga gccatacaga cttcatgaag atgataaaga gcaagatatt gcagataaaa    3540
tgaaagaaga tgaaccatgg cgaataacag ataatgagct tgaactttat aagaccaaga    3600
cataccggca gatcaggtta aatgagttat taaggaaca ttcaagcaca gctaatatta    3660
ttgtcatgag tctcccagtt gcacgaaaag gtgctgtgtc tagtgctctc tacatggcat    3720
ggttagaagc tctatctaag gacctaccac caatcctcct agttcgtggg aatcatcaga    3780
gtgtccttac cttctattca taaatgttct atacagtgga cagccctcca gaatggtact    3840
tcagtgccta gtgtagtaac tgaaatcttc aatgacacat taacatcaca atggcgaatg    3900 gtgactttc tttcacgatt tcattaattt gaaagcacac aggaaagttg ctccattgat    3960
aacgtgtatg gagacttcgg ttttagtcaa ttccatatct caatcttaat ggtgattctt    4020
ctctgttgaa ctgaagtttg tgagagtagt tttcctttgc tacttgaata gcaataaaag    4080
cgtgttaact ttttgattga tgaaagaagt acaaaaagcc tttagccttg aggtgccttc    4140
tgaaattaac caaatttcat ccatatatcc tcttttataa acttatagaa tgtcaaactt    4200
tgccttcaac tgttttttatt tctagtctct tccactttaa aacaaaatga acactgcttg    4260
tcttcttcca ttgaccattt agtgttgagt actgtatgtg ttttgttaat tctataaagg    4320
tatctgttag atattaaagg tgagaattag ggcaggttaa tcaaaaatgg ggaagggaa     4380 atggtaacca aaaagtaacc ccatggtaag gtttatatga gtatatgtga atatagagct    4440
aggaaaaaaa gccccccccaa ataccttttt aaccccctctg attggctatt attactatat   4500
ttattattat ttattgaaac cttagggaag attgaagatt catcccatac ttctatatac    4560
catgcttaaa aatcacgtca ttctttaaac aaaaatactc aagatcattt atatttattt    4620
ggagagaaaa ctgtcctaat ttagaatttc cctcaaatct gagggacttt taagaaatgc    4680
taacagattt ttctggagga aatttagaca aaacaatgtc atttagtaga atatttcagt    4740
atttaagtgg aatttcagta tactgtacta tcctttataa gtcattaaaa taatgttttca   4800 tcaaatggtt aaatggacca ctggtttctt agagaaatgt ttttaggctt aattcattca    4860
attgtcaagt acactagtc ttaatacact caggtttgaa cagattattc tgaatattaa     4920
aatttaatcc attcttaata ttttaaaact tttgttaaga aaaactgcca gtttgtgctt    4980
ttgaaatgtc tgttttgaca tcatagtcta gtaaaatttt gacagtgcat atgtactgtt    5040
actaaaagct ttatatgaaa ttattaatgt gaagtttttc atttataatt caaggaagga    5100
tttcctgaaa acatttcaag ggatttatgt ctacatattt gtgtgtgtgt gtgtatatat    5160
atgtaatatg catacacaga tgcatatgtg tatatataat gaaatttatg ttgctggtat    5220
tttgcatttt aaagtgatca agattcatta ggcaaacttt ggtttaagta aacatatgtt    5280
caaaatcaga ttaacagata caggtttcat agagaacaaa ggtgatcatt tgaagggcat    5340
```

```
gctgtaattt cacacaattt tccagttcaa aaatggagaa tacttcgcct aaaatactgt    5400
taagtgggtt aattgataca agtttctgtg gtggaaaatt tatgcaggtt ttcacgaatc    5460
cttttttttt tttttttttt tttttgagac ggagtcttgc tctgttgcca cgctggaatg    5520
cagtaacgtg atcttggctc actgcgacct ccacctcccc agttcaagcg attctcctgc    5580
ctcagcctcc ctagtagctg ggactacggg tgcacgccac catgcccagc taattttttgt    5640 attttgagta gagacagggt ttcaccgtgt tggctaggat ggtgtctatc tcttgacctt    5700
gtgatccacc cgcctcagcc tcccagagtg ctgggattac aggtgcgagc cactgcgcct    5760
ggctggtttt catgaatctt gatagacatc tattttcag tggtgtgcag    5820 cattttttgct tcatgagtat gacctaggta tagagatctg ataacttgaa ttcagaatat    5880
taagaaaatg aagtaactga ttttctaaaa aaaaaaaaa aaaaaatttc tacattataa    5940
ctcacagcat tgttccattg caggttttgc aatgtttggg ggtaaagaca gtagaaatat    6000
tattcagtaa acaataatgt gtgaactttt aagatggata atagggcatg gactgagtgc    6060
tgctatcttg aaatgtgcac aggtacactt acctttttt tttttttttt taagttttc     6120 ccattcagga aaacaacatt gtgatctgta ctacaggaac caaatgtcat gcgtcataca    6180
tgtgggtata aagtacataa aatatatcta actattcata atgtggggtg ggtaatactg    6240
tctgtgaaat aatgtaagaa gcttttcact taaaaaaaat gcattacttt cacttaacac    6300
tagacaccag gtcgaaaatt ttcaaggtta tagtacttat ttcaacaatt cttagagatg    6360
ctagctagtt ttgaagctaa aaatagcttt attttatgctg aattgtgatt ttttatgcc    6420 aaattttttt tagttctaat cattgatgat agcttggaaa taaataatta tgccatggca    6480
tttgacagtt cattattcct ataagaatta aattgagttt agagagaatg gtggtgttga    6540
gctgattatt aacagttact gaaatcaaat atttatttgt tacattattc catttgtatt    6600
ttaggtttcc ttttacattc tttttatatg cattctgaca ttacatattt tttaagacta    6660
tggaaataat ttaaagattt aagctctggt ggatgattat ctgctaagta agtctgaaaa    6720
tgtaatattt tgataatact gtaatatacc tgtcacacaa atgctttttct aatgttttaa    6780 ccttgagtat tgcagttgct gctttgtaca gaggttactg caataaagga agtggattca    6840
ttaaacctat ttaatgtcca                                                6860
```

<210> SEQ ID NO 21
<211> LENGTH: 3745
<212> TYPE: DNA
<213> ORGANISM: Homo sapiens

<400> SEQUENCE: 21

```
cgcaaagcaa gtgggcacaa ggagtatggt tctaacgtga ttggggtcat gaagacgttg      60
ctgttggact tggctttgtg gtcactgctc ttccagcccg ggtggctgtc ctttagttcc     120
caggtgagtc agaactgcca caatggcagc tatgaaatca cgtcctgat gatgggcaac     180 tcagcctttg cagagcccct gaaaaacttg gaagatgcgg tgaatgaggg gctggaaata    240
gtgagaggac gtctgcaaaa tgctggccta aatgtgactg tgaacgctac tttcatgtat    300
tcggatggtc tgattcataa ctcaggcgac tgccggagta gcacctgtga aggcctcgac    360
ctactcagga aaatttcaaa tgcacaacgg atgggctgtg tcctcatagg gcctcatgt    420 acatactcca ccttccagat gtaccttgac acagaattga gctacccat gatctcagct    480 ggaagttttg gattgtcatg tgactataaa gaaaccttaa ccaggctgat gtctccagct    540
agaaagttga tgtacttctt ggttaacttt tggaaaacca acgatctgcc cttcaaaact    600
```

```
tattcctgga gcacttcgta tgtttacaag aatggtacag aaactgagga ctgtttctgg    660
taccttaatg ctctggaggc tagcgtttcc tatttctccc acgaactcgg ctttaaggtg    720
gtgttaagac aagataagga gtttcaggat atcttaatgg accacaacag gaaaagcaat    780
gtgattatta tgtgtggtgg tccagagttc ctctacaagc tgaagggtga ccgagcagtg    840
gctgaagaca ttgtcattat tctagtggat cttttcaatg accagtactt ggaggacaat    900
gtcacagccc ctgactatat gaaaaatgtc cttgttctga cgctgtctcc tgggaattcc    960
cttctaaata gctctttctc caggaatcta tcaccaacaa aacgagactt tgctcttgcc   1020
tatttgaatg gaatcctgct ctttggacat atgctgaaga tatttcttga aaatggagaa   1080
aatattacca cccccaaatt tgctcatgct ttcaggaatc tcacttttga agggtatgac   1140
ggtccagtga ccttggatga ctgggggat gttgacagta ccatggtgct tctgtatacc   1200
tctgtggaca ccaagaaata caaggttctt ttgacctatg atacccacgt aaataagacc   1260
tatcctgtgg atatgagccc cacattcact tggaagaact ctaaacttcc taatgatatt   1320
acaggccggg gccctcagat cctgatgatt gcagtcttca ccctcactgg agctgtggtg   1380
ctgctcctgc tcgtcgctct cctgatgctc agaaaatata gaaaagatta tgaacttcgt   1440
cagaaaaaat ggtcccacat tcctcctgaa aatatctttc ctctggagac caatgagacc   1500
aatcatgtta gcctcaagat cgatgatgac aaaagacgag atacaatcca gagactacga   1560
cagtgcaaat acgacaaaaa gcgagtgatt ctcaaagatc tcaagcacaa tgatggtaat   1620
ttcactgaaa acagaagat agaattgaac aagttgcttc agattgacta ttacaacctg   1680
accaagttct acggcacagt gaaacttgat accatgatct tcggggtgat agaatactgt   1740
gagagaggat ccctccggga agttttaaat gacacaattt cctaccctga tggcacattc   1800
atggattggg agtttaagat ctctgtcttg tatgacattg ctaagggaat gtcatatctg   1860
cactccagta agacagaagt ccatggtcgt ctgaaatcta ccaactgcgt agtggacagt   1920
agaatggtgg tgaagatcac tgattttggc tgcaattcca ttttacctcc aaaaaaggac   1980
ctgtggacag ctccagagca cctccgccaa gccaacatct ctcagaaagg agatgtgtac   2040
agctatggga tcatcgcaca ggagatcatt ctgcggaaag aaaccttcta cacttttgagc   2100 tgtcgggacc ggaatgagaa gattttcaga gtggaaaatt ccaatggaat gaaacccttc   2160
cgcccagatt tattcttgga aacagcagag gaaaaagagc tagaagtgta cctacttgta   2220
aaaaactgtt gggaggaaga tccagaaaag agaccagatt tcaaaaaaat tgagactaca   2280
cttgccaaga tatttggact ttttcatgac caaaaaaatg aaagctatat ggataccttg   2340
atccgacgtc tacagctata ttctcgaaac ctggaacatc tggtagagga aggacacagg   2400
ctgtacaagg cagagaggga cagggctgac agacttaact ttatgttgct tccaaggcta   2460
gtggtaaagt ctctgaagga gaaggctttg tgggagccgg aactatatga ggaagttaca   2520
atctacttca gtgacattgt aggtttcact actatctgca aatacagcac ccccatggaa   2580
gtggtggaca tgcttaatga catctataag agttttgacc acattgttga tcatcatgat   2640
gtctacaagg tggaaaccat cggtgatgcg tacatggtgg ctagtggttt gcctaagaga   2700
aatggcaatc ggcatgcaat agacattgcc aagatggcct tggaaatcct cagcttcatg   2760
gggacctttg agctggagca tcttcctggc ctcccaatat ggattcgcat ggagttcac    2820 tctggtccct gtgctgctgg agttgtggga atcaagatgc ctcgttattg tctatttgga   2880
gatacggtca acacagcctc taggatggaa tccactggcc tcccctttgag aattcacgtg   2940
```

| | |
|---|---|
| agtggctcca ccatagccat cctgaagaga actgagtgcc agttccttta tgaagtgaga | 3000 |
| ggagaaacat acttaaaggg aagaggaaat gagactacct actggctgac tgggatgaag | 3060 |
| gaccagaaat tcaacctgcc aacccctcct actgtggaga atcaacagcg tttgcaagca | 3120 |
| gaattttcag acatgattgc caactcttta cagaaaagac aggcagcagg gataagaagc | 3180 |
| caaaaaccca gacgggtagc cagctataaa aaaggcactc tggaatactt gcagctgaat | 3240 |
| accacagaca aggagagcac ctattttta acctaaatga ggtataagga ctcacacaaa | 3300 |
| ttaaaataca gctgcactga ggcagcgacc tcaagtgtcc tgaaagctta cattttcctg | 3360 |
| agacctcaat gaagcagaaa tgtacttagg cttggctgcc ctgtctggaa catggacttt | 3420 |
| cttgcatgaa tcagatgtgt gttctcagtg aaataactac cttccactct ggaaccttat | 3480 |
| tccagcagtt gttccaggga gcttctacct ggaaaagaaa agaatgaat agactatcta | 3540 |
| gaacttgaga agattttatt cttatttcat ttatttttg tttgtttatt tttatcgttt | 3600 |
| ttgtttactg gctttccttc tgtattcata agattttta aattgtcata attatattt | 3660 |
| aaatacccat cttcattaaa gtatatttaa ctcataattt ttgcagaaaa tatgctatat | 3720 |
| attaggcaag aataaaagct aaagg | 3745 |

```
<210> SEQ ID NO 22
<211> LENGTH: 1428
<212> TYPE: DNA
<213> ORGANISM: Homo sapiens

<400> SEQUENCE: 22
```

| | |
|---|---|
| cttcaggtca gggagaatgt ataaatgtcc attgccatcg aggttctgct attttгaga | 60 |
| agctgaagca actccaagga cacagttcac agaaatttgg ttctcagccc caaaatactg | 120 |
| attgaattgg agacaattac aaggactctc tggccaaaaa cccttgaaga ggccccgtga | 180 |
| aggaggcagt gaggagcttt tgattgctga cctgtgtcgt accacccag aatgtgcact | 240 |
| gggggctgtg ccagatgcct gggggggacc ctcattcccc ttgcttttt tggcttcctg | 300 |
| gctaacatcc tgttattttt tcctggagga aaagtgatag atgacaacga ccacctttcc | 360 |
| caagagatct ggtttttcgg aggaatatta ggaagcggtg tcttgatgat cttccctgcg | 420 |
| ctggtgttct tgggcctgaa gaacaatgac tgctgtgggt gctgcggcaa cgagggctgt | 480 |
| gggaagcgat ttgcgatgtt cacctccacg atatttgctg tggttggatt cttgggagct | 540 |
| ggatactcgt ttatcatctc agccatttca atcaacaagg gtcctaaatg cctcatggcc | 600 |
| aatagtacat ggggctaccc cttccacgac ggggattatc tcaatgatga ggccttatgg | 660 |
| aacaagtgcc gagagcctct caatgtggtt ccctggaatc tgaccctctt ctccatcctg | 720 |
| ctggtcgtag gaggaatcca gatggttctc tgcgccatcc aggtggtcaa tggcctcctg | 780 |
| gggaccctct gtgggactg ccagtgttgt ggctgctgtg ggggagatgg acccgtttaa | 840 |
| acctccgaga tgagctgctc agactctaca gcatgacgac tacaatttct tttcataaaa | 900 |
| cttcttctct tcttggaatt attaattcct atctgcttcc tagctgataa gcttagaaa | 960 |
| aggcagttat tccttctttc caaccagctt tgctcgagtt agaattttgt tattttcaaa | 1020 |
| taaaaatag tttggccact taacaaattt gatttataaa tctttcaaat tagttccttt | 1080 |
| ttagaattta ccaacaggtt caaagcatac ttttcatgat ttttttatta caaatgtaaa | 1140 |
| atgtataaag tcacatgtac tgccatacta cttctttgta tataaagatg tttatatctt | 1200 |
| tggaagtttt acataaatca aggaagaaa gcacatttaa aatgagaaac taagaccaat | 1260 |
| ttctgttttt aagaggaaaa agaatgattg atgtatccta agtattgtta tttgttgtct | 1320 |

```
tttttttgctg ccttgcttga gttgcttgtg actgatcttt tgaggctgtc atcatggcta    1380 ggggttctttt atgtatgtta aattaaaacc tgaattcaga ggtaacgt                1428

<210> SEQ ID NO 23
<211> LENGTH: 4090
<212> TYPE: DNA
<213> ORGANISM: Homo sapiens

<400> SEQUENCE: 23
ctggagagcc tgctgcccgc ccgcccgtaa aatggtcccc tcggctggac agctcgccct      60
gttcgctctg ggtattgtgt tggctgcgtg ccaggccttg gagaacagca cgtcccgct     120 gagtgcagac ccgcccgtgg ctgcagcagt ggtgtcccat tttaatgact gcccagattc    180
ccacactcag ttctgcttcc atggaacctg caggttttg gtgcaggagg acaagccagc     240
atgtgtctgc cattctgggt acgttggtgc acgctgtgag catgcggacc tcctggccgt    300
ggtggctgcc agccagaaga agcaggccat caccgccttg tggtggtct ccatcgtggc     360 cctggctgtc cttatcatca catgtgtgct gatacactgc tgccaggtcc gaaaacactg    420
tgagtggtgc cgggccctca tctgccggca cgagaagccc agcgccctcc tgaagggaag    480
aaccgcttgc tgccactcag aaacagtggt ctgaagagcc cagaggagga gtttggccag    540
gtggactgtg gcagatcaat aaagaaaggc ttcttcagga cagcactgcc agagatgcct    600
gggtgtgcca cagaccttcc tacttggcct gtaatcacct gtgcagcctt ttgtgggcct    660
tcaaaactct gtcaagaact ccgtctgctt ggggttattc agtgtgacct agagaagaaa    720
tcagcggacc acgatttcaa gacttgttaa aaagaactg caaagagacg gactcctgtt     780 caccctaggtg aggtgtgtgc agcagttggt gtctgagtcc acatgtgtgc agttgtcttc    840
tgccagccat ggattccagg ctatatattt cttttttaatg gccacctcc ccacaacaga     900 attctgccca acacaggaga tttctatagt tattgttttc tgtcatttgc ctactgggga    960
agaaagtgaa ggagggaaaa ctgtttaata tcacatgaag accctagctt aagagaagc    1020 tgtatcctct aaccacgaga ctctcaacca gcccaacatc ttccatggac acatgacatt   1080
gaagaccatc ccaagctatc gccacccttg agatgatgt cttatttatt agatggataa    1140
tggttttatt tttaatctct taagtcaatg taaaaagtat aaaacccctt cagacttcta   1200
cattaatgat gtatgtgttg ctgactgaaa agctatactg attagaaatg tctggcctct   1260
tcaagacagc taaggcttgg gaaaagtctt ccagggtgcg gagatggaac cagaggctgg   1320
gttactggta ggaataaagg tagggggttca gaaatggtgc cattgaagcc acaaagccgg   1380
taaatgcctc aatacgttct gggagaaaac ttagcaaatc catcagcagg gatctgtccc   1440
ctctgttggg gagagaggaa gagtgtgtgt gtctacacag gataaaccca atacatattg   1500
tactgctcag tgattaaatg ggttcacttc ctcgtgagcc ctcggtaagt atgtttagaa   1560
atagaacatt agccacgagc cataggcatt tcaggccaaa tccatgaaag ggggaccagt   1620
catttatttt ccatttgtt gcttggttgg tttgttgctt tatttttaaa aggagaagtt    1680
taactttgct atttatttc gagcactagg aaaactattc cagtaatttt ttttcctca    1740 tttccattca ggatgccggc tttattaaca aaaactctaa caagtcacct ccactatgtg   1800
ggtcttcctt tcccctcaag agaaggagca attgttcccc tgacatctgg gtccatctga   1860
cccatggggc ctgcctgtga gaaacagtgg gtcccttcaa atacatagtg gatagctcat   1920
ccctaggaat tttcattaaa aatttggaaac agagtaatga agaaataata tataaactcc   1980
```

```
ttatgtgagg aaatgctact aatatctgaa aagtgaaaga tttctatgta ttaactctta    2040
agtgcaccta gcttattaca tcgtgaaagg tacatttaaa atatgttaaa ttggcttgaa    2100
attttcagag aattttgtct tccctaatt cttcttcctt ggtctggaag aacaatttct    2160
atgaattttc tctttatttt ttttttataa ttcagacaat tctatgaccc gtgtcttcat    2220
ttttggcact cttatttaac aatgccacac ctgaagcact tggatctgtt cagagctgac    2280
cccctagcaa cgtagttgac acagctccag gttttaaat tactaaaata agttcaagtt    2340
tacatccctt gggccagata tgtgggttga ggcttgactg tagcatcctg cttagagacc    2400
aatcaatgga cactggtttt tagacctcta tcaatcagta gttagcatcc aagagacttt    2460
gcagaggcgt aggaatgagg ctggacagat ggcggaacga gaggttccct gcgaagactt    2520
gagatttagt gtctgtgaat gttctagttc ctaggtccag caagtcacac ctgccagtgc    2580
cctcatcctt atgcctgtaa cacacatgca gtgagaggcc tcacatatac gcctccctag    2640
aagtgccttc caagtcagtc ctttggaaac cagcaggtct gaaaagagg ctgcatcaat    2700 gcaagcctgg ttgaccatt gtccatgcct caggatgaa cagcctggct tatttgggga    2760 ttttttcttct agaaatcaaa tgactgataa gcattggctc cctctgccat ttaatggcaa    2820
tggtagtctt tggttagctg caaaaatact ccatttcaag ttaaaaatgc atcttctaat    2880
ccatctctgc aagctccctg tgtttccttg cccttagaa aatgaattgt tcactacaat    2940
tagagaatca tttaacatcc tgacctggta agctgccaca cacctggcag tggggagcat    3000
cgctgtttcc aatggctcag gagacaatga aaagccccca tttaaaaaaa taacaaacat    3060 ttttaaaag gcctccaata ctcttatgga gcctggattt ttcccactgc tctacaggct    3120 gtgactttt ttaagcatcc tgacaggaaa tgtttcttc tacatggaaa gatagacagc    3180
agccaaccct gatctggaag acagggcccc ggctggacac acgtggaacc aagccaggga    3240
tgggctggcc attgtgtccc cgcaggagag atgggcagaa tggccctaga gttcttttcc    3300
ctgagaaagg agaaaagat gggattgcca ctcacccacc cacactggta agggaggaga    3360
atttgtgctt ctggagcttc tcaagggatt gtgttttgca ggtacagaaa actgcctgtt    3420
atcttcaagc caggttttcg agggcacatg ggtcaccagt tgcttttca gtcaatttgg    3480 ccgggatgga ctaatgaggc tctaacactg ctcaggagac ccctgccctc tagttggttc    3540
tgggctttga tctcttccaa cctgcccagt cacagaagga ggaatgactc aaatgcccaa    3600
aaccaagaac acattgcaga agtaagacaa acatgtatat ttttaaatgt tctaacataa    3660
gacctgttct ctctagccat tgatttacca ggctttctga aagatctagt ggttcacaca    3720
gagagagaga gagtactgaa aaagcaactc ctcttcttag tcttaataat ttactaaaat    3780
ggtcaacttt tcattatctt tattataata aacctgatgc tttttttag aactccttac    3840 tctgatgtct gtatatgttg cactgaaaag gttaatattt aatgttttaa tttattttgt    3900
gtggtaagtt aattttgatt tctgtaatgt gttaatgtga ttagcagtta ttttccttaa    3960
tatctgaatt atacttaaag agtagtgagc aatataagac gcaattgtgt ttttcagtaa    4020
tgtgcattgt tattgagttg tactgtacct tatttggaag gatgaaggaa tgaacctttt    4080
tttcctaaaa                                                          4090
```

<210> SEQ ID NO 24
<211> LENGTH: 1180
<212> TYPE: DNA
<213> ORGANISM: Homo sapiens

<400> SEQUENCE: 24

-continued

```
gaatagtcta ccccccttgc actctacctg acacagctgc agcctgcaat tcactcgcac    60
tgcctgggat tgcactggat ccgtgtgctc agaacaaggt gaacgcccag ctgcagccat   120
gaagatctgt agcctcaccc tgctctcctt cctcctactg gctgctcagg tgctcctggt   180
ggagggaaa aaaaaagtga agaatggact tcacagcaaa gtggtctcag aacaaaagga   240
cactctgggc aacacccaga ttaagcagaa aagcaggccc ggaacaaag gcaagtttgt   300
caccaaagac caagccaact gcagatgggc tgctactgag caggaggagg gcatctctct   360
caaggttgag tgcactcaat tggaccatga atttcctgt gtctttgctg caatccaac   420
ctcatgccta aagctcaagg atgagagagt ctattggaaa caagttgccc ggaatctgcg   480
ctcacagaaa gacatctgta gatattccaa gacagctgtg aaaccagag tgtgcagaaa   540
ggatttcca gaatccagtc ttaagctagt cagctccact ctatttggga acacaaagcc   600
caggaaggag aaaacagaga tgtcccccag ggagcacatc aaaggcaaag agaccacccc   660
ctctagccta gcagtgaccc agaccatggc caccaaagct cccgagtgtg tggaggaccc   720
agatatggca aaccagagga agactgcccc tggagttctgt ggagagactt ggagctctct   780
ctgcacattc ttcctcagca tagtgcagga cacgtcatgc taatgaggtc aaaagagaac   840
gggttccctt aagagatgtc atgtcgtaag tccctctgta tactttaaag ctctctacag   900
tcccccaaa atatgaactt tgtgcttag tgagtgcaac gaaatattta aacaagttt    960
gtatttttg cttttgtgtt ttggaattg ccttatttt cttggatgcg atgttcagag  1020
gctgtttcct gcagcatgta tttccatggc ccacacagct atgtgtttga gcagcgaaga  1080
gtctttgagc tgaatgagcc agagtgataa tttcagtgca acgaactttc tgctgaatta  1140
atggtaataa aactctgggt gttttcaga aatacattca                        1180
```

<210> SEQ ID NO 25
<211> LENGTH: 2510
<212> TYPE: DNA
<213> ORGANISM: Homo sapiens

<400> SEQUENCE: 25

```
gctgggccac agcctggtcc tgccgctgcg cccgcccgcc atggtgtccc gggaccaggc    60
tcacctgggc cccaagtatg tgggcctctg ggacttcaag tcccggacgg acgaggagct   120
gagcttccgc gcgggggacg tcttccacgt ggccaggaag gaggagcagt ggtggtgggc   180
cacgctgctg acgaggcgg gtggggccgt ggcccagggc tatgtgcccc acaactacct   240
ggccgagagg gagacggtgg agtcggaacc gtggttctt ggctgcatct cccgctcgga   300
agctgtgcgt cggctgcagg ccgagggcaa cgccacgggc gccttcctga tcagggtcag   360
cgagaagccg agtgccgact acgtcctgtc ggtgcgggac acgcaggctg tcggcacta   420
caagatctgg cggcgtgccg ggggccggct gcacctgaac gaggcggtgt ccttcctcag   480
cctgcccgag cttgtgaact accacagggc ccagagcctg tcccacggcc tgcggctggc   540
cgcgccctgc cggaagcacg agcctgagcc cctgccccat gggatgact gggagaggcc   600
gaggaggag ttcacgctct gcaggaagct ggggtccggc tactttgggg aggtcttcga   660
ggggctctgg aaagaccggg tccaggtggc cattaaggtg atttctcgag acaacctcct   720
gcaccagcag atgctgcagt cggagatcca ggccatgaag aagctgcggc acaaacacat   780
cctggcgctg tacgccgtgg tgtccgtggg ggaccccgtg tacatcatca cggagctcat   840
ggccaagggc agcctgctgg agctgctccg cgactctgat gagaaagtcc tgcccgtttc   900
```

-continued

```
ggagctgctg gacatcgcct ggcaggtggc tgagggcatg tgttacctgg agtcgcagaa      960
ttacatccac cgggacctgg ccgccaggaa catcctcgtc ggggaaaaca ccctctgcaa     1020
agttggggac ttcgggttag ccaggcttat caaggaggac gtctacctct cccatgacca     1080
caatatcccc tacaagtgga cggccccgga agcgctctcc cgaggccatt actccaccaa     1140
atccgacgtc tggtcctttg ggattctcct gcatgagatg ttcagcaggg gtcaggtgcc     1200
ctacccaggc atgtccaacc atgaggcctt cctgagggtg gacgccggct accgcatgcc     1260
ctgccctctg gagtgcccgc ccagcgtgca aagctgatg ctgacatgct ggtgcaggga     1320
ccccgagcag agaccctgct tcaaggccct gcgggagagg ctctccagct tcaccagcta     1380
cgagaacccg acctgagctg ctgtggagcg gcatggccg ggccctgctg aggaggggcc     1440
tgggcagagg gcctggacct gggatcaagg cccacgcgct tccctggggt ttactgaggt     1500
gatgggtgca ggaaaggttc acaaatgtgg agtgtctgcg tccaatacac gcgtgtgctc     1560
ctctccttac tccatcgtgt gtgccttggg tctcagctgc tgacacgcag cctgctctgg     1620
agcctgcaga tgagatccgg gagactgaca cgaagccagc agaggtcaga ggggactctg     1680
accacagccc gctctctggc tgtctgtctg cagtgcccgg ctgagggtgg aggcaaaca     1740
cgccttgttc ctgctcttcc cagttcagct tggtgggaga aagtcattcg cgtggctcgg     1800
gacgctcatg taaatttggt tttggtgctc aaggggttctt tcctcccagg ggcaggtgtt     1860
tctttcctgt ttgtcttgtg tcttgagagc ttggccttat gaccagtgag aactctctcc     1920
ctggtctctg ccagcccaag catcactgcc cgaggcgcca gctcagtttc accgtccacg     1980
tccacaaggg gcttttccca ccttcacctt tgtcgctggg tcagtgctgg aaagcgcccc     2040
tcactcctgc gctgacaagg gcccttctct actgtctgtg gggtggttcc gggctggggg     2100
ggctgcctcc tttgcacctg attttgaagg tgtctctttc atccatggtt aagtcataaa     2160
aagcttattg gttttggttt tgactcacct gaaagttttt ttggtttaaa agaagaatag     2220
gcggggcacg gtggctcatg cctgtaatcc cagcactttg ggaggctgag gcaggtggat     2280
cacgaggtca ggagatcgac accatcctgg ctaacacggt gaaacccgt ctctactaaa     2340
aaatacaaaa aattagctgg gtgtggtggt gggggtgggc gcctgtagtc ccagctacgt     2400
gggaggctga gcagcagac tggtgtgaac ccgggaggtg gagcttgcag tgagccgaga     2460
tcgcgccact gcactccagc ctgggcgaca gagcgagact ccatctcaaa                2510
```

<210> SEQ ID NO 26
<211> LENGTH: 2620
<212> TYPE: DNA
<213> ORGANISM: Homo sapiens

<400> SEQUENCE: 26

```
acaggcacag gtgaggaact caactcaaac tcctctctct gggaaaacgc ggtgcttgct       60
cctcccggag tggccttggc agggtgttgg agccctcggc ctgccccgtc cggtctctgg      120
ggccaaggct gggtttccct catgtatggc aagagctcta ctcgtgcggt gcttcttctc      180
cttggcatac agctcacagc tctttggcct atagcagctg tggaaattta tacctcccgg      240
gtgctggagg ctgttaatgg gacagatgct cggttaaaat gcactttctc cagctttgcc      300
cctgtgggta tgctctaac agtgacctgg aattttcgtc ctctagacgg ggacctgag       360
cagtttgtat tctactacca catagatccc ttccaaccca tgagtgggcg gtttaaggac      420
cgggtgtctt gggatgggaa tcctgagcgg tacgatgcct ccatccttct ctggaaactg      480
cagttcgacg acaatgggac atacacctgc aggtgaaga acccacctga tgttgatggg      540
```

```
gtgataggg  agatccggct  cagcgtcgtg  cacactgtac  gcttctctga  gatccacttc      600
ctggctctgg  ccattggctc  tgcctgtgca  ctgatgatca  taatagtaat  tgtagtggtc      660
ctcttccagc  attaccggaa  aaagcgatgg  gccgaaagag  ctcataaagt  ggtggagata      720
aaatcaaaag  aagaggaaag  gctcaaccaa  gagaaaaagg  tctctgttta  tttagaagac      780
acagactaac  aatttagat   ggaagctgag  atgatttcca  agaacaagaa  ccctagtatt      840
tcttgaagtt  aatggaaact  tttctttggc  ttttccagtt  gtgacccgtt  ttccaaccag      900
ttctgcagca  tattagattc  tagacaagca  acacccctct  ggagccagca  cagtgctcct      960
ccatatcacc  agtcatacac  agcctcatta  ttaaggtctt  atttaatttc  agagtgtaaa     1020
ttttttcaag  tgctcattag  gttttataaa  caagaagcta  cattttttgcc ccttaagacac    1080 tacttacagt  gttatgactt  gtatacacat  atattggtat  caaaagggat  aaaagccaat     1140
ttgtctgtta  catttccttt  cacgtatttc  ttttagcagc  acttctgcta  ctaaagttaa     1200
tgtgtttact  ctcttttcctt cccacattct  caattaaaag  gtgagctaag  cctcctcggt     1260
gtttctgatt  aacagtaaat  cctaaattca  aactgttaaa  tgacattttt  atttttatgt     1320
ctctccttaa  ctatgagaca  catcttgttt  tactgaattt  ctttcaatat  tccaggtgat     1380
agatttttgt  tgttttgtta  attaatccaa  gatttacaat  agcacaacgc  taaatcacac     1440
agtaactaca  aaaggttaca  tagatatgaa  aagattggca  gaggccattg  caggatgaat     1500
cacttgtcac  ttttcttctg  tgctgggaaa  ataatcaac   aatgtgggtc  tttcatgagc     1560
agtgacggat  agtttagctt  actatgtttc  cccccccaatt caatgatcta  taacaacaga     1620
gcaaagtcta  tgctcatttg  cagactggaa  tcattaagta  atttaataaa  aaaattgtga     1680
aacagcatat  tacaagtttg  aaaattcagg  gctggtgaaa  aaaatcaact  ctaaatgatg     1740
ataattttgt  acagttttat  ataaaactct  gagaactaga  agaaattatt  aactttttt      1800 cttttttaat  tctaattcac  ttgtttattt  tgggggagga  agactttggt  atggagcaaa     1860
gaaataccaa  aactacttta  aatggaataa  aaccaacttt  attcttttt   tcccccatac     1920 tggtagataa  agcaaacttt  ataagtgggc  tattgaaaga  aaagttacaa  gcttaagata     1980
cagaagcatt  tgttcaaagg  atagaaagca  tctaaaagtt  taggctcaag  atcaatcttt     2040
acagattgat  attttcagtt  tttaatcgac  tggactgcag  atgttttttc  ttttaacaaa     2100
ctggaatttt  caaacagatt  atctgtattt  aaatgtatag  accttgatat  ttttccaata     2160
ctatttttta  aaaaattgta  tgatttacat  atgaacctca  gttctgaaat  tcattacata     2220
tctgtctcat  tctgccttt   atactgtcta  aaaaagcaaa  gttttaaagt  gcaattttaa     2280
aactgtaaat  tacatctgaa  ggctatatat  cctttaatca  catttatat   tttttcttca     2340 caattctaac  ctttgaaaat  attataactg  gatatttctt  caaacagatg  tcctggatga     2400
tggtccataa  gaataatgaa  gaagtagtta  aaaatgtatg  acagttttt   ccggcaaaat     2460 ttgtagctta  tgtcttggct  aaatagtcaa  ggggtaatat  gggcctgttg  tttagtgtct     2520
ccttcctaaa  gagcactttt  gtattgtaat  ttatttttta  ttatgcttta  aacactatgt     2580
aaataaacct  ttagtaataa  agaattatca  gttataaaaa                             2620

<210> SEQ ID NO 27
<211> LENGTH: 3950
<212> TYPE: DNA
<213> ORGANISM: Homo sapiens

<400> SEQUENCE: 27
```

```
attaaggact cggggcagga ggggcagaag ttgcgcgcag gccggcgggc gggagcggac    60
accgaggccg gcgtgcaggc gtgcgggtgt gcgggagccg ggctcggggg gatcggaccg   120
agagcgagaa gcgcggcatg gagctccagg cagcccgcgc ctgcttcgcc ctgctgtggg   180
gctgtgcgct ggccgcggcc gcggcggcgc agggcaagga agtggtactg ctggactttg   240
ctgcagctgg aggggagctc ggctggctca cacacccgta tggcaaaggg tgggacctga   300
tgcagaacat catgaatgac atgccgatct acatgtactc cgtgtgcaac gtgatgtctg   360
gcgaccagga caactggctc cgcaccaact gggtgtaccg aggagaggct gagcgtatct   420
tcattgagct caagtttact gtacgtgact gcaacagctt ccctggtggc gccagctcct   480
gcaaggagac tttcaacctc tactatgccg agtcggacct ggactacggc accaacttcc   540
agaagcgcct gttcaccaag attgacacca ttgcgcccga tgagatcacc gtcagcagcg   600
acttcgaggc acgccacgtg aagctgaacg tggaggagcg ctccgtgggg ccgctcaccc   660
gcaaaggctt ctacctggcc ttccaggata tcggtgcctg tgtggcgctg ctctccgtcc   720
gtgtctacta caagaagtgc cccgagctgc tgcagggcct ggcccacttc cctgagacca   780
tcgccggctc tgatgcacct tccctggcca ctgtggccgg cacctgtgtg gaccatgccg   840
tggtgccacc ggggggtgaa gagccccgta tgcactgtgc agtggatggc gagtggctgg   900
tgcccattgg gcagtgcctg tgccaggcag gctacgagaa ggtggaggat gcctgccagg   960
cctgctcgcc tggatttttt aagtttgagg catctgagag ccccTgcttg gagtgccctg  1020
agcacacgct gccatcccct gagggtgcca cctcctgcga gtgtgaggaa ggcttcttcc  1080
gggcacctca ggacccagcg tcgatgcctt gcacacgacc cccctccgcc ccacactacc  1140
tcacagccgt gggcatgggt gccaaggtgg agctgcgctg gacgcccccct caggacagcg  1200
ggggccgcga ggacattgtc tacagcgtca cctgcgaaca gtgctggccc gagtctgggg  1260
aatgcgggcc gtgtgaggcc agtgtgcgct actcggagcc tcctcacgga ctgacccgca  1320
ccagtgtgac agtgagcgac ctggagcccc acatgaacta caccttcacc gtggaggccc  1380
gcaatggcgt ctcaggcctg gtaaccagcc gcagcttccg tactgccagt gtcagcatca  1440
accagacaga gccccccaag gtgaggctgg agggccgcag caccacctcg cttagcgtct  1500
cctggagcat cccccccgccg cagcagagcc gagtgtggaa gtacgaggtc acttaccgca  1560
agaagggaga ctccaacagc tacaatgtgc gccgcaccga gggtttctcc gtgaccctgg  1620
acgacctggc cccagacacc acctacctgg tccaggtgca ggcactgacg caggagggcc  1680
aggggccgg cagcaaggtg cacgaattcc agacgctgtc cccggaggga tctggcaact  1740
tggcggtgat tggcggcgtg gctgtcggtg tggtcctgct tctggtgctg gcaggagttg  1800
gcttctttat ccaccgcagg aggaagaacc agcgtgcccg ccagtccccg gaggacgttt  1860
acttctccaa gtcagaacaa ctgaagcccc tgaagacata cgtggacccc cacacatatg  1920
aggaccccaa ccaggctgtg ttgaagttca ctaccgagat ccatccatcc tgtgtcactc  1980
ggcagaaggt gatcggagca ggagagtttg ggaggtgta caagggcatg ctgaagacat  2040
cctcggggaa gaaggaggtg ccggtggcca tcaagacgct gaaagccggc tacacagaga  2100
agcagcgagt ggacttcctc ggcgaggccg gcatcatggg ccagttcagc caccacaaca  2160
tcatccgcct agagggcgtc atctccaaat acaagcccat gatgatcatc actgagtaca  2220
tggagaatgg ggccctggac aagttccttc gggagaagga tggcgagttc agcgtgctgc  2280
agctggtggg catgctgcgg ggcatcgcag ctggcatgaa gtacctggcc aacatgaact  2340
atgtgcaccg tgacctggct gcccgcaaca tcctcgtcaa cagcaacctg gtctgcaagg  2400
```

-continued

```
tgtctgactt tggcctgtcc cgcgtgctgg aggacgaccc cgaggccacc tacaccacca      2460
gtggcggcaa gatccccatc cgctggaccg ccccggaggc catttcctac cggaagttca      2520
cctctgccag cgacgtgtgg agctttggca ttgtcatgtg ggaggtgatg acctatggcg      2580
agcggcccta ctgggagttg tccaaccacg aggtgatgaa agccatcaat gatggcttcc      2640
ggctccccac acccatggac tgcccctccg ccatctacca gctcatgatg cagtgctggc      2700
agcaggagcg tgcccgccgc ccaagttcg ctgacatcgt cagcatcctg acaagctca       2760
ttcgtgcccc tgactccctc aagacccctgg ctgactttga ccccgcgtg tctatccggc     2820
tccccagcac gagcggctcg aggggggtgc ccttccgcac ggtgtccgag tggctggagt      2880
ccatcaagat gcagcagtat acggagcact tcatggcggc cggctacact gccatcgaga      2940
aggtggtgca gatgaccaac gacgacatca agaggattgg ggtgcggctg cccggccacc      3000
agaagcgcat cgcctacagc ctgctgggac tcaaggacca ggtgaacact gtggggatcc      3060
ccatctgagc ctcgacaggg cctggagccc catcggccaa gaatacttga agaaacagag      3120
tggcctccct gctgtgccat gctgggccac tggggacttt atttatttct agttctttcc      3180
tcccctgca acttccgctg aggggtctcg gatgacaccc tggcctgaac tgaggagatg       3240
accagggatg ctgggctggg ccctctttcc ctgcgagacg cacacagctg agcacttagc      3300
aggcaccgcc acgtcccagc atccctggag caggagcccc gccacagcct tcggacagac      3360
atataggata ttcccaagcc gaccttccct ccgccttctc ccacatgagg ccatctcagg      3420
agatggaggg cttggcccag cgccaagtaa acagggtacc tcaagcccca tttcctcaca      3480
ctaagagggc agactgtgaa cttgactggg tgagacccaa agcggtccct gtccctctag      3540
tgccttcttt agaccctcgg gccccatcct catccctgac tggccaaacc cttgctttcc      3600
tgggcctttg caagatgctt ggttgtgttg aggtttttaa atatatattt tgtactttgt      3660
ggagagaatg tgtgtgtgtg gcaggggggcc ccgccagggc tggggacaga gggtgtcaaa     3720
cattcgtgag ctggggactc agggaccggt gctgcaggag tgtcctgccc atgccccagt      3780
cggcccatc tctcatcctt ttggataagt ttctattctg tcagtgttaa agattttgtt      3840
ttgttggaca ttttttttcga atcttaattt attatttttt ttatatttat tgttagaaaa      3900
tgacttattt ctgctctgga ataaagttgc agatgattca aaccgaaaaa                 3950
```

<210> SEQ ID NO 28
<211> LENGTH: 5810
<212> TYPE: DNA
<213> ORGANISM: Homo sapiens

<400> SEQUENCE: 28

```
aacgggctca ttcagcggtc gcgagctgcc cgcgaggggg agcggccgga cggagagcgc       60
gacccgtccc gggggtgggg ccgggcgcag cggcgagagg aggcgaaggt ggctgcggta      120
gcagcagcgc ggcagcctcg gacccagccc ggagcgcagg gcggccgctg caggtccccg      180
ctcccctccc cgtgcgtccg cccatggccg ccgccgggca gctgtgcttg ctctacctgt      240
cggcggggct cctgtcccgg ctcggcgcag ccttcaactt ggacactcgg gaggacaacg      300
tgatccggaa atatgagac cccgggagcc tcttcggctt ctcgctggcc atgcactggc      360
aactgcagcc cgaggacaag cggctgttgc tcgtgggggc cccgcgggca gaagcgcttc      420
cactgcagag agccaacaga acgggagggc tgtacagctg cgacatcacc gcccgggggc      480
catgcacgcg gatcgagttt gataacgatg ctgaccccac gtcagaaagc aaggaagatc      540
```

```
agtggatggg ggtcaccgtc cagagccaag gtccagggggg caaggtcgtg acatgtgctc    600
accgatatga aaaaaggcag catgttaata cgaagcagga atcccgagac atctttgggc    660
ggtgttatgt cctgagtcag aatctcagga ttgaagacga tatggatggg ggagattgga    720
gcttttgtga tgggcgattg agaggccatg agaaatttgg ctcttgccag caaggtgtag    780
cagctacttt tactaaagac tttcattaca ttgtatttgg agccccgggt acttataact    840
ggaagggat tgttcgtgta gagcaaaaga ataacacttt ttttgacatg aacatctttg     900
aagatgggcc ttatgaagtt ggtggagaga ctgagcatga tgaaagtctc gttcctgttc    960
ctgctaacag ttacttaggt ttttctttgg actcagggaa aggtattgtt tctaaagatg   1020
agatcacttt tgtatctggt gctcccagag ccaatcacag tggagccgtg gttttgctga   1080
agagagacat gaagtctgca catctcctcc ctgagcacat attcgatgga aaggtctgg    1140
cctcttcatt tggctatgat gtggcggtgg tggacctcaa caaggatggg tggcaagata   1200
tagttattgg agccccacag tattttgata gagatggaga agttggaggt gcagtgtatg   1260
tctacatgaa ccagcaaggc agatggaata atgtgaagcc aattcgtctt aatggaacca   1320
aagattctat gtttggcatt gcagtaaaaa atattggaga tattaatcaa gatggctacc   1380
cagatattgc agttggagct ccgtatgatg acttgggaaa ggttttatc tatcatggat    1440
ctgcaaatgg aataaatacc aaaccaacac aggttctcaa gggtatatca ccttattttg   1500
gatattcaat tgctggaaac atggaccttg atcgaaattc ctaccctgat gttgctgttg   1560
gttccctctc agattcagta actatttca gatcccggcc tgtgattaat attcagaaaa    1620
ccatcacagt aactcctaac agaattgacc tccgccagaa acagcgtgt ggggcgccta    1680
gtgggatatg cctccaggtt aaatcctgtt ttgaatatac tgctaacccc gctggttata   1740
atccttcaat atcaattgtg ggcacacttg aagctgaaaa agaaagaaga aaatctgggc   1800
tatcctcaag agttcagttt cgaaaccaag gttctgagcc caaatatact caagaactaa   1860
ctctgaagag gcagaaacag aaagtgtgca tggaggaaac cctgtggcta caggataata   1920
tcagagataa actgcgtccc attcccataa ctgcctcagt ggagatccaa gagccaagct   1980
ctcgtaggcg agtgaattca cttccagaag ttcttccaat tctgaattca gatgaaccca   2040
agacagctca tattgatgtt cacttcttaa agagggatg tggagacgac aatgtatgta   2100
acagcaacct taaactagaa tataaatttt gcacccgaga aggaaatcaa gacaaatttt   2160
cttatttacc aattcaaaaa ggtgtaccag aactagttct aaaagatcag aaggatattg   2220
ctttagaaat aacagtgaca aacagcccctt ccaacccaag gaatcccaca aaagatggcg   2280
atgacgccca tgaggctaaa ctgattgcaa cgtttccaga cactttaacc tattctgcat   2340
atagagaact gagggctttc cctgagaaac agttgagttg tgttgccaac cagaatggct   2400
cgcaagctga ctgtgagctc ggaaatcctt ttaaagaaa ttcaaatgtc acttttttatt    2460
tggttttaag tacaactgaa gtcacctttg acaccccaga tctggatatt aatctgaagt   2520
tagaaacaac aagcaatcaa gataatttgg ctccaattac agctaaagca aaagtggtta   2580
ttgaactgct tttatcggtc tcgggagttg ctaaaccttc ccagtgtat tttgaggta    2640
cagttgttgg cgagcaagct atgaaatctg aagatgaagt gggaagttta atagagtatg   2700
aattcagggt aataaactta ggtaaacctc ttacaaacct cggcacagca accttgaaca   2760
ttcagtggcc aaaagaaatt agcaatggga aatggttgct ttatttggtg aaagtagaat   2820
ccaaaggatt ggaaaggta acttgtgagc cacaaaagga gataaactcc ctgaacctaa   2880
cggagtctca caactcaaga aagaaacggg aaattactga aaaacagata gatgataaca   2940
```

```
gaaaattttc tttatttgct gaaagaaaat accagactct taactgtagc gtgaacgtga    3000
actgtgtgaa catcagatgc ccgctgcggg ggctggacag caaggcgtct cttattttgc    3060
gctcgaggtt atggaacagc acatttctag aggaatattc caaactgaac tacttggaca    3120
ttctcatgcg agccttcatt gatgtgactg ctgctgccga aaatatcagg ctgccaaatg    3180
caggcactca ggttcgagtg actgtgtttc cctcaaagac tgtagctcag tattcgggag    3240
taccttggtg gatcatccta gtggctattc tcgctgggat cttgatgctt gctttattag    3300
tgtttatact atggaagtgt ggtttcttca agagaaataa gaaagatcat tatgatgcca    3360
catatcacaa ggctgagatc catgctcagc catctgataa agagaggctt acttctgatg    3420
catagtattg atctacttct gtaattgtgt ggattcttta aacgctctag gtacgatgac    3480
agtgttcccc gataccatgc tgtaaggatc cggaaagaag agcgagagat caaagatgaa    3540
aagtatattg ataaccttga aaaaaaacag tggatcacaa agtggaacga aaatgaaagc    3600
tactcatagc gggggcctaa aaaaaaaaag cttcacagta cccaaactgc ttttccaac    3660 tcagaaattc aatttggatt taaaagcctg ctcaatccct gaggactgat ttcagagtga    3720
ctacacacag tacgaaccta cagttttaac tgtggatatt gttacgtagc ctaaggctcc    3780
tgttttgcac agccaaattt aaaactgttg gaatggattt ttctttaact gccgtaattt    3840
aactttctgg gttgccttta tttttggcgt ggctgactta catcatgtgt tggggaaggg    3900
cctgcccagt tgcactcagg tgacatcctc cagatagtgt agctgaggag gcacctacac    3960
tcacctgcac taacagagtg gccgtcctaa cctcgggcct gctgcgcaga cgtccatcac    4020
gttagctgtc ccacatcaca agactatgcc attggggtag ttgtgtttca acggaaagtg    4080
ctgtcttaaa ctaaatgtgc aatagaaggt gatgttgcca tcctaccgtc ttttcctgtt    4140
tcctagctgt gtgaatacct gctcacgtca aatgcataca agtttcattc tcccttttcac   4200 taaaacacac aggtgcaaca gacttgaatg ctagttatac ttatttgtat atggtatttta   4260 ttttttcttt tctttacaaa ccatttgtt attgactaac aggccaaaga gtctccagtt    4320 taccctcag gttggtttaa tcaatcagaa ttagagcatg ggaggtcatc actttgacct    4380
aaattattta ctgcaaaaag aaaatcttta taaatgtacc agagagagtt gttttaataa    4440
cttatctata aactataacc tctccttcat gacagcctcc accccacaac ccaaaaggtt    4500
taagaaatag aattataact gtaaagatgt ttatttcagg cattggatat ttttttacttt   4560 agaagcctgc ataatgtttc tggatttcat actgtaacat tcaggaattc ttggagaaaa    4620
tgggtttatt cactgaactc tagtgcggtt tactcactgc tgcaaatact gtatattcag    4680
gacttgaaag aaatggtgaa tgcctatggt ggatccaaac tgatccagta taagactact    4740
gaatctgcta ccaaaacagt taatcagtga gtcgatgttc tatttttgt tttgtttcct     4800 ccctatctg tattcccaaa aattactttg gggctaattt aacaagaact ttaaattgtg     4860
ttttaattgt aaaaatggca gggggtggaa ttattactct atacattcaa cagagactga    4920
atagatatga aagctgattt ttttttaatta ccatgcttca caatgttaag ttatatgggg   4980
agcaacagca aacaggtgct aatttgtttt ggatatagta taagcagtgt ctgtgttttg    5040
aaagaataga acacagtttg tagtgccact gttgttttgg gggggctttt ttcttttcgg    5100
aaatcttaaa ccttaagata ctaaggacgt tgttttggtt gtactttgga attcttagtc    5160 acaaatatata ttttgtttac aaaaattct gtaaaacagg ttataacagt gtttaaagtc    5220
tcagtttctt gcttggggaa cttgtgtccc taatgtgttt agattgctag attgctaagg    5280
```

```
agctgatact tgacagtgt ttttagacct gtgttactaa aaaaaagatg aatgtcctga    5340
aaagggtgtt gggagggtgg ttcaacaaag aaacaaagat gttatggtgt ttagatttat    5400
ggttgttaaa aatgtcatct caagtcaagt cactggtctg tttgcatttg atacatttt     5460 gtactaacta gcattgtaaa attatttcat gattagaaat tacctgtgga tatttgtata    5520
aaagtgtgaa ataaattttt tataaaagtg ttcattgttt cgtaacacag cattgtatat    5580
gtgaagcaaa ctctaaaatt ataaatgaca acctgaatta tctatttcat caaaccaaag    5640
ttcagtgttt ttattttttgg tgtctcatgt aatctcagat cagccaaaga tactagtgcc    5700
aaagcaatgg gattcggggt ttttttctgt tttcgctcta tgtaggtgat cctcaagtct    5760 ttcatttttcc ttctttatga ttaaaagaaa cctacaggta tttaacaacc              5810
```

<210> SEQ ID NO 29
<211> LENGTH: 3640
<212> TYPE: DNA
<213> ORGANISM: Homo sapiens

<400> SEQUENCE: 29

```
gccaccacgt gtgtccctgc gcccggtggc caccgactca gtccctcgcc gaccagtctg      60
ggcagcggag gagggtggtt ggcagtggct ggaagcttcg ctatgggaag ttgttccttt    120
gctctctcgc gcccagtcct cctccctggt tctcctcagc cgctgtcgga ggagagcacc    180
cggagacgcg ggctgcagtc gcggcggctt ctccccgcct gggcggccgc gccgctgggc    240
aggtgctgag cgcccctaga gcctcccttg ccgcctccct cctctgcccg gccgcagcag    300
tgcacatggg gtgttggagg tagatgggct cccggcccgg gaggcggcgg tggatgcggc    360
gctgggcaga agcagccgcc gattccagct gccccgcgcg ccccgggcgc ccctgcgagt    420
ccccggttca gccatgggga cctctccgag cagcagcacc gccctcgcct cctgcagccg    480
catcgcccgc cgagccacag ccacgatgat cgcgggctcc cttctcctgc ttggattcct    540
tagcaccacc acagctcagc cagaacagaa ggcctcgaat ctcattggca cataccgcca    600
tgttgaccgt gccaccggcc aggtgctaac ctgtgacaag tgtccagcag gaacctatgt    660
ctctgagcat tgtaccaaca caagcctgcg cgtctgcagc agttgccctg tggggacctt    720
taccaggcat gagaatggca tagagaaatg ccatgactgt agtcagccat gcccatggcc    780
aatgattgag aaattacctt gtgctgcctt gactgaccga gaatgcactt gcccacctgg    840
catgttccag tctaacgcta cctgtgcccc ccataccggtg tgtcctgtgg gttggggtgt    900
gcggaagaaa gggacagaga ctgaggatgt gcggtgtaag cagtgtgctc ggggtacctt    960
ctcagatgtg ccttctagtg tgatgaaatg caaagcatac acagactgtc tgagtcagaa   1020
cctggtggtg atcaagccgg ggaccaagga gacagacaac gtctgtggca cactcccgtc   1080
cttctccagc tccacctcac cttcccctgg cacagccatc tttccacgcc ctgagcacat   1140
ggaaacccat gaagtcccctt cctccactta tgttcccaaa ggcatgaact caacagaatc   1200
caactcttct gcctctgtta gaccaaaggt actgagtagc atccaggaag ggacagtccc   1260
tgacaacaca agctcagcaa gggggaagga agacgtgaac aagaccctcc caaaccttca   1320
ggtagtcaac caccagcaag gcccccacca cagacacatc ctgaagctgc tgccgtccat   1380
ggaggccact gggggcgaga agtccagcac gcccatcaag gccccaagga ggggacatcc   1440
tagacagaac ctacacaagc attttgacat caatgagcat ttgccctgga tgattgtgct   1500
tttcctgctg ctggtgcttg tgtgattgt ggtgtgcagt atccggaaaa gctcgaggac   1560
tctgaaaaag gggccccggc aggatcccag tgccattgtg gaaaaggcag ggctgaagaa   1620
```

```
atccatgact ccaacccaga accgggagaa atggatctac tactgcaatg gccatggtat    1680
cgatatcctg aagcttgtag cagcccaagt gggaagccag tggaaagata tctatcagtt    1740
tctttgcaat gccagtgaga gggaggttgc tgctttctcc aatgggtaca cagccgacca    1800
cgagcgggcc tacgcagctc tgcagcactg gaccatccgg ggccccgagg ccagcctcgc    1860
ccagctaatt agcgccctgc gccagcaccg gagaaacgat gttgtggaga agattcgtgg    1920
gctgatggaa gacaccaccc agctggaaac tgacaaacta gctctcccga tgagccccag    1980
cccgcttagc ccgagcccca tccccagccc aacgcgaaa cttgagaatt ccgctctcct    2040
gacggtggag ccttccccac aggacaagaa caagggcttc ttcgtggatg agtcggagcc    2100
ccttctccgc tgtgactcta catccagcgg ctcctccgcg ctgagcagga acggttcctt    2160
tattaccaaa gaaaagaagg acacagtgtt gcggcaggta cgcctggacc cctgtgactt    2220
gcagcctatc tttgatgaca tgctccactt tctaaatcct gaggagctgc gggtgattga    2280
agagattccc caggctgagg acaaactaga ccggctattc gaaattattg gagtcaagag    2340
ccaggaagcc agccagaccc tcctggactc tgtttatagc catcttcctg acctgctgta    2400 gaacatagggg atactgcatt ctggaaatta ctcaatttag tggcagggtg gttttttaat    2460
tttcttctgt ttctgatttt tgttgtttgg ggtgtgtgtg tgtgtttgtg tgtgtgtgtg    2520
tgtgtgtgtg tgtgtgtgtg tttaacagag aatatggcca gtgcttgagt tctttctcct    2580
tctctctctc tcttttttttt ttaaataact cttctgggaa gttggtttat aagcctttgc    2640
caggtgtaac tgttgtgaaa tacccaccac taaagttttt taagttccat attttctcca    2700
ttttgccttc ttatgtattt tcaagattat tctgtgcact ttaaatttac ttaacttacc    2760
ataaatgcag tgtgacttt  cccacacact ggattgtgag gctcttaact tcttaaaagt    2820
ataatggcat cttgtgaatc ctataagcag tctttatgtc tcttaacatt cacacctact    2880
ttttaaaaac aaatattatt actattttta ttattgtttg tcctttataa attttcttaa    2940
agattaagaa aatttaagac cccattgagt tactgtaatg caattcaact ttgagttatc    3000
ttttaaatat gtcttgtata gttcatattc atggctgaaa cttgaccaca ctattgctga    3060
ttgtatggtt ttcacctgga caccgtgtag aatgcttgat tacttgtact cttcttatgc    3120
taatatgctc tgggctggag aaatgaaatc ctcaagccat caggatttgc tatttaagtg    3180
gcttgacaac tgggccacca agaacttga  acttcacctt ttaggatttg agctgttctg    3240
gaacacattg ctgcactttg gaaagtcaaa atcaagtgcc agtggcgccc tttccataga    3300
gaatttgccc agctttgctt taaaagatgt cttgtttttt atatacacat aatcaatagg    3360
tccaatctgc tctcaaggcc ttggtcctgg tgggattcct tcaccaatta ctttaattaa    3420
aaatggctgc aactgtaaga acccttgtct gatatatttg caactatgct cccatttaca    3480
aatgtacctt ctaatgctca gttgccaggt tccaatgcaa aggtggcgtg gactcccttt    3540
gtgtgggtgg ggtttgtggg tagtggtgaa ggaccgatat cagaaaaatg ccttcaagtg    3600 tactaatttta ttaataaaca ttaggtgttt gttaaaaaaa                         3640

<210> SEQ ID NO 30
<211> LENGTH: 1130
<212> TYPE: DNA
<213> ORGANISM: Homo sapiens

<400> SEQUENCE: 30
agtgccccag gagctatgac aagcaaagga acatacttgc ctggagatag cctttgcgat    60
```

```
atttaaatgt ccgtggatac agaaatctct gcaggcaagt tgctccagag catattgcag      120
gacaagcctg taacgaatag ttaaattcac ggcatctgga ttcctaatcc tttccgaaa       180 tggcaggtgt gagtgcctgt ataaaatatt ctatgtttac cttcaacttc ttgttctggc      240
tatgtggtat cttgatccta gcattagcaa tatgggtacg agtaagcaat gactctcaag      300
caatttttgg ttctgaagat gtaggctcta gctcctacgt tgctgtggac atattgattg      360
ctgtaggtgc catcatcatg attctgggct tcctgggatg ctgcgtgct ataaaagaaa       420 gtcgctgcat gcttctgttg tttttcatag gcttgcttct gatcctgctc ctgcaggtgg      480
cgacaggtat cctaggagct gttttcaaat ctaagtctga tcgcattgtg aatgaaactc      540
tctatgaaaa cacaaagctt ttgagcgcca caggggaaag tgaaaaacaa ttccaggaag      600
ccataattgt gtttcaagaa gagtttaaat gctgcggttt ggtcaatgga gctgctgatt      660
ggggaaataa ttttcaacac tatcctgaat tatgtgcctg tctagataag cagagaccat      720
gccaaagcta taatggaaaa caagtttaca agagacctg tatttctttc ataaaagact       780
tcttggcaaa aaatttgatt atagttattg gaatatcatt tggactggca gttattgaga      840
tactgggttt ggtgtttct atggtcctgt attgccagat cgggaacaaa tgaatctgtg       900
gatgcatcaa cctatcgtca gtcaaacccc tttaaaatgt tgctttggct ttgtaaattt      960
aaatatgtaa gtgctatata agtcaggagc agctgtcttt ttaaaatgtc tcggctagct      1020
agaccacaga tatcttctag acatattgaa cacatttaag atttgaggga tataagggaa      1080
aatgatatga atgtgtattt ttactcaaaa taaaagtaac tgtttacgtt                 1130
```

<210> SEQ ID NO 31
<211> LENGTH: 1145
<212> TYPE: DNA
<213> ORGANISM: Homo sapiens

<400> SEQUENCE: 31

```
attctctccc cagcttgctg agcccttttgc tcccctggcg actgcctgga cagtcagcaa     60
ggaattgtct cccagtgcat tttgccctcc tggctgccaa ctctggctgc taaagcggct     120
gccacctgct gcagtctaca cagcttcggg aagaggaaag gaacctcaga ccttccagat    180
cgcttcctct cgcaacaaac tatttgtcgc aggaataaag atggctgctg aaccagtaga    240
agacaattgc atcaactttg tggcaatgaa atttattgac aatacgcttt actttatagc    300
tgaagatgat gaaaacctgg aatcagatta ctttggcaag cttgaatcta aattatcagt    360
cataagaaat ttgaatgacc aagttctctt cattgaccaa ggaaatcggc tctatttga    420 agatatgact gattctgact gtagagataa tgcaccccgg accatattta ttataagtat    480
gtataaagat agccagccta gaggtatggc tgtaactatc tctgtgaagt gtgagaaaat    540
ttcaactctc tcctgtgaga acaaaattat ttccttttaag gaatgaatc ctcctgataa     600 catcaaggat acaaaagtg acatcatatt ctttcagaga agtgtcccag acatgataa     660 taagatgcaa tttgaatctt catcatacga aggatacttt ctagcttgtg aaaaagagag    720
agaccttttt aaactcattt tgaaaaaga ggatgaattg ggggatagat ctataatgtt     780
cactgttcaa aacgaagact agctattaaa atttcatgcc gggcgcagtg gctcacgcct    840
gtaatcccag ccctttggga ggctgaggcg ggcagatcac cagaggtcag gtgttcaaga    900
ccagcctgac caacatggtg aaacctcatc tctactaaaa atacaaaaaa ttagctgagt    960
gtagtgacgc atgccctcaa tcccagctac tcaagaggct gaggcaggag aatcacttgc    1020
actccggagg tagaggttgt ggtgagccga gattgcacca ttgcgctcta gcctgggcaa    1080
```

```
caacagcaaa actccatctc aaaaaataaa ataaataaat aaacaaataa aaaattcata    1140
atgtg                                                                1145

<210> SEQ ID NO 32
<211> LENGTH: 1790
<212> TYPE: DNA
<213> ORGANISM: Homo sapiens

<400> SEQUENCE: 32
gagggagggg ccgccgggga agaggaggag gaaggaaaga aagaaagcga gggagggaaa      60
gaggaggaag gaagatgcga gaaggcagag gaggagggag ggagggaagg agcgcggagc     120
ccggcccgga agctaggagc cattccgtag tgccatcccg agcaacgcac tgctgcagct     180
tccctgagcc tttccagcaa gtttgttcaa gattggctgt caagaatcat ggactgttat     240
tatatgcctt gttttctgtc aagacaccat gattcctggt aaccgaatgc tgatggtcgt     300
tttattatgc caagtcctgc taggaggcgc gagccatgct agtttgatac ctgagacggg     360
gaagaaaaaa gtcgccgaga ttcagggcca cgcgggagga cgccgctcag ggcagagcca     420
tgagctcctg cgggacttcg aggcgacact tctgcagatg tttgggctgc cgcgccgccc     480
gcagcctagc aagagtgccg tcattccgga ctacatgcgg gatctttacc ggcttcagtc     540
tggggaggag gaggaagagc agatcccacag cactggtctt gagtatcctg agcgcccggc     600
cagccgggcc aacaccgtga ggagcttcca ccacgaagaa catctggaga acatcccagg     660
gaccagtgaa aactctgctt ttcgtttcct ctttaacctc agcagcatcc ctgagaacga     720
ggcgatctcc tctgcagagc ttcggctctt ccgggagcag gtggaccagg gccctgattg     780 ggaaagggc ttccaccgta taaacattta tgaggttatg aagccccag cagaagtggt      840 gcctgggcac ctcatcacac gactactgga cacgagactg gtccaccaca atgtgacacg     900
gtgggaaact tttgatgtga gccctgcggt ccttcgctgg acccgggaga agcagccaaa     960
ctatgggcta gccattgagg tgactcacct ccatcagact cggacccacc agggccagca    1020
tgtcaggatt agccgatcgt tacctcaagg gagtgggaat tgggcccagc tccggccct     1080 cctggtcacc tttggccatg atggccgggg ccatgccttg acccgacgcc ggagggccaa    1140
gcgtagccct aagcatcact cacagcgggc caggaagaag aataagaact gccggcgcca    1200
ctcgctctat gtggacttca gcgatgtggg ctggaatgac tggattgtgg ccccaccagg    1260
ctaccaggcc ttctactgcc atgggggactg ccccttttcca ctggctgacc acctcaactc    1320
aaccaaccat gccattgtgc agaccctggt caattctgtc aattccagta tccccaaagc    1380
ctgttgtgtg cccactgaac tgagtgccat ctccatgctg tacctggatg agtatgataa    1440
ggtggtactg aaaaattatc aggagatggt agtagaggga tgtgggtgcc gctgagatca    1500
ggcagtcctt gaggatagac agatatacac accacacaca cacaccacat acaccacaca    1560
cacacgttcc catccactca cccacacact acacagactg cttccttata gctggacttt    1620
tatttaaaaa aaaaaaaaa aaaatggaaa aaatccctaa acattcacct tgaccttatt    1680
tatgacttta cgtgcaaatg ttttgaccat attgatcata tattttgaca aaatatattt    1740
ataactacgt attaaaagaa aaaaataaaa tgagtcatta ttttaaaggt             1790

<210> SEQ ID NO 33
<211> LENGTH: 1880
<212> TYPE: DNA
<213> ORGANISM: Homo sapiens
```

<400> SEQUENCE: 33

```
ccagatcata ccctgctggg caaaggagga agagccagag gatccagacg ccttggagga      60
cttggaacac ctgtaacagg caaggagtt ctgctcaggc acgtggccac agaaaactac     120
ttaggaagcc tgtggtgaga acaacaacag tgcctgaaa tcccacggct ctggggaagt     180
gagccccgag gatgaggctg ctcgcctggc tgattttcct ggctaactgg ggaggtgcca     240
gggctgaacc agggaagttc tggcacatcg ctgacctgca ccttgaccct gactacaagg     300
tatccaaaga cccccttccag gtgtgcccat cagctggatc ccagccagtg cccgacgcag     360
gccccctgggg tgactacctc tgtgattctc cctgggccct catcaactcc tccatctatg     420
ccatgaagga gattgagcca gagccagact tcattctctg gactggtgat gacacgcctc     480
atgtgcccga tgagaaactg ggagaggcag ctgtactgga aattgtggaa cgcctgacca     540
agctcatcag agaggtcttt ccagatacta aagtctatgc tgctttggga aatcatgatt     600
ttcaccccaa aaaccagttc ccagctggaa gtaacaacat ctacaatcag atagcagaac     660
tatggaaacc ctggcttagt aatgagtcca tcgctctctt caaaaaaggt gccttctact     720
gtgagaagct gccgggtccc agcggggctg ggcgaattgt ggtcctcaac accaatctgt     780
actataccag caatgcgctg acagcagaca tggcggaccc tggccagcag ttccagtggc     840
tggaagatgt gctgaccgat gcatccaaag ctggggacat ggtgtacatt gtcggccacg     900
tgcccccggg gttctttgag aagacgcaaa acaaggcatg gttccgggag ggcttcaatg     960
aaaaatacct gaaggtggtc cggaagcatc atcgcgtcat agcagggcag ttcttcgggc    1020
accaccacac cgacagcttt cggatgctct atgatgatgc aggtgtcccc ataagcgcca    1080
tgttcatcac acctggagtc accccatgga aaaccacatt acctggagtg gtcaatgggg    1140
ccaacaatcc agccatccgg gtgttcgaat atgaccgagc cacactgagc ctgaaggaca    1200
tggtgaccta cttcatgaac ctgagccagg cgaatgctca ggggacgccg cgctgggagc    1260
tcgagtacca gctgaccgag gcctatgggg tgccggacgc cagcgcccac tccatgcaca    1320
cagtgctgga ccgcatcgct ggcgaccaga gcacactgca gcgctactac gtctataact    1380
cagtcagcta ctctgctggg gtctgcgacg aggcctgcag catgcagcac gtgtgtgcca    1440
tgcgccaggt ggacattgac gcttacacca cctgtctgta tgcctctggc accacgcccg    1500
tgccccagct cccgctgctg ctgatggccc tgctgggcct gtgcacgctc gtgctgtgac    1560
ctgccaggct caccttcttc ctggtaacgg gtaacggggg cagcgcccag gatcacccag    1620
agctgggcct tccaccattt cctccgcgcc tgaggagtga actgaaatag gacaaccgaa    1680
tcaggaagcg aagccccagg agctgcagcc atccgtgatc gcgccactgc actccagcct    1740
gggcgacaaa gccagactct ctccaaaaac aaaccagaaa cagaaagaa atgacgaccc    1800
aagacccccc tacaagcata cttctttgc gtattatgtt ttactcacaa aacaaagctc    1860
atcatgcgtt tgaaaaaaaa                                                 1880
```

<210> SEQ ID NO 34
<211> LENGTH: 3200
<212> TYPE: DNA
<213> ORGANISM: Homo sapiens

<400> SEQUENCE: 34

```
cgcgagctaa gcaggaggcg gaggcggagg cggagggcga ggggcgggga gcgccgcctg      60
gagcgcggca ggtcatattg aacattccag ataccatca ttactcgatg ctgttgataa     120
cagcaagatg gctttgaact cagggtcacc accagctatt ggaccttact atgaaaacca     180
```

```
tggataccaa ccggaaaacc cctatcccgc acagcccact gtggtcccca ctgtctacga     240
ggtgcatccg gctcagtact acccgtcccc cgtgccccag tacgcccga gggtcctgac      300 gcaggcttcc aacccgtcg tctgcacgca gcccaaatcc ccatccggga cagtgtgcac     360
ctcaaagact aagaaagcac tgtgcatcac cttgaccctg ggaccttcc tcgtgggagc     420 tgcgctggcc gctggcctac tctggaagtt catgggcagc aagtgctcca actctgggat    480
agagtgcgac tcctcaggta cctgcatcaa cccctctaac tggtgtgatg cgtgtcaca    540 ctgcccggc ggggaggacg agaatcggtg tgttcgcctc tacggaccaa acttcatcct    600
tcagatgtac tcatctcaga ggaagtcctg gcaccctgtg tgccaagacg actggaacga    660
gaactacggg cgggcggcct gcagggacat gggctataag aataatttt actctagcca    720 aggaatagtg gatgacagcg gatccaccag ctttatgaaa ctgaacacaa gtgccggcaa    780
tgtcgatatc tataaaaaac tgtaccacag tgatgcctgt tcttcaaaag cagtggtttc    840
tttacgctgt atagcctgcg gggtcaactt gaactcaagc cgccagagca ggatcgtggg    900
cggtgagagc gcgctcccgg gggcctggcc ctggcaggtc agcctgcacg tccagaacgt    960
ccacgtgtgc ggaggctcca tcatcacccc cgagtggatc gtgacagccg cccactgcgt   1020
ggaaaaacct cttaacaatc catggcattg acggcatt gcggggatt tgagacaatc     1080 tttcatgttc tatggagccg gataccaagt agaaaaagtg atttctcatc caaattatga   1140
ctccaagacc aagaacaatg acattgcgct gatgaagctg cagaagcctc tgactttcaa   1200
cgacctagtg aaaccagtgt gtctgcccaa cccaggcatg atgctgcagc agaacagct   1260 ctgctggatt tccgggtggg gggccaccga ggagaaaggg aagacctcag aagtgctgaa   1320
cgctgccaag gtgcttctca ttgagacaca gagatgcaac agcagatatg tctatgacaa   1380
cctgatcaca ccagccatga tctgtgccgg cttcctgcag gggaacgtcg attcttgcca   1440
gggtgacagt ggagggcctc tggtcacttc gaagaacaat atctggtggc tgataggga    1500 tacaagctgg ggttctggct gtgccaaagc ttacagacca ggagtgtacg gaatgtgat   1560 ggtattcacg gactggattt atcgacaaat gagggcagac ggctaatcca catggtcttc   1620
gtccttgacg tcgttttaca agaaaacaat ggggctggtt ttgcttcccc gtgcatgatt   1680
tactcttaga gatgattcag aggtcacttc attttatta aacagtgaac ttgtctggct    1740
ttggcactct ctgccattct gtgcaggctg cagtggctcc cctgcccagc tgctctccc    1800 taaccccttg tccgcaaggg gtgatggccg gctggttgtg ggcactggcg gtcaagtgtg   1860
gaggagaggg gtggaggctg ccccattgag atcttcctgc tgagtccttt ccaggggcca   1920
attttggatg agcatggagc tgtcacctct cagctgctgg atgacttgag atgaaaaagg   1980
agagacatgg aaagggagac agccaggtgg cacctgcagc ggctgccctc tggggccact   2040
tggtagtgtc cccagcctac ctctccacaa ggggatttg ctgatgggtt cttagagcct    2100
tagcagccct ggatggtggc cagaaataaa gggaccagcc cttcatgggt ggtgacgtgg   2160
tagtcacttg taaggggaac agaaacattt ttgttcttat ggggtgagaa atagacagt   2220 gcccttggtg cgagggaagc aattgaaaag gaacttgccc tgagcactcc tggtgcaggt   2280
ctccacctgc acattgggtg gggtcctgg gaggagact cagccttcct cctcatcctc     2340
cctgaccctg ctcctagcac cctggagagt gcacatgccc cttggtcctg caggggcgcc   2400
aagtctggca ccatgttggc ctcttcaggc ctgctagtca ctggaaattg aggtccatgg   2460
gggaaatcaa ggatgctcag tttaaggtac actgtttcca tgttatgttt ctacacattg   2520
```

-continued

| | |
|---|---:|
| ctacctcagt gctcctggaa acttagcttt tgatgtctcc aagtagtcca ccttcattta | 2580 |
| actctttgaa actgtatcac ctttgccaag taagagtggg ggcctatttc agctgctttg | 2640 |
| acaaaatgac tggctcctga cttaacgttc tataaatgaa tgtgctgaag caaagtgccc | 2700 |
| atggtggcgg cgaagaagag aaagatgtgt tttgttttgg actctctgtg gtcccttcca | 2760 |
| atgctgtggg tttccaacca ggggaagggt cccttttgca ttgccaagtg ccataaccat | 2820 |
| gagcactact ctaccatggt tctgcctcct ggccaagcag gctggtttgc aagaatgaaa | 2880 |
| tgaatgattc tacagctagg acttaacctt gaaatggaaa gtcttgcaat cccatttgca | 2940 |
| ggatccgtct gtgcacatgc ctctgtagag agcagcattc ccagggacct tggaaacagt | 3000 |
| tggcactgta aggtgcttgc tccccaagac acatcctaaa aggtgttgta atggtgaaaa | 3060 |
| cgtcttcctt ctttattgcc ccttcttatt tatgtgaaca actgtttgtc ttttttgta | 3120 |
| tcttttttaa actgtaaagt tcaattgtga aaatgaatat catgcaaata aattatgcga | 3180 |
| ttttttttc aaagcaaaaa | 3200 |

<210> SEQ ID NO 35
<211> LENGTH: 5430
<212> TYPE: DNA
<213> ORGANISM: Homo sapiens

<400> SEQUENCE: 35

| | |
|---|---:|
| gtagggagcc agcccctggg cgcggcctgc agggtaccgg caaccgcccg ggtaagcggg | 60 |
| ggcaggacaa ggccggagcc tgtgtccgcc cggcagccgc ccgcagctgc agagagtccc | 120 |
| gctgcgtctc cgccgcgtgc gccctcctcg accagcagac ccgcgctgcg ctccgccgct | 180 |
| gacatgtgtg ccgctcagat gccgcccctg gcgcacatct tccgagggac gttcgtccac | 240 |
| tccacctgga cctgccccat ggaggtgctg cgggatcacc tcctcggcgt gagcgacagc | 300 |
| ggcaaaatag tgttttagaa agaagcatct caacaggaaa aactggccaa agaatggtgc | 360 |
| ttcaagccgt gtgaaataag agaactgagc caccatgagt tcttcatgcc tgggctggtt | 420 |
| gatacacaca tccatgcctc tcagtattcc tttgctggaa gtagcataga cctgccactc | 480 |
| ttggagtggc tgaccaagta cacatttcct gcagaacaca gattccagaa catcgacttt | 540 |
| gcagaagaag tatataccag agttgtcagg agaacactaa agaatggaac aaccacagct | 600 |
| tgttactttg caacaattca cactgactca tctctgctcc ttgccgacat tacagataaa | 660 |
| tttggacagc gggcatttgt gggcaaagtt tgcatggatt tgaatgacac ttttccagaa | 720 |
| tacaaggaga ccactgagga atcgatcaag gaaactgaga gatttgtgtc agaaatgctc | 780 |
| caaaagaact attctagagt gaagcccata gtgacaccac gttttcccct ctcctgctct | 840 |
| gagactttga tgggtgaact gggcaacatt gctaaaaccc gtgatttgca cattcagagc | 900 |
| catataagtg aaaatcgtga tgaagttgaa gctgtgaaaa acttataccc cagttataaa | 960 |
| aactacacat ctgtgtatga taaaaacaat cttttgacaa ataagacagt gatggcacac | 1020 |
| ggctgctacc tctctgcaga agaactgaac gtattccatg aacgaggagc atccatcgca | 1080 |
| cactgtccca attctaattt atcgctcagc agtggatttc taaatgtgct agaagtcctg | 1140 |
| aaacatgaag tcaagatagg gctgggtaca gacgtggctg gtggctattc atattccatg | 1200 |
| cttgatgcaa tcagaagagc agtgatggtt tccaatatcc ttttaattaa taaggtaaat | 1260 |
| gagaaaagcc tcaccctcaa agaagtcttc agactagcta ctcttggagg aagccaagcc | 1320 |
| ctggggctgg atggtgagat tggaaacttt gaagtgggca aggaatttga tgccatcctg | 1380 |
| atcaacccca agcatccga ctctcccatt gacctgtttt atggggactt ttttggtgat | 1440 |

```
atttctgagg ctgttatcca gaagttcctc tatctaggag atgatcgaaa tattgaagag    1500
gtttatgtgg gcggaaagca ggtggttccg ttttccagct cagtgtaaga ccctcgggcg    1560
tctacaaagt tctcctggga ttagcgtggt tctgcatctc ccttgtgccc aggtggagtt    1620
agaaagtcaa aaatagtac cttgttcttg ggatgactat ccctttctgt gtctagttac     1680
agtattcact tgacaaatag ttcgaaggaa gttgcactaa ttctcaactc tggttgagag    1740
ggttcataaa tttcatgaaa atatctccct ttggagctgc tcagacttac tttaagctca    1800
aacagaaggg aatgctatta ctggtggtgt tcctacggta agacttaagc aaagccttt     1860 tcatatttga aaatgtggaa agaaaagatg ttcctaaaag gttagatatt ttgagctaat    1920
aattgcaaaa attagaagac tgaaaatgga cccatgagag tatattttta tgagggagca    1980
aaagttagac tgagaacaaa cgttagaaaa tcacttcaga ttgtgtttga aaattatata    2040
ctgagcatac taatttaaaa agagaacttg ttgaaattta aaacgtgttt ctaggttgac    2100
cttgtgtttt agaaatttgc acttaatgga atttgcattt cagagatgtg ttagtgttgt    2160
gctttgcctt ctttggcgat gaatgtcaga aattgaatgc cacatgcttt cataatatag    2220
ttttgtgctt caaagtgttt gacagaagtt gggtattaaa gatttaaagt ctcttaggaa    2280
tattattcat gtaactccat ggcataaata gttgtatttt tgtgtacttt aaaatcaact    2340
tataactgtg agatgttatt gcttccattt tattagaaga gaaacaaatt ccatgcttta    2400
tggaatttat gtagactgga gtcttcgtga actggggcaa atgctggcat ccaggagccg    2460
ccaatactaa caggacaggt tccattgcca tggcctattc cacccaaaca atatgttgta    2520
gtttctggaa attccatact cagatatcag tctgctagaa ctttaaaatg aaggacaaat    2580
cctgttaaag aaatattgtt aaaaatcttt aaaccctgtg tattgaaagc actctatttt    2640
ctaattttat ccagttttct gtttaactcc ttataatgtt taggatatta aaattttagg    2700
ataatgaaga gtacataatg tcctacttaa tatttatgtt aataggactt aattcttact    2760
agacatctag gaacattaca aagcaaagac tattttatg cttccataac ctagaattaa     2820
aaccaaatta tgaccttatg ataaatcttt aagtattggt gtgaatgtta tttaaattct    2880 atattttct tatttaatta caaatactat aaatgagcaa ggaaaggaa tagactttct      2940 taatatatta taacactcat tcctagagct taggggtgac tctttaatat taccttatag    3000
tagaaacttt atgtaatata gctaactccg tatttacaga acaaaaaaac acagttcccc    3060
ctcctgtagt ataaatttta ttttcacata cttagctaat ttagcagtaa ttggcccagt    3120 ttttccta atagaaatac ttttagattt gattatgtat acatgacacc taagagggga     3180 acaaagtta gttttatttt tttaataaac aacagagtttt gttttgtgag ataagtatct    3240
tagtaaaccc aatttccagt cttagtctgt atttccaata tttctaattc ctgagccacg    3300
tcaaagatgc cttgccaaat ttctccccat ttctctacgg ggctagcaaa atcttcagc    3360 tttatcactc aacccctgcc aaaggaactt gattacatgg tgtctaacca atgagcagg    3420 cttaggaatt tagatgagat gtgtaagatt cacttacagg cagtagctgc ttctagcatt    3480
tgcaagatcc tacactttta ccttctttaa gggtgtacat tttgatgttg aacatcagtt    3540
ttcatgtaga cttaggactc atgtgcagta aatataaata agtgtagcat cagaagcagt    3600
aggaatggcc gtatacaacc atcctgttaa acatttaaat ttagctctga tagtgtgtta    3660
agacctgaat atctttccta gtaaaaatag gatgtgttga aatatttata tgtactttga    3720
tctctccaca tcacttataa cttatgtgtt ttatttctcc aagtgcggtg ttcctgaatg    3780
```

| | | |
|---|---|---|
| ttatgtatgc tttttttct gtaccacagg cattatctat acctgggcc agattttctg | 3840 |
| cactttgaaa tgttgccttt gcctaatgta ggttgacttt ctgaattgtg gagaggcact | 3900 |
| tttccaagcc aatcttattt gtcacttttt gttttaatat cttgctctct gacaggaaag | 3960 |
| aaacaattca cttaccagcc tcctcacccc atcctccacc atttccttaa tgttccatgg | 4020 |
| tattttcaac ggaatacact ttgaaaggta aaacaattc aaaagtatcg attatcataa | 4080 |
| attcacaaaa tattttgca accagaacac aaaagcaggc tagtcagcta aggtaaattt | 4140 |
| cattttcaaa cgagagggaa acatgggaag taaaagatta ggatgtgaaa ggttgtccta | 4200 |
| aacagaccaa ggagactgtt ccctaattta ttctcttggc tggttctctc attgaattat | 4260 |
| cagaccccaa gaggagatat tggaacaggc tcccttcatg ccaagggtct ttctaagtta | 4320 |
| atactgtgag cattgagccc ccattaaaac tcttttttac ttcagaaaga attttacagg | 4380 |
| ttaaagggaa agaaatggtg ggaaactctc cccgtaatgc ttagccaact ttaaagtgta | 4440 |
| cccttcaata tccccattgg caactgcagc tgagatctta gagaggaaat ataaccggtg | 4500 |
| tgagatctag caatgcattt tgaatcttca ctccctacca ggctcttcct attttttaatc | 4560 |
| tcttcacctc agaactagac atatggagag ctttaaaggc aagctggaag gcacattgta | 4620 |
| tcaattctac cttgtgctat acgtaggaga gatccaaaat ttggatgctt ctggagactc | 4680 |
| ttagacatct tttcattgtt gtccattttt aaagttgatg attgctggaa acattcacac | 4740 |
| gcttaaaagc aatggtgtga gttattaatg ggtaaactaa gaagtgttat aggcaatgac | 4800 |
| ttgaaatggt ttttaaattg tatggattgt taagaattgt tgaaaaaaaa tttttttttt | 4860 |
| ttggacagct tcaaggagat gttagcaatt tcagatatac tagccagttt aggtatgact | 4920 |
| ttggaagtgc agaaacagaa ggatactgtt agaaaatcct aacattggtc tccgtgcatg | 4980 |
| tgttcacacc tggtctcact gcctttcctt cccacagacc tgagtgtgaa agactgagag | 5040 |
| ttgaggagtt actttgtgga tcttgtccaa atttagtgaa atgtggaagt caaccagacc | 5100 |
| aatgatggaa ttaaatgtaa attccaagag ggctttcaca gtccacaggg ttcaaatgac | 5160 |
| ttgggtaaca gaagttattc ttagcttacc tgttatgtga cagtgattta cctgtccatt | 5220 |
| tccaacccaa aagcctgtca gaaagcattc tttagagaaa accactttac atttgttgtt | 5280 |
| aaactcctga tcgctactct taagaatata catgtatgta ttcataggaa cattttttct | 5340 |
| caatatttgt atgattcgct tactgttatt gtgctgagtg agctcctgtg tgcttcagac | 5400 |
| aaaaataaat gagactttgt gtttacgtta | 5430 |

<210> SEQ ID NO 36
<211> LENGTH: 4541
<212> TYPE: DNA
<213> ORGANISM: Homo sapiens

<400> SEQUENCE: 36

| | | |
|---|---|---|
| ggatcctcta gggtcccagc tcgcctcgat ggagctcctc ccgccgctgc ctcagtcctt | 60 |
| cctgttgctg ctgctgttgc ctgccaagcc cgcggcgggc gaggactggc agtgcccgcg | 120 |
| cacccccctac gcggcctctc gcgactttga cgtgaagtac gtggtgccca gcttctccgc | 180 |
| cggaggcctg gtacaggcca tggtgaccta cgagggcgac agaaatgaga gtgctgtgtt | 240 |
| tgtagccata cgcaatcgcc tgcatgtgct tgggcctgac ctgaagtctg tccagagcct | 300 |
| ggccacgggc cctgctggag accctggctg ccagacgtgt gcagcctgtg gcccaggacc | 360 |
| ccacggccct cccggtgaca cagacacaaa ggtgctggtg ctggatcccg cgctgcctgc | 420 |
| gctggtcagt tgtggctcca gcctgcaggg ccgctgcttc ctgcatgacc tagagcccca | 480 |

-continued

```
agggacagcc gtgcatctgg cagcgccagc ctgcctcttc tcagcccacc ataaccggcc      540
cgatgactgc cccgactgtg tggccagccc attgggcacc cgtgtaactg tggttgagca      600
aggccaggcc tcctatttct acgtggcatc ctcactggac gcagccgtgg ctggcagctt      660
cagcccacgc tcagtgtcta tcaggcgtct caaggctgac gcctcgggat tcgcaccggg      720
ctttgtggcg ttgtcagtgc tgcccaagca tcttgtctcc tacagtattg aatacgtgca      780
cagcttccac acgggagcct tcgtatactt cctgactgta cagccggcca gcgtgacaga      840
tgatcctagt gccctgcaca cacgcctggc acggcttagc gccactgagc cagagttggg      900
tgactatcgg gagctggtcc tcgactgcag atttgctcca aaacgcaggc gccgggggc      960 cccagaaggc ggacagccct accctgtgct gcaggtggcc cactccgctc cagtgggtgc      1020
ccaacttgcc actgagctga gcatcgccga gggccaggaa gtactatttg ggtctttgt      1080 gactggcaag gatggtggtc ctggcgtggg ccccaactct gtcgtctgtg ccttccccat      1140
tgacctgctg gacacactaa ttgatgaggg tgtggagcgc tgttgtgaat ccccagtcca      1200
tccaggcctc cggcgaggcc tcgacttctt ccagtcgccc agttttttgcc ccaacccgcc      1260 tggcctggaa gccctcagcc ccaacaccag ctgccgccac ttccctctgc tggtcagtag      1320
cagcttctca cgtgtggacc tattcaatgg gctgttggga ccagtacagg tcactgcatt      1380
gtatgtgaca cgccttgaca acgtcacagt ggcacacatg ggcacaatgg atgggcgtat      1440
cctgcaggtg gagctggtca ggtcactaaa ctacttgctg tatgtgtcca acttctcact      1500
gggtgacagt gggcagcccg tgcagcggga tgtcagtcgt cttggggacc acctactctt      1560
tgcctctggg gaccaggttt tccaggtacc tatccgaggc cctggctgcc gccacttcct      1620
gacctgtggg cgttgcctaa gggcatggca tttcatgggc tgtggctggt gtgggaacat      1680
gtgcggccag cagaaggagt gtcctggctc ctggcaacag gaccactgcc cacctaagct      1740
tactgagttc cacccccaca gtggacctct aaggggcagt acaaggctga ccctgtgtgg      1800
ctccaacttc taccttcacc cttctggtct ggtgcctgag ggaacccatc aggtcactgt      1860
gggccaaagt ccctgccggc cactgccccaa ggacagctca aaactcagac cagtgccccg      1920
gaaagacttt gtagaggagt ttgagtgtga actggagccc ttgggcaccc aggcagtggg      1980
gcctaccaac gtcagcctca ccgtgactaa catgccaccg ggcaagcact tccgggtaga      2040
cggcacctcc gtgctgagag gcttctcttt catggagcca gtgctgatag cagtgcaacc      2100
cctctttggc ccacgggcag gaggcacctg tctcactctt gaaggccaga gtctgtctgt      2160
aggcaccagc cgggctgtgc tggtcaatgg gactgagtgt ctgctagcac gggtcagtga      2220
ggggcagctt ttatgtgcca cacccctgg gccacggtg gccagtgtcc cccttagcct      2280
gcaggtgggg ggtgcccagg tacctggttc ctggaccttc cagtacagag aagaccctgt      2340
cgtgctaagc atcagcccca actgtggcta catcaactcc cacatcacca tctgtggcca      2400
gcatctaact tcagcatggc acttagtgct gtcattccat gacgggctta gggcagtgga      2460
aagcaggtgt gagaggcagc ttccagagca gcagctgtgc cgccttcctg aatatgtggt      2520 ccgagaccccc cagggatggg tggcagggaa tctgagtgcc cgaggggatg gagctgctgg      2580
ctttacactg cctggctttc gcttcctacc cccaccccat ccaccagtg ccaacctagt      2640 tccactgaag cctgaggagc atgccattaa gtttgagtat attgggctgg gcgctgtggc      2700
tgactgtgtg ggtatcaacg tgaccgtggg tggtgagagc tgccagcacg agttccgggg      2760
ggacatggtt gtctgccccc tgccccatc cctgcagctt ggccaggatg gtgccccatt      2820
```

```
gcaggtctgc gtagatggtg aatgtcatat cctgggtaga gtggtgcggc cagggccaga   2880
tggggtccca cagagcacgc tccttggtat cctgctgcct ttgctgctgc ttgtggctgc   2940
actggcgact gcactggtct tcagctactg gtggcggagg aagcagctag ttcttcctcc   3000
caacctgaat gacctggcat ccctggacca gactgctgga gccacacccc tgcctattct   3060
gtactcgggc tctgactaca gaagtggcct tgcactccct gccattgatg gtctggattc   3120
caccacttgt gtccatggag catccttctc cgatagtgaa gatgaatcct gtgtgccact   3180
gctgcggaaa gagtccatcc agctaaggga cctggactct gcgctcttgg ctgaggtcaa   3240
ggatgtgctg attccccatg agcgggtggt cacccacagt gaccgagtca ttggcaaagg   3300
ccactttgga gttgtctacc acggagaata catagaccag gcccagaatc gaatccaatg   3360
tgccatcaag tcactaagtc gcatcacaga gatgcagcag gtggaggcct tcctgcgaga   3420
ggggctgctc atgcgtggcc tgaaccaccc gaatgtgctg gctctcattg gtatcatgtt   3480
gccacctgag ggcctgcccc atgtgctgct gccctatatg tgccacggtg acctgctcca   3540
gttcatccgc tcacctcagc ggaaccccac cgtgaaggac ctcatcagct ttggcctgca   3600
ggtagcccgc ggcatggagt acctggcaga gcagaagttt gtgcacaggg acctggctgc   3660
gcggaactgc atgctggacg agtcattcac agtcaaggtg gctgactttg gtttggcccg   3720
cgacatcctg acagggagt actatagtgt tcaacagcat cgccacgctc gcctacctgt   3780
gaagtggatg gcgctggaga gcctgcagac ctatagattt accaccaagt ctgatgtgtg   3840
gtcatttggt gtgctgctgt gggaactgct gacacgggt gccccaccat accgccacat   3900 tgacccttt gaccttaccc acttcctggc ccagggtcgg cgcctgcccc agcctgagta   3960
ttgccctgat tctctgtacc aagtgatgca gcaatgctgg gaggcagacc cagcagtgcg   4020
acccaccttc agagtactag tgggggaggt ggagcagata gtgtctgcac tgcttgggga   4080
ccattatgtg cagctgccag caacctacat gaacttgggc cccagcacct cgcatgagat   4140
gaatgtgcgt ccagaacagc cgcagttctc acccatgcca gggaatgtac gccggccccg   4200
gccactctca gagcctcctc ggcccacttg acttagttct tgggctggac ctgcttagct   4260
gccttgagct aaccccaagg ctgcctctgg gccatgccag gccagagcag tggccctcca   4320
ccttgttcct gcccttttaac tttcagaggc aataggtaaa tgggcccatt aggtccctca   4380
ctccacagag tgagccagtg agggcagtcc tgcaacatgt atttatggag tgcctgctgt   4440
ggaccctgtc ttctgggcac agtggactca gcagtgacca caccaacact gacccttgaa   4500
ccaataaagg aacaaatgac tattaaagca caaaaaaaa a                        4541

<210> SEQ ID NO 37
<211> LENGTH: 5920
<212> TYPE: DNA
<213> ORGANISM: Homo sapiens

<400> SEQUENCE: 37
gcgctgcccg cctcgtcccc accccccaa ccccgcgcc cgcctcgga cagtccctgc         60 tcgcccgcgc gctgcagccc catctcctag cggcagccca ggcgcggagg gagcgagtcc     120
gccccgaggt aggtccagga cgggcgcaca gcagcagccg aggctggccg ggagagggag     180
gaagaggatg gcagggccac gccccagccc atgggccagg ctgctcctgg cagccttgat     240
cagcgtcagc ctctctggga ccttggcaaa ccgctgcaag aaggcccag tgaagagctg     300 cacggagtgt gtccgtgtgg ataaggactg cgcctactgc acagacgaga tgttcaggga    360
ccggcgctgc aacacccagg cggagctgct ggccgcgggc tgccagcggg agagcatcgt    420
```

-continued

```
ggtcatggag agcagcttcc aaatcacaga ggagacccag attgacacca ccctgcggcg    480
cagccagatg tccccccaag gcctgcgggt ccgtctgcgg cccggtgagg agcggcattt    540
tgagctggag gtgtttgagc cactggagag ccccgtggac ctgtacatcc tcatggactt    600
ctccaactcc atgtccgatg atctggacaa cctcaagaag atggggcaga acctggctcg    660
ggtcctgagc cagctcacca gcgactacac tattggattt ggcaagtttg tggacaaagt    720
cagcgtcccg cagacggaca tgaggcctga gaagctgaag gagccctggc ccaacagtga    780
cccccccttc tccttcaaga acgtcatcag cctgacagaa gatgtggatg agttccggaa    840
taaactgcag ggagagcgga tctcaggcaa cctggatgct cctgagggcg cttcgatgc     900 catcctgcag acagctgtgt gcacgaggga cattggctgg cgcccggaca gcacccacct    960
gctggtcttc tccaccgagt cagccttcca ctatgaggct gatggcgcca acgtgctggc   1020
tggcatcatg agccgcaacg atgaacggtg ccacctggac accacgggca cctacaccca   1080
gtacaggaca caggactacc cgtcggtgcc caccctggtg cgcctgctcg ccaagcacaa   1140
catcatcccc atctttgctg tcaccaacta ctcctatagc tactacgaga agcttcacac   1200
ctatttccct gtctcctcac tgggggtgct gcaggaggac tcgtccaaca tcgtggagct   1260
gctggaggag gccttcaatc ggatccgctc caacctggac atccgggccc tagacagccc   1320
ccgaggcctt cggacagagg tcacctccaa gatgttccag aagacgagga ctgggtcctt   1380
tcacatccgg cgggggaag tgggtatata ccaggtgcag ctgcgggccc ttgagcacgt   1440
ggatgggacg cacgtgtgcc agctgccgga ggaccagaag gcaacatcc atctgaaacc    1500 ttccttctcc gacggcctca agatggacgc gggcatcatc tgtgatgtgt gcacctgcga   1560
gctgcaaaaa gaggtgcggt cagctcgctg cagcttcaac ggagacttcg tgtgcggaca   1620
gtgtgtgtgc agcgagggct ggagtggcca gacctgcaac tgctccaccg gctctctgag   1680
tgacattcag ccctgcctgc ggagggcga ggacaagccg tgctccggcc gtggggagtg    1740
ccagtgcggg cactgtgtgt gctacggcga aggccgctac gagggtcagt ctgcgagta    1800 tgacaacttc cagtgtcccc gcacttccgg gttcctctgc aatgaccgag acgctgctc    1860 catgggccag tgtgtgtgtg agcctggttg gacaggccca agctgtgact gtcccctcag   1920
caatgccacc tgcatcgaca gcaatggggg catctgtaat ggacgtggcc actgtgagtg   1980
tggccgctgc cactgccacc agcagtcgct ctacacggac accatctgcg agatcaacta   2040
ctcggcgatc caccgggcc tctgcgagga cctacgctcc tgcgtgcagt gccaggcgtg   2100
gggcaccggc gagaagaagg ggcgcacgtg tgaggaatgc aacttcaagg tcaagatggt   2160
ggacgagctt aagagagccg aggaggtggt ggtgcgctgc tccttccggg acgaggatga   2220
cgactgcacc tacagctaca ccatggaagg tgacggcgcc cctgggccca acagcactgt   2280
cctggtgcac aagaagaagg actgccctcc gggctccttc tggtggctca tcccctgct    2340 cctcctcctc ctgccgctcc tggccctgct actgctgcta tgctggaagt actgtgcctg   2400 ctgcaaggc tgcctggcac ttctcccgtg ctgcaaccga ggtcacatgg tgggctttaa   2460
ggaagaccac tacatgctgc gggagaacct gatggcctct gaccacttgg acacgcccat   2520
gctgcgcagc gggaacctca agggccgtga cgtggtccgc tggaaggtca ccaacaacat   2580
gcagcggcct ggcttttgcca ctcatgccgc cagcatcaac cccacagagc tggtgcccta   2640
cgggctgtcc ttgcgcctgg cccgcctttg caccgagaac ctgctgaagc ctgacactcg   2700
ggagtgcgcc cagctgcgcc aggaggtgga ggagaacctg aacgaggtct acaggcagat   2760
```

```
ctccggtgta cacaagctcc agcagaccaa gttccggcag cagcccaatg ccgggaaaaa    2820
gcaagaccac accattgtgg acacagtgct gatggcgccc cgctcggcca agccggccct    2880
gctgaagctt acagagaagc aggtggaaca gagggccttc cacgacctca aggtggcccc    2940
cggctactac accctcactg cagaccagga cgcccggggc atggtggagt tccaggaggg    3000
cgtggagctg gtggacgtac gggtgcccct ctttatccgg cctgaggatg acgacgagaa    3060
gcagctgctg gtggaggcca tcgacgtgcc cgcaggcact gccaccctcg gccgccgcct    3120
ggtaaacatc accatcatca aggagcaagc cagagacgtg gtgtcctttg agcagcctga    3180
gttctcggtc agccgcgggg accaggtggc ccgcatccct gtcatccggc gtgtcctgga    3240
cggcgggaag tcccaggtct cctaccgcac acaggatggc accgcgcagg caaccgggga    3300
ctacatcccc gtggagggtg agctgctgtt ccagcctggg gaggcctgga aagagctgca    3360
ggtgaagctc ctggagctgc aagaagttga ctccctcctg cggggccgcc aggtccgccg    3420
tttccacgtc cagctcagca accctaagtt tggggcccac ctgggccagc cccactccac    3480
caccatcatc atcagggacc agatgaact  ggaccggagc ttcacgagtc agatgttgtc    3540
atcacagcca ccccctcacg gcgacctggg cgccccgcag aacccaatg  ctaaggccgc    3600
tgggtccagg aagatccatt tcaactggct gccccttct  ggcaagccaa tggggtacag    3660
ggtaaagtac tggattcagg gtgactccga atccgaagcc cacctgctcg acagcaaggt    3720
gccctcagtg gagctcacca acctgtaccc gtattgcgac tatgagatga aggtgtgcgc    3780
ctacggggct cagggcgagg accctacag  ctccctggtg tcctgccgca cccaccagga    3840
agtgcccagc gagccagggc gtctggcctt caatgtcgtc tcctccacgg tgacccagct    3900
gagctgggct gagccggctg agaccaacgg tgagatcaca gcctacgagg tctgctatgg    3960
cctggtcaac gatgacaacc gacctattgg gcccatgaag aaagtgctgg ttgacaaccc    4020
taagaaccgg atgctgctta ttgagaacct tcgggagtcc cagccctacc gctacacggt    4080
gaaggcgcgc aacggggccg gctgggggcc tgagcgggag gccatcatca acctggccac    4140
ccagcccaag aggcccatgt ccatccccat catccctgac atccctatcg tggacgccca    4200
gagcggggag gactacgaca gcttccttat gtacagcgat gacgttctac gctctccatc    4260
gggcagccag aggcccagcg tctccgatga cactggctgc ggctggaagt tcgagcccct    4320
gctgggggag gagctggacc tgcggcgcgt cacgtggcgg ctgcccccgg agctcatccc    4380
gcgcctgtcg gccagcagcg ggcgctcctc cgacgcgag  gcgccccacg ggccccggga    4440
cgacggcggc gcgggcggga agggcggcag cctgccccgc agtgcgacac ccgggccccc    4500
cggagagcac ctggtgaatg gccggatgga cttt gccttc ccgggcagca ccaactccct    4560
gcacaggatg accacgacca gtgctgctgc ctatggcacc cacctgagcc acacgtgcc    4620
ccaccgcgtg ctaagcacat cctccaccct cacacgggac tacaactcac tgacccgctc    4680
agaacactca cactcgacca cactgcccag ggactactcc accctcacct ccgtctcctc    4740
ccacgactct cgcctgactg ctggtgtgcc cgacacgccc accgcctgg  tgttctctgc    4800
cctgggcccc acatctctca gagtgagctg gcaggagccg cggtgcgagc ggccgctgca    4860
gggctacagt gtggagtacc agctgctgaa cggcggtgag ctgcatcggc tcaacatccc    4920
caacccctgcc cagacctcgg tggtggtgga agacctcctg cccaaccact cctacgtgtt    4980
ccgcgtgcgg gcccagagcc aggaaggctg gggccgagag cgtgagggtg tcatcaccat    5040
tgaatcccag gtgcacccgc agagcccact gtgtcccctg ccaggctccg ccttcacttt    5100
gagcactccc agtgccccag gccgctggt  gttcactgcc ctgagcccag actcgctgca    5160
```

| | |
|---|---|
| gctgagctgg gagcggccac ggaggcccaa tggggatatc gtcggctacc tggtgacctg | 5220 |
| tgagatggcc caaggaggag ggccagccac cgcattccgg gtggatggag acagccccga | 5280 |
| gagccggctg accgtgccgg gcctcagcga aacgtgccc tacaagttca aggtgcaggc | 5340 |
| caggaccact gagggcttcg ggccagagcg cgagggcatc atcaccatag agtcccagga | 5400 |
| tggaggaccc ttcccgcagc tgggcagccg tgccgggctc ttccagcacc cgctgcaaag | 5460 |
| cgagtacagc agcatcacca ccacccacac cagcgccacc gagcccttcc tagtggatgg | 5520 |
| gctgaccctg ggggcccagc acctggaggc aggcggctcc ctcacccggc atgtgaccca | 5580 |
| ggagtttgtg agccggacac tgaccaccag cggaacccct agcacccaca tggaccaaca | 5640 |
| gttcttccaa acttgaccgc accctgcccc accccgcca cgtcccacta ggcgtcctcc | 5700 |
| cgactcctct cccggagcct cctcagctac tccatccttg caccctggg ggcccagccc | 5760 |
| acccgcatgc acagagcagg ggctaggtgt ctcctgggag gcatgaaggg ggcaaggtcc | 5820 |
| gtcctctgtg ggcccaaacc tatttgtaac caaagagctg ggagcagcac aaggacccag | 5880 |
| cctttgttct gcacttaata aatggttttg ctactgctaa | 5920 |

<210> SEQ ID NO 38
<211> LENGTH: 1620
<212> TYPE: DNA
<213> ORGANISM: Homo sapiens
<400> SEQUENCE: 38

| | |
|---|---|
| gggtggggaa gcttagagac cggtgaggga gcagagctgg ggcgcctgtg tacagggata | 60 |
| gagcccggcg gcagcagggc gcggcttccc tttcccgggg cctggggccg caatcaggtg | 120 |
| gagtcgagag gccggaggag gggcaggagg aaggggtgcg gtcgcgatcc ggacccggag | 180 |
| ccagcgcgga gcacctgcgc ccgcggctga caccttcgct cgcagtttgt tcgcagttta | 240 |
| ctcgcacacc agtttccccc accgcgcttt ggattagtgt gatctcagct caaggcaaag | 300 |
| gtgggatatc atggcatcta tctgggttgg acaccgagga acagtaagag attatccaga | 360 |
| ctttagccca tcagtggatg ctgaagctat tcagaaagca atcagaggaa ttggaactga | 420 |
| tgagaaaatg ctcatcagca ttctgactga gaggtcaaat gcacagcggc agctgattgt | 480 |
| taaggaatat caagcagcat atggaaagga gctgaaagat gacttgaagg gtgatctctc | 540 |
| tggccacttt gagcatctca tggtggccct agtgactcca ccagcagtct ttgatgcaaa | 600 |
| gcagctaaag aaatccatga agggcgcggg aacaaacgaa gatgccttga ttgaaatctt | 660 |
| aactaccagg acaagcaggc aaatgaagga tatctctcaa gcctattata cagtatacaa | 720 |
| gaagagtctt ggagatgaca ttagttccga aacatctggt gacttccgga agctctgtt | 780 |
| gactttggca gatggcagaa gagatgaaag tctgaaagtg gatgagcatc tggccaaaca | 840 |
| agatgcccag attctctata agctggtga aacagatgg ggcacggatg aagacaaatt | 900 |
| cactgagatc ctgtgtttaa ggagctttcc tcaattaaaa ctaacatttg atgaatacag | 960 |
| aaatatcagc caaaaggaca ttgtggacag cataaaagga gaattatctg gcatttttga | 1020 |
| agacttactg ttggccatag ttaattgtgt gaggaacacg ccggccttt tagccgaaag | 1080 |
| actgcatcga gccttgaagg gtattggaac tgatgagttt actctgaacc gaataatggt | 1140 |
| gtccagatca gaaattgacc ttttggacat tcgaacagag ttcaagaagc attatggcta | 1200 |
| ttccctatat tcagcaatta aatcggatac ttctggagac tatgaaatca cactcttaaa | 1260 |
| aatctgtggt ggagatgact gaaccaagaa gataatctcc aaaggtccac gatgggcttt | 1320 |

| | | |
|---|---|---|
| cccaacagct ccaccttact tcttctcata ctatttaaga gaacaagcaa atataaacag | 1380 |
| caacttgtgt tcctaacagg aattttcatt gttctataac aacaacaaca aaagcgatta | 1440 |
| ttattttaga gcatctcatt tataatgtag cagctcataa atgaaattga aaatggtatt | 1500 |
| aaagatctgc aactactatc caactatat ttctgctttc aaagttaaga atctttatag | 1560 |
| ttctactcca ttaaatataa agcaagataa taaaaattgt tgcttttgtt aaaagtaaaa | 1620 |

<210> SEQ ID NO 39
<211> LENGTH: 955
<212> TYPE: DNA
<213> ORGANISM: Homo sapiens

<400> SEQUENCE: 39

| | |
|---|---|
| tgcagactga tatggattca ccactgctaa cacctcctgg ttggaactac aggaatagaa | 60 |
| ctggaaaggg aaaaaaggca gcattcacca catcccaatc ctgaatccaa gagtctaaga | 120 |
| tagtccccca ctcctatctc aggcttagag gattagatta atctcctgga gggaagactc | 180 |
| ttccttgaaa catttttttt tatctgcctg tagctattgg gataattcgg gaaatccaca | 240 |
| gggacagttc aagtcatctt tgtcctctac ttttctgttgc actctcagcc ttgttctctt | 300 |
| tttagaaact gcatggtaac tattatatag ctaaagaaga gcattctgac ctctgccctg | 360 |
| ggacttcctg gatcctcctc ttcttataaa tacaagggca gagctggtat cccgggggagc | 420 |
| caggaagcag tgagcccagg agtcctcggc cagccctgcc tgcccaccag gaggatgaag | 480 |
| gtctccgtgg ctgccctctc ctgcctcatg cttgttgctg tccttggatc ccaggcccag | 540 |
| ttcataaatg atgcagagac agagttaatg atgtcaaagc ttccactgga aaatccagta | 600 |
| gttctgaaca gctttcactt tgctgctgac tgctgcacct cctacatctc acaaagcatc | 660 |
| ccgtgttcac tcatgaaaag ttattttgaa acgagcagcg agtgctccaa gccaggtgtc | 720 |
| atattcctca ccaagaaggg gcggcaagtc tgtgccaaac ccagtggtcc gggagttcag | 780 |
| gattgcatga aaaagctgaa gccctactca atataataat aaagagacaa aagaggccag | 840 |
| ccacccacct ccaacacctc ctgtgagttt cttggtctga aatacttaaa aaatatatat | 900 |
| attgttgtgt ctggtaatga aagtaatgca tctaataaag agtattcaat ttttt | 955 |

<210> SEQ ID NO 40
<211> LENGTH: 1738
<212> TYPE: DNA
<213> ORGANISM: Homo sapiens

<400> SEQUENCE: 40

| | |
|---|---|
| cgggggggta ctgtgcgagc cctcaaggag gtggctgttc tgtagctgga gagctccgtg | 60 |
| ggtggcagga ctgaacttga acaccagaaa caaccccaa gccttgtgac ctgggaggca | 120 |
| ggaggcgggt ctgtctccct gggacttggg tggctgagcc gaggtactcg ggaccctgtc | 180 |
| ccgcgcatgg cagagtggct cctcacagcc tgaagctcat ccttctgcac gggccagcca | 240 |
| ggccagcaca gaggcaccag ggcagcagtg cacacaggtc cccggggacc ccaccatgtg | 300 |
| gagcggatgt tggctgtggc cccttgtggc cgtctgcact gcagacttct ttcgggacga | 360 |
| ggcagagagg atcatgaggg actccctgt cattgatggg cacaatgacc tccctggca | 420 |
| gctgctggat atgttcaaca accggctgca ggacgagagg gccaacctga ccaccttggc | 480 |
| cggcacacac accaacatcc caagctgag gccggctttt gtgggaggcc agttctggtc | 540 |
| cgtgtacacg ccctgcgaca cccagaacaa agacgccgtg cggaggacgc tggagcagat | 600 |
| ggacgtggtc caccgcatgt gccggatgta cccggagacc ttcctgtatg tcaccagcag | 660 |

-continued

```
tgcaggcatt cggcaggcct tccgggaagg gaaggtggcc agcctgatcg gcgtggaggg      720
cggccactcc attgacagca gtttgggcgt cctgcgggca ctctatcagc tgggcatgcg      780
gtacctgacc ctcacccaca gctgcaacac gccctgggct gacaactggc tggtggacac      840
gggagacagc gagccccaga gccaaggctt gtcacccttt gggcagcgtg tggtgaagga      900
gctgaaccgt ctgggggtcc tcatcgactt ggctcacgtg tctgtggcca ccatgaaggc      960
caccctgcag ctgtccagag ccccggtcat cttcagccac tcctcggcct acagcgtgtg     1020
cgcaagccgg cgcaacgtgc ctgacgacgt cctgaggctg gtgaaacaga cagacagcct     1080
ggtgatggtg aacttctaca caattacat ttcctgcacc aacaaggcca acctgtccca      1140
agtggccgac catctggatc acatcaagga ggtggcagga gccagagccg tgggttttgg     1200
tggggacttt gatggtgttc caagggtccc tgaggggctg gaggacgtct ccaagtatcc     1260
agacctgatc gctgagctgc tcaggaggaa ctggacggag gcggaggtca agggcgcact     1320
ggctgacaac ctgctgaggg tcttcgaggc tgtggaacag gccagcaacc tcacacaggc     1380
tcccgaggag gagcccatcc cgctggacca gctgggtggc cctgcagga cccattacgg      1440 ctactcctct ggggcttcca gcctccatcg ccactggggg ctcctgctgg cctccctcgc     1500 tccctggtc ctctgtctgt ctctcctgtg aaacctggga gaccagagtc ccctttaggg      1560
ttcccggagc tccgggaaga cccgcccatc ccaggactcc agatgccagg agccctgctg     1620
cccacatgca aggaccagca tctcctgaga ggacgcctgg gcttacctgg ggggcaggat     1680
gcctggggac agttcaggac acacacacag taggcccgca ataaaagcaa caccccctt     1738
```

<210> SEQ ID NO 41
<211> LENGTH: 1132
<212> TYPE: DNA
<213> ORGANISM: Homo sapiens

<400> SEQUENCE: 41

```
agccatggca ggcccccgat acccagtttc agtgcaaggg gcagccctgg tgcagatcaa       60
gaggctccaa acgtttgcct tctctgtgcg ctggtcagac ggcagcgaca ccttcgtgcg      120
caggagttgg gacgaattca ggcagctcaa gaagaccctc aaggagacct tcccggtgga      180
ggcgggcctg ctgcggagat ctgaccgcgt tctcccaaag cttctcgatg caccactgtt      240
gggacgcgtg gggcgcacga gccgcggcct ggcgcgcctg cagctgttgg aaacctattc      300
tcggaggctg ctggcgactg cagagcgcgt ggcacggagc ccgacgatca ctggcttctt      360
cgcaccgcaa ccctggacc tggagcccgc gctgccaccc ggcagccggg tgatcctgcc      420 cacccccagag gagcagcctc tttctcgcgc tgcgggccgc ctctccatcc acagtctgga     480
ggctcagagc ctgcgctgcc tgcagccctt ctgtacccag gacacgcggg ataggccttt     540
tcaggcgcag gcccaggaga gcctggacgt gctgctgcgg caccccctcag gctggtggct    600 ggtggagaac gaagaccggc agaccgcctg gtttccagcg ccctacctgg aggaggcggc     660
cccgggccaa ggccgggagg gaggccccgtc cctagggagc agcggtcccc agttctgtgc    720
ttcccgcgcc tacgagagca gccgcgcaga tgagctgtcc gtgcccgcgg gggcgcgcgt     780
gcgcgtgttg gaaacgtcag accgcggctg gtggctatgc aggtacgcg accgggcggg     840 cctactcccc gcggtgctgc tgcggccgga agggctgggc gctctcctga gcgggacggg     900
gttccgtgga ggagacgacc cggcgggtga ggcccgggc ttccctgaac cctcccaggc      960
caccgcccct cccccaccg tgcccacccg accttcgccg ggcgccatcc agagccgctg     1020
```

```
ctgcaccgtc acacgcaggg ccctggagcg gcgcccacgg cgccagggcc gccctcgagg    1080
gtgcgtggac tctgtgccgc accccacgac ggagcagtga gcgcgaggat cc            1132

<210> SEQ ID NO 42
<211> LENGTH: 656
<212> TYPE: DNA
<213> ORGANISM: Homo sapiens

<400> SEQUENCE: 42
gggaacacat ccaagcttaa gacggtgagg tcagcttcac attctcagga actctccttc      60
tttgggtctg gctgaagttg aggatctctt actctctagg ccacggaatt aacccgagca    120
ggcatggagg cctctgctct cacctcatca gcagtgacca gtgtggccaa agtggtcagg    180
gtggcctctg gctctgccgt agttttgccc ctggccagga ttgctacagt tgtgattgga    240
ggagttgtgg ctgtgcccat ggtgctcagt gccatgggct tcactgcggc gggaatcgcc    300
tcgtcctcca tagcagccaa gatgatgtcc gcggcggcca ttgccaatgg gggtggagtt    360
gcctcgggca gccttgtggc tactctgcag tcactgggag caactggact ctccggattg    420
accaagttca tcctgggctc cattgggtct gccattgcgg ctgtcattgc gaggttctac    480
tagctccctg cccctcgccc tgcagagaag agaaccatgc caggggagaa ggcacccagc    540
catcctgacc cagcgaggag ccaactatcc caaatatacc tggggtgaaa tataccaaat    600
tctgcatctc cagaggaaaa taagaaataa agatgaattg ttgcaactct tcaaaa         656

<210> SEQ ID NO 43
<211> LENGTH: 2164
<212> TYPE: DNA
<213> ORGANISM: Homo sapiens

<400> SEQUENCE: 43
acctctgggc agagaaacaa agctctatat gcacagccca gcaaagagca gcacacagct      60
gaaagaaaaa ctcagaagac agagctgaaa aagaaaactg gtgatggatc tcattccaaa    120 cttttgccatg gaaacatggg ttcttgtggc taccagcctg gtactcctct atatttatgg    180
gacccattca cataaacttt ttaagaagct gggaattcct gggccaaccc ctctgccttt    240
tctgggaact attttgttct accttagggg tcttttggaat tttgacagag aatgtaatga    300
aaaatacgga gaaatgtggg ggctgtatga ggggcaacag cccatgctgg tcatcatgga    360
tcccgacatg atcaaaacag tgttagtgaa agaatgttac tctgtcttca caaaccagat    420
gcctttaggt ccaatgggat ttctgaaaag tgccttaagt tttgctgaag atgaagaatg    480
gaagagaata cgaacattgc tatctccagc tttcaccagt gtaaaattca aggaaatggt    540
ccccatcatt tcccaatgtg gagatatgtt ggtgagaagc ctgaggcagg aagcagagaa    600
cagcaagtcc atcaacttga aagatttctt tggggcctac accatggatg taatcactgg    660
cacattattt ggagtgaact tggattctct caacaatcca caagatccct ttctgaaaaa    720
tatgaagaag ctttttaaaat tggatttttt ggatcccttt ttactcttaa tatcactctt    780
tccatttctt acccccagttt ttgaagccct aaatatcggt ttgtttccaa agatgttac    840 ccattttta aaaaattcca ttgaaaggat gaaagaaagt cgcctcaaag ataaacaaaa    900
gcatcgagta gatttctttc aacagatgat cgactcccag aattccaaag aaacaaagtc    960
ccataaagct ctgtctgatc tggagcttgt ggcccagtca attatcatca tttttgctgc   1020
ctatgacaca actagcacca ctctccccctt cattatgtat gaactggcca ctcaccctga   1080
tgtccagcag aaactgcagg aggagattga cgcagttttta cccaataagg cacctgtcac   1140
```

```
ctacgatgcc ctggtacaga tggagtacct tgacatggtg gtgaatgaaa cgctcagatt   1200
attcccagtt gttagtagag ttacgagagt ctgcaagaaa gatattgaaa tcaatggagt   1260
gttcattccc aaagggttag cagtgatggt tccaatctat gctcttcacc atgacccaaa   1320
gtactggaca gagcctgaga agttctgccc tgaaaggttc agtaagaaga caaggacag    1380 catagatctt tacagataca tacctttgg agctggaccc cgaaactgca ttggcatgag    1440
gtttgctctc acaaacataa aacttgctgt cattagagca ctgcagaact tctccttcaa   1500
accttgtaaa gagactcaga tcccactgaa attagacaat ctaccaattc ttcaaccaga   1560
aaaacctatt gttctaaaag tgcacttaag agatgggatt acaagtggac cctgactttc   1620
cctaaggact tccactttgt tcaagaaagc tgtatcccag aacactagac acttcaaatt   1680
gttttgtgaa taaaactcag aaatgaagat gagcttaatt aacctagtat actgggtgaa   1740
taattagaaa ttctctacat tcattgagct ctcattgtct gggtagagta ttacacgttg   1800
catactacaa agcaggtgac aaatcaatgc caaataagta cagtcatctt ctctagttct   1860
cataagacta tctccccgcc acctatagtt agtaccctca agtcctcctg agctgtgatc   1920
agagaataaa catttctcaa caattttacc aacaattttt aatgaaaagg aaaattatac   1980
ttgtgattct cgtagtgaca tttatattac atgttccatt tgtgatattc tataataagt   2040
attatattga gaaagtcaac aagcacctct ttacaaaact gttatctgat gtcttcctgc   2100
atattaagga tgaatctaca gaattagatc aataaggatc aacaaataaa tatttttggt   2160
catt                                                               2164

<210> SEQ ID NO 44
<211> LENGTH: 4380
<212> TYPE: DNA
<213> ORGANISM: Homo sapiens

<400> SEQUENCE: 44
gtggcggctt cgcccgcgag tccagaggca ggcgagcagc tcggtcgccc ccaccggccc     60
catggcagcc cccggcgccc cagctgagta cggctacatc cggaccgtcc tgggccagca    120
gatcctggga caactggaca gctccagcct ggcgctgccc tccgaggcca agctgaagct    180
ggcggggagc agcggccgcg gcggccagac agtcaagagc ctgcggatcc aggagcaggt    240
gcagcagacc ctcgcccgga agggccgcag ctccgtgggc aacggaaatc ttcaccgaac    300
cagcagtgtt cctgagtatg tctacaacct acacttggtt gaaaatgatt tgttggagg     360 ccgttcccct gttcctaaaa cctatgacat gctaaaggct ggcacaactg ccacttatga    420
aggtcgctgg ggaagaggaa cagcacagta cagctcccag aagtccgtgg aagaaaggtc    480
cttgaggcat cctctgagga gactggagat ttctcctgac agcagcccgg agagggctca    540
ctacacgcac agcgattacc agtacagcca gagaagccag gctgggcaca ccctgcacca    600
ccaagaaagc aggcgggccg ccctcctagt gccaccgaga tatgctcgtt ccgagatcgt    660
gggggtcagc cgtgctggca ccacaagcag gcagcgccac tttgacacat accacagaca    720
gtaccagcat ggctctgtta gcgacaccgt ttttgacagc atccctgcca acccggccct    780
gctcacgtac cccaggccag ggaccagccg cagcatgggc aacctcttgg agaaggagaa    840
ctacctgacg gcagggctca ctgtcgggca ggtcaggccc tggtgcccc tgcagccgt     900 cactcagaac agggcttcca ggtcctcctg gcatcagagc tccttccaca gcacccgcac    960
gctgagggaa gctgggccca gtgtcgccgt ggattccagc gggaggagag cgcacttgac   1020
```

```
tgtcggccag gcggccgcag ggggaagtgg gaatctgctc actgagagaa gcactttcac   1080
tgactcccag ctggggaatg cagacatgga gatgactctg gagcgagcag tgagtatgct   1140
cgaggcagac cacatgccgc catccaggat ttctgctgca gctactttca tacagcacga   1200
gtgcttccag aaatctgaag ctcggaagag ggttaaccag cttcgtggca tcctcaagct   1260
tctgcagctc ctaaaagttc agaatgaaga cgttcagcga gctgtgtgtg gggccttgag   1320
aaacttagta tttgaagaca atgacaacaa attggaggtg gctgaactaa atggggtacc   1380
tcggctgctc caggtgctga agcaaaccag agacttggag actaaaaaac aaataacaga   1440
ccatacagtc aatttaagaa gtaggaatgg ctggccgggc gcggtggctc acgcctgtaa   1500
tcccagcact ttgggaggcc aaggcgggcg gatcacgagg tcaggagttc gagaccagcc   1560
tgaccaacat ggtttgctgt ggaatttgtc atctaatgac aaactcaaga atctcatgat   1620
aacagaagca ttgcttacgc tgacggagaa tatcatcatc ccctttttctg ggtggcctga   1680 aggagactac ccaaaagcaa atggtttgct cgattttgac atattctaca acgtcactgg   1740
atgcctaaga aacatgagtt ctgctggcgc tgatgggaga aaagcgatga aagatgtga    1800 cggactcatt gactcactgg tccattatgt cagaggaacc attgcagatt accagccaga   1860
tgacaaggcc acggagaatt gtgtgtgcat tcttcataac ctctcctacc agctggaggc   1920
agagctccca gagaaatatt cccagaatat ctatattcaa aaccggaata tccagactga   1980
caacaacaaa agtattggat gttttggcag tcgaagcagg aaagtaaaag agcaatacca   2040
ggacgtgccg atgccggagg aaaagagcaa ccccaagggc gtggagtggc tgtggcattc   2100
cattgttata aggatgtatc tgtccttgat cgccaaaagt gtccgcaact acacacaaga   2160
agcatcctta ggagctctgc agaacctcac ggccggaagt ggaccaatgc cgacatcagt   2220
ggctcagaca gttgtccaga aggaaagtgg cctgcagcac acccgaaaga tgctgcatgt   2280
tggtgaccca agtgtgaaaa agacagccat ctcgctgctg aggaatctgt cccggaatct   2340
ttctctgcag aatgaaattg ccaaagaaac tctccctgat ttggtttcca tcattcctga   2400
cacagtcccg agtactgacc ttctcattga aactacagcc tctgcctgtt acacattgaa   2460
caacataatc caaaacagtt accagaatgc acgcgacctt ctaaacaccg ggggcatcca   2520
gaaaattatg gccattagtg caggcgatgc ctatgcctcc aacaaagcaa gtaaagctgc   2580
ttccgtcctt ctgtattctc tgtgggcaca cacggaactg catcatgcct acaagaaggc   2640
tcagtttaag aagacagatt ttgtcaacag ccggactgcc aaagcctacc actcccttaa   2700
agactgagga aaatgacaaa gtattctcgg ctgcaaaaat ccccaaagga aaacacctat   2760
ttttctacta cccagcccaa gaaacctcaa aagcatgcct tgtttctatc cttctctatt   2820
tccgtggtcc cctgaatcca gaaaacaaat agaacataat tttatgagtc ttccagaaga   2880
cctttgcaag tttgccacca gtagataccg gccacaggct cgacaaatag tggtctttgt   2940
tattagggct tatggtacat ggcttcctgg aatcaaaatg tgaattcatg tggaagggac   3000
attaatccaa taaataagga aagaagctgt tgcattactg ggattttaaa agtttgattt   3060
acatttatat tcctttttctg gttcccatgt tttgtcactc atgtgcacat tgcttcgcca   3120
ttgggcctcc agtgtattgt tctgcagtgt tgaaacagaa tggaaatgac aagaaatatc   3180
tgcagttatc caggagaaag tataatggca aaattattgg tttctttctt tactttgtgc   3240
ttgtttttat ccccttgggt tgttttttctc tgatttttaa ataaacttaa gaaatttaga   3300
ttacagagta tgcatgactg taagaaaaag aaattgagag gaagtgatca tagcaaatta   3360
aagaagtctt ttcctcccag aacttaaagt aaaataaaaa ataaataaat aaataaaatc   3420
```

```
-continued tttccacag agaaaggcaa ctgtgatgat aaaatttaac gttccccaa acactgagtc    3480 aatgagattt ttctcaggag atactttacc tataacaacg ccgttaaatc caaatctctt    3540
ctaaacgatg gcattctatg taatgccttt cctggacttt tttggccact gccctggact    3600
agtgaaagaa tggactctat ctttatctgc aagaggaact aaggccttct atcagactgc    3660
ctggccagcc tggggcactg aaaatacggc tcatgttaat gagttacatt atcagccagc    3720
ccagccttgc ccaccattta agaaatatca cagagccact agatctcata tgatcttctt    3780
caagccatta ttttaactca agaaaactct agagaagaaa agtgaagaag tcatgttgaa    3840
gaagatgtaa gaatgtgtca agaccatcca gaaatgatat gagaaatact gatattttaa    3900
atggttgaca tcatccagcg aaatgaatct acattaaatg ttgttttaac tgcgctatga    3960
ttaaaaccat tcatatagag ttagtcttta caactactat tctgttattt tttttttttaa    4020 tctgacaaca tttgtcctaa gtaagataag caaaaaaatt cttcaactcc ttttggcaag    4080
aaaactgtaa cagaaaataa attttgaatg tgtacttaag tctttattat atttgaagca    4140
attttttttc aattttaaaa gctgaatgaa gacaacttag gttgctaacc tagttcaaaa    4200
tgaaattatt tagataccaa tttttaaaat actggagaga atttatatgt cttttccag      4260 agttctgatg ataagcattt ggagtgcatt tattcctcca gataataaat gtgtgttcag    4320
aactttttgt gttttttaag gcattaataa agccttcgat aatattaaat acaaaatgaa    4380
```